United States Patent
Nakamura et al.

(10) Patent No.: US 10,160,727 B2
(45) Date of Patent: Dec. 25, 2018

(54) HETEROCYCLE AND CARBOCYCLE DERIVATIVES HAVING TRKA INHIBITORY ACTIVITY

(71) Applicant: Shionogi & Co., Ltd., Osaka (JP)

(72) Inventors: Kenichiroh Nakamura, Osaka (JP); Takatsugu Inoue, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 15/501,749

(22) PCT Filed: Aug. 5, 2015

(86) PCT No.: PCT/JP2015/072209
§ 371 (c)(1),
(2) Date: Feb. 3, 2017

(87) PCT Pub. No.: WO2016/021629
PCT Pub. Date: Feb. 11, 2016

(65) Prior Publication Data
US 2017/0240512 A1 Aug. 24, 2017

(30) Foreign Application Priority Data

Aug. 6, 2014 (JP) ................ 2014-160655
Dec. 26, 2014 (JP) ................ 2014-263731
May 29, 2015 (JP) ................ 2015-109262

(51) Int. Cl.
| | | |
|---|---|---|
| C07D 213/72 | (2006.01) |
| C07D 231/40 | (2006.01) |
| C07D 401/14 | (2006.01) |
| C07D 403/12 | (2006.01) |
| C07D 403/14 | (2006.01) |
| C07D 405/14 | (2006.01) |
| C07D 409/14 | (2006.01) |
| C07D 413/14 | (2006.01) |
| C07D 417/14 | (2006.01) |
| C07D 471/04 | (2006.01) |
| C07D 487/08 | (2006.01) |

(52) U.S. Cl.
CPC ......... *C07D 231/40* (2013.01); *C07D 213/72* (2013.01); *C07D 401/14* (2013.01); *C07D 403/12* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 487/08* (2013.01)

(58) Field of Classification Search
None
See application file for complete search history.

(56) References Cited

U.S. PATENT DOCUMENTS

| | | |
|---|---|---|
| 4,855,316 A | 8/1989 | Horwell et al. |
| 4,906,655 A | 3/1990 | Horwell et al. |
| 2015/0166564 A1* | 6/2015 | Allen ............... C07D 401/14 514/236.5 |
| 2016/0000783 A1 | 1/2016 | Takeuchi et al. |
| 2016/0280684 A1 | 9/2016 | Takeuchi et al. |
| 2017/0027939 A1 | 2/2017 | Takeuchi et al. |
| 2017/0340634 A1 | 11/2017 | Takeuchi et al. |

FOREIGN PATENT DOCUMENTS

| | | |
|---|---|---|
| EP | 0 372 466 A2 | 6/1990 |
| EP | 2 842 955 A1 | 3/2015 |
| WO | WO 99/016431 | 4/1999 |
| WO | WO 00/35452 A1 | 6/2000 |
| WO | WO 2004/110993 A2 | 12/2004 |
| WO | WO 2005/026113 A | 3/2005 |
| WO | WO 2005/110994 A2 | 11/2005 |
| WO | WO 2009/074260 A1 | 6/2009 |
| WO | WO 2009/131196 A1 | 10/2009 |

(Continued)

OTHER PUBLICATIONS

Ito et al. in Cancer Science 94(1), 3-8 (2003).*
STN Registry database entry for CAS RN 410069-68-0, STN entry date May 2, 2002; Accessed Oct. 2, 2017.*
International Preliminary Report on Patentability for International Application No. PCT/JP2015/072209, The International Bureau of WIPO, Geneva, Switzerland, dated Feb. 7, 2017, 10 pages.
International Search Report and Written Opinion for International Application No. PCT/JP2015/072209, Japan Patent Office, Tokyo, Japan, dated Sep. 15, 2015, 28 pages.

(Continued)

*Primary Examiner* — Alicia L Otton
(74) *Attorney, Agent, or Firm* — Sterne, Kessler, Goldstein & Fox P.L.L.C.

(57) ABSTRACT

The present invention relates to a compound represented by Formula (I):

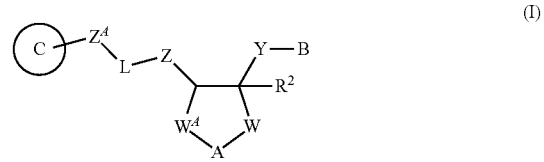

(I)

wherein -L- is —C(=X)—, or the like, —Z— is —NR$^5$—, or the like, —Z$^A$— is —NR$^{5A}$—, or the like, —W— is —C(R$^8$R$^9$)n-, —W$^A$— is —C(R$^3$R$^4$)m-, B is substituted or unsubstituted aromatic carbocyclyl, or the like, Y is a bond, or the like, the ring C is a substituted or unsubstituted aromatic heterocycle, or the like, R$^2$ is a hydrogen atom, or the like, or a pharmaceutically acceptable salt thereof, or a pharmaceutical composition comprising thereof.

12 Claims, No Drawings

(56) References Cited

FOREIGN PATENT DOCUMENTS

| WO | WO 2014/052563 A2 | 4/2012 |
|---|---|---|
| WO | WO 2012/158413 A2 | 11/2012 |
| WO | WO 2012/174199 A1 | 12/2012 |
| WO | WO 2014/053965 | 4/2014 |
| WO | WO 2014/053967 | 4/2014 |
| WO | WO 2014/053968 | 4/2014 |
| WO | WO 2014/078322 | 5/2014 |
| WO | WO 2014/078323 | 5/2014 |
| WO | WO 2014/078325 A1 | 5/2014 |
| WO | WO 2014/078328 | 5/2014 |
| WO | WO 2014/078331 | 5/2014 |
| WO | WO 2014/078372 | 5/2014 |
| WO | WO 2014/078378 | 5/2014 |
| WO | WO 2014/078408 | 5/2014 |
| WO | WO 2014/078417 | 5/2014 |
| WO | WO 2014/078454 | 5/2014 |
| WO | WO 2015/039333 A1 | 3/2015 |
| WO | WO 2015/039334 A1 | 3/2015 |
| WO | WO 2015/042085 A2 | 3/2015 |
| WO | WO 2015/042088 A1 | 3/2015 |
| WO | WO 2015/159175 A1 | 10/2015 |
| WO | WO 2015/170218 A1 | 11/2015 |
| WO | WO 2015/175788 A1 | 11/2015 |
| WO | WO 2016/116900 A1 | 7/2016 |
| WO | WO 2017/006953 A1 | 1/2017 |
| WO | WO 2017/135399 A1 | 8/2017 |

OTHER PUBLICATIONS

Allen, S.J., and Dawbarn, D."Clinical relevance of the neurotrophins and their receptors," *Clinical Science* 110:175-191, The Biochemical Society, England (2006).

Chao, M.V., "Neurotrophins and Their Receptors: A Convergence Point for Many Signalling Pathways," *Nature Reviews Neuroscience* 14: 299-309, Nature Publishing Group, England (2003).

Ghilardi, J., et al. "Administration of a tropomyosin receptor kinase inhibitor attenuates sarcoma-induced nerve sprouting, neuroma formation and bone cancer pain," *Molecular Pain* 6:87 Biomedcentral, England (2010).

Ghilardi, J., et al., "Sustained blockade of neurotrophin receptors TrkA, TrkB and TrkC reduces non-malignant skeletal pain but not the maintenance of sensory and sympathetic nerve fibers" *Bone 48*: 389-398, Elsevier, The Netherlands (2011).

Halfpenny, P.R., et al., "Highly Selective K-Opioid Analgesics. 2. Synthesis and Structure-Activity Relationships of Novel N-[(2-Aminocyclohexyl)aryl]acetamide Derivatives," *Journal of Medicinal Chemistry* 32(7): 1620-1626, American Chemical Society, United States, American Chemical Society, United States (1989).

Halfpenny, P.R., et al., "Highly Selective K-Opioid Analgesics. 3. Synthesis and Structure-Activity Relationships of Novel N-[2-(1-Pyrrolidinyl)-4- or -5-substituted-cyclohexyl]arylacetamide Derivatives," *Journal of Medicinal Chemistry* 33(1): 286-291, American Chemical Society, United States (1990).

Indo, Y., "Nerve growth factor and the physiology of pain: lessons from congenital insensitivity to pain with anhidrosis," *Clinical Genetics 82*: 341-350 (2012).

Mantyh, P.W., et al., "Antagonism of Nerve Growth Factor-TrkA Signaling and the Relief of Pain," *Anesthesiology* 115:189-204, The American Society of Anesthesiologists, United States (2011).

McCarthy, C., and Walker, E., "Tropomyosin receptor kinase inhibitors: a patent update 2009-2013," *Expert Opinion on Therapeutic Patents 24*: 731-744, Informa Healthcare, England (2014).

McKelvey, L., et al., "Nerve growth factor-mediated regulation of pain signalling and proposed new intervention strategies in clinical pain management," *Journal of Neurochemistry 124*: 276-289, International Society for Neurochemistry (2013).

Meyer, J., et al., "Remarkable leukemogenic potency and quality of a constitutively active neurotrophin receptor, DTrkA," *Leukemia 21*: 2171-2180, Nature Publishing Group (2007).

Pinski, J., et al., "Trk Receptor Inhibition Induces Apoptosis of Proliferating but not Quiescent Human Osteoblasts," *Cancer Research 62*: 986-989, American Association for Cancer Research, United States (2002).

Stachel, S.J., et al., "Maximizing Diversity from a Kinase Screen: Identification of Novel and Selective pan-Trk Inhibitors for Chronic Pain," *Journal of Medicinal Chemistry 57*: 5800-5816, American Chemical Society, United States (2014).

Truzzi, F., et al. "Neurotrophins in healthy and diseased skin," *Dermato-Endocrinology, 3*: 32-36, Landes Bioscience, United States (2011).

Vaishnavi, A., et al., "Oncogenic and drug-sensitive NTRK1 rearrangements in lung cancer," *Nature Medicine 19*: 1469-1472, Nature Publishing Group, England (2013).

Wang, T., et al., "Trk kinase inhibitors as new treatments for cancer and pain," *Expert Opinion on Therapeutic Patents 19*: 305-319, Informa UK Ltd, England (2009).

Avontis, F., "2-2-Dimethyl-3-[N'-alkyl(aryl) ureido]-1-[[N'-alkyl(aryl)ureido]methyl] cyclobutanes", *LATVIJAS KIMIJAS ZURNALS*;715-720, Riga, Latviia (1991).

File Registry on STN, RN 410069-68-0, American Chemical Society, United States (2016).

\* cited by examiner

HETEROCYCLE AND CARBOCYCLE DERIVATIVES HAVING TRKA INHIBITORY ACTIVITY

TECHNICAL FIELD

The present invention relates to a compound that has a TrkA inhibitory activity and is useful in the treatment and/or prevention of TrkA mediated disorders, or a pharmaceutically acceptable salt thereof, and a pharmaceutical composition comprising thereof.

BACKGROUND ART

The tropomyosin receptor kinase (Trk) is a family of receptor tyrosine kinases and has a function as a receptor of neurotrophin (NT). Three maj or subtypes of Trk receptors are TrkA high-affinity receptor for nerve growth factor (NGF), TrkB high-affinity receptor for brain-derived neutrophic factor (BDNF) and NT-4/5, and TrkC high-affinity receptor for NT-3. All receptors involve in various physiological function in vivo. TrkA is mainly expressed in peripheral and central nerves, and involves in neuronal development and differentiation, and maintenance of neuronal functions. The gene mutation in TrkA is associated with painless anhidrosis in human (Patent Documents 1, 2 and Non-patent Documents 1 to 3). The activation of NGF-TrkA signal produces hypralgesia (Non-patent Documents 4 to 6). Clinical and non-clinical researches regarding anti-NGF antibodies and non-clinical researches regarding Trk inhibitors reveal the involvement of NGF-TrkA signal or NT-Trk signal in the pain of osteoarthritis, rheumatoid arthritis, bone fracture, interstitial cystitis, chronic pancreatitis and prostatitis in addition to nociceptive pain such as chronic low back pain, neuropathic pain such as diabetic peripheral neuropathic pain, acute pain such as postoperative pain and chronic pain such as pelvic pain and cancer pain (Patent Documents 1, 2 and Non-patent documents 7, 8).

Trk receptors are also expressed in several types of cancer cells such as neuroblastoma, prostate cancer, lung cancer, breast cancer, gastric cancer and pancreatic cancer, and involve in the proliferation and migration of cancer cells. The fusion protein combined with TrkA kinase domain causes the proliferation of lung cancer cells. Trk inhibitor is shown to suppress the proliferation and metastasis of cancer cells in animal model. (Patent Document 1 and Non-patent Documents 9 to 12). Furthermore, Trk receptors are expressed in mast cells, eosinophils, immunocompetent cells such as T and B cells and keratinocytes, and NGF-trkA signal or NT-Trk signal involves in inflammatory bowel diseases such as ulcerative colitis and Crohn's disease, allergic diseases such as asthma and rhinitis, and skin diseases such as psoriasis, atopic dermatitis and pruritus (Patent Documents 1, 2). In addition, the inhibition of NGF-TrkA signal improves the overactive bladder (Patent Document 1). NT-Trk signal also involves in Sjogren's syndrome (Patent Document 1) and endometriosis (Patent Document 1). TrkA receptor plays a critical role in the infection process of the parasitic infection of *Trypanosoma cruzi* (Chagas disease) (Patent Document 1). Therefore, the compounds having an inhibitory activity for TrkA will be effective for various diseases including nociceptive pain, neuropathic pain, cancer, inflammatory diseases, allergic diseases and dermatological diseases.

The compounds that have an inhibitory activity for TrkA are disclosed in Patent Documents 1 to 15 and Non-patent Documents 6, 13 to 14. However, the compounds related to the present invention aren't indicated and suggested in any documents.

Cyclohexane compounds that produce analgesic effect are disclosed in Patent Documents 16 to 19 and Non-patent Documents 15 to 16, but these compounds don't show an inhibitory activity for TrkA.

PRIOR ART REFERENCES

Patent Document

[Patent Document 1] International Publication No. 2014/078325 pamphlet
[Patent Document 2] International Publication No. 2013/161919 pamphlet
[Patent Document 3] International Publication No. 2012/158413 pamphlet
[Patent Document 4] International Publication No. 2014/078454 pamphlet
[Patent Document 5] International Publication No. 2014/078417 pamphlet
[Patent Document 6] International Publication No. 2014/078408 pamphlet
[Patent Document 7] International Publication No. 2014/078378 pamphlet
[Patent Document 8] International Publication No. 2014/078372 pamphlet
[Patent Document 9] International Publication No. 2014/078331 pamphlet
[Patent Document 10] International Publication No. 2014/078328 pamphlet
[Patent Document 11] International Publication No. 2014/078323 pamphlet
[Patent Document 12] International Publication No. 2014/078322 pamphlet
[Patent Document 13] International Publication No. 2014/053967 pamphlet
[Patent Document 14] International Publication No. 2014/053965 pamphlet
[Patent Document 15] International Publication No. 2014/053968 pamphlet
[Patent Document 16] International Publication No. 99/16431 pamphlet
[Patent Document 17] European Patent Publication No. 372466 pamphlet
[Patent Document 18] U.S. Pat. No. 4,906,655 pamphlet
[Patent Document 19] U.S. Pat. No. 4,855,316 pamphlet
[Non-patent Document 1] Clinical Science, Vol. 110, 175-191 (2006)
[Non-patent Document 2] Nature Reviews Neuroscience, Vol. 4, 299-309 (2003)
[Non-patent Document 3] Clinical Genetics, Vol. 82, 341-350 (2012)
[Non-patent Document 4] Anesthesiology, Vol. 115, 189-204 (2011)
[Non-patent Document 5] Journal of Neurochemistry, Vol. 124, 276-289 (2013)
[Non-patent Document 6] Expert Opinion on Therapeutic Patents, Vol. 24, 731-744 (2014)
[Non-patent Document 7] Bone, Vol. 48, 389-398 (2011)
[Non-patent Document 8] Molecular Pain, Vol. 6, 87 (2010)
[Non-patent Document 9] Dermato-Endocrinology, Vol. 3, 32-36 (2011)
[Non-patent Document 10] Leukemia, Vol. 21, 2171-2180 (2007)

[Non-patent Document 11] Cancer Research, Vol. 62, 986-989 (2002)
[Non-patent Document 12] Nature Medicine, Vol. 19, 1469-1472 (2013)
[Non-patent Document 13] Journal of Medicinal Chemistry, Vol. 57, 5800-5816 (2014)
[Non-patent Document 14] Expert Opinion on Therapeutic Patents, Vol. 19, 305-319 (2009)
[Non-patent Document 15] Journal of Medicinal Chemistry, Vol. 33 (1), 286-291 (1990)
[Non-patent Document 16] Journal of Medicinal Chemistry, Vol. 32 (7), 1620-1626 (1989)

SUMMARY OF THE INVENTION

Problems to be Solved by the Invention

The purpose of the present invention is to provide a compound that has a TrkA inhibitory activity or a pharmaceutically acceptable salt thereof, or a pharmaceutical composition comprising thereof.

Means for Solving the Problem

The present invention relates to a compound that has a TrkA inhibitory activity and is useful in the treatment and/or prevention of TrkA mediated disorders, or a pharmaceutically acceptable salt thereof.

The present invention relates to the following 1A) to 42A).

1A) A compound represented by Formula (I):

[Chemical Formula 1]

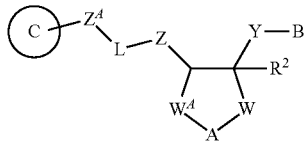

(I)

wherein, -L- is —C(=X)— or —SO$_2$—;
=X is =O, =S, =NR$^{10}$ or =CR$^{11}$R$^{12}$;
—Z— is —NR$^5$—, —O— or —CR$^6$R$^7$—;
—Z$^A$— is —NR$^{5A}$— or —CR$^{6A}$R$^{7A}$—;
—W— is —C(R$^8$R$^9$)n-;
—W$^A$— is —C(R$^3$R$^4$)m-;
n is 0, 1 or 2;
m is 1 or 2;
provided that n=0, 1 or 2 when m=1; and n=0 when m=2;
-A- is —NR$^1$—, —N$^+$(O$^-$)(R$^{1A}$)—, —N$^+$R$^{1B}$R$^{1C}$— or —CR$^{1D}$R$^{1E}$—;
—Y— is a bond, or substituted or unsubstituted alkylene which may be intervened by an oxygen atom;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;
Ring C is a substituted or unsubstituted aromatic heterocycle, or a substituted, or unsubstituted non-aromatic heterocycle;
R$^1$ is a hydrogen atom, cyano, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1A}$ and R$^{1B}$ are each independently substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1D}$ is a hydrogen atom, substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1C}$ and R$^{1E}$ are each independently a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or
R$^{1D}$ and R$^{1E}$ may be taken together to form =CR$^{1F}$R$^{1G}$, oxo, =N—O—R$^{1H}$, or a substituted or unsubstituted non-aromatic carbocycle, or a substituted or unsubstituted non-aromatic heterocycle;
R$^{1F}$ and R$^{1G}$ are each independently a hydrogen atom, substituted or unsubstituted alkyl, substituted or unsubstituted alkyloxy, or substituted or unsubstituted alkyloxycarbonyl;
R$^{1H}$ is a hydrogen atom, substituted or unsubstituted alkyl, substituted or unsubstituted alkenyl, or substituted or unsubstituted alkynyl;
R$^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen or hydroxy, or
R$^2$ may be taken together with "—Y—B" to form a substituted or unsubstituted non-aromatic carbocycle, or a substituted or unsubstituted non-aromatic heterocycle;
R$^3$ is each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;

R[4] is each independently a hydrogen atom, substituted or unsubstituted alkyl, substituted or unsubstituted alkenyl, or substituted or unsubstituted alkynyl, or R[4] may be taken together with one of R[8] to form (C2-C4) bridge, in which one of the carbon atoms consisting of the bridge may be replaced with an oxygen atom or a nitrogen atom; the carbon atoms consisting of the bridge are each independently substituted with a substituent selected from R[a]; and the nitrogen atom consisting the bridge is substituted with a substituent selected from R[b];

R[a] is each independently a hydrogen atom, halogen, hydroxy, cyano, oxo, substituted or unsubstituted carbamoyl, substituted or unsubstituted amino, or substituted or unsubstituted alkyl;

R[b] is each independently a hydrogen atom, substituted or unsubstituted alkyl, substituted or unsubstituted acyl, substituted or unsubstituted alkyloxycarbonyl, or substituted or unsubstituted alkylsulfonyl;

R[5] and R[5A] are each independently a hydrogen atom, or substituted or unsubstituted alkyl;

R[6], R[6A], R[7] and R[7A] are each independently a hydrogen atom, halogen, hydroxy, substituted or unsubstituted alkyl, substituted or unsubstituted alkenyl, substituted or unsubstituted alkynyl, substituted or unsubstituted alkyloxy, or substituted or unsubstituted amino;

R[8] is each independently a hydrogen atom, halogen, hydroxy, substituted or unsubstituted alkyl, substituted or unsubstituted alkenyl, substituted or unsubstituted alkynyl, or substituted or unsubstituted alkyloxy;

R[9] is each independently a hydrogen atom, halogen, hydroxy, substituted or unsubstituted alkyl, substituted or unsubstituted alkenyl, substituted or unsubstituted alkynyl, or substituted or unsubstituted alkyloxy, or R[8] and R[9] may be taken together to form oxo;

R[10] is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxyl;

R[11] is a hydrogen atom, cyano, substituted or unsubstituted acyl, substituted or unsubstituted alkyloxycarbonyl, substituted or unsubstituted alkylcarbamoyl, substituted or unsubstituted alkylsulfonyl, or nitro;

R[12] is a hydrogen atom or cyano;

provided that:

(1) B is not aromatic carbocyclyl optionally substituted with halogen, —CF$_3$, —OCF$_3$, alkyloxy, hydroxyalkyl, alkyl or cyano; and is not aromatic heterocyclyl optionally substituted with halogen, hydroxy, —NH$_2$, —CF$_3$, hydroxyalkyl or alkyl when the group of "—Y—B" and the group of "—Z-L-Z[A]-(Ring C)" are in trans conformation, —W— is —CH$_2$—, —W[A]— is —CH$_2$—, —Y— is a bond, -L- is —C(=O), —Z— is —NH—, —Z[A]— is —NH—, -A- is —NR[1]—, and R[1] is a group represented by the following group:

[Chemical Formula 2]

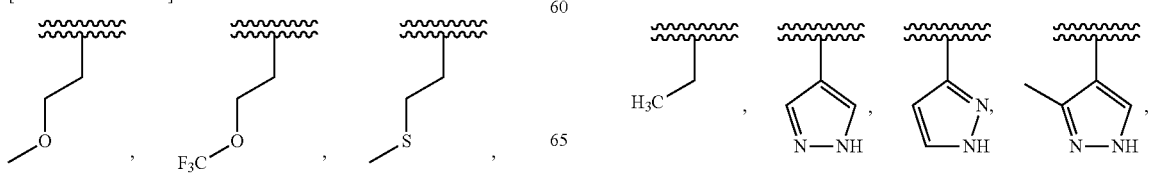

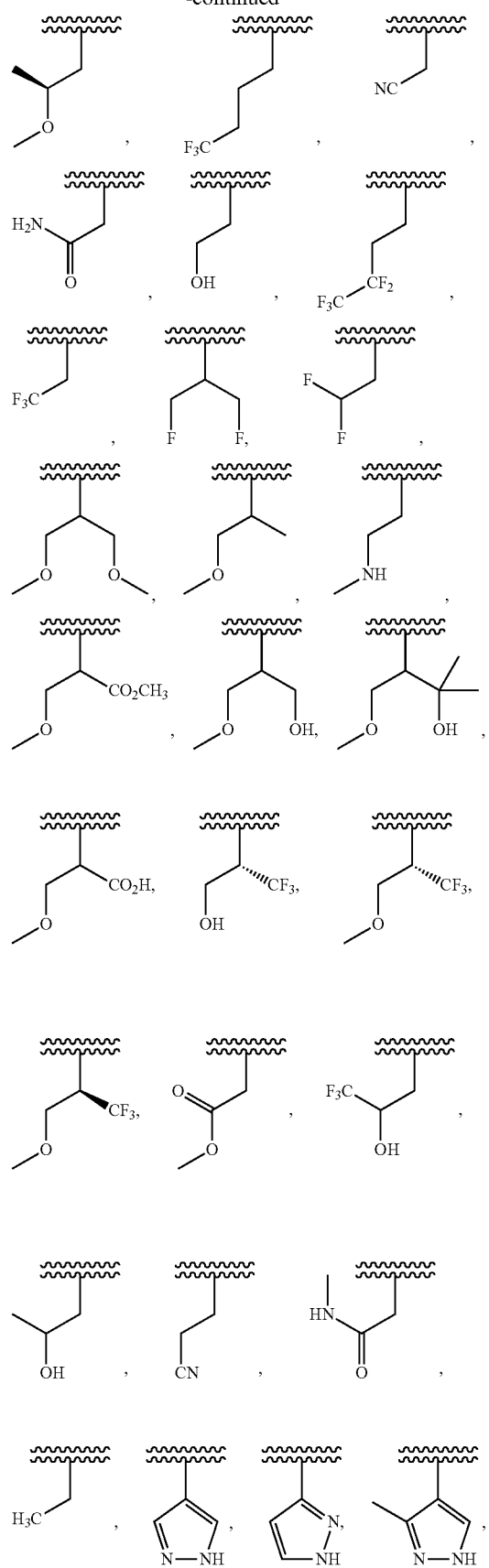

-continued

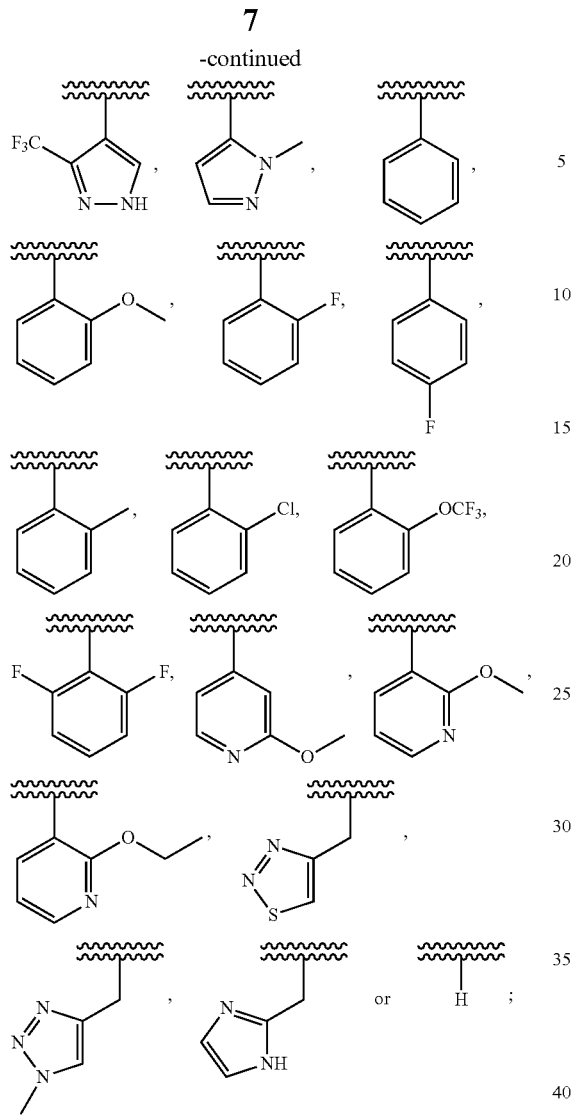

(2) Ring C is not

[Chemical Formula 3]

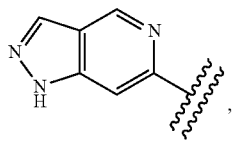

when -A- is —NR$^1$—, —W— is —C(R$^8$R$^9$)— and —W$^4$— is —C(R$^3$R$^4$)—;

(3) Ring C is not substituted or unsubstituted pyrimidine, when -A- is —CR$^{1D}$R$^{1E}$—, —W— is —C(R$^8$R$^9$)$_2$— and —W$^4$— is —C(R$^3$R$^4$)—;

(4) B is not substituted or unsubstituted pyrrolidyl, when -A- is —CR$^{1D}$R$^{1E}$—, —W— is —C(R$^8$R$^9$)$_2$—, —W$^4$— is —C(R$^3$R$^4$)— and Y is a bond; and (5) B is not unsubstituted cyclopropyl, when -A- is —NR$^1$—, —W— is —CH$_2$—, —W$^4$— is —CH$_2$— and —Y— is a bond;

provided that the following compounds are excluded:

[Chemical Formula 4]

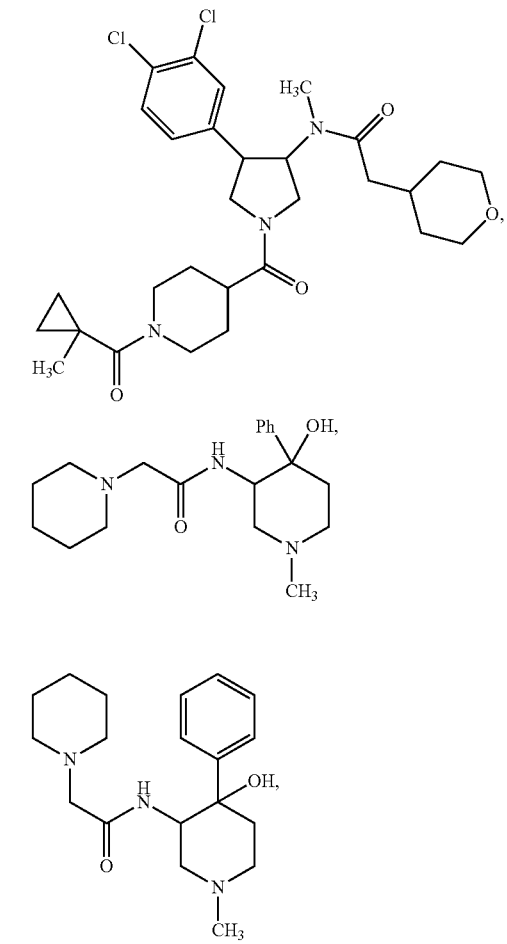

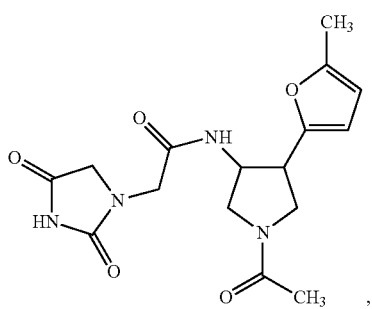

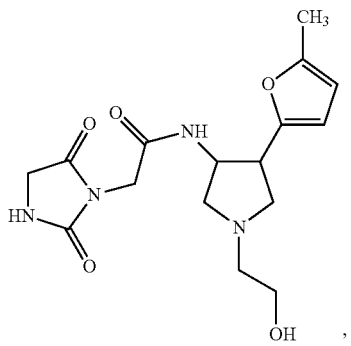

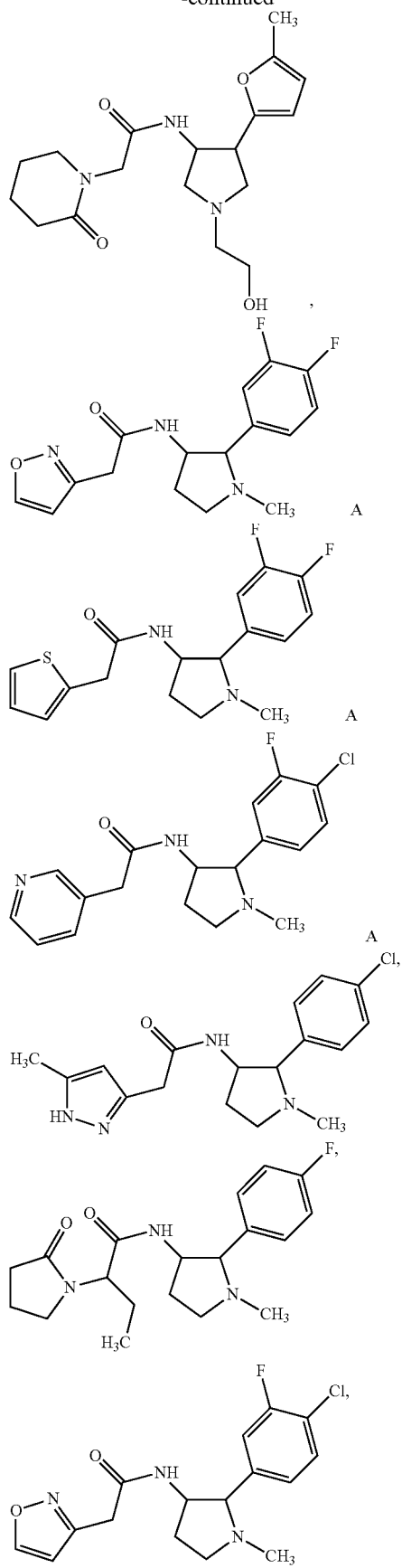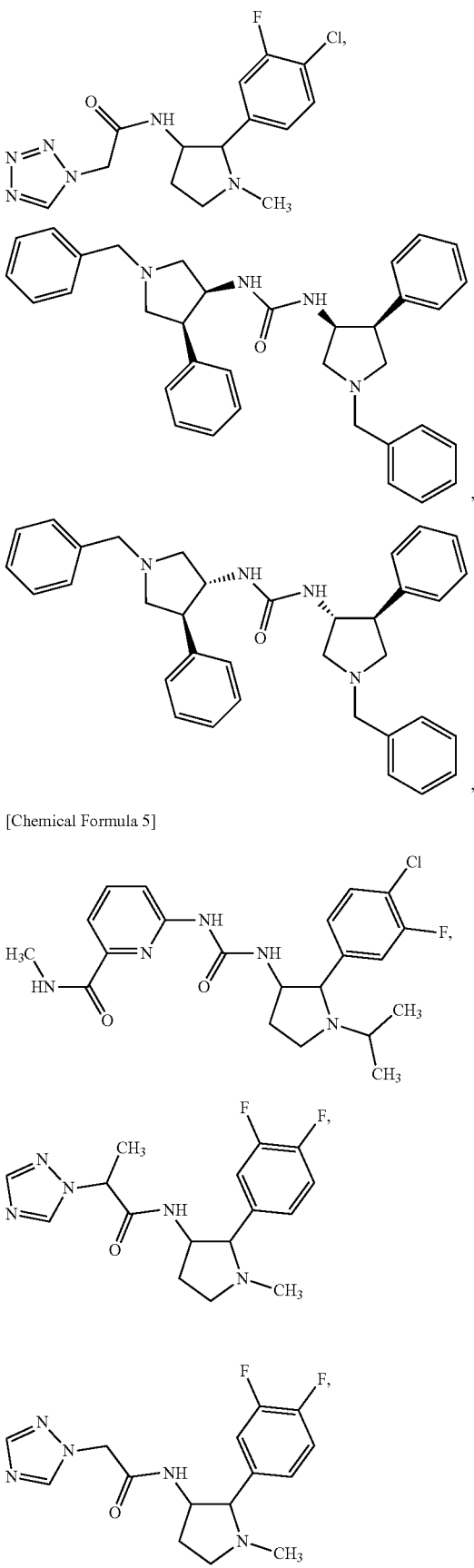
[Chemical Formula 5]

-continued

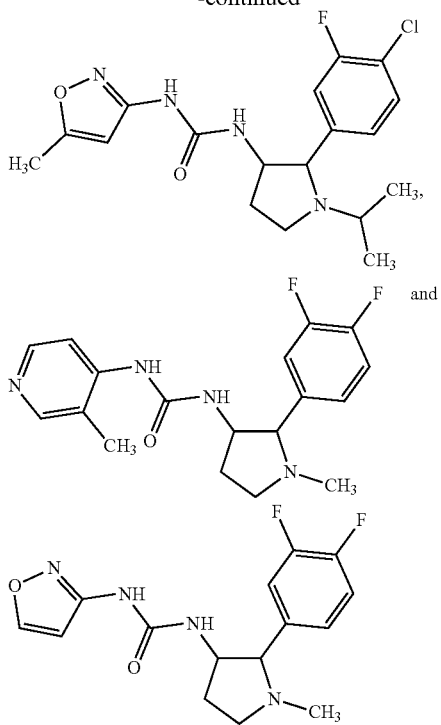

or its pharmaceutically acceptable salt.

2A) The compound according to the above item 1A),
wherein -L- is —C(=X)—,
=X is =O or =S,
Y is a bond,
$R^{1D}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or its pharmaceutically acceptable salt.

3A) The compound according to the above item 1A) or 2A),
wherein m=1 and n=1,
or its pharmaceutically acceptable salt.

4A) The compound according to any one of the above items 1A) to 3A),
wherein -A- is —N$^+$(O$^-$)(R$^{1A}$)— or —CR$^{1D}$R$^{1E}$—,
or its pharmaceutically acceptable salt.

5A) The compound according to any one of the above items 1A) to 4A),
wherein -A- is —NR$^1$—,
$R^1$ is
alkyl substituted with
halogenoethyloxy,
substituted or unsubstituted aromatic carbocyclyloxy,
substituted or unsubstituted non-aromatic carbocyclyloxy,
substituted or unsubstituted non-aromatic heterocyclyl,
substituted or unsubstituted alkyloxycarbonylamino,
substituted or unsubstituted alkylcarbonylamino,
substituted or unsubstituted alkylsulfonylamino,
substituted or unsubstituted alkylsulfonyl,
substituted or unsubstituted non-aromatic carbocyclyl,
carboxy,
substituted or unsubstituted alkyloxyalkyloxy, or
acyl;
alkyl substituted with furyl substituted with
carboxy,
halogen,
cyano,
alkyl or
hydroxylalkyl;
alkyl substituted with
substituted or unsubstituted alkyloxy and substituted or unsubstituted amino,
substituted or unsubstituted alkyloxy and cyano,
substituted or unsubstituted alkyloxy and halogen,
substituted or unsubstituted alkyloxy and substituted or unsubstituted aromatic heterocyclyl,
substituted or unsubstituted alkyloxy and hydroxy,
substituted or unsubstituted alkyloxy and substituted or unsubstituted non-aromatic heterocyclyl,
substituted or unsubstituted aromatic heterocyclyl and hydroxy,
substituted or unsubstituted alkyloxy and substituted or unsubstituted carbamoyl,
substituted or unsubstituted alkyloxy and substituted or unsubstituted alkyloxycarbonyl,
substituted or unsubstituted alkyloxy and substituted or unsubstituted alkylthio, or
substituted or unsubstituted alkyloxycarbonyl and substituted or unsubstituted aromatic heterocyclyl;
substituted or unsubstituted alkyloxycarbonyl;
substituted or unsubstituted acyl;
substituted or unsubstituted non-aromatic heterocyclyl, or
substituted or unsubstituted non-aromatic carbocyclyl,
or its pharmaceutically acceptable salt.

6A) The compound according to any one of the above items 1A) to 5A),
wherein B is phenyl substituted with substituted or unsubstituted alkyloxycarbonyl, phenyl substituted with substituted or unsubstituted carbamoyl, phenyl substituted with substituted or unsubstituted aromatic carbocyclyl, phenyl substituted with substituted or unsubstituted aromatic heterocyclyl, phenyl substituted with substituted or unsubstituted alkenyl, phenyl substituted with substituted or unsubstituted non-aromatic carbocyclyl, phenyl substituted with carboxy, phenyl substituted with alkylamino, phenyl substituted with substituted or unsubstituted acyl, substituted or unsubstituted naphthyl, substituted or unsubstituted non-aromatic heterocyclyl, or substituted or unsubstituted bicyclic aromatic heterocyclyl,
or its pharmaceutically acceptable salt.

7A) The compound according to any one of the above items 1A) to 6A),
wherein m=2 and n=0,
or its pharmaceutically acceptable salt.

8A) The compound according to any one of the above items 1A) to 7A),
wherein m=1 and n=0,
or its pharmaceutically acceptable salt.

9A) The compound according to any one of the above items 1A) to 8A),
wherein -A- is —NR$^1$—,
or a pharmaceutically acceptable salt thereof.

10A) The compound according to any one of the above items 1A) to 9A),
wherein —Z— is —NH—, =X is =O and —Z$^A$— is —NH—,
or a pharmaceutically acceptable salt thereof.

11A) The compound according to any one of the above items 1A) to 10A),
wherein —Z— is —NR$^5$—, =X is =O and —Z$^A$— is —NR$^{5A}$—,
or its pharmaceutically acceptable salt.

12A) The compound according to any one of the above items 1A) to 11A),
wherein R$^5$ and R$^{5A}$ are hydrogen atoms,
or its pharmaceutically acceptable salt.

13A) The compound according to any one of the above items 1A) to 12A),
wherein —Z— is —NR$^5$—, =X is =O and —Z$^A$— is —CR$^{6A}$R$^{7A}$—,
or its pharmaceutically acceptable salt.

14A) The compound according to any one of the above items 1A) to 13A),
wherein R$^5$, R$^{6A}$ and R$^{7A}$ are hydrogen atoms,
or its pharmaceutically acceptable salt.

15A) The compound according to any one of the above items 1A) to 14A),
wherein —Z— is —CR$^6$R$^7$—, =X is =O and —Z$^A$— is —NR$^{5A}$—,
or its pharmaceutically acceptable salt.

16A) The compound according to any one of the above items 1A) to 15A),
wherein R$^6$, R$^7$ and R$^{5A}$ are hydrogen atoms,
or its pharmaceutically acceptable salt.

17A) The compound according to any one of the above items 1A) to 16A),
wherein —Z— is —O—, =X is =O and —Z$^A$— is —NR$^{5A}$—,
or its pharmaceutically acceptable salt.

18A) The compound according to any one of the above items 1A) to 17A),
wherein R$^{5A}$ is a hydrogen atom,
or its pharmaceutically acceptable salt.

19A) The compound according to any one of the above items 1A) to 18A),
wherein R$^8$ and R$^9$ are hydrogen atoms, or R$^8$ and R$^9$ are taken together to form oxo,
or its pharmaceutically acceptable salt.

20A) The compound according to any one of the above items 1A) to 19A),
wherein R$^3$ and R$^4$ are hydrogen atoms,
or its pharmaceutically acceptable salt.

21A) The compound according to any one of the above items 1A) to 20A),
wherein Ring C is a substituted or unsubstituted aromatic heterocycle,
or its pharmaceutically acceptable salt.

22A) The compound according to any one of the above items 1A) to 21A),
wherein Ring C is a substituted or unsubstituted pyrazole,
or its pharmaceutically acceptable salt.

23A) The compound according to any one of the above items 1A) to 22A),
wherein Ring C is a group represented by Formula:

[Chemical Formula 6]

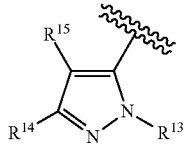

wherein R$^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

R$^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

R$^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylthio, substituted or unsubstituted alkenylthio, substituted or unsubstituted alkynylthio, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

R$^{14}$ and R$^{15}$ may be taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle,
or its pharmaceutically acceptable salt.

24A) The compound according to any one of the above items 1A) to 23A),
wherein R$^{13}$ is a hydrogen atom, or substituted or unsubstituted aromatic carbocyclyl, R$^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, and $R^{15}$ is substituted or unsubstituted alkyl,
or its pharmaceutically acceptable salt.

25A) The compound according to any one of the above items 1A) to 24A),
wherein $R^1$ is substituted or unsubstituted alkyl,
or its pharmaceutically acceptable salt.

26A) The compound according to any one of the above items 1A) to 25A),
wherein $R^{1A}$ is substituted or unsubstituted alkyl,
or its pharmaceutically acceptable salt.

27A) The compound according to any one of the above items 1A) to 26A),
wherein $R^{1E}$ is a hydrogen atom,
or its pharmaceutically acceptable salt.

28A) The compound according to any one of the above items 1A) to 27A),
wherein $R^2$ is a hydrogen atom, or substituted or unsubstituted alkyl,
or its pharmaceutically acceptable salt.

29A) The compound according to any one of the above items 1A) to 28A),
wherein the compound is represented by Formula (I'):

[Chemical Formula 7]

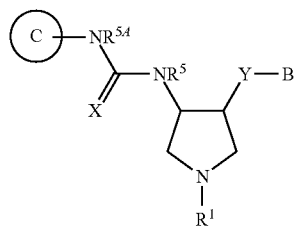

(I')

wherein X, Ring C, $R^5$ and $R^{5A}$ are the same as the above item 1A);
Y is a bond;
$R^1$ and B are
(a) $R^1$ is
alkyl substituted with
halogenoethyloxy,
substituted or unsubstituted aromatic carbocyclyloxy,
substituted or unsubstituted non-aromatic carbocyclyloxy,
substituted or unsubstituted non-aromatic heterocyclyl,
substituted or unsubstituted alkyloxycarbonylamino,
substituted or unsubstituted alkylcarbonylamino,
substituted or unsubstituted alkylsulfonylamino,
substituted or unsubstituted alkylsulfonyl,
substituted or unsubstituted non-aromatic carbocyclyl,
carboxy,
substituted or unsubstituted alkyloxyalkyloxy, or
acyl;
alkyl substituted with furyl substituted with
carboxy,
halogen,
cyano,
alkyl or
hydroxyalkyl;

alkyl substituted with
substituted or unsubstituted alkyloxy and substituted or unsubstituted amino,
substituted or unsubstituted alkyloxy and cyano,
substituted or unsubstituted alkyloxy and halogen,
substituted or unsubstituted alkyloxy and substituted or unsubstituted aromatic heterocyclyl,
substituted or unsubstituted alkyloxy and hydroxy,
substituted or unsubstituted alkyloxy and substituted or unsubstituted non-aromatic heterocyclyl,
substituted or unsubstituted aromatic heterocyclyl and hydroxy,
substituted or unsubstituted alkyloxy and substituted or unsubstituted carbamoyl,
substituted or unsubstituted alkyloxy and substituted or unsubstituted alkyloxycarbonyl,
substituted or unsubstituted alkyloxy and substituted or unsubstituted alkylthio,
or substituted or unsubstituted alkyloxycarbonyl and substituted or unsubstituted aromatic heterocyclyl;
substituted or unsubstituted alkyloxycarbonyl;
substituted or unsubstituted acyl;
substituted or unsubstituted non-aromatic heterocyclyl, or
substituted or unsubstituted non-aromatic carbocyclyl;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;
or (b) $R^1$ is a hydrogen atom, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
B is phenyl substituted with substituted or unsubstituted alkyloxycarbonyl, phenyl substituted with substituted or unsubstituted carbamoyl, phenyl substituted with substituted or unsubstituted aromatic carbocyclyl, phenyl substituted with substituted or unsubstituted aromatic heterocyclyl, phenyl substituted with substituted or unsubstituted alkenyl, phenyl substituted with substituted or unsubstituted non-aromatic carbocyclyl, phenyl substituted with carboxy, phenyl substituted with alkylamino, phenyl substituted with substituted or unsubstituted acyl, substituted or unsubstituted naphthyl, substituted or unsubstituted non-aromatic heterocyclyl, or substituted or unsubstituted bicyclic aromatic heterocyclyl,
or its pharmaceutically acceptable salt.

30A) The compound according to any one of the above items 1A) to 29A), wherein the compound is represented by Formula (I''):

[Chemical Formula 8]

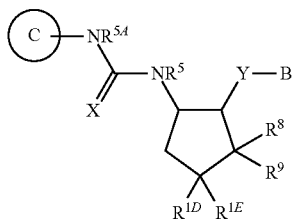

(I'')

wherein X, Ring C, $R^5$, $R^{5A}$, $R^8$ and $R^9$ are the same as the above item 1A);

Y is a bond;

B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1D}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1E}$ is a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^{1D}$ and $R^{1E}$ may be taken together to form $=CR^{1F}R^{1G}$, oxo, $=N-O-R^{1H}$ or a substituted or unsubstituted non-aromatic carbocycle, or a substituted or unsubstituted non-aromatic heterocycle, $R^{1F}$, $R^{1G}$ and $R^{1H}$ are the same as the above item 1A), or its pharmaceutically acceptable salt.

31A) The compound according to any one of the above items 1A) to 30A), wherein the compound is represented by Formula (I'''):

[Chemical Formula 9]

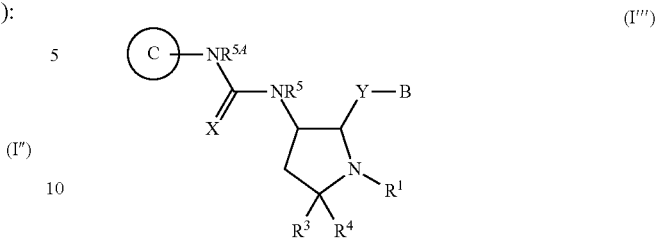

(I''')

wherein X, Ring C, $R^1$, $R^3$, $R^5$ and $R^{5A}$ are the same as the above item 1A);

Y is a bond;

B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $R^4$ is a hydrogen atom, substituted or unsubstituted alkyl, substituted or unsubstituted alkenyl, or substituted or unsubstituted alkynyl, or its pharmaceutically acceptable salt.

32A) A pharmaceutical composition comprising the compound according to any one of the above items 1A) to 31A), or its pharmaceutically acceptable salt.

33A) The pharmaceutical composition according to the above item 32A), wherein the composition has a TrkA inhibitory activity.

34A) A method for treating or preventing a disease related to TrkA comprising administering the compound according to any one of the above items 1A) to 31A), or its pharmaceutically acceptable salt.

35A) The compound according to any one of the above items 1A) to 31A), or its pharmaceutically acceptable salt, for use in a method for treating or preventing a disease related to TrkA.

36A) A pharmaceutical composition comprising the compound of any one of the above items 1A) to 31A), or a pharmaceutically acceptable salt thereof, for oral administration.

37A) The pharmaceutical composition according to the above item 36A), which is a tablet, powder, granule, capsule, pill, film, suspension, emulsion, elixir, syrup, lemonade, spirit, aromatic water, extract, decoction or tincture.

38A) The pharmaceutical composition according to the above item 37A), which is a sugar-coated tablet, film-coated tablet, enteric-coated tablet, sustained-release tablet, troche tablet, sublingual tablet, buccal tablet, chewable tablet, orally disintegrated tablet, dry syrup, soft capsule, micro capsule or sustained-release capsule.

39A) A pharmaceutical composition comprising the compound of any one of the above items 1A) to 31A), or a pharmaceutically acceptable salt thereof, for parenteral administration.

40A) The pharmaceutical composition according to the above item 39A), for dermal, subcutaneous, intravenous, intraarterial, intramuscular, intraperitoneal, transmucosal, inhalation, transnasal, ophthalmic, inner ear or vaginal administration.

41A) The pharmaceutical composition according to the above item 39A) or 40A), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

42A) A pharmaceutical composition comprising the compound of any one of the above items 1A) to 31A), or a pharmaceutically acceptable salt thereof, for a pediatric or geriatric patient.

In addition, the present invention relates to the following items 1) to 31).

1) A compound represented by Formula (I):

[Chemical Formula 10]

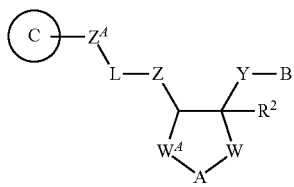

(I)

wherein, -L- is —C(=X)— or —SO$_2$—;
=X is =O, =S, =NR$^{10}$ or =CR$^{11}$R$^{12}$;
—Z— is —NR$^5$—, —O— or —CR$^6$R$^7$—;
—Z$^A$— is —NR$^{5A}$— or —CR$^{6A}$R$^{7A}$—;
—W— is —C(R$^8$R$^9$)n-;
—W$^A$— is —C(R$^3$R$^4$)m-;
n is 0, 1 or 2;
m is 1 or 2;
provided that n=0, 1 or 2 when m=1; and n=0 when m=2;
-A- is —NR$^1$—, —N$^+$(O$^-$)(R$^{1A}$)—, —N$^+$R$^{1B}$R$^{1C}$— or —CR$^{1D}$R$^{1E}$—;
—Y— is a bond or substituted or unsubstituted alkylene which may be intervened by an oxygen atom;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;
Ring C is a substituted or unsubstituted aromatic heterocycle, or a substituted or unsubstituted non-aromatic heterocycle;
R$^1$ is a hydrogen atom, cyano, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1A}$ and R$^{1B}$ are each independently substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1D}$ is a hydrogen atom, substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1C}$ and R$^{1E}$ are each independently a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or
R$^{1D}$ and R$^{1E}$ may be taken together to form =CR$^{1F}$R$^{1G}$, oxo, =N—O—R$^{1H}$, or a substituted or unsubstituted non-aromatic carbocycle, or a substituted or unsubstituted non-aromatic heterocycle;
R$^{1F}$ and R$^{1G}$ are each independently a hydrogen atom, substituted or unsubstituted alkyl, substituted or unsubstituted alkyloxy or substituted or unsubstituted alkyloxycarbonyl;
R$^{1H}$ is a hydrogen atom, substituted or unsubstituted alkyl, substituted or unsubstituted alkenyl, or substituted or unsubstituted alkynyl;
R$^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen or hydroxy, or
R$^2$ may be taken together with "—Y—B" to form a substituted or unsubstituted non-aromatic carbocycle, or a substituted or unsubstituted non-aromatic heterocycle;
R$^3$ is each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;
R$^4$ is each independently a hydrogen atom, substituted or unsubstituted alkyl, substituted or unsubstituted alkenyl or substituted or unsubstituted alkynyl, or
R$^4$ may be taken together with one of R$^8$ to form (C2-C4) bridge, in which one of the carbon atoms consisting of the bridge may be replaced with an oxygen atom or a nitrogen atom; the carbon atoms consisting of the bridge are each independently substituted with a substituent selected from R$^a$; and the nitrogen atom consisting the bridge is substituted with a substituent selected from R$^b$;
R$^a$ is each independently a hydrogen atom, halogen, hydroxy, cyano, oxo, substituted or unsubstituted carbamoyl, substituted or unsubstituted amino, or substituted or unsubstituted alkyl;
R$^b$ is each independently a hydrogen atom, substituted or unsubstituted alkyl, substituted or unsubstituted acyl, substituted or unsubstituted alkyloxycarbonyl, or substituted or unsubstituted alkylsulfonyl;
R$^5$ and R$^{5A}$ are each independently a hydrogen atom, or substituted or unsubstituted alkyl;
R$^6$, R$^{6A}$, R$^7$ and R$^{7A}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, or substituted or unsubstituted amino;

$R^8$ is each independently a hydrogen atom, halogen, hydroxy, substituted or unsubstituted alkyl, substituted or unsubstituted alkenyl, substituted or unsubstituted alkynyl, or substituted or unsubstituted alkyloxy;

$R^9$ is each independently a hydrogen atom, halogen, hydroxy, substituted or unsubstituted alkyl, substituted or unsubstituted alkenyl, substituted or unsubstituted alkynyl, or substituted or unsubstituted alkyloxy, or $R^8$ and $R^9$ may be taken together to form oxo;

$R^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxyl;

$R^{11}$ is a hydrogen atom, cyano, substituted or unsubstituted acyl, substituted or unsubstituted alkyloxycarbonyl, substituted or unsubstituted alkylcarbamoyl, substituted or unsubstituted alkylsulfonyl, or nitro;

$R^{12}$ is a hydrogen atom or cyano;

provided that:

(1) B is not aromatic carbocyclyl optionally substituted with halogen, $-CF_3$, $-OCF_3$, alkyloxy, hydroxyalkyl, alkyl or cyano, and is not aromatic heterocyclyl optionally substituted with halogen, hydroxy, $-NH_2$, $-CF_3$, hydroxyalkyl or alkyl when the group of "—Y—B" and the group of "—Z-L-$Z^4$-(Ring C)" are in trans conformation, —W— is $-CH_2-$, $-W^4-$ is $-CH_2-$, —Y— is a bond, -L- is $-C(=O)$, —Z— is —NH—, $-Z^4-$ is —NH—, -A- is $-NR^1-$, and $R^1$ is a group represented by the following group:

[Chemical Formula 11]

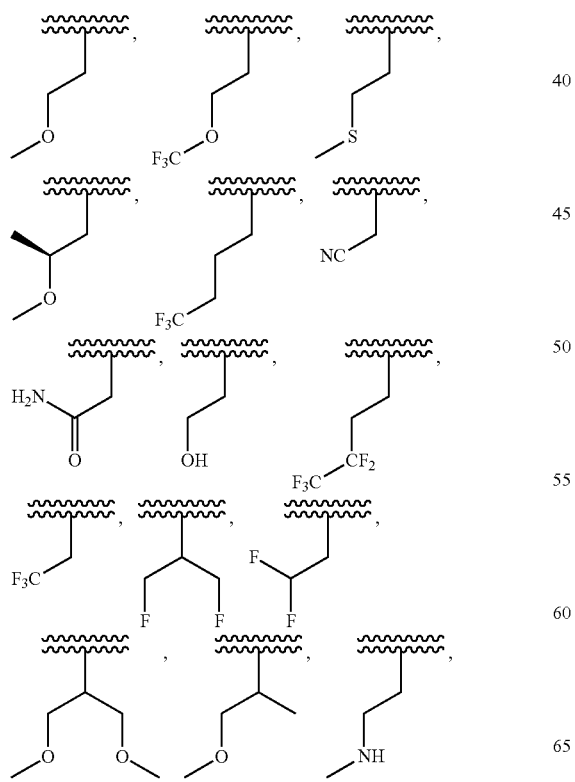

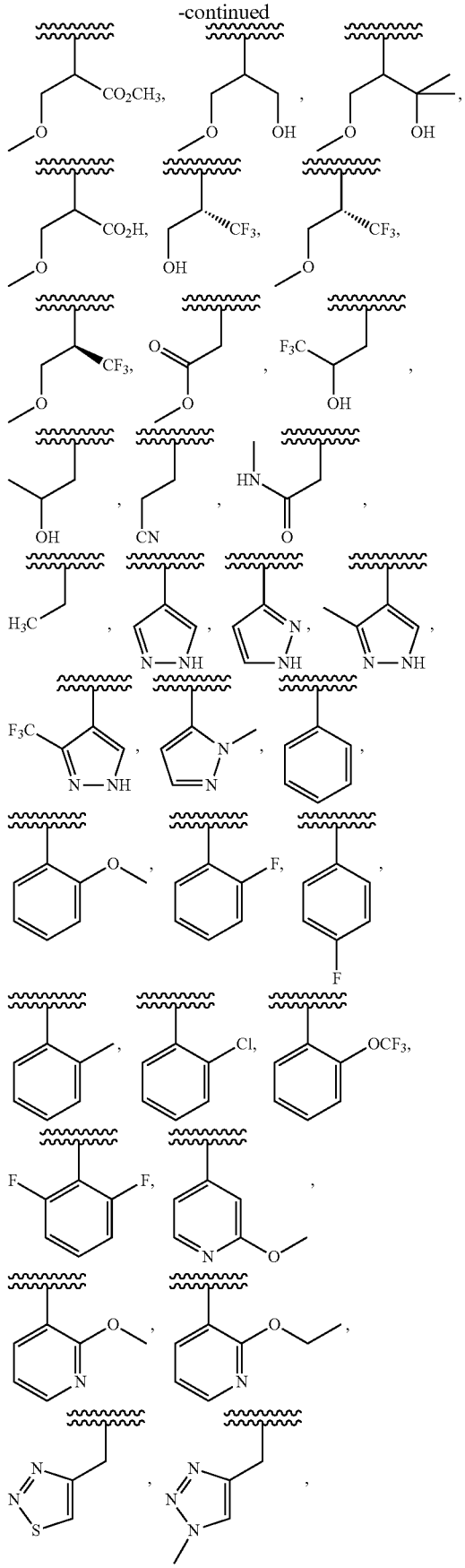

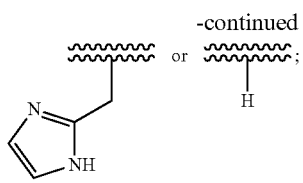

(2) Ring C is not

[Chemical Formula 12]

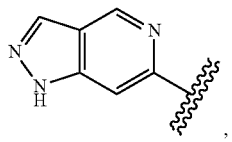

when -A- is —NR$^1$—, —W— is —C(R$^8$R$^9$)— and —W$^A$— is —C(R$^3$R$^4$)—;

(3) Ring C is not substituted or unsubstituted pyrimidine, when -A- is —CR$^{1D}$R$^{1E}$—, —W— is —C(R$^8$R$^9$)$_2$— and —W$^A$— is —C(R$^3$R$^4$)—;

(4) B is not substituted or unsubstituted pyrrolidyl, when -A- is —CR$^{1D}$R$^{1E}$—, —W— is —C(R$^8$R$^9$)$_2$—, —W$^A$— is —C(R$^3$R$^4$)— and Y is a bond; and (5) B is not unsubstituted cyclopropyl, when -A- is —NR$^1$—, —W— is —CH$_2$—, —W$^A$— is —CH$_2$— and —Y— is a bond;

provided that the following compounds are excluded:

[Chemical Formula 13]

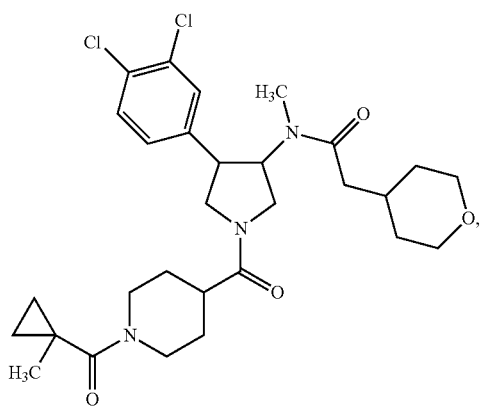

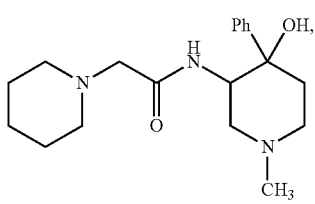

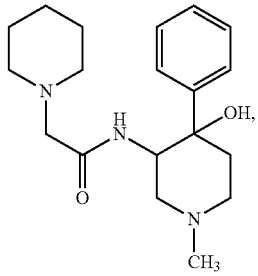

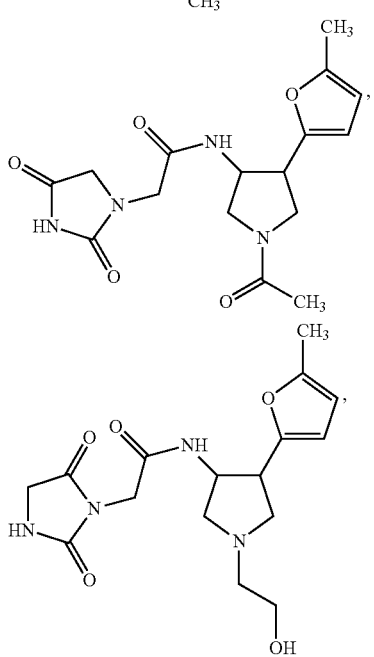

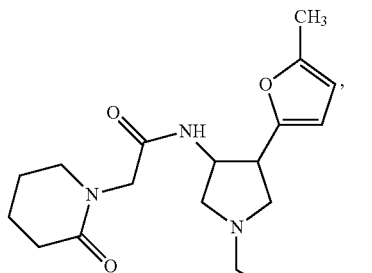

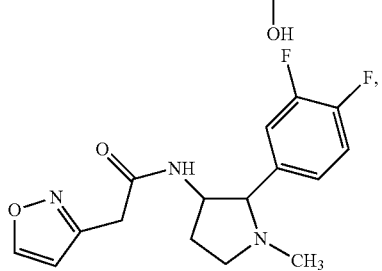

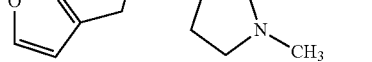

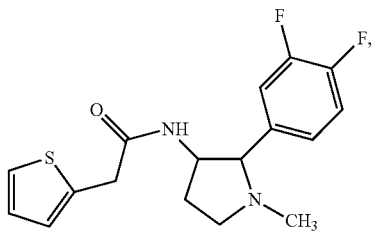

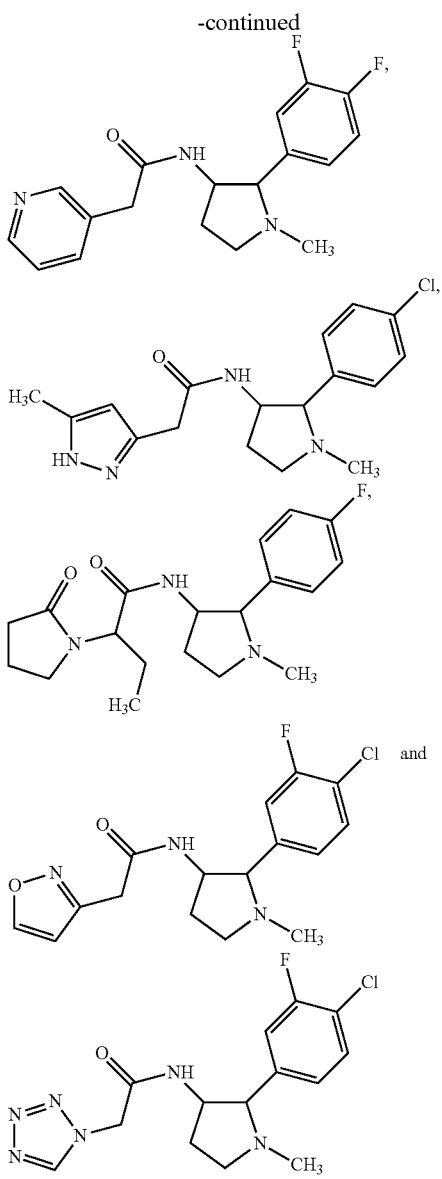

or its pharmaceutically acceptable salt.

2) The compound according to the above item 1),
wherein -L- is —C(=X)—,
=X is =O or =S,
Y is a bond,
$R^{1D}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or its pharmaceutically acceptable salt.

3) The compound according to the above item 1) or 2), wherein m=1 and n=1,
or its pharmaceutically acceptable salt.

4) The compound according to any one of the above items 1) to 3),
wherein -A- is —$N^+(O^-)(R^{1A})$— or —$CR^{1D}R^{1E}$—,
or its pharmaceutically acceptable salt.

5) The compound according to any one of the above items 1) to 4),
wherein -A- is —$NR^1$—,
$R^1$ is
alkyl substituted with
halogenoethyloxy,
substituted or unsubstituted aromatic carbocyclyloxy,
substituted or unsubstituted non-aromatic heterocyclyl,
substituted or unsubstituted alkyloxycarbonylamino,
substituted or unsubstituted alkylcarbonylamino,
substituted or unsubstituted alkylsulfonylamino,
substituted or unsubstituted alkylsulfonyl,
substituted or unsubstituted non-aromatic carbocyclyl,
carboxy,
substituted or unsubstituted alkyloxyalkyloxy, or
acyl;
alkyl substituted with furyl substituted with
carboxy,
halogen,
alkyl or
hydroxylalkyl;
alkyl substituted with
substituted or unsubstituted alkyloxy and substituted or unsubstituted amino,
substituted or unsubstituted alkyloxy and cyano,
substituted or unsubstituted alkyloxy and halogen,
substituted or unsubstituted alkyloxy and substituted or unsubstituted aromatic heterocyclyl,
substituted or unsubstituted alkyloxy and hydroxy,
substituted or unsubstituted alkyloxy and substituted or unsubstituted non-aromatic heterocyclyl,
substituted or unsubstituted aromatic heterocyclyl and hydroxy,
substituted or unsubstituted alkyloxy and substituted or unsubstituted carbamoyl,
substituted or unsubstituted alkyloxy and substituted or unsubstituted alkyloxycarbonyl,
substituted or unsubstituted alkyloxy and substituted or unsubstituted alkylthio, or
substituted or unsubstituted alkyloxycarbonyl and substituted or unsubstituted aromatic heterocyclyl;
substituted or unsubstituted alkyloxycarbonyl;
substituted or unsubstituted acyl;
substituted or unsubstituted non-aromatic heterocyclyl, or
substituted or unsubstituted non-aromatic carbocyclyl,
or its pharmaceutically acceptable salt.

6) The compound according to any one of the above items 1) to 5),
wherein B is phenyl substituted with substituted or unsubstituted alkyloxycarbonyl, phenyl substituted with substituted or unsubstituted carbamoyl, phenyl substituted with substituted or unsubstituted aromatic carbocyclyl, phenyl substituted with substituted or unsubstituted aromatic heterocyclyl, phenyl substituted with substituted or unsubstituted alkenyl, phenyl substituted with substituted or unsubstituted non-aromatic carbocyclyl, phenyl substituted with carboxy, phenyl substituted with alkylamino, substituted or unsubstituted naphthyl, substituted or unsubstituted non-aromatic heterocyclyl, or substituted or unsubstituted bicyclic aromatic heterocyclyl, or its pharmaceutically acceptable salt.

7) The compound according to any one of the above items 1) to 6),
wherein m=2 and n=0,
or its pharmaceutically acceptable salt.

8) The compound according to any one of the above items 1) to 7),
wherein m=1 and n=0,
or its pharmaceutically acceptable salt.

9) The compound according to any one of the above items 1) to 8),
wherein -A- is —NR$^1$—,
or a pharmaceutically acceptable salt thereof.

10) The compound according to any one of the above items 1) to 9),
wherein —Z— is —NH—, =X is =O and —Z$^A$— is —NH—,
or a pharmaceutically acceptable salt thereof.

11) The compound according to any one of the above items 1) to 10),
wherein —Z— is —NR$^5$—, =X is =O and —Z$^A$— is —NR$^{5A}$—,
or its pharmaceutically acceptable salt.

12) The compound according to any one of the above items 1) to 11),
wherein R$^5$ and R$^{5A}$ are hydrogen atoms,
or its pharmaceutically acceptable salt.

13) The compound according to any one of the above items 1) to 12),
wherein —Z— is —NR$^5$—, =X is =O and —Z$^A$— is —CR$^{6A}$R$^{7A}$—,
or its pharmaceutically acceptable salt.

14) The compound according to any one of the above items 1) to 13),
wherein R$^5$, R$^{6A}$ and R$^{7A}$ are hydrogen atoms,
or its pharmaceutically acceptable salt.

15) The compound according to any one of the above items 1) to 14),
wherein —Z— is —CR$^6$R$^7$—, =X is =O and —Z$^A$— is —NR$^{5A}$—,
or its pharmaceutically acceptable salt.

16) The compound according to any one of the above items 1) to 15),
wherein R$^6$, R$^7$ and R$^{5A}$ are hydrogen atoms,
or its pharmaceutically acceptable salt.

17) The compound according to any one of the above items 1) to 16),
wherein —Z— is —O—, =X is =O and —Z$^A$— is —NR$^{5A}$—,
or its pharmaceutically acceptable salt.

18) The compound according to any one of the above items 1) to 17),
wherein R$^{5A}$ is a hydrogen atom,
or its pharmaceutically acceptable salt.

19) The compound according to any one of the above items 1) to 18),
wherein R$^8$ and R$^9$ are hydrogen atoms, or R$^8$ and R$^9$ are taken together to form oxo,
or its pharmaceutically acceptable salt.

20) The compound according to any one of the above items 1) to 19),
wherein R$^3$ and R$^4$ are hydrogen atoms,
or its pharmaceutically acceptable salt.

21) The compound according to any one of the above items 1) to 20),
wherein Ring C is a substituted or unsubstituted aromatic heterocycle,
or its pharmaceutically acceptable salt.

22) The compound according to any one of the above items 1) to 21),
wherein Ring C is a substituted or unsubstituted pyrazole,
or its pharmaceutically acceptable salt.

23) The compound according to any one of the above items 1) to 22),
wherein R$^1$ is substituted or unsubstituted alkyl,
or its pharmaceutically acceptable salt.

24) The compound according to any one of the above items 1) to 23),
wherein R$^{1A}$ is substituted or unsubstituted alkyl,
or its pharmaceutically acceptable salt.

25) The compound according to any one of the above items 1) to 24),
wherein R$^{1E}$ is a hydrogen atom,
or its pharmaceutically acceptable salt.

26) The compound according to any one of the above items 1) to 25),
wherein R$^2$ is a hydrogen atom or substituted or unsubstituted alkyl,
or its pharmaceutically acceptable salt.

27) The compound according to the above item 1),
wherein the compound is represented by Formula (I'):

[Chemical Formula 14]

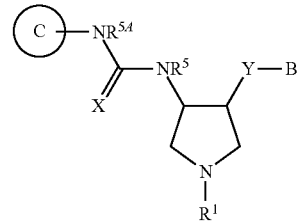

(I')

wherein X, Ring C, R$^5$ and R$^{5A}$ are the same as the above item 1);
Y is a bond;
R$^1$ and B are
(a) R$^1$ is
alkyl substituted with
halogenoethyloxy,
substituted or unsubstituted aromatic carbocyclyloxy,
substituted or unsubstituted non-aromatic heterocyclyl,
substituted or unsubstituted alkyloxycarbonylamino,
substituted or unsubstituted alkylcarbonylamino,
substituted or unsubstituted alkylsulfonylamino,
substituted or unsubstituted alkylsulfonyl,
substituted or unsubstituted non-aromatic carbocyclyl,
carboxy,
substituted or unsubstituted alkyloxyalkyloxy, or
acyl;
alkyl substituted with furyl substituted with
carboxy,
halogen, alkyl or
hydroxyalkyl;
alkyl substituted with
substituted or unsubstituted alkyloxy and substituted or unsubstituted amino,
substituted or unsubstituted alkyloxy and cyano,
substituted or unsubstituted alkyloxy and halogen,
substituted or unsubstituted alkyloxy and substituted or unsubstituted aromatic heterocyclyl,
substituted or unsubstituted alkyloxy and hydroxy,
substituted or unsubstituted alkyloxy and substituted or unsubstituted non-aromatic heterocyclyl,
substituted or unsubstituted aromatic heterocyclyl and hydroxy,
substituted or unsubstituted alkyloxy and substituted or unsubstituted carbamoyl,
substituted or unsubstituted alkyloxy and substituted or unsubstituted alkyloxycarbonyl,
substituted or unsubstituted alkyloxy and substituted or unsubstituted alkylthio, or
substituted or unsubstituted alkyloxycarbonyl and substituted or unsubstituted aromatic heterocyclyl;
substituted or unsubstituted alkyloxycarbonyl;
substituted or unsubstituted acyl;
substituted or unsubstituted non-aromatic heterocyclyl, or
substituted or unsubstituted non-aromatic carbocyclyl;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy; or (b) $R^1$ is a hydrogen atom, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

B is phenyl substituted with substituted or unsubstituted alkyloxycarbonyl, phenyl substituted with substituted or unsubstituted carbamoyl, phenyl substituted with substituted or unsubstituted aromatic carbocyclyl, phenyl substituted with substituted or unsubstituted aromatic heterocyclyl, phenyl substituted with substituted or unsubstituted alkenyl, phenyl substituted with substituted or unsubstituted non-aromatic carbocyclyl, phenyl substituted with carboxy, phenyl substituted with alkylamino, substituted or unsubstituted naphthyl, substituted or unsubstituted non-aromatic heterocyclyl, or substituted or unsubstituted bicyclic aromatic heterocyclyl, or its pharmaceutically acceptable salt.

28) The compound according to the above items 1), wherein the compound is represented by Formula (I''):

[Chemical Formula 15]

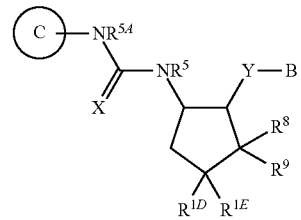

(I'')

wherein X, Ring C, $R^5$, $R^{5A}$, $R^8$ and $R^9$ are the same as the above item 1);
Y is a bond;
B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^{1D}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^{1E}$ is a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or
$R^{1D}$ and $R^{1E}$ may be taken together to form =$CR^{1F}R^{1G}$, oxo, =N—O—$R^{1H}$, or a substituted or unsubstituted non-aromatic carbocycle or a substituted or unsubstituted non-aromatic heterocycle,
$R^{1F}$, $R^{1G}$ and $R^{1H}$ are the same as the above item 1), or its pharmaceutically acceptable salt.

29) The compound according to the above items 1), wherein the compound is represented by Formula (I'''):

[Chemical Formula 16]

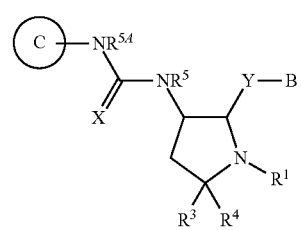

(I''')

wherein X, Ring C, $R^1$, $R^3$, $R^5$ and $R^{5A}$ are the same as the above item 1);

Y is a bond;

B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $R^4$ is a hydrogen atom, substituted or unsubstituted alkyl, substituted or unsubstituted alkenyl, or substituted or unsubstituted alkynyl, or its pharmaceutically acceptable salt.

30) A pharmaceutical composition comprising the compound according to any one of the above items 1) to 29), or its pharmaceutically acceptable salt.

31) The pharmaceutical composition according to the above item 30), wherein the composition has a TrkA inhibitory activity.

Moreover, the present invention relates to the following items 1') to 28').

1') A compound represented by Formula (I):

[Chemical Formula 17]

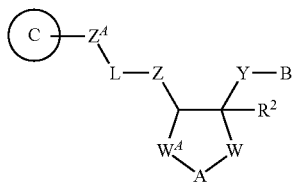

(I)

wherein, -L- is —C(=X)— or —SO$_2$—;
=X is =O, =S, =NR$^{10}$ or =CR$^{11}$R$^{12}$;
—Z— is —NR$^5$—, —O— or —CR$^6$R$^7$—;
—Z$^A$— is —NR$^{5A}$— or —CR$^{6A}$R$^{7A}$—;
—W— is —C(R$^8$R$^9$)n-;
—W$^A$— is —C(R$^3$R$^4$)m-;
n is 0, 1 or 2;
m is 1 or 2;
provided that n=0, 1 or 2 when m=1; and n=0 when m=2;
-A- is —NR$^1$—, —N$^+$(O$^-$)(R$^{1A}$)—, —N$^+$R$^{1B}$R$^{1C}$— or —CR$^{1D}$R$^{1E}$—;
—Y— is a bond, or substituted or unsubstituted alkylene which may be intervened by an oxygen atom;

B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl or substituted or unsubstituted alkyloxy;

Ring C is a substituted or unsubstituted aromatic heterocycle, or a substituted or unsubstituted non-aromatic heterocycle;

$R^1$ is a hydrogen atom, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1A}$ and $R^{1B}$ are each independently substituted or unsubstituted alkyl, substituted or unsubstituted alkenyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1D}$ is a hydrogen atom, substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1C}$ and $R^{1E}$ are each independently a hydrogen atom, hydroxy, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^{1D}$ and $R^{1E}$ may be taken together to form =CR$^{1F}$R$^{1G}$, oxo, =N—O—R$^{1H}$, or a substituted or unsubstituted non-aromatic carbocycle, or a substituted or unsubstituted non-aromatic heterocycle;

$R^{1F}$ and $R^{1G}$ are each independently a hydrogen atom, substituted or unsubstituted alkyl, substituted or unsubstituted alkyloxy, or substituted or unsubstituted alkyloxycarbonyl;

$R^{1H}$ is a hydrogen atom, substituted or unsubstituted alkyl, substituted or unsubstituted alkenyl, or substituted or unsubstituted alkynyl;

$R^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen or hydroxy, or $R^2$ may be taken together with "—Y—B" to form a substituted or unsubstituted non-aromatic carbocycle, or a substituted or unsubstituted non-aromatic heterocycle;

$R^3$ is each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;

$R^4$ is each independently a hydrogen atom, substituted or unsubstituted alkyl, substituted or unsubstituted alkenyl, or substituted or unsubstituted alkynyl, or $R^4$ may be taken together with one of $R^8$ to form (C2-C4) bridge, in which one of the carbon atoms consisting of the bridge may be replaced with an oxygen atom or a nitrogen atom; the carbon atoms consisting of the bridge are each independently substituted with a substituent selected from R$^a$; and the nitrogen atom consisting the bridge is substituted with a substituent selected from R$^b$;

R$^a$ is each independently a hydrogen atom, halogen, hydroxy, cyano, oxo, substituted or unsubstituted carbamoyl, substituted or unsubstituted amino, or substituted or unsubstituted alkyl;

R$^b$ is each independently a hydrogen atom, substituted or unsubstituted alkyl, substituted or unsubstituted acyl, substituted or unsubstituted alkyloxycarbonyl, or substituted or unsubstituted alkylsulfonyl;

R$^5$ and R$^{5A}$ are each independently a hydrogen atom, or substituted or unsubstituted alkyl;

R$^6$, R$^{6A}$, R$^7$ and R$^{7A}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, or substituted or unsubstituted amino;

R$^8$ is each independently a hydrogen atom, halogen, hydroxy, substituted or unsubstituted alkyl, substituted or unsubstituted alkenyl, substituted or unsubstituted alkynyl, or substituted or unsubstituted alkyloxy;

R$^9$ is each independently a hydrogen atom, halogen, hydroxy, substituted or unsubstituted alkyl, substituted or unsubstituted alkenyl, substituted or unsubstituted alkynyl, or substituted or unsubstituted alkyloxy, or R$^8$ and R$^9$ may be taken together to form oxo;

R$^{10}$ is substituted or unsubstituted alkyl, substituted or unsubstituted acyl, substituted or unsubstituted alkyloxycarbonyl, substituted or unsubstituted alkylsulfonyl, or nitro;

R$^{11}$ is a hydrogen atom, cyano, substituted or unsubstituted acyl, substituted or unsubstituted alkyloxycarbonyl, substituted or unsubstituted alkylcarbamoyl, substituted or unsubstituted alkylsulfonyl, or nitro;

R$^{12}$ is a hydrogen atom or cyano;

provided that:

(1) B is not aromatic carbocyclyl optionally substituted with halogen, hydroxyl, —NH$_2$, —CF$_3$, —OCF$_3$, alkyloxy, hydroxyalkyl, alkyl or cyano, and is not aromatic heterocyclyl optionally substituted with halogen, hydroxy, —NH$_2$, —CF$_3$, —OCF$_3$, alkyloxy, hydroxyalkyl, alkyl or cyano, when the group of "—Y—B" and the group of "—Z-L-Z$^A$-(Ring C)" are in trans conformation, —W— is —C(R$^8$R$^9$)—, —W$^A$— is —(R$^3$R$^4$)—, —Y— is a bond, -A- is —NR$^1$—, and R$^1$ is (i) unsubstituted alkyl,
(ii) alkyl substituted with
alkyloxy,
trifluoromethoxy,
sulfanyl,
monofluoro,
difluoro,
trifluoro,
tetrafluoro,
pentafluoro,
cyano,
aminocarbonyl,
hydroxyl,
dihydroxy,
alkylamino,
alkyloxycarbonyl,
amino,
hydroxyalkyloxy,
dialkyloxy,
alkyloxytrifluoro,
hydroxytrifluoro,
alkyloxycarbonylalkyloxy,
hydroxycarbonylalkyloxy, substituted or unsubstituted aromatic heterocyclyl, or substituted or unsubstituted aromatic carbocyclyl, (iii) substituted or unsubstituted aromatic heterocyclyl,
(iv) substituted or unsubstituted aromatic carbocyclyl, or
(v) a hydrogen atom;

(2) Ring C is not

[Chemical Formula 18]

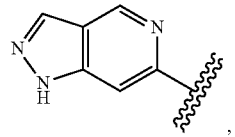

when -A- is —NR$^1$—, —W— is —C(R$^8$R$^9$)— and —W$^A$— is —C(R$^3$R$^4$)—;

(3) Ring C is not a substituted or unsubstituted pyrimidine, when -A- is —CR$^{1D}$R$^{1E}$—, —W— is —C(R$^8$R$^9$)$_2$— and —W$^A$— is —C(R$^3$R$^4$)—;

(4) B is not substituted or unsubstituted pyrrolidyl, when -A- is —CR$^{1D}$R$^{1E}$—, —W— is —C(R$^8$R$^9$)$_2$—, —W$^A$— is —C(R$^3$R$^4$)— and Y is a bond; and (5) B is not unsubstituted cyclopropyl, when -A- is —NR$^1$—, —W— is —CH$_2$—, —W$^A$— is —CH$_2$— and —Y— is a bond;

provided that the following compounds are excluded:

[Chemical Formula 19]

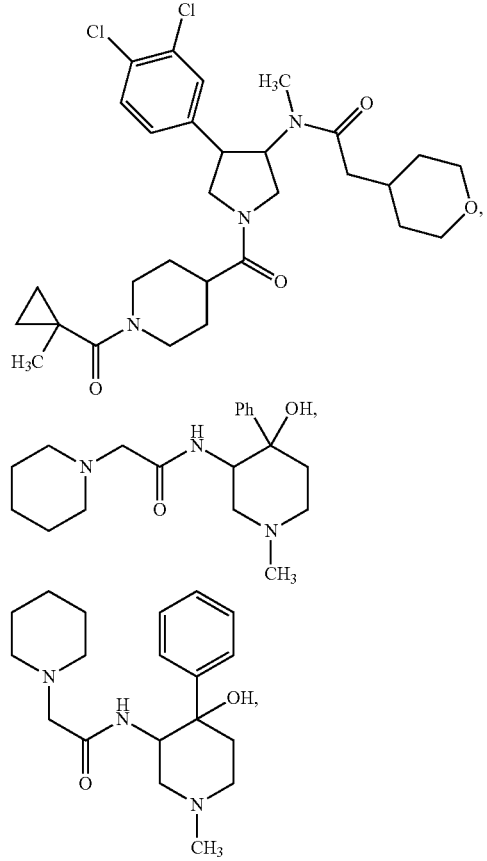

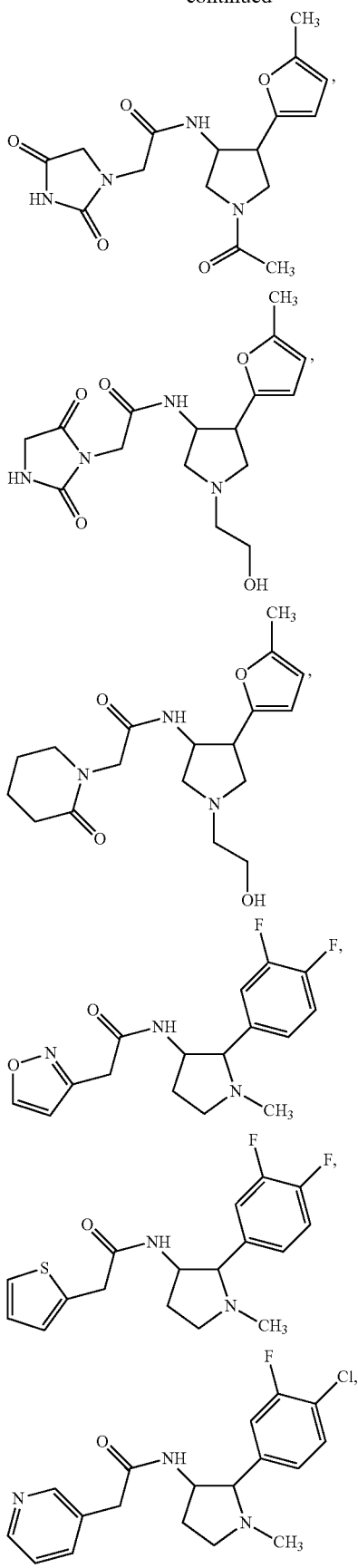
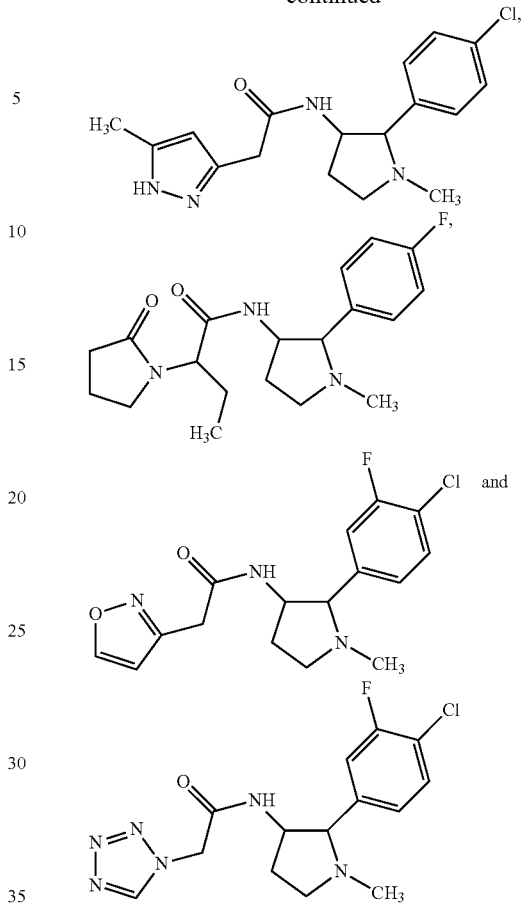

or its pharmaceutically acceptable salt.

2') The compound according to the above item 1'),
wherein -L- is —C(═X)—,
═X is ═O or ═S,
Y is a bond,
R[1D] is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or its pharmaceutically acceptable salt.

3') The compound according to the above item 1') or 2'),
wherein m=1 and n=1,
or its pharmaceutically acceptable salt.

4') The compound according to any one of the above items 1') to 3'),
wherein -A- is —N$^+$(O$^-$)(R$^{1A}$)— or —CR$^{1D}$R$^{1E}$—,
or its pharmaceutically acceptable salt.

5') The compound according to any one of the above items 1') to 4'),
wherein -A- is —NR$^1$—,
R$^1$ is
alkyl substituted with
halogenoethyloxy,
substituted or unsubstituted aromatic carbocyclyloxy,
substituted or unsubstituted non-aromatic heterocyclyl,
substituted or unsubstituted alkyloxycarbonylamino,
substituted or unsubstituted alkylcarbonylamino,
substituted or unsubstituted alkylsulfonylamino,
substituted or unsubstituted alkylsulfonyl,
substituted or unsubstituted non-aromatic carbocyclyl,
carboxy, or
substituted or unsubstituted alkyloxyalkyloxy,
substituted or unsubstituted alkyloxycarbonyl,
substituted or unsubstituted acyl,
substituted or unsubstituted non-aromatic heterocyclyl, or
substituted or unsubstituted non-aromatic carbocyclyl,
or its pharmaceutically acceptable salt.

6') The compound according to any one of the above items 1') to 5'),
wherein B is phenyl substituted with substituted or unsubstituted alkyloxycarbonyl, phenyl substituted with substituted or unsubstituted carbamoyl, phenyl substituted with substituted or unsubstituted aromatic carbocyclyl, phenyl substituted with substituted or unsubstituted aromatic heterocyclyl, phenyl substituted with substituted or unsubstituted alkenyl, phenyl substituted with substituted or unsubstituted non-aromatic carbocyclyl, phenyl substituted with carboxy, substituted or unsubstituted naphthyl, or substituted or unsubstituted non-aromatic heterocyclyl,
or its pharmaceutically acceptable salt.

7') The compound according to any one of the above items 1') to 6'),
wherein m=2 and n=0,
or its pharmaceutically acceptable salt.

8') The compound according to any one of the above items 1') to 7'),
wherein m=1 and n=0,
or its pharmaceutically acceptable salt.

9') The compound according to any one of the above items 1') to 8'),
wherein -A- is —NR$^1$—,
or a pharmaceutically acceptable salt thereof.

10') The compound according to any one of the above items 1') to 9'),
wherein —Z— is —NH—, =X is =O and —Z$^A$— is —NH—,
or a pharmaceutically acceptable salt thereof.

11') The compound according to any one of the above items 1') to 10'),
wherein —Z— is —NR$^5$—, =X is =O and —Z$^A$— is —NR$^{5A}$—,
or its pharmaceutically acceptable salt.

12') The compound according to any one of the above items 1') to 11'),
wherein R$^5$ and R$^{5A}$ are hydrogen atoms,
or its pharmaceutically acceptable salt.

13') The compound according to any one of the above items 1') to 12'),
wherein —Z— is —NR$^5$—, =X is =O and —Z$^A$— is —CR$^{6A}$R$^{7A}$—,
or its pharmaceutically acceptable salt.

14') The compound according to any one of the above items 1') to 13'),
wherein R$^5$, R$^{6A}$ and R$^{7A}$ are hydrogen atoms,
or its pharmaceutically acceptable salt.

15') The compound according to any one of the above items 1') to 14'),
wherein —Z— is —CR$^6$R$^7$—, =X is =O and —Z$^A$— is —NR$^{5A}$—,
or its pharmaceutically acceptable salt.

16') The compound according to any one of the above items 1') to 15'),
wherein R$^6$, R$^7$ and R$^{5A}$ are hydrogen atoms,
or its pharmaceutically acceptable salt.

17') The compound according to any one of the above items 1') to 16'),
wherein —Z— is —O—, =X is =O and —Z$^A$— is —NR$^{5A}$—,
or its pharmaceutically acceptable salt.

18') The compound according to any one of the above items 1') to 17'),
wherein R$^{5A}$ is a hydrogen atom,
or its pharmaceutically acceptable salt.

19') The compound according to any one of the above items 1') to 18'),
wherein R$^8$ and R$^9$ are hydrogen atoms, or R$^8$ and R$^9$ are taken together to form oxo,
or its pharmaceutically acceptable salt.

20') The compound according to any one of the above items 1') to 19'),
wherein R$^3$ and R$^4$ are hydrogen atoms,
or its pharmaceutically acceptable salt.

21') The compound according to any one of the above items 1') to 20'),
wherein Ring C is a substituted or unsubstituted aromatic heterocycle,
or its pharmaceutically acceptable salt.

22') The compound according to any one of the above items 1') to 21'),
wherein Ring C is a substituted or unsubstituted pyrazole,
or its pharmaceutically acceptable salt.

23') The compound according to any one of the above items 1') to 22'),
wherein R$^1$ is substituted or unsubstituted alkyl,
or its pharmaceutically acceptable salt.

24') The compound according to any one of the above items 1') to 23'),
wherein R$^{1A}$ is substituted or unsubstituted alkyl,
or its pharmaceutically acceptable salt.

25') The compound according to any one of the above items 1') to 24'),
wherein R$^{1E}$ is a hydrogen atom,
or its pharmaceutically acceptable salt.

26') The compound according to any one of the above items 1') to 25'),
wherein R$^2$ is a hydrogen atom or substituted or unsubstituted alkyl,
or its pharmaceutically acceptable salt.

27') A pharmaceutical composition comprising the compound according to any one of the above items 1') to 26'), or its pharmaceutically acceptable salt.

28') The pharmaceutical composition according to the above item 27'), wherein the composition has a TrkA inhibitory activity.

Effect of the Invention

The present invention provides a compound useful in the treatment and/or prevention of TrkA mediated disorder, or a pharmaceutically acceptable salt thereof. The compound of the present invention shows an excellent TrkA kinase inhibitory activity as described in the following test examples. Thereby, a pharmaceutical composition of the present invention is available for therapeutic agent and/or prophylactic agent for pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease, immune disease, visceral disease, infection disease and the like.

A compound of the present invention is the one having utility as a medicament. Herein, utility as a medicament includes the following points: the compound has good solubility; good metabolic stability; the induction of a drug-metabolizing enzyme is low; the inhibition of a drug-metabolizing enzyme which metabolizes another drug is low; the compound has high oral absorbency; the inhibition of hERG is low; the clearance is low; and/or the half-life is sufficiently long to express the efficacy; or the like.

MODE FOR CARRYING OUT THE INVENTION

Hereinafter, the present invention is described with reference to embodiments. It should be understood that, throughout the present specification, the expression of a singular form includes the concept of its plural form unless specified otherwise. Accordingly, it should be understood that an article in singular form (for example, in the English language, "a," "an," "the," and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

Terms used in this description are explained below. Each term, unless otherwise indicated, has the same meaning when it is used alone or together with other terms.

The term of "consisting of" means having only components.

The term of "comprising" means not restricting with components and not excluding undescribed factors.

The term "halogen" includes a fluorine atom, a chlorine atom, a bromine atom and an iodine atom. A fluorine atom and a chlorine atom are especially preferable.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

The term "alkynyl" includes a C2 to C10, preferably a C2 to C8, more preferably a C2 to C6 and further preferably a C2 to C4 linear or branched hydrocarbon group having one or more triple bond(s) at any position(s). Furthermore, it may have double bond(s) at any position(s). Examples include ethynyl, propynyl, butynyl, pentynyl, hexynyl, heptynyl, octynyl, nonynyl, decynyl and the like.

A preferred embodiment of "alkynyl" is ethynyl, propynyl, butynyl or pentynyl.

The term "alkylene" includes a C1 to C15, preferably a C1 to C10, more preferably a C1 to C6 and further preferably a C1 to C4 liner or branched divalent hydrocarbon group. Examples include methylene, ethylene, trimethylene, propylene, tetramethylene, pentamethylene, hexamethylene and the like.

The term "aromatic carbocyclyl" means a cyclic aromatic hydrocarbon group which is monocyclic or polycyclic having two or more rings. Examples include phenyl, naphthyl, anthryl, phenanthryl and the like.

A preferred embodiment of "aromatic carbocyclyl" is phenyl.

The term "aromatic carbocycle" means a cyclic aromatic hydrocarbon ring which is monocyclic or polycyclic having two or more rings. Examples include a benzene ring, a naphthalene ring, an anthracene ring, a phenanthrene ring, and the like.

A preferred embodiment of "aromatic carbocycle" is a benzene ring and a naphthalene ring.

The term "non-aromatic carbocyclyl" means a cyclic saturated hydrocarbon group or a cyclic unsaturated non-aromatic hydrocarbon group, which is monocyclic or polycyclic having two or more rings. The "non-aromatic carbocyclyl" which is polycyclic having two or more rings includes a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

[Chemical Formula 20]

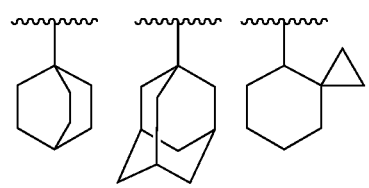

The non-aromatic carbocyclyl which is monocyclic is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

Examples of non-aromatic carbocyclyl, which is polycyclic having two or more rings, include indanyl, indenyl, acenaphthyl, tetrahydronaphthyl, fluorenyl and the like.

The term "non-aromatic carbocycle" means a cyclic saturated hydrocarbon ring or a cyclic unsaturated non-aromatic hydrocarbon ring, which is monocyclic or polycyclic having two or more rings. The "non-aromatic carbocycle", which is polycyclic having two or more rings, includes a fused ring wherein the non-aromatic carbocycle, which is monocyclic or polycyclic having two or more rings, is fused with a ring of the above "aromatic carbocycle".

In addition, examples of the "non-aromatic carbocycle" also include a ring having a bridge or a ring to form a spiro ring as follows:

[Chemical Formula 21]

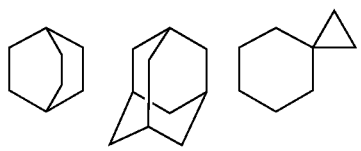

The non-aromatic carbocycle which is monocyclic is preferably C3 to C16, more preferably C3 to C12 and further preferably C4 to C8 carbocyclyl. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene, and the like.

Examples of a non-aromatic carbocycle, which is polycyclic having two or more rings, include indane, indene, acenaphthene, tetrahydronaphthalene, fluorene, and the like.

Examples of a non-aromatic carbocycle in which $R^{1D}$ and $R^{1E}$ may be taken together to form, include a ring as follows:

[Chemical Formula 22]

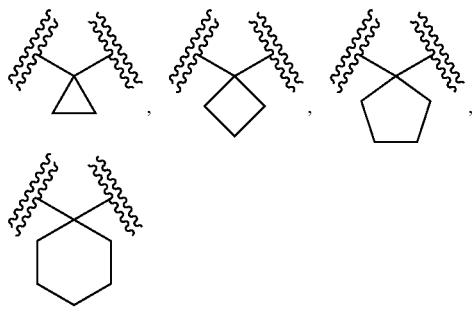

Examples of a non-aromatic carbocycle in which $R^2$ and —Y—B may be taken together to form, include a ring as follows:

[Chemical Formula 23]

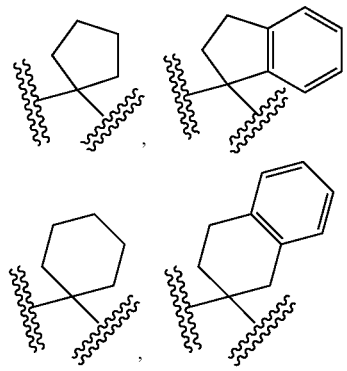

The term "aromatic heterocyclyl" means an aromatic cyclyl, which is monocyclic or polycyclic having two or more rings, containing one or more, same or different heteroatom(s) selected independently from O, S and N. The "aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered ring and more preferably a 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like. Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl, thienopyridyl, furopyridyl, pyrrolopyridyl and the like.

Examples of aromatic heterocyclyl, which is bicyclic, include a group as follows:

[Chemical Formula 24]

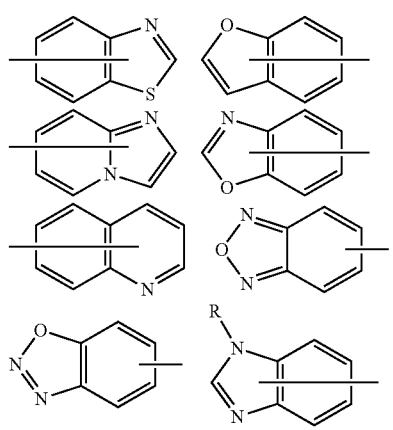

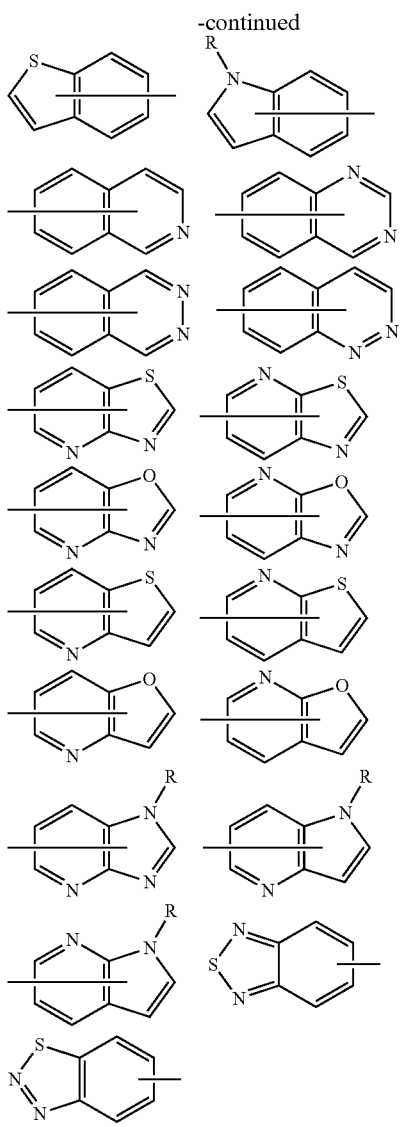

wherein R is a hydrogen atom, CH₃, CH₂CF₃, in the case that one of the binding group attaches to one ring, it may be attached to a connectable atom that constitutes the ring, in the case that one of the binding group attached to two rings, it may be attached to a connectable atom that constitutes the two rings.

Examples of aromatic heterocyclyl, which is polycyclic having three or more rings, include carbazolyl, acridinyl, xanthenyl, phenothiazinyl, phenoxathiinyl, phenoxazinyl, dibenzofuryl and the like.

The term "aromatic heterocycle" means an aromatic ring, which is monocyclic or polycyclic having two or more rings, containing one or more, same or different heteroatom(s) selected independently from O, S and N.

The "aromatic heterocycle", which is polycyclic having two or more rings, includes a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered ring and more preferably a 5- or 6-membered ring. Examples include pyrrole, imidazole, pyrazole, pyridine, pyridazine, pyrimidine, pyrazine, pyridone, triazole, triazine, tetrazole, furan, thiophen, isoxazole, oxazole, oxadiazole, isothiazole, thiazole, thiadiazole, and the like.

Examples of an aromatic heterocycle, which is bicyclic, include, indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, thiazolopyridine, and the like.

Examples of an aromatic heterocycle, which is polycyclic having three or more rings, include carbazole, acridine, xanthene, phenothiazine, phenoxathiine, phenoxazine, dibenzofuran, and the like.

The term "non-aromatic heterocyclyl" means a non-aromatic cyclyl, which is monocyclic or polycyclic having two or more rings, containing one or more, same or different heteroatom(s) selected independently from O, S and N. The "non-aromatic heterocyclyl", which is polycyclic having two or more rings, include an above-mentioned non-aromatic heterocyclyl fused with a ring of the above "aromatic carbocyclyl", "non-aromatic carbocyclyl" and/or "aromatic heterocyclyl".

In addition, examples of the "non-aromatic heterocyclyl" also include a group having a bridge or a group to form a spiro ring as follows:

[Chemical Formula 25]

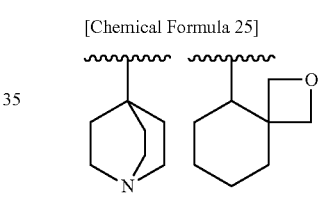

The non-aromatic heterocyclyl, which is monocyclic, is preferably a 3- to 8-membered and more preferably a 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolynyl, oxepanyl, thiolanyl, thiinyl, thiazinyl and the like.

Examples of non-aromatic heterocyclyl, which is polycyclic having two or more rings, include indolinyl, isoindolinyl, chromanyl, isochromanyl and the like.

The term "non-aromatic heterocycle" means a cyclic non-aromatic ring, which is monocyclic or polycyclic having two or more rings, containing one or more, same or different heteroatom(s) selected from O, S and N.

The "non-aromatic heterocycle", which is polycyclic having two or more rings, includes an above-mentioned non-aromatic heterocycle fused with a ring of the above "aromatic carbocycle", "non-aromatic carbocycle" and/or "aromatic heterocycle". In addition, the "non-aromatic heterocycle" also includes a ring having a bridge or a ring to form a spiro ring as follows:

[Chemical Formula 26]

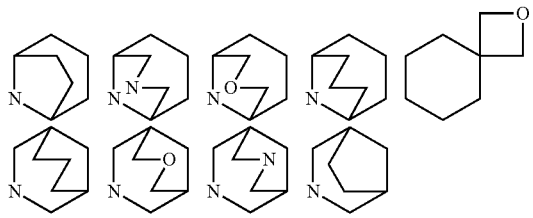

The non-aromatic heterocycle which is non-bridged is preferably a 3 to 8-membered ring, more preferably a 4 to 8-membered ring, and further preferably a 5 or 6-membered ring.

The non-aromatic heterocycle which is bridged is preferably a 6 to 10-membered ring and more preferably a 8 or 9-membered ring. Herein, a number of members mean a number of all atoms which constitutes a bridged non-aromatic heterocycle.

The non-aromatic heterocycle which is monocyclic is preferably a 3 to 8-membered ring, and more preferably a 5 or 6-membered ring. For example, dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiine, thiazine and the like.

Examples of a non-aromatic heterocycle, which is polycyclic having two or more rings, include indoline, isoindoline, chromane, isochromane, and the like.

Examples of a non-aromatic heterocycle in which $R^{1D}$ and $R^{1E}$ may be taken together to form, include a ring as follows:

[Chemical Formula 27]

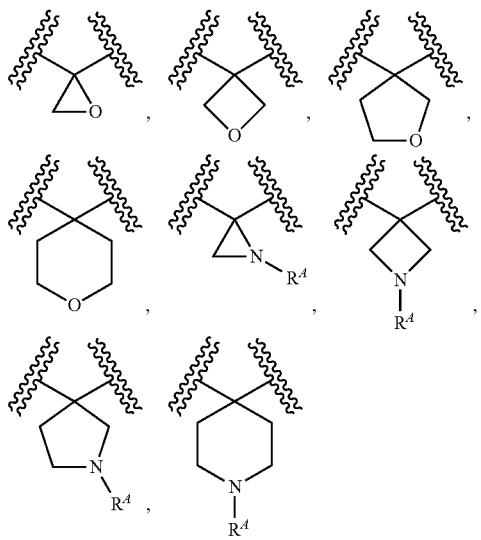

wherein, $R^A$ is substituted or unsubstituted alkyl, substituted or unsubstituted alkenyl, substituted or unsubstituted alkyloxycarbonyl, or substituted or unsubstituted alkylcarbonyl.

Examples of a non-aromatic heterocycle in which $R^2$ and —Y—B group may be taken together to form, include a ring as follows:

[Chemical Formula 28]

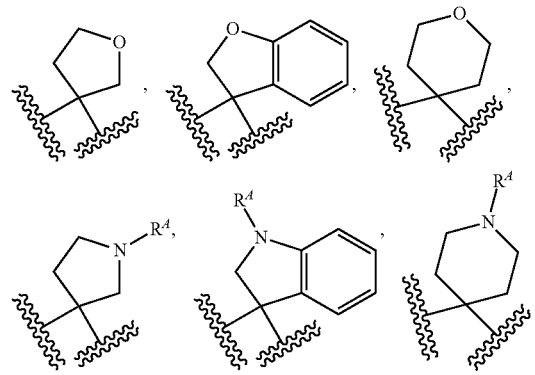

wherein $R^A$ is substituted or unsubstituted alkyl, substituted or unsubstituted alkenyl, substituted or unsubstituted alkyloxycarbonyl, or substituted or unsubstituted alkylcarbonyl.

The term "hydroxyalkyl" means a group wherein one or more hydrogen atom(s) attached to a carbon atom of the above "alkyl" is replaced with a hydroxyl group. Examples include hydroxymethyl, 1-hydroxyethyl, 2-hydroxyethyl, 1-hydroxypropyl, 2-hydroxypropyl, 1,2-dihydroxyethyl, and the like.

A preferred embodiment of "hydroxyalkyl" is hydroxymethyl.

The term "alkyloxy" means a group wherein the above "alkyl" is bonded to an oxygen atom. Examples include methoxy, ethoxy, n-propyloxy, isopropyloxy, n-butyloxy, tert-butyloxy, isobutyloxy, sec-butyloxy, pentyloxy, isopentyloxy, hexyloxy, and the like.

A preferred embodiment of "alkyloxy" is methoxy, ethoxy, n-propyloxy, isopropyloxy, and tert-butyloxy.

The term "alkenyloxy" means a group wherein the above "alkenyl" is bonded to an oxygen atom. Examples include vinyloxy, allyloxy, 1-propenyloxy, 2-butenyloxy, 2-pentenyloxy, 2-hexenyloxy, 2-heptenyloxy, 2-octenyloxy, and the like.

The term "alkynyloxy" means a group wherein the above "alkynyl" is bonded to an oxygen atom. Examples include ethynyloxy, 1-propynyloxy, 2-propynyloxy, 2-butynyloxy, 2-pentynyloxy, 2-hexynyloxy, 2-heptynyloxy, 2-octynyloxy, and the like.

The term "haloalkyl" includes a group wherein one or more hydrogen atom(s) attached to a carbon atom of the above "alkyl" is replaced with the above "halogen". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropane-2-yl, and the like.

A preferred embodiment of "haloalkyl" is trifluoromethyl and trichloromethyl.

The term "haloalkyloxy" means a group wherein the above "haloalkyl" is bonded to an oxygen atom. Examples include monofluoromethoxy, monofluoroethoxy, trifluoromethoxy, trichloromethoxy, trifluoroethoxy, trichloroethoxy, and the like.

A preferred embodiment of "haloalkyloxy" is trifluoromethoxy and trichloromethoxy.

The term "alkyloxyalkyl" means a group wherein the above "alkyloxy" is bonded to the above "alkyl". Examples include methoxymethyl, methoxyethyl, ethoxymethyl, and the like.

The term "alkyloxyalkyloxy" means a group wherein the above "alkyloxy" is bonded to the above "alkyloxy". Examples include methoxymethoxy, methoxyethoxy, ethoxymethoxy, ethoxyethoxy, and the like.

The term "alkylcarbonyl" means a group wherein the above "alkyl" is bonded to a carbonyl group. Examples include methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl, and the like.

A preferred embodiment of "alkylcarbonyl" is methylcarbonyl, ethylcarbonyl and n-propylcarbonyl.

The term "alkenylcarbonyl" means a group wherein the above "alkenyl" is bonded to a carbonyl group. Examples include ethylenylcarbonyl, propenylcarbonyl and the like.

The term "alkynylcarbonyl" means a group wherein the above "alkynyl" is bonded to a carbonyl group. Examples include ethynylcarbonyl, propynylcarbonyl and the like.

The term "alkylamino" means a group wherein one or two hydrogen atom(s) attached to a nitrogen atom of an amino group is(are) replaced with the above "alkyl". Examples include methylamino, dimethylamino, ethylamino, diethylamino, isopropylamino, N,N-diisopropylamino, N-methyl-N-ethylamino, and the like.

A preferred embodiment of "alkylamino" is methylamino and ethylamino.

The term "alkylsulfonyl" means a group wherein the above "alkyl" is bonded to a sulfonyl group. Examples include methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylulfonyl" is methylsulfonyl and ethylsulfonyl.

The term "alkenylsulfonyl" means a group wherein the above "alkenyl" is bonded to a sulfonyl group. Examples include ethylenylsulfonyl, propenylsulfonyl, and the like.

The term "alkynylsulfonyl" means a group wherein the above "alkynyl" is bonded to a sulfonyl group. Examples include ethynylsulfonyl, propynylsulfonyl, and the like.

The term "alkylcarbonylamino" means a group wherein one or two hydrogen atom(s) attached to a nitrogen atom of an amino group is(are) replaced with the above "alkylcarbonyl". Examples include methylcarbonylamino, dimethylcarbonylamino, ethylcarbonylamino, diethylcarbonylamino, propylcarbonylamino, isopropylcarbonylamino, N,N-diisopropylcarbonylamino, tert-butylcarbonylamino, isobutylcarbonylamino, sec-butylcarbonylamino, and the like.

The term "alkylsulfonylamino" means a group wherein one or two hydrogen atom(s) attached to a nitrogen atom of an amino group is(are) replaced with the above "alkylsulfonyl". Examples include methyl sulfonylamino, dimethyl sulfonylamino, ethylsulfonylamino, diethyl sulfonylamino, propyl sulfonylamino, isopropyl sulfonylamino, N,N-diisopropyl sulfonylamino, tert-butyl sulfonylamino, isobutyl sulfonylamino, sec-butylsulfonylamino and the like.

A preferred embodiment of "alkylsulfonylamino" is methylsulfonylamino and ethyl sulfonyl amino.

The term "alkylimino" means a group wherein a hydrogen atom attached to a nitrogen atom of an imino group is replaced with the above "alkyl". Examples include methylimino, ethylimino, n-propylimino, isopropylimino and the like.

The term "alkenylimino" means a group wherein a hydrogen atom attached to a nitrogen atom of an imino group is replaced with the above "alkenyl". Examples include ethylenylimino, propenylimino and the like.

The term "alkynylimino" means a group wherein a hydrogen atom attached to a nitrogen atom of an imino group is replaced with the above "alkynyl". Examples include ethynylimino, propynylimino and the like.

The term "alkylcarbonylimino" means a group wherein a hydrogen atom attached to a nitrogen atom of an imino group is replaced with the above "alkylcarbonyl". Examples include methylcarbonylimino, ethylcarbonylimino, n-propylcarbonylimino, isopropylcarbonylimino and the like.

The term "alkenylcarbonylimino" means a group wherein a hydrogen atom attached to a nitrogen atom of an imino group is replaced with the above "alkenylcarbonyl". Examples include ethylenylcarbonylimino, propenylcarbonylimino and the like.

The term "alkynylcarbonylimino" means a group wherein a hydrogen atom attached to a nitrogen atom of an imino group is replaced with the above "alkynylcarbonyl". Examples include ethynylcarbonylimino, propynylcarbonylimino and the like.

The term "alkyloxyimino" means a group wherein a hydrogen atom attached to a nitrogen atom of an imino group is replaced with the above "alkyloxy". Examples include methyloxyimino, ethyloxyimino, n-propyloxyimino, isopropyloxyimino and the like.

The term "alkenyloxyimino" means a group wherein a hydrogen atom attached to a nitrogen atom of an imino group is replaced with the above "alkenyloxy". Examples include ethylenyloxyimino, propenyloxyimino and the like.

The term "alkynyloxyimino" means a group wherein a hydrogen atom attached to a nitrogen atom of an imino group is replaced with the above "alkynyloxy". Examples include ethynyloxyimino, propynyloxyimino and the like.

The term "alkylcarbonyloxy" means a group wherein the above "alkylcarbonyl" is bonded to an oxygen atom. Examples include methylcarbonyloxy, ethylcarbonyloxy, propylcarbonyloxy, isopropylcarbonyloxy, tert-butylcarbonyloxy, isobutylcarbonyloxy, sec-butylcarbonyloxy, and the like.

A preferred embodiment of "alkylcarbonyloxy" is methylcarbonyloxy and ethylcarbonyloxy.

The term "alkenylcarbonyloxy" means a group wherein the above "alkenylcarbonyl" is bonded to an oxygen atom. Examples include ethylenylcarbonyloxy and propenylcarbonyloxy.

The term "alkynylcarbonyloxy" means a group wherein the above "alkynylcarbonyl" is bonded to an oxygen atom. Examples include ethynylcarbonyloxy and propynylcarbonyloxy.

The term "alkyloxycarbonyl" means a group wherein the above "alkyloxy" is bonded to a carbonyl group. Examples include methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like.

A preferred embodiment of "alkyloxycarbonyl" is methyloxycarbonyl, ethyloxycarbonyl and propyloxycarbonyl.

The term "alkenyloxycarbonyl" means a group wherein the above "alkenyloxy" is bonded to a carbonyl group. Examples include ethylenyloxycarbonyl and propenyloxycarbonyl.

The term "alkynyloxycarbonyl" means a group wherein the above "alkynyloxy" is bonded to a carbonyl group. Examples include ethynyloxycarbonyl and propynyloxycarbonyl.

The term "alkylsulfanyl" means a group wherein a hydrogen atom attached to a sulfur atom of a sulfanyl group is replaced with the above "alkyl". Examples include methylsulfanyl, ethylsulfanyl, n-propylsulfanyl, isopropylsulfanyl and the like.

The term "alkenylsulfanyl" means a group wherein a hydrogen atom attached to a sulfur atom of a sulfanyl group is replaced with the above "alkenyl". Examples include ethylenylsulfanyl, propenylsulfanyl and the like.

The term "alkynylsulfanyl" means a group wherein a hydrogen atom attached to a sulfur atom of a sulfanyl group is replaced with the above "alkynyl". Examples include ethynylsulfanyl, propynylsulfanyl and the like.

The term "alkylsulfinyl" means a group wherein the above "alkyl" is bonded to a sulfinyl group. Examples include methylsulfinyl, ethylsulfinyl, n-propylsulfinyl, isopropylsulfinyl and the like.

The term "alkenylsulfinyl" means a group wherein the above "alkenyl" is bonded to a sulfinyl group. Examples include ethylenylsulfinyl, propenylsulfinyl and the like.

The term "alkynylsulfinyl" means a group wherein the above "alkynyl" is bonded to a sulfinyl group. Examples include ethynylsulfinyl, propynylsulfinyl and the like.

The term "alkylcarbamoyl" means a group wherein one or two hydrogen atom(s) attached to a nitrogen atom of a carbamoyl group is(are) replaced with the above "alkyl". Examples include methylcarbamoyl, dimethylcarbamoyl, ethylcarbamoyl, diethylcarbamoyl and the like.

The term "alkylsulfamoyl" means a group wherein one or two hydrogen atom(s) attached to a nitrogen atom of a sulfamoyl group is(are) replaced with the above "alkyl". Examples include methylsulfamoyl, dimethylsulfamoyl, dimethylsulfamoyl, diethylsulfamoyl and the like.

The term "trialkylsilyl" means a group wherein three of the above "alkyl" are bonded to a silyl atom. Three alkyl groups may be the same or different. Examples include trimethylsilyl, triethylsilyl, tert-butyldimethylsilyl and the like.

The alkyl part of "aromatic carbocyclylalkyl", "non-aromatic carbocyclylalkyl", "aromatic heterocyclylalkyl", and "non-aromatic heterocyclylalkyl", "aromatic carbocyclylalkyloxy", "non-aromatic carbocyclylalkyloxy", "aromatic heterocyclylalkyloxy", and "non-aromatic heterocyclylalkyloxy", "aromatic carbocyclylalkyloxycarbonyl", "non-aromatic carbocyclylalkyloxycarbonyl", "aromatic heterocyclylalkyloxycarbonyl", and "non-aromatic heterocyclylalkyloxycarbonyl", "aromatic carbocyclylalkyloxyalkyl", "non-aromatic carbocyclylalkyloxyalkyl", "aromatic heterocyclylalkyloxyalkyl", and "non-aromatic heterocyclylalkyloxyalkyl", and "aromatic carbocyclylalkylamino", "non-aromatic carbocyclyl alkylamino", "aromatic heterocyclylalkylamino", and "non-aromatic heterocyclylalkylamino" is also the same as above "alkyl".

The term "aromatic carbocyclylalkyl" means an alkyl substituted with one or more "aromatic carbocyclyl" described above. Examples include benzyl, phenethyl, phenylpropyl, benzhydryl, trityl, naphthylmethyl, a group of the formula of

[Chemical Formula 29]

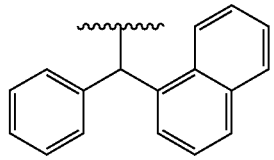

and the like.

A preferred embodiment of "aromatic carbocyclylalkyl" is benzyl, phenethyl or benzhydryl.

The term "non-aromatic carbocyclylalkyl" means an alkyl substituted with one or more "non-aromatic carbocyclyl" described above. The "non-aromatic carbocyclylalkyl" also includes "non-aromatic carbocyclylalkyl" wherein the alkyl part is substituted with the above "aromatic carbocyclyl". Examples include cyclopropylmethyl, cyclobutylmethyl, cyclopentylmethyl, cyclohexylmethyl, a group of the formula of

[Chemical Formula 30]

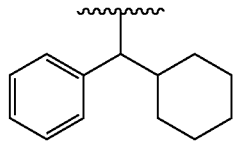

and the like.

The term "aromatic heterocyclylalkyl" means an alkyl substituted with one or more "aromatic heterocyclyl" described above. The "aromatic heterocyclylalkyl" also includes "aromatic heterocyclylalkyl" wherein the alkyl part is substituted with the above "aromatic carbocyclyl" and/or "non-aromatic carbocyclyl". Examples include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, groups of the formula of

[Chemical Formula 31]

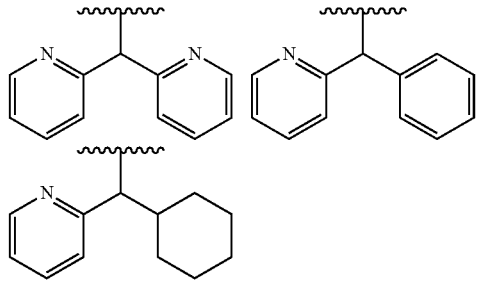

and the like.

The term "non-aromatic heterocyclylalkyl" means an alkyl substituted with one or more "non-aromatic heterocyclyl" described above. The "non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". Examples include tetrahydropyranylmethyl, morpholinylethyl, piperidinylmethyl, piperazinylmethyl, groups of the formula of

[Chemical Formula 32]

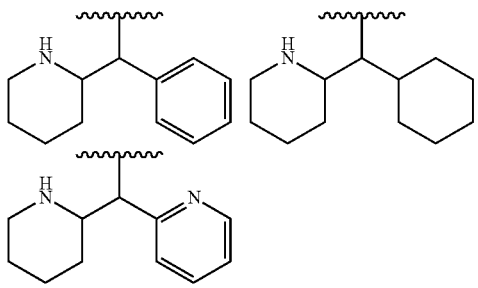

and the like.

The term "aromatic carbocyclylalkyloxy" means an alkyloxy substituted with one or more "aromatic carbocyclyl" described above. Examples include benzyloxy, phenethyloxy, phenylpropyloxy, benzhydryloxy, trityloxy, naphthylmethyloxy, a group of the formula of

[Chemical Formula 33]

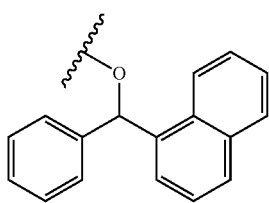

and the like.

The term "non-aromatic carbocyclylalkyloxy" means an alkyloxy substituted with one or more "non-aromatic carbocyclyl" described above. The "non-aromatic carbocyclylalkyloxy" also includes "non-aromatic carbocyclylalkyloxy" wherein the alkyl part is substituted with the above "aromatic carbocyclyl". Examples include cyclopropylmethyloxy, cyclobutylmethyloxy, cyclopentylmethyloxy, cyclohexylmethyloxy, a group of the formula of

[Chemical Formula 34]

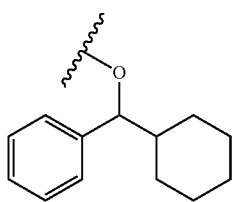

and the like.

The term "aromatic heterocyclylalkyloxy" means an alkyloxy substituted with one or more "aromatic heterocyclyl" described above. The "aromatic heterocyclylalkyloxy" also includes "aromatic heterocyclylalkyloxy" wherein the alkyl part is substituted with the above "aromatic carbocyclyl" and/or "non-aromatic carbocyclyl". Example include pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, groups of the formula of

[Chemical Formula 35]

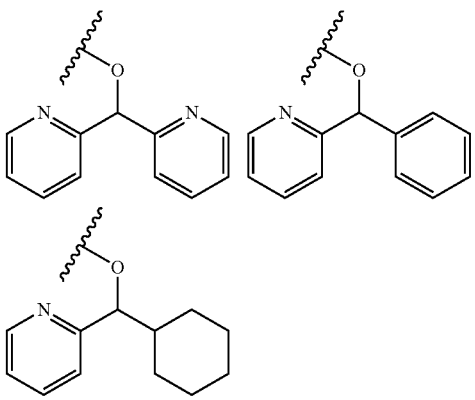

and the like.

The term "non-aromatic heterocyclylalkyloxy" means an alkyloxy substituted with one or more "non-aromatic heterocyclyl" described above. The "non-aromatic heterocyclylalkyloxy" also includes "non-aromatic heterocyclylalkyloxy" wherein the alkyl part is substituted with the above "aromatic carbocyclyl", "non-aromatic carbocyclyl" and/or "aromatic heterocyclyl". Examples include tetrahydropyranylmethyloxy, morpholinylmethyloxy, morpholinylethyloxy, piperidinylmethyloxy, piperazinylmethyloxy, groups of the formula of

[Chemical Formula 36]

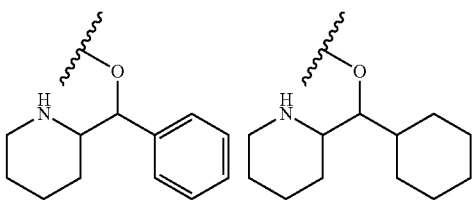

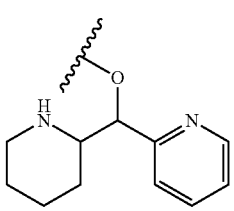

and the like.

The term "aromatic carbocyclylalkyloxycarbonyl" means an alkyloxycarbonyl substituted with one or more "aromatic carbocyclyl" described above. Examples include benzyloxycarbonyl, phenethyloxycarbonyl, phenylpropyloxycarbonyl, benzhydryloxycarbonyl, trityloxycarbonyl, naphthylmethyloxycarbonyl, a group of the formula of

[Chemical Formula 37]

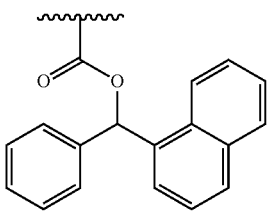

and the like.

The term "non-aromatic carbocyclylalkyloxycarbonyl" means an alkyloxycarbonyl substituted with one or more "non-aromatic carbocyclyl" described above. The "non-aromatic carbocyclylalkyloxycarbonyl" also includes "non-aromatic carbocyclylalkyloxycarbonyl" wherein the alkyl part is substituted with the above "aromatic carbocyclyl". Examples include cyclopropylmethyloxycarbonyl, cyclobutylmethyloxycarbonyl, cyclopentylmethyloxycarbonyl, cyclohexylmethyloxycarbonyl, a group of the formula of

[Chemical Formula 38]

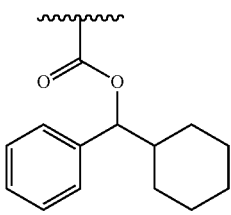

and the like.

The term "aromatic heterocyclylalkyloxycarbonyl" means an alkyloxycarbonyl substituted with one or more "aromatic heterocyclyl" described above. The "aromatic heterocyclylalkyloxycarbonyl" also include "aromatic heterocyclylalkyloxycarbonyl" wherein the alkyl part is substituted with the above "aromatic carbocyclyl" and/or "non-aromatic carbocyclyl". Examples include pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, groups of the formula of

[Chemical Formula 39]

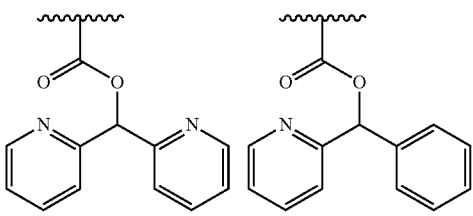

and the like.

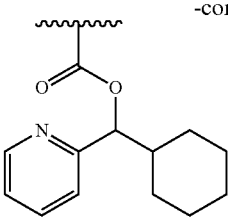

and the like.

The term "non-aromatic heterocyclylalkyloxycarbonyl" means an alkyloxycarbonyl substituted with one or more "non-aromatic heterocyclyl" described above. The "non-aromatic heterocyclylalkyloxycarbonyl" also includes "non-aromatic heterocyclylalkyloxycarbonyl" wherein the alkyl part is substituted with the above "aromatic carbocyclyl", "non-aromatic carbocyclyl" and/or "aromatic heterocyclyl". Examples include tetrahydropyranylmethyl oxycarbonyl, morpholinylmethyloxycarbonyl, morpholinyl ethyloxycarbonyl, piperidinylmethyloxycarbonyl, piperazinylmethyloxycarbonyl, groups of the formula of

[Chemical Formula 40]

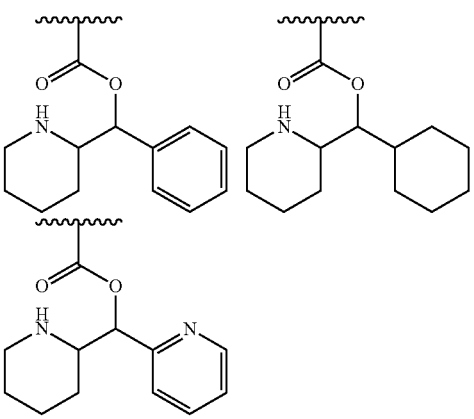

and the like.

The term "aromatic carbocyclylalkyloxyalkyl" means an alkyloxyalkyl substituted with one or more "aromatic carbocyclyl" described above. Examples include benzyloxymethyl, phenethyloxymethyl, phenylpropyloxymethyl, benzhydryloxymethyl, trityloxymethyl, naphthylmethyloxymethyl, a group of the formula of

[Chemical Formula 41]

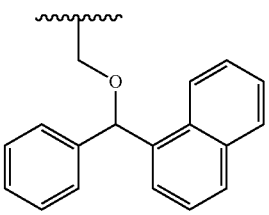

and the like.

The term "non-aromatic carbocyclylalkyloxyalkyl" means an alkyloxyalkyl substituted with one or more "non-aromatic carbocyclyl" described above. The "non-aromatic carbocyclylalkyloxyalkyl" also includes "non-aromatic carbocyclylalkyloxyalkyl" wherein the alkyl part bonded to the non-aromatic carbocycle is substituted with the above "aromatic carbocyclyl". Examples include cyclopropylmethyloxymethyl, cyclobutylmethyloxymethyl, cyclopenthylmethyloxymethyl, cyclohexylmethyloxymethyl, a group of the formula of

[Chemical Formula 42]

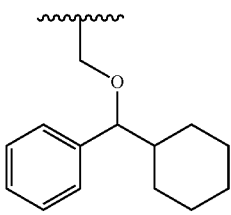

and the like.

The term "aromatic heterocyclylalkyloxyalkyl" means an alkyloxyalkyl substituted with one or more "aromatic heterocyclyl" described above. The "aromatic heterocyclylalkyloxyalkyl" also includes "aromatic heterocyclylalkyloxyalkyl" wherein the alkyl part bonded to the aromatic heterocycle is substituted with the above "aromatic carbocyclyl" and/or "non-aromatic carbocyclyl". Examples include pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, groups of the formula of

[Chemical Formula 43]

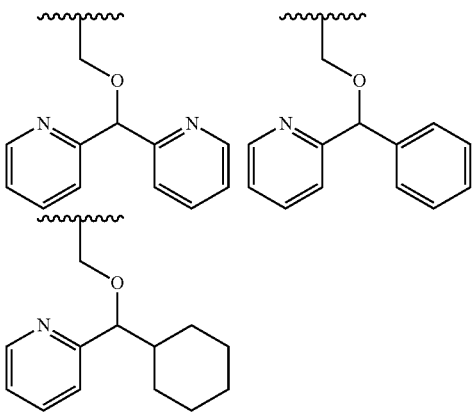

and the like.

The term "non-aromatic heterocyclylalkyloxyalkyl" means an alkyloxyalkyl substituted with one or more "non-aromatic heterocyclyl" described above. The "non-aromatic heterocyclylalkyloxyalkyl" also includes "non-aromatic heterocyclylalkyloxyalkyl" wherein the alkyl part bonded to the non-aromatic heterocycle is substituted with the above "aromatic carbocyclyl", "non-aromatic carbocyclyl" and/or "aromatic heterocyclyl". Examples include tetrahydropyranylmethyl oxymethyl, morpholinylmethyloxymethyl, morpholinyl ethyloxymethyl, piperidinylmethyloxymethyl, piperazinylmethyloxymethyl, groups of the formula of

[Chemical Formula 44]

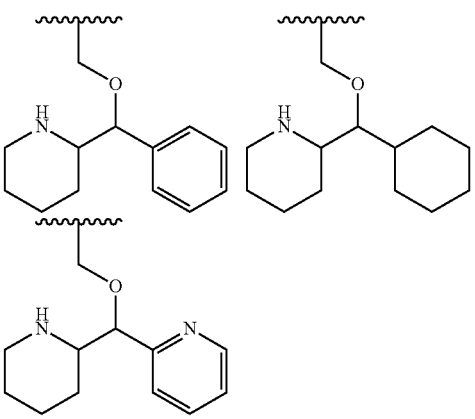

and the like.

The term "aromatic carbocyclylalkylamino" means a group wherein one or two hydrogen atom(s) attached to a nitrogen atom of an amino group is(are) replaced with the above "aromatic carbocyclylalkyl". Examples include benzylamino, phenethylamino, phenylpropylamino, benzhydrylamino, tritylamino, naphthylmethylamino, dibenzylamino and the like.

The term "non-aromatic carbocyclylalkylamino" means a group wherein one or two hydrogen atom(s) attached to a nitrogen atom of an amino group is(are) replaced with the above "non-aromatic carbocyclylalkyl". Examples include cyclopropylmethylamino, cyclobutylmethylamino, cyclopentylmethylamino, cyclohexylmethylamino and the like.

The term "aromatic heterocyclylalkylamino" means a group wherein one or two hydrogen atom(s) attached to a nitrogen atom of an amino group is(are) replaced with the above "aromatic heterocyclylalkyl". Examples include pyridylmethylamino, furanylmethylamino, imidazolylmethylamino, indolylmethylamino, benzothiophenylmethylamino, oxazolylmethyl amino, isoxazolylmethylamino, thiazolylmethylamino, isothiazolylmethylamino, pyrazolylmethylamino, isopyrazolylmethylamino, pyrrolylmethylamino, benzoxazolylmethylamino and the like.

The term "non-aromatic heterocyclylalkylamino" means a group wherein one or two hydrogen atom(s) attached to a nitrogen atom of an amino group is(are) replaced with the above "non-aromatic heterocyclylalkyl". Examples include tetrahydropyranylmethylamino, morpholinyl ethylamino, piperidinylmethylamino, piperazinylmethylamino and the like.

The aromatic carbocycle part of "aromatic carbocycyloxy", "aromatic carbocyclylcarbonyl", "aromatic carbocyclyloxycarbonyl", "aromatic carbocyclylsulfanyl", and "aromatic carbocyclylsulfonyl" is also the same as above "aromatic carbocyclyl".

The term "aromatic carbocyclyloxy" means a group wherein the "aromatic carbocycle" is bonded to an oxygen atom. Examples include phenyloxy, naphthyloxy and the like.

The term "aromatic carbocyclylcarbonyl" means a group wherein the "aromatic carbocycle" is bonded to a carbonyl group. Examples include phenylcarbonyl, naphthylcarbonyl and the like.

The term "aromatic carbocyclyloxycarbonyl" means a group wherein the above "aromatic carbocyclyloxy" is bonded to a carbonyl group. Examples include phenyloxycarbonyl, naphthyloxycarbonyl.

The term "aromatic carbocyclylsulfanyl" means a group wherein a hydrogen atom attached to a sulfur atom of a sulfanyl group is replaced with the "aromatic carbocycle". Examples include phenylsulfanyl, naphthylsulfanyl and the like.

The term "aromatic carbocyclylsulfonyl" means a group wherein the "aromatic carbocycle" is bonded to a sulfonyl group. Examples include phenylsulfonyl, naphthylsulfonyl and the like.

The non-aromatic carbocycle part of "non-aromatic carbocyclyloxy", "non-aromatic carbocyclylcarbonyl", "non-aromatic carbocyclyloxycarbonyl", "non-aromatic carbocyclylsulfanyl", and "non-aromatic carbocyclylsulfonyl" is also the same as above "non-aromatic carbocyclyl".

The term "non-aromatic carbocyclyloxy" means a group wherein the "non-aromatic carbocycle" is bonded to an oxygen atom. Examples include cyclopropyloxy, cyclohexyloxy, cyclohexenyloxy and the like.

The term "non-aromatic carbocyclylcarbonyl" means a group wherein the "non-aromatic carbocycle" is bonded to a carbonyl group. Examples include cyclopropylcarbonyl, cyclohexylcarbonyl, cyclohexenylcarbonyl and the like.

The term "non-aromatic carbocyclyloxycarbonyl" means a group wherein the above "non-aromatic carbocyclyloxy" is bonded to a carbonyl group. Examples include cyclopropyloxycarbonyl, cyclohexyloxycarbonyl, cyclohexenyloxycarbonyl and the like.

The term "non-aromatic carbocyclylsulfanyl" means a group wherein a hydrogen atom attached to a sulfur atom of a sulfanyl group is replaced with the "non-aromatic carbocycle". Examples include cyclopropylsulfanyl, cyclohexylsulfanyl, cyclohexenylsulfanyl and the like.

The term "non-aromatic carbocyclylsulfonyl" means a group wherein the "non-aromatic carbocycle" is bonded to a sulfonyl group. Examples include cyclopropylsulfonyl, cyclohexylsulfonyl, cyclohexenylsulfonyl and the like.

The aromatic heterocycle part of "aromatic heterocyclyloxy", "aromatic heterocyclylcarbonyl", "aromatic heterocyclyloxycarbonyl", "aromatic heterocyclylsulfanyl", and "aromatic heterocyclylsulfonyl" is also the same as above "aromatic heterocyclyl". The term "aromatic heterocyclyloxy" means a group wherein the "aromatic heterocycle" is bonded to an oxygen atom. Examples include pyridyloxy, oxazolyloxy and the like.

The term "aromatic heterocyclylcarbonyl" means a group wherein the "aromatic heterocycle" is bonded to a carbonyl group. Examples include pyridylcarbonyl, oxazolylcarbonyl and the like.

The term "aromatic heterocyclyloxycarbonyl" means a group wherein the above "aromatic heterocyclyloxy" is bonded to a carbonyl group. Examples include pyridyloxycarbonyl, oxazolyloxycarbonyl and the like.

The term "aromatic heterocyclylsulfanyl" means a group wherein a hydrogen atom attached to a sulfur atom of a sulfanyl group is replaced with the "aromatic heterocycle". Examples include pyridylsulfanyl, oxazolylsulfanyl and the like.

The term "aromatic heterocyclylsulfonyl" means a group wherein the "aromatic heterocycle" is bonded to a sulfonyl group. Examples include pyridylsulfonyl, oxazolylsulfonyl and the like.

The non-aromatic heterocycle part of "non-aromatic heterocyclyloxy", "non-aromatic heterocyclylcarbonyl", "non-aromatic heterocyclyloxycarbonyl", "non-aromatic heterocyclylsulfanyl", and "non-aromatic heterocyclylsulfonyl" is also the same as above "non-aromatic heterocyclyl".

The term "non-aromatic heterocyclyloxy" means a group wherein the "non-aromatic heterocycle" is bonded to an oxygen atom. Examples include piperidinyloxy, tetrahydrofuryloxy and the like.

The term "non-aromatic heterocyclylcarbonyl" means a group wherein the "non-aromatic heterocycle" is bonded to a carbonyl group. Examples include piperidinylcarbonyl, tetrahydrofurylcarbonyl and the like.

The term "non-aromatic heterocyclyloxycarbonyl" means a group wherein the above "non-aromatic heterocyclyloxy" is bonded to a carbonyl group. Examples include piperidinyloxycarbonyl, tetrahydrofuryloxycarbonyl and the like.

The term "non-aromatic heterocyclylsulfanyl" means a group wherein a hydrogen atom attached to a sulfur atom of a sulfanyl group is replaced with the "non-aromatic heterocycle". Examples include piperidinylsulfanyl, tetrahydrofurylsulfanyl and the like.

The term "non-aromatic heterocyclylsulfonyl" means a group wherein the "non-aromatic heterocycle" is bonded to a sulfonyl group. Examples include piperidinylsulfonyl, tetrahydrofuryl sulfonyl.

The term "acyl" includes "formyl", "alkylcarbonyl", "alkenylcarbonyl", "alkynylcarbonyl", "aromatic heterocyclylcarbonyl", "non-aromatic heterocyclylcarbonyl", "aromatic heterocyclylcarbonyl" and "non-aromatic heterocyclylcarbonyl".

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkenylcarbonyl", "substituted or unsubstituted alkynylcarbonyl", "substituted or unsubstituted alkylamino", "substituted or unsubstituted alkylamino", "substituted or unsubstituted alkylsulfonyl", "substituted or unsubstituted alkenylsulfonyl", "substituted or unsubstituted alkynylsulfonyl", "substituted or unsubstituted alkyl carbonylamino", "substituted or unsubstituted alkylcarbonylamino", "substituted or unsubstituted alkyl sulfonylamino", "substituted or unsubstituted alkyl sulfonylamino", "substituted or unsubstituted alkylimino", "substituted or unsubstituted alkenylimino", "substituted or unsubstituted alkynylimino", "substituted or unsubstituted alkylcarbonylimino", "substituted or unsubstituted alkenylcarbonylimino", "substituted or unsubstituted alkynylcarbonylimino", "substituted or unsubstituted alkyloxyimino", "substituted or unsubstituted alkenyloxyimino", "substituted or unsubstituted alkynyloxyimino", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfanyl", "substituted or unsubstituted alkenylsulfanyl", "substituted or unsubstituted alkynylsulfanyl", "substituted or unsubstituted alkylsulfinyl", "substituted or unsubstituted alkenylsulfinyl", "substituted or unsubstituted alkynylsulfinyl", "substituted or unsubstituted alkylcarbamoyl", "substituted or unsubstituted alkylcarbamoyl", "substituted or unsubstituted alkylsulfamoyl" and "substituted or unsubstituted alkylsulfamoyl" include the following substituents. A carbon atom at any positions may be bonded to one or more group(s) selected from the following substituents.

A substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, alkylamino, alkylamino, alkylsulfonyl, alkenylsulfonyl, alkynylsulfonyl, alkylcarbonylamino, alkylcarbonylamino, alkylsulfonylamino, alkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylcarbamoyl, alkylcarbamoyl, alkylsulfamoyl, alkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclyl alkyloxycarbonyl, non-aromatic carbocyclyl alkyloxycarbonyl, aromatic heterocyclylalkyloxycarbonyl, non-aromatic heterocyclylalkyloxycarbonyl, aromatic carbocyclyl alkylamino, non-aromatic carbocyclylalkylamino, aromatic heterocyclyl alkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

The substituents on the ring of "aromatic carbocycle", "non-aromatic carbocycle", "aromatic heterocycle", and "non-aromatic heterocycle" part of "substituted or unsubstituted aromatic carbocyclyl", "substituted or unsubstituted non-aromatic carbocyclyl", "substituted or unsubstituted aromatic heterocyclyl", "substituted or unsubstituted bicyclic aromatic heterocyclyl" and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocycly loxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", and "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl" include the following substituents. An atom at any position(s) on the ring may be bonded to one or more group(s) selected from the following substituents.

A substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, alkylamino, alkylamino, alkylsulfonyl, alkenylsulfonyl, alkynylsulfonyl, alkylcarbonylamino, alkylcarbonylamino, alkylsulfonylamino, alkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylcarbamoyl, alkylcarbamoyl, alkylsulfamoyl, alkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclyl alkylamino, aromatic heterocyclylalkylamino, non-aromatic heterocyclyl alkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on the same carbon atom are substituted as below.

[Chemical Formula 45]

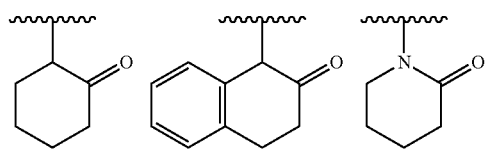

-continued

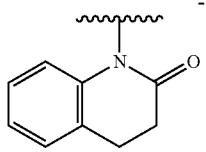

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylcarbonyl", "substituted or unsubstituted non-aromatic heterocyclylcarbonyl", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfanyl", "substituted or unsubstituted non-aromatic heterocyclylsulfanyl", "substituted or unsubstituted non-aromatic carbocyclylsulfonyl", and "substituted or unsubstituted non-aromatic heterocyclylsulfonyl" may be substituted with "oxo" as described above.

The (C2-C4) bridge in which $R^4$ taken together with one of $R^8$ forms includes the following structures.

[Chemical Formula 46]

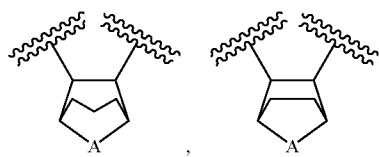

The substituent of "substituted or unsubstituted alkyl" in $R^1$ includes, for example,
halogenoethyloxy;
carboxy;
substituted or unsubstituted aromatic carbocyclyloxy (the substituent: halogen, alkyloxy);
substituted or unsubstituted non-aromatic carbocyclyloxy (the substituent: halogen, alkyloxy);
substituted or unsubstituted non-aromatic heterocyclyl (the substituent: halogen, alkyloxy);
substituted or unsubstituted alkyloxycarbonylamino (the substituent: halogen);
substituted or unsubstituted alkylcarbonylamino (the substituent: halogen, alkyloxy);
substituted or unsubstituted alkylsulfonylamino (the substituent: halogen, alkyloxy);
substituted or unsubstituted alkylsulfonyl (the substituent: halogen);
substituted or unsubstituted non-aromatic carbocyclyl (the substituent: halogen, alkyloxy); and
substituted or unsubstituted alkyloxyalkyloxy (the substituent: halogen). It may be optionally substituted with one or more group(s) selected from the above substituents.

The substituent of "substituted or unsubstituted alkyl" in $R^1$ includes, alkyloxy;
halogen;
hydroxyl;
cyano;
alkyloxycarbonyl;
alkylcarbonyl;
alkylthio;
substituted or unsubstituted alkyloxy (the substituent: halogen);
substituted or unsubstituted aromatic carbocyclyl (the substituent: halogen, alkyloxy);
substituted or unsubstituted aromatic heterocyclyl (the substituent: halogen, alkyloxy, alkyl, cyano, carboxy, hydroxyalkyl, non-aromatic carbocyclyl);
substituted or unsubstituted non-aromatic heterocyclyl (the substituent: halogen);
substituted or unsubstituted carbamoyl (the substituent: alkyl, alkyloxy); and
substituted or unsubstituted amino (the substituent: alkylcarbonyl, alkyl, hydroxy, carbamoyl, alkyloxy, alkylsulfonyl, amidino). It may be optionally substituted with one or more group(s) selected from the above substituents.

For example, the substituent of "substituted or unsubstituted alkyl" in $R^1$ includes,
alkyloxy and substituted or unsubstituted amino (the substituent: alkylcarbonyl, alkyl, hydroxy, carbamoyl, alkyloxy, alkylsulfonyl, amidino, guanidino, alkyloxycarbonyl);
alkyloxy and cyano;
alkyloxy and halogen;
alkyloxy and substituted or unsubstituted aromatic heterocyclyl (the substituent: halogen, alkyloxy, alkyl, cyano, carboxy, hydroxyalkyl, non-aromatic carbocyclyl),
alkyloxy and hydroxyl;
alkyloxy and substituted or unsubstituted non-aromatic heterocyclyl (the substituent: halogen, hydroxy, alkyl);
alkyloxy and substituted or unsubstituted carbamoyl (the substituent: alkyl, alkyloxy);
alkyloxy and substituted or unsubstituted alkyloxycarbonyl;
alkyloxy and alkylthio;
aromatic heterocyclyl and hydroxyl;
substituted or unsubstituted alkyloxycarbonyl and substituted or unsubstituted aromatic heterocyclyl;
alkyloxy and substituted or unsubstituted alkyloxyimino; and
furyl substituted with carboxy, halogen, cyano, alkyl or hydroxyalkyl.

The substituent of "substituted or unsubstituted alkyloxycarbonyl" in $R^1$ includes halogen.

The substituent of "substituted or unsubstituted acyl" in $R^1$ includes halogen and alkyloxy. It may be substituted with one or more group(s) selected from the above substituents.

The substituent of "substituted or unsubstituted non-aromatic heterocyclyl" in $R^1$ includes halogen, alkyloxy and oxo. It may be substituted with one or more group(s) selected from the above substituents.

The substituent of "substituted or unsubstituted aromatic heterocyclyl" in $R^1$ includes alkyl. It may be substituted with one or more group(s) selected from the above substituents.

The substituent of "substituted or unsubstituted non-aromatic carbocyclyl" in $R^1$ includes halogen and alkyloxy. It may be substituted with one or more group(s) selected from the above substituents.

The substituent of "substituted or unsubstituted alkylsulfonyl" in $R^1$ includes halogen.

The substituent of "substituted or unsubstituted alkyloxy" in $R^1$ includes alkyloxy.

The substituent of "substituted or unsubstituted alkyl" in $R^{1A}$ includes alkyloxy.

The substituent of "substituted or unsubstituted alkyl" in $R^{1B}$ and $R^{1C}$ includes halogen and alkyloxy. It may be substituted with one or more group(s) selected from the above substituents.

The substituent of "substituted or unsubstituted alkyl" in $R^{1D}$ and $R^{1E}$ includes halogen and alkyloxy. It may be substituted with one or more group(s) selected from the above substituents.

The substituent of "substituted or unsubstituted phenyl" in B includes, alkyloxycarbonyl;
carboxy;
hydroxyl;
acyl;
substituted or unsubstituted carbamoyl (the substituent: alkyl, aromatic carbocyclyl, aromatic heterocyclyl);
substituted or unsubstituted aromatic carbocyclyl (the substituent: halogen, alkyloxy, cyano, alkyloxycarbonyl);
substituted or unsubstituted aromatic heterocyclyl (the substituent: halogen, alkyloxy, cyano);
substituted or unsubstituted non-aromatic carbocyclyl (the substituent: halogen, alkyloxy);
substituted or unsubstituted alkenyl (the substituent: aromatic carbocyclyl); and
substituted or unsubstituted amino (the substituent: alkyl).
It may be optionally substituted with one or more group(s) selected from the above substituents.

The substituent of "substituted or unsubstituted aromatic carbocyclyl" in B includes, halogen, hydroxy, substituted or unsubstituted alkyl (the substituent: halogen or hydroxy), substituted or unsubstituted alkyloxy (the substituent: halogen), and cyano.

The substituent of "substituted or unsubstituted non-aromatic carbocyclyl" in B includes halogen and alkyloxy. It may be optionally substituted with one or more group(s) selected from the above substituents.

The substituent of "substituted or unsubstituted aromatic heterocyclyl" in B includes, cyano, non-aromatic heterocyclyl, halogen, hydroxy, substituted or unsubstituted amino, substituted or unsubstituted alkyl (the substituent: hydroxyl, halogen). It may be optionally substituted with one or more group(s) selected from the above substituents.

The substituent of "substituted or unsubstituted aromatic heterocycle" in C includes, substituted or unsubstituted alkyl (the substituent: halogen, alkyloxy);
substituted or unsubstituted aromatic carbocyclyl (the substituent: halogen, alkyloxy, alkyloxycarbonyl);
substituted or unsubstituted aromatic heterocyclyl (the substituent: alkyl, halogen, alkyloxy); and
substituted or unsubstituted alkyloxy (the substituent: hydroxyl). It may be optionally
substituted with one or more group(s) selected from the above substituents.

The substituent of "substituted or unsubstituted alkyloxycarbonyl" in $R^3$ includes halogen and hydroxyl. It may be optionally substituted with one or more group(s) selected from the above substituents.

The substituent of "substituted or unsubstituted alkyl" in $R^3$ and $R^4$ includes halogen, hydroxyl and alkyloxy. It may be optionally substituted with one or more group(s) selected from the above substituents.

Embodiments of the present invention are exemplified below.

In Formula (I), -L- includes —C(=X).
=X includes =O.
—Z— includes —NR$^5$—, —CH$_2$— or —O—.
$R^5$ includes a hydrogen atom.
—Z$^A$— includes —NR$^{5A}$ or —CH$_2$—.
$R^{5A}$ includes a hydrogen atom.

—W— includes an absence, —CH$_2$— or —CH$_2$—CH$_2$—.
—W$^A$— includes —CH$_2$— or —CH$_2$—CH$_2$—.
-A- includes —NR$^1$—, —N$^+$(O$^-$)(R$^{14}$)— or —CR$^{1D}$R$^{1E}$—.
$R^1$ includes substituted or unsubstituted alkyl, substituted or unsubstituted alkyloxycarbonyl, substituted or unsubstituted acyl, substituted or unsubstituted non-aromatic heterocyclyl, or substituted or unsubstituted non-aromatic carbocyclyl.
$R^{14}$ includes substituted or unsubstituted alkyl.
$R^{1D}$ includes substituted or unsubstituted alkyl.
$R^{1E}$ includes a hydrogen atom.
$R^{1D}$ and $R^{1E}$ in which they may be taken together includes =CR$^{1F}$R$^{1G}$.
$R^2$ includes a hydrogen atom or substituted or unsubstituted alkyl.

For example, the following embodiments are included.
A compound represented by Formula (I'-A):

[Chemical Formula 47]

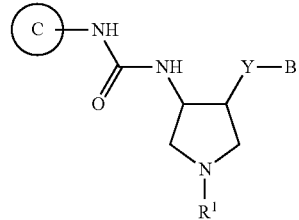

(I'-A)

wherein Y is a bond,
or a pharmaceutically acceptable salt thereof.
Embodiments of $R^1$, B and Ring C are exemplified below. The embodiment of compounds represented by Formula (I'-A) includes the compounds indicated by all possible combination of the following each substituent.

$R^1$ and B include,
(a) $R^1$ is
alkyl substituted with
halogenoethyloxy,
substituted or unsubstituted aromatic carbocyclyloxy,
substituted or unsubstituted non-aromatic carbocyclyloxy,
substituted or unsubstituted non-aromatic heterocyclyl,
substituted or unsubstituted alkyloxycarbonylamino,
substituted or unsubstituted alkylcarbonylamino,
substituted or unsubstituted alkylsulfonylamino,
substituted or unsubstituted alkylsulfonyl,
substituted or unsubstituted non-aromatic carbocyclyl,
carboxy,
substituted or unsubstituted alkyloxyalkyloxy, or
acyl;
alkyl substituted with furyl substituted with
carboxy,
halogen,
cyano,
alkyl or
hydroxyalkyl;
alkyl substituted with
substituted or unsubstituted alkyloxy and substituted or unsubstituted amino, substituted or unsubstituted alkyloxy and cyano, substituted or unsubstituted alkyloxy and halogen,
substituted or unsubstituted alkyloxy and substituted or unsubstituted aromatic heterocyclyl,
substituted or unsubstituted alkyloxy and hydroxy,
substituted or unsubstituted alkyloxy and substituted or unsubstituted non-aromatic heterocyclyl,
substituted or unsubstituted aromatic heterocyclyl and hydroxy,
substituted or unsubstituted alkyloxy and substituted or unsubstituted carbamoyl,
substituted or unsubstituted alkyloxy and substituted or unsubstituted alkyloxycarbonyl,
substituted or unsubstituted alkyloxy and substituted or unsubstituted alkylthio, or
substituted or unsubstituted alkyloxycarbonyl and substituted or unsubstituted aromatic heterocyclyl;
substituted or unsubstituted alkyloxycarbonyl;
substituted or unsubstituted acyl;
substituted or unsubstituted non-aromatic heterocyclyl; or
substituted or unsubstituted non-aromatic carbocyclyl;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy; or (b) $R^1$ is a hydrogen atom, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl or substituted or unsubstituted non-aromatic heterocyclyl;
B is phenyl substituted with substituted or unsubstituted alkyloxycarbonyl, phenyl substituted with substituted or unsubstituted carbamoyl, phenyl substituted with substituted or unsubstituted aromatic carbocyclyl, phenyl substituted with substituted or unsubstituted aromatic heterocyclyl, phenyl substituted with substituted or unsubstituted alkenyl, phenyl substituted with substituted or unsubstituted non-aromatic carbocyclyl, phenyl substituted with carboxy, phenyl substituted with alkylamino, phenyl substituted with substituted or unsubstituted acyl, substituted or unsubstituted naphthyl, substituted or unsubstituted non-aromatic heterocyclyl, or substituted or unsubstituted bicyclic aromatic heterocyclyl. (hereinafter, referred to as A-1)

$R^1$ and B include,
$R^1$ is
alkyl substituted with
halogenoethyloxy,
substituted or unsubstituted aromatic carbocyclyloxy,
substituted or unsubstituted non-aromatic carbocyclyloxy,
substituted or unsubstituted non-aromatic heterocyclyl,
substituted or unsubstituted alkyloxycarbonylamino,
substituted or unsubstituted alkylcarbonylamino,
substituted or unsubstituted alkylsulfonylamino,
substituted or unsubstituted alkylsulfonyl,
substituted or unsubstituted non-aromatic carbocyclyl,
carboxy,
substituted or unsubstituted alkyloxyalkyloxy, or
acyl; or
alkyl substituted with furyl substituted with
carboxy,
halogen,
cyano,
alkyl or
hydroxyalkyl,
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy. (hereinafter, referred to as A-2)

$R^1$ and B include,
$R^1$ is
alkyl substituted with
substituted or unsubstituted alkyloxy and substituted or unsubstituted amino,
substituted or unsubstituted alkyloxy and cyano,
substituted or unsubstituted alkyloxy and halogen,
substituted or unsubstituted alkyloxy and substituted or unsubstituted aromatic heterocyclyl,
substituted or unsubstituted alkyloxy and hydroxy,
substituted or unsubstituted alkyloxy and substituted or unsubstituted non-aromatic heterocyclyl,
substituted or unsubstituted aromatic heterocyclyl and hydroxy,
substituted or unsubstituted alkyloxy and substituted or unsubstituted carbamoyl,
substituted or unsubstituted alkyloxy and substituted or unsubstituted alkyloxycarbonyl,
substituted or unsubstituted alkyloxy and substituted or unsubstituted alkylthio, or
substituted or unsubstituted alkyloxycarbonyl and substituted or unsubstituted aromatic heterocyclyl,
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy. (hereinafter, referred to as A-3)

$R^1$ and B include,
$R^1$ is substituted or unsubstituted alkyloxycarbonyl;
substituted or unsubstituted acyl;
substituted or unsubstituted non-aromatic heterocyclyl; or
substituted or unsubstituted non-aromatic carbocyclyl,
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy. (hereinafter, referred to as A-4)

$R^1$ and B include,
$R^1$ is a hydrogen atom, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, B is phenyl substituted with substituted or unsubstituted alkyloxycarbonyl, phenyl substituted with substituted or unsubstituted carbamoyl, phenyl substituted with substituted or unsubstituted aromatic carbocyclyl, phenyl substituted with substituted or unsubstituted aromatic heterocyclyl, phenyl substituted with substituted or unsubstituted alkenyl, phenyl substituted with substituted or unsubstituted non-aromatic carbocyclyl, phenyl substituted with carboxy, phenyl substituted with alkylamino, or phenyl substituted with substituted or unsubstituted acyl. (hereinafter, referred to as A-5)

$R^1$ and B include, $R^1$ is a hydrogen atom, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, B is substituted or unsubstituted naphthyl, substituted or unsubstituted non-aromatic heterocyclyl, or substituted or unsubstituted bicyclic aromatic heterocyclyl. (hereinafter, referred to as A-6)

Ring C includes the group represented by Formula:

[Chemical Formula 48]

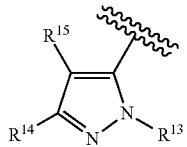

wherein $R^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylthio, substituted or unsubstituted alkenylthio, substituted or unsubstituted alkynylthio, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ and $R^{15}$ may be taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle. (hereinafter, referred to as B-1)

Ring C includes the group represented by Formula:

[Chemical Formula 49]

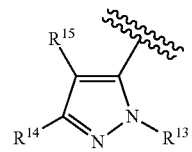

wherein $R^{13}$ is a hydrogen atom, or substituted or unsubstituted aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, $R^{15}$ is substituted or unsubstituted alkyl. (hereinafter, referred to as B-2)

For example, the following embodiments are included.

A compound represented by Formula (I″-A):

[Chemical Formula 50]

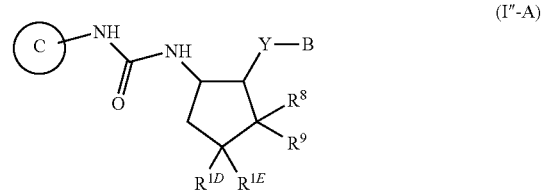

(I″-A)

wherein Y is a bond, or a pharmaceutically acceptable salt thereof.

Embodiments of $R^{1D}$, $R^{1E}$, $R^8$, $R^9$, B and Ring C are exemplified below. The embodiment of compounds represented by Formula (I″-A) includes the compounds indicated by all possible combination of the following each substituent.

$R^{1D}$ includes substituted or unsubstituted alkyl, substituted or unsubstituted alkenyl, substituted or unsubstituted acyl, substituted or unsubstituted alkyloxy, substituted or unsubstituted aromatic carbocycyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl. (hereinafter, referred to as C-1)

$R^{1D}$ includes substituted or unsubstituted alkyl, substituted or unsubstituted alkyloxy, substituted or unsubstituted aromatic carbocyclyloxy, or substituted or unsubstituted aromatic heterocyclyloxy. (hereinafter, referred to as C-2)

$R^{1D}$ includes substituted or unsubstituted alkyl. (hereinafter, referred to as C-3)

$R^{1E}$ includes a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl. (hereinafter, referred to as D-1)

$R^{1E}$ includes a hydrogen atom, or substituted or unsubstituted alkyl. (hereinafter, referred to as D-2)

$R^{1D}$ and $R^{1E}$ may be taken together to form $=CR^{1F}R^{1G}$, $R^{1F}$ and $R^{1G}$ are each independently a hydrogen atom, substituted or unsubstituted alkyl, substituted or unsubstituted alkyloxy, or substituted or unsubstituted alkyloxycarbonyl. (hereinafter, referred to as D-3)

$R^8$ includes a hydrogen atom, or substituted or unsubstituted alkyl. (hereinafter, referred to as E-1)

$R^8$ includes a hydrogen atom. (hereinafter, referred to as E-2)

$R^9$ includes a hydrogen atom, or substituted or unsubstituted alkyl. (hereinafter, referred to as F-1)

$R^9$ includes a hydrogen atom. (hereinafter, referred to as F-2)

B includes substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy. (hereinafter, referred to as G-1)

B includes substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl. (hereinafter, referred to as G-2)

B includes substituted or unsubstituted aromatic carbocyclyl, or substituted or unsubstituted aromatic heterocyclyl. (hereinafter, referred to as G-3)

Ring C includes the group represented by Formula:

[Chemical Formula 51]

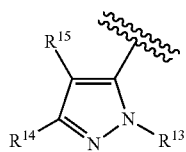

wherein $R^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylthio, substituted or unsubstituted alkenylthio, substituted or unsubstituted alkynylthio, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ and $R^{15}$ may be taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle. (hereinafter, referred to as H-1)

Ring C includes the group represented by Formula:

[Chemical Formula 52]

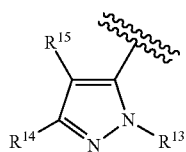

wherein $R^{13}$ is a hydrogen atom or substituted or unsubstituted aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, $R^{15}$ is substituted or unsubstituted alkyl. (hereinafter, referred to as H-2)

For example, the following embodiments are included.

A compound represented by Formula (I′′′-A):

[Chemical Formula 53]

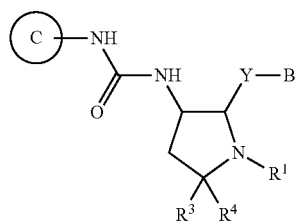

(I′′′-A)

wherein Y is a bond, or a pharmaceutically acceptable salt thereof.

Embodiments of $R^1$, $R^3$, $R^4$, B and Ring C are exemplified below. The embodiment of compounds represented by Formula (I′′′-A) includes the compounds indicated by all possible combination of the following each substituent.

$R^1$ includes a hydrogen atom, cyano, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl. (hereinafter, referred to as J-1)

$R^1$ includes a hydrogen atom, or substituted or unsubstituted alkyl. (hereinafter, referred to as J-2)

$R^3$ includes a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl. (hereinafter, referred to as K-1)

$R^3$ includes a hydrogen atom, or substituted or unsubstituted alkyl. (hereinafter, referred to as K-2)

$R^3$ includes alkyl substituted with alkyloxy. (hereinafter, referred to as K-3)

$R^3$ includes alkyl substituted with hydroxy and alkyloxy. (hereinafter, referred to as K-4)

$R^4$ includes a hydrogen atom, substituted or unsubstituted alkyl, substituted or unsubstituted alkenyl, or substituted or unsubstituted alkynyl. (hereinafter, referred to as L-1)

$R^4$ includes a hydrogen atom, or substituted or unsubstituted alkyl. (hereinafter, referred to as L-2)

B includes substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy. (hereinafter, referred to as M-1)

B includes substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl. (hereinafter, referred to as M-2)

B includes substituted or unsubstituted aromatic carbocyclyl, or substituted or unsubstituted aromatic heterocyclyl. (hereinafter, referred to as M-3)

Ring C includes the group represented by Formula:

[Chemical Formula 54]

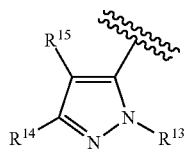

wherein $R^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylthio, substituted or unsubstituted alkenylthio, substituted or unsubstituted alkynylthio, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ and $R^{15}$ may be taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle. (hereinafter, referred to as N-1)

Ring C includes the group represented by Formula:

[Chemical Formula 55]

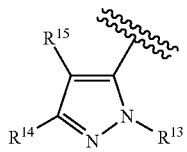

wherein $R^{13}$ is a hydrogen atom, or substituted or unsubstituted aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, $R^{15}$ is substituted or unsubstituted alkyl. (hereinafter, referred to as N-2)

The compounds of Formula (I) are not limited to specific isomers but include all possible isomers (e.g., keto-enol isomers, imine-enamine isomers, diastereoisomers, enantiomers, rotamers or the like), racemates or mixtures thereof.

One or more hydrogen, carbon and/or other atom(s) in the compounds of Formula (I) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl respectively. The compounds of Formula (I) include the compounds replaced with these isotopes. The compounds replaced with the above isotopes are useful as medicines and include all of radiolabeled compounds of the compound of Formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds of Formula (I) can be prepared using well-known methods in this field of the invention. For example, a tritium-labeled compound of Formula (I) can be prepared by introducing a tritium to a certain compound of Formula (I) through a catalytic dehalogenation reaction using a tritium. This method comprises reacting an appropriately-halogenated precursor of the compound of Formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}$C-labeled compound can be prepared by using a raw material having $^{14}$C.

The pharmaceutically acceptable salts of the compounds of Formula (I) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, diethanolamine, ethylenediamine, pyridine, picoline, quinoline or the like), amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds of Formula (I) of the present invention or pharmaceutically acceptable salts thereof may form solvates (e.g., hydrates or the like), co-crystal and/or crystal polymorphs. The present invention encompasses those various solvates, co-crystal and crystal polymorphs. "Solvates" may be those wherein any numbers of solvent molecules (e.g., water molecules or the like) are coordinated with the compounds of Formula (I). When the compounds of Formula (I) or pharmaceutically acceptable salts thereof are allowed to stand in the atmosphere, the compounds may absorb water, resulting in attachment of adsorbed water or formation of hydrates. Recrystallization of the compounds of Formula (I) or pharmaceutically acceptable salts thereof may produce crystal polymorphs. "Co-crystal" means that a compound of Formula (I) or a salt thereof and a counter-molecule exist in the same crystal lattice, and it can be formed with any number of counter-molecules.

The compounds of Formula (I) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of Formula (I) through enzymatic oxidation, reduction, hydrolysis or the like under physiological conditions in vivo, compounds that are converted to the compounds of Formula (I) through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds of Formula (I) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, $p-CH_3O-PhSO_3-$, $PhSO_3-$ and $p-CH_3PhSO_3-$.

General procedures for the synthesis of the compounds of the present invention are described below. Starting materials and reaction reagents used in such synthesis are commercially available or can be synthesized according to methods well known in the art using compounds commercially available. Further, extraction, purification and the like may be performed in accordance with the methods carried out in the art.

In the following all steps, when a substituent which impedes a reaction, e.g. hydroxy, mercapto, amino, formyl, carbonyl, carboxy, is possessed, the substituent is protected by the method described in Protective Groups in organic Synthesis, and Theodora W Greene (John Wiley & Sons, hereinafter referred to as literature A) in advance, and the protecting group may be removed at a desirable stage. In addition, in the all steps, an order of steps to be implemented may be appropriately changed, and each intermediate may be isolated, and used in a next step. All of reaction time, reaction temperature, solvents, reagents, protecting groups, etc. are mere exemplification and not limited as long as they do not cause an adverse effect on a reaction.

For example, the compounds represented by Formula (I) of the present invention can be prepared by the general synthetic methods described below.

[Chemical Formula 56]

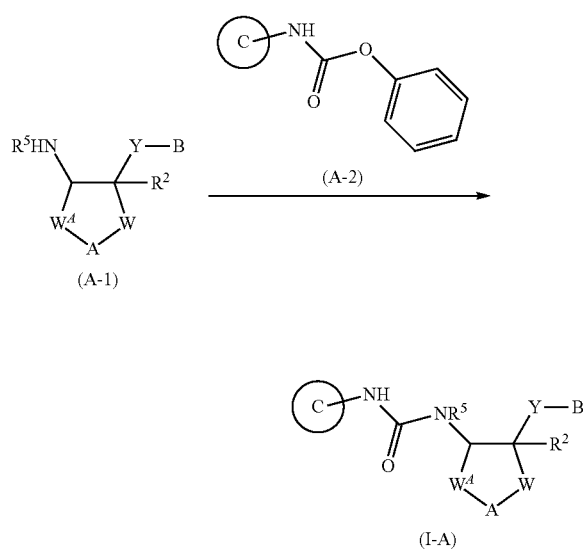

(A-1)

(I-A)

wherein, each symbol in the formula is the same as above.

(Method A)

Compound (I-A) can be synthesized by reacting Compound (A-1) with Compound (A-2) in the presence of a base.

Compound (A-1) is commercially available or can be synthesized according to the methods well known in the art.

For example, Compound (A-1) can be synthesized by reduction of azido derivative which is described in Tetrahedron, 2006, 62, pp. 6882-6892.

Compound (A-2) can be synthesized by the method described in WO2012158413. It can be used at 1 to 1.5 mol equivalent(s) relative to Compound (A-1).

As the base, pyridine, triethylamine, diisopropylethylamine, N-methylmorpholine and the like are exemplified, and it can be used at 1 to 5 mol equivalent(s) relative to Compound (A-1).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, dichloromethane, chloroform, THF, toluene, DMF, DMSO, NMP, dioxane and the like are exemplified, and it can be used alone or in combination.

[Chemical Formula 57]

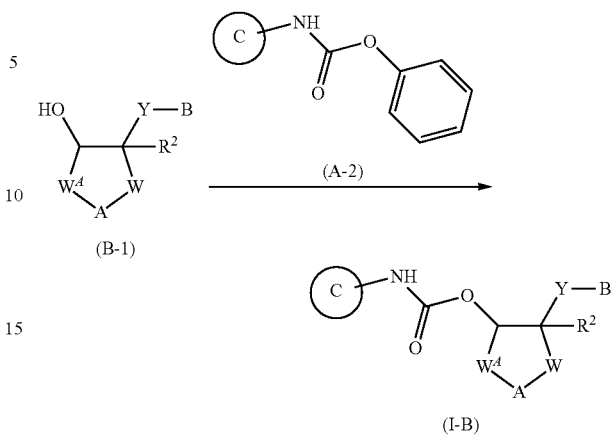

(B-1)

(I-B)

wherein, each symbol in the formula is the same as above.

(Method B)

Compound (I-B) can be synthesized by reacting Compound (B-1) with Compound (A-2) in the presence of a catalyst and a base.

Compound (B-1) is commercially available or can be synthesized according to the methods well known in the art.

Compound (A-2) can be synthesized in accordance with the above Method A. It can be used at 1 to 1.5 mol equivalent(s) relative to Compound (B-1).

As the catalyst, DMAP and the like are exemplified, and it can be used at 0.1 to 1 mol equivalent relative to Compound (B-1).

As the base, pyridine, triethylamine, diisopropylethylamine, N-methylmorpholine and the like are exemplified, and it can be used at 1 to 5 mol equivalent(s) relative to Compound (B-1).

The reaction temperature is 0° C. to the reflux temperature of the solvent, preferably room temperature to 100° C.

The reaction time is 0.1 to 72 hour(s), preferably 0.5 to 60 hour(s).

As the reaction solvent, dichloromethane, chloroform, THF, toluene, DMF, DMSO, NMP, dioxane and the like are exemplified, and it can be used alone or in combination.

[Chemical Formula 58]

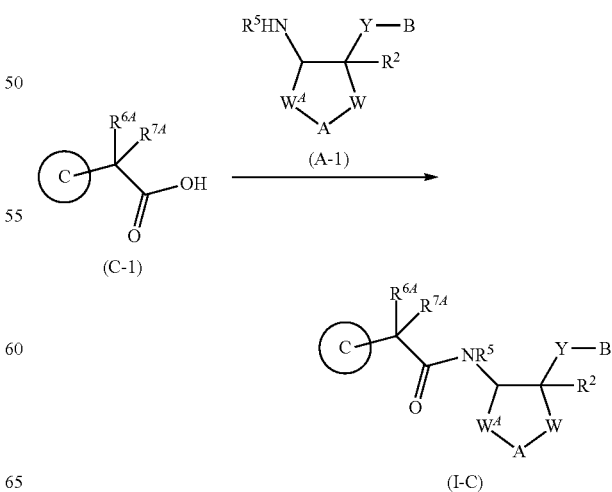

(C-1)

(I-C)

wherein, each symbol in the formula is the same as above.
(Method C)

Compound (I-C) can be synthesized by reacting Compound (C-1) with Compound (A-1) in the presence of a condensing agent and a base.

Compound (C-1) is commercially available or can be synthesized according to the methods well known in the art.

Compound (A-1) can be synthesized in accordance with the above Method A. It can be used at 1 to 3 mol equivalent(s) relative to Compound (C-1).

As the condensing agent, HATU, COMU, EDC and the like are exemplified, and it can be used at 1 to 5 mol equivalent(s) relative to Compound (C-1).

As the base, pyridine, triethylamine, diisopropylethylamine, N-methylmorpholine and the like are exemplified, and it can be used at 1 to 5 mol equivalent(s) relative to Compound (C-1).

The reaction temperature is −20° C. to the reflux temperature of the solvent, preferably −10 to 50° C.

The reaction time is 0.1 to 24 hour(s), preferably 0.5 to 12 hour(s).

As the reaction solvent, dichloromethane, chloroform, THF, toluene, DMF, DMSO, NMP, dioxane and the like are exemplified, and it can be used alone or in combination.

[Chemical Formula 59]

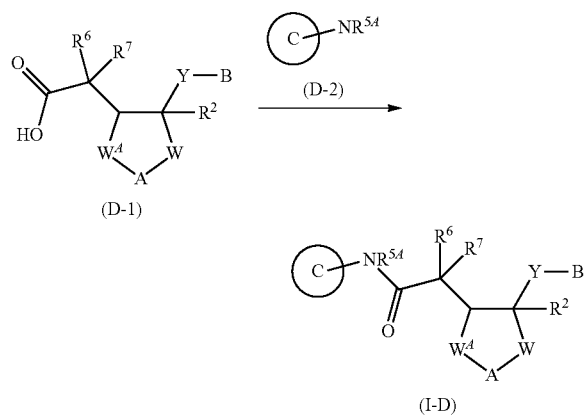

(D-1)

(I-D)

wherein each symbol in the formula is the same as above.
(Method D)

Compound (I-D) can be obtained in accordance with the above Method C.

Compound (D-1) is commercially available or can be synthesized according to the methods well known in the art.

Compound (D-2) is commercially available or can be synthesized according to the methods well known in the art.

[Chemical Formula 60]

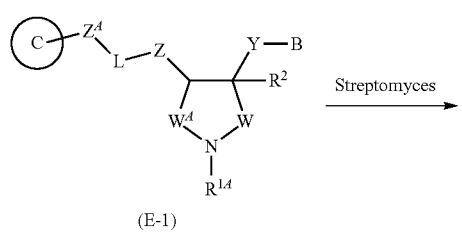

(E-1)

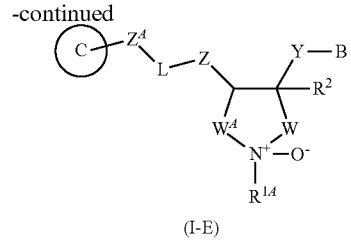

(I-E)

wherein each symbol in the formula is the same as above.
(Method E)

The microbiological properties of this strain were as follows.

The taxonomic analysis of the strain SB-134726 were done by morphometric characteristic, cultural characteristic, physiological characteristic, availability of carbon sources, cellular constituents and 16S rRNA gene sequence.

The analysis was carried out by a method described in "Identification Manual of Actinomycetes edited by The Society for Actinomycetes Japan, published by Business Center for Academic Societies Japan, 2001".

(I) Morphometric Characteristic

The strain SB-134726 was cultured with yeast malt agar medium (ISP No. 2) at 28° C. for 14 days, and observed under an optical microscope.

Substrate mycelia was 0.2-0.3 m and well developed, branched irregularly and fragmentation was not observed.

Diameter of the aerial mycelia was 0.2-0.3 m and branched simply.

Head part of the aerial mycelia was divided and formed the spore-chain.

The spore-chain was irregularly curved.

Each spore was cylindrical.

Spore size was 0.3-0.8×0.8-2.0 m and non-motile.

The sporangia and sclerotium were not observed.

(II) Cultural Characteristic

Growth state of the strain SB-134726 after cultured at 28° C. for 14 days was shown in the following table.

This strain was grown in all medium association with colorless aerial mycelia.

Along with the sporulation, the color of the colony showed gray.

The notation of the detailed color obeyed JIS color standard (Japan Standards Association) and Munsell color system code was noted in parentheses.

TABLE 1

| medium | growth | aerial mycelium color | Reverse color | Soluble pigment |
|---|---|---|---|---|
| Yeast malt agar (ISP No. 2) | good | abundant, light gray (N7/0) | blackish brown (10YR3/2) | + |
| Oatmeal agar (ISP No. 3) | good | abundant, light gray (N7/0) | grayish white (2.5Y8/1) | − |
| Inorganic salt-starch agar(ISP-No. 4) | good | abundant, light gray (N7/0) | ash olive (5Y5/2) | − |
| Glycerol asparagine agar(ISP-No. 5) | good | abundant, light gray (N7/0) | dark greenish blue (2.5B3/2) | − |
| Peptone Yeast Extract Iron Agar (ISP-No. 6) | moderate | poor | Cream (2.5Y9/2) | + |

TABLE 1-continued

| medium | growth | aerial mycelium color | Reverse color | Soluble pigment |
|---|---|---|---|---|
| Tyrosine Agar (ISP-No. 7) | good | abundant, light gray (N7/0) | dark grayish yellow (2.5Y4/2) | + |

(III) Physiological Characteristic
(1) Growing temperature range:
Growth occurred in the temperature range of 15–38° C. on yeast malt agar medium (ISP No. 2). The optimum growth temperature was around 32° C. No growth occurred at 40° C.
(2) Liquefaction of Gelatin: positive
(3) Hydrolysis of starch: positive
(4) Peptonization/coagulation of skim milk: negative
(5) Salt tolerance: Growth occurred on yeast malt agar medium (ISP No. 2) with 5% salt. No growth occurred with 7% salt.
(6) Production of melanin: negative
(IV) Bioavailability of Carbon Sources
(1) Available sugar: D-glucose, L-alabinose, D-xylose, D-ribose
(2) Unavailable sugar: D-fructose, m-inositol, D-mannitol, D-raffinose, L-rhamunose, saccarose
(V) Cellular Constituents
The main isomer of the diaminopimeric acid was LL type. The main menaquinones were MK-9($H_8$) and MK-9($H_{10}$) and occupied in total approximately 90%. MK-7($H_{10}$) was also detected as minor component.

From these morphological properties and cell body ingredient analyses, it was strongly suggested that the strain SB-134726 belonged to the genus *Streptomyces*.
(VI) 16S rRNA Gene Sequence Analysis
The partial sequence (960 bp) of the 16S rRNA of the strain SB-134726 was decoded. As a result of database retrieval, homogeny with *Streptomyces bikiniensis* (Ess amA-1) was the highest with 99%. And it was included in a cluster of the genus *Streptomyces*.

Based upon the foregoing, the strain SB-134726 had been shown to belong to genus *Streptomyces*. This strain was named to *Streptomyces* sp. SB-134726.

This strain was deposited internationally to the Patent Microorganisms Depositary of the National Institute of Technology and Evaluation (NITE) as receipt number NITE BP-01897 on Dec. 10, 2014.

[Chemical Formula 61]

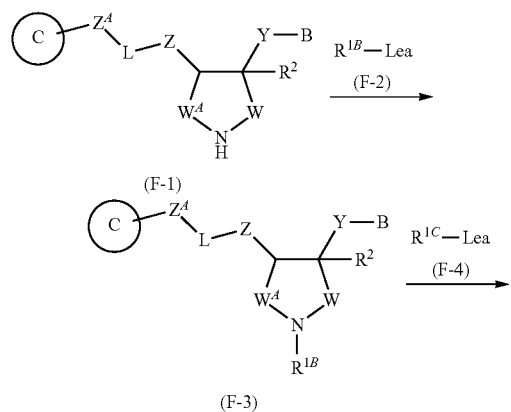

wherein, each symbol in the formula is the same as above, Lea is a leaving group, such as halogen, tosylate, mesylate and the like.
(Method F)
(Step 1)
Compound (F-3) can be obtained by reacting Compound (F-1) with Compound (F-2) in the presence of a base.

Compound (F-1) can be synthesized in accordance with the above Method A to Method D.

Compound (F-2) is commercially available or can be synthesized according to the methods well known in the art. It can be used at 0.8 to 1.2 mol equivalent(s) relative to Compound (F-1).

As the base, triethylamine, diisopropylethylamine, diazabicycloundecene and the like are exemplified, and it can be used at 1 to 5 mol equivalent(s) relative to Compound (F-1).

The reaction temperature is 0° C. to the reflux temperature of the solvent, preferably room temperature to 80° C.

The reaction time is 0.1 to 24 hour(s), preferably 0.5 to 12 hour(s).

As the reaction solvent, dichloromethane, chloroform, THF, toluene, DMF, DMSO, NMP, dioxane, water and the like are exemplified, and it can be used alone or in combination.
(Step 2)
Compound (I-F) can be obtained by reacting Compound (F-3) with Compound (F-4).

Compound (F-4) can be used at 1.0 to 1.5 mol equivalent (s) relative to Compound (F-3).

The reaction temperature is 0° C. to the reflux temperature of the solvent, preferably room temperature to 80° C.

The reaction time is 0.1 to 24 hour(s), preferably 0.5 to 12 hour(s).

As the reaction solvent, dichloromethane, chloroform, THF, toluene, DMF, DMSO, NMP, dioxane, water and the like are exemplified, and it can be used alone or in combination.

[Chemical Formula 62]

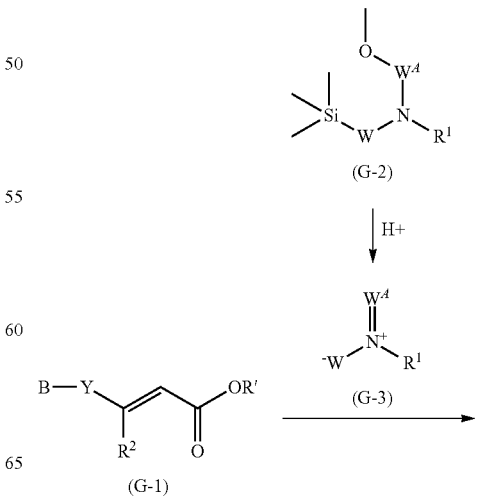

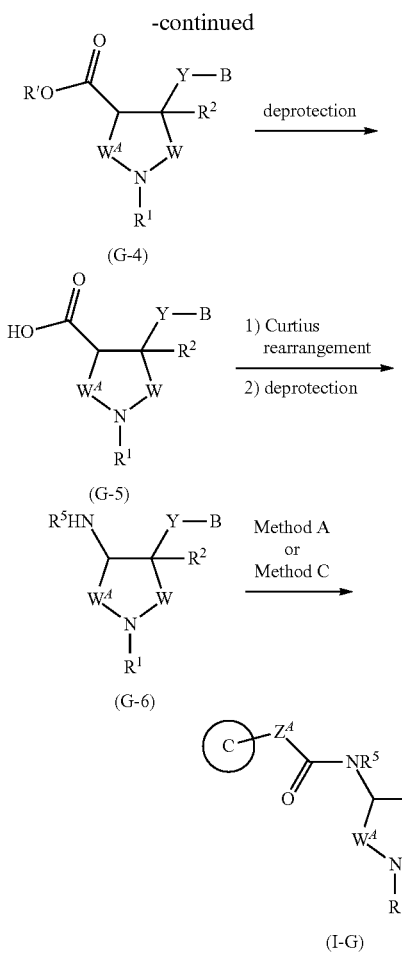

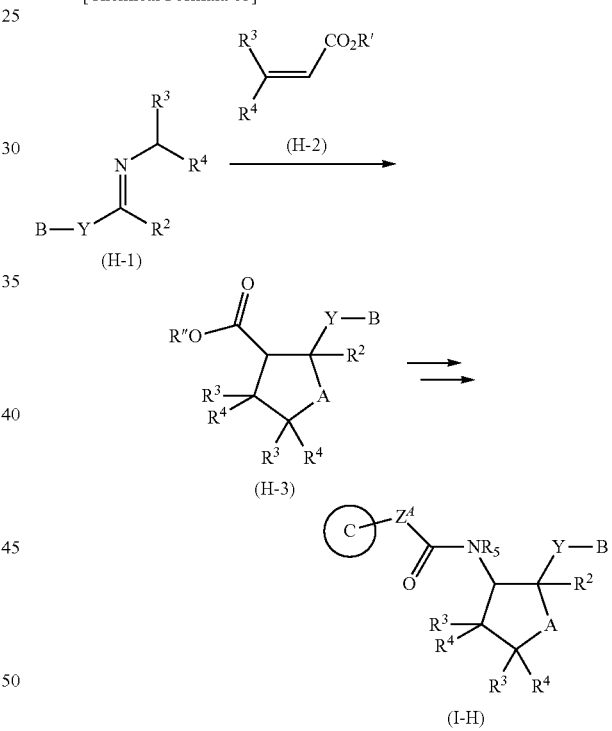

As the reagent used for Curtius rearrangement, DPPA and the like are exemplified, and it can be used at 1 to 5 mol equivalent(s) relative to Compound (G-5).

The reaction temperature is room temperature to the reflux temperature of the solvent, preferably 50 to 100° C.

The reaction time is 0.1 to 24 hour(s), preferably 0.5 to 12 hour(s).

As the reaction solvent, 2-(trimethylsilyl)ethanol, t-BuOH, benzylalcohol and the like can be used.

As the reaction solvent, toluene, benzene and the like can be also used. In this case, carbamate can be obtained by adding the above alcohol after preparation of isocyanate.

The above alcohol can be used at 1 to 5 mol equivalent(s) relative to Compound (G-5).

The obtained carbamate can be deprotected in accordance with the method described in the above literature A to give Compound (G-6).

(Step 4)

Compound (I-G) can be synthesized from Compound (G-6) which is obtained in the above step 3 in accordance with the above Method A or Method C.

[Chemical Formula 63]

wherein, each symbol in the formula is the same as above, and $R^1$ is C1-C4 alkyl.

(Method G)

(Step 1)

Compound (G-4) can be obtained by 1,3-dipolar cycloaddition reaction of Compound (G-1) and Compound (G-3).

Compound (G-1) is commercially available or can be synthesized according to the methods well known in the art.

Compound (G-2) is commercially available or can be synthesized according to the methods well known in the art.

Compound (G-3) can be synthesized by treating Compound (G-2) with acid.

As the acid, hydrochloric acid, sulfuric acid, trifluoroacetic acid and the like are exemplified, and it can be used at 0.1 to 0.5 mol equivalent relative to Compound (G-2).

The reaction temperature is −20° C. to the reflux temperature of the solvent, preferably 0 to 60° C.

The reaction time is 0.1 to 24 hour(s), preferably 0.5 to 12 hour(s).

As the reaction solvent, dichloromethane, chloroform, toluene, and the like are exemplified, and it can be used alone or in combination.

(Step 2)

Compound (G-5) can be obtained by deprotection of protecting group for carboxyl group of Compound (G-4) which is obtained in the above step 1. For example, the method disclosed in the above literature A can be used.

(Step 3)

The carboxyl group of Compound (G-5) which is obtained in the above step 2 can be converted to an amino group by Curtius rearrangement.

wherein, each symbol in the formula is the same as above, and $R^1$ is C1 to C4 alkyl.

(Method H)

(Step 1)

Compound (H-3) can be obtained by 1,3-dipolar cycloaddition reaction of Compound (H-1) and Compound (H-2) in the presence of a catalyst and a ligand.

Compound (H-1) is commercially available or can be synthesized according to the methods well known in the art.

Compound (H-2) is commercially available or can be synthesized according to the methods well known in the art.

As the catalyst, copper acetate, copper perchlorate and the like are exemplified, and it can be used at 0.01 to 0.1 mol equivalent relative to Compound (H-1).

As the ligand, BINAP and the like are exemplified, and it can be used at 0.01 to 0.1 mol equivalent relative to Compound (H-1).

The reaction temperature is −30° C. to the reflux temperature of the solvent, preferably 0° C. to room temperature.

The reaction time is 0.1 to 24 hour(s), preferably 0.5 to 12 hour(s).

As the reaction solvent, methanol, THF and the like are exemplified, and it can be used alone or in combination.
(Step 2)

Compound (I-H) can be synthesized from Compound (H-3) which is obtained in the above step 1 in accordance with the above Method G.

The Compounds of Formula (I) of the present invention prepared by the above general synthetic method can be purified by referring to the known methods (e.g., chromatography, recrystallization and the like).

The compound of the present invention has TrkA inhibitory activity and it can be available for therapeutic agent and/or prophylactic agent for pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease and the like.

The compound of the present invention has not only TrkA inhibitory activity but also are useful as a medicine and has any or all of the following excellent characteristics:

a) The compound is a weak inhibitor of CYP enzymes (e.g., CYP1A2, CYP2C9, CYP2C19, CYP2D6, CYP3A4 and the like).

b) The compound demonstrates good pharmacokinetics, such as a high bioavailability, moderate clearance and the like.

c) The compound has a high metabolic stability.

d) The compound has no irreversible inhibitory action against CYP enzymes (e.g., CYP3A4) when the concentration is within the range described in the present description as the measurement conditions.

e) The compound has no mutagenicity.

f) The compound is associated with a low cardiovascular risk.

g) The compound has a high solubility.

h) The compound is highly selective for TrkA receptor.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In the case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrated tablets. Powders and granules can be dry syrups. Capsules can be soft capsules, micro capsules or sustained-release capsules.

In the case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, diluents and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The compound of the present invention can be used in combination of therapeutic agents for pain, anti-inflammatory agents, anticancer agents, or the like (hereinafter referred to as a co-administered drug) to increase the activity of the compound or reduce the dose of the compound, or the like. In this case, the timing of administration for a compound of the present invention and the co-administered drug is not limited. They can be administered to the subjects to be treated, at a time or at different times. Furthermore, a compound of the present invention and the co-administered drug can be administered as two formulations independently comprising each active ingredient or a single formulation comprising the both active ingredients.

The dose for co-administered drugs may be appropriately selected in reference to the clinical dose. The compounding ratio of the compounds of the present invention and co-administered drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of co-administered drugs.

For example, the therapeutic agent for pain includes cyclooxygenase inhibitor (e.g., ketoprofen, celecoxib), neuropathic disorder agent (e.g., pregabalin), antidepressant (e.g., duloxetine, amitriptyline), opioid receptor agonist (e.g., morphine, tramadol), regional anesthetic (e.g., lidocaine), ketamine, acetaminophen and the like.

For example, the anti-inflammatory agent includes steroid agent (e.g., prednisolone), antihistamine agent (e.g., loratadine) and the like.

For example, the anticancer agent includes molecularly-targeted agent (e.g., lapatinib, rituximab), alkylating agent (e.g., cyclophosphamide), antimetabolite (e.g., methotrexate), alkaloid agent (e.g., paclitaxel), platinum agent (e.g., oxaliplatin), hormonal agent (e.g., tamoxifen, leuprorelin) and the like.

EXAMPLES

The present invention will be described in more detail with reference to, but not limited to, the following Examples, Reference Examples and Test Examples.

In this description, meaning of each abbreviation is as follows:
BINAP: 2,2'-bis(diphenylphosphino)-1,1'-binaphthyl
Bn: benzyl
Boc: tert-butoxycarbonyl
DIEA: N,N-diisopropylethylamine
DMAP: 4-dimethylaminopyridine
DMF: N,N-dimethylformamide
DMSO: dimethylsulfoxide
DPPA: diphenylphosphoryl azide
EDC: 1-ethyl-3-(3-dimethylaminopropyl)carbodiimide
Et: ethyl
HATU: O-(7-azabenzotriazol-1-yl)-1,1,3,3-tetramethyluronium hexafluorophosphate
Ms: methanesulfonyl
Ph: phenyl
TBAF: tetrabutylammonium fluoride
TMS: trimethylsilyl
t-Bu: tert-butyl
TFA: trifluoroacetic acid
HPLC: high performance liquid chromatography
NMP: N-methylpyrrolidone
COMU: (1-cyano-2-ethoxy-2-oxoethylidenaminooxy)dimethylaminomorpholinocarbenium hexafluorophosphate
THF: tetrahydrofuran NMR analysis of each example was performed by 400 MHz using DMSO-$d_6$ or CDCl$_3$. In the case of indicating NMR data, there are cases in which not all measured peaks are described.

"RT" in the following tables means a retention time of LC/MS: liquid chromatography/mass spectrometry, and the measurement conditions are as follows.

(Method 1)
Column: Shim-pack XR-ODS (2.2 m, i.d. 50×3.0 mm) (Shimadzu)
Flow rate: 1.6 mL/min
UV detection wavelength: 254 nm
Mobile phase: [A] is 0.1% formic acid in aqueous solution, and [B] is 0.1% formic acid in acetonitrile solution.
Gradient: Linear gradient of 10% to 100% solvent [B] for 3 minutes was performed, and 100% solvent [B] was maintained for 0.5 minute.

(Method 2)
Column: ACQUITY UPLC™ BEH C18 (1.7 μm i.d. 2.1×50 mm) (Waters)
Flow rate: 0.8 mL/min
UV detection wavelength: 254 nm
Mobile phase: [A] is 0.1% formic acid in aqueous solution, and [B] is 0.1% formic acid in acetonitrile solution.
Gradient: Linear gradient of 5% to 100% solvent [B] for 3.5 minutes was performed, and 100% solvent [B] was maintained for 0.5 minute.

(Method 3) (Shimadzu UHPLC)
Column: ACQUITY UPLC™ BEH C18 (1.7 μm i.d. 2.1×50 mm) (Waters)
Flow rate: 0.8 mL/min
UV detection wavelength: 254 nm
Mobile phase: [A] is 10 mM ammonium carbonate in aqueous solution, and [B] is acetonitrile.
Gradient: Linear gradient of 5% to 100% solvent [B] for 3.5 minutes was performed, and 100% solvent [B] was maintained for 0.5 minute.

(Method 4) (Waters UPLC)
Column: ACQUITY UPLC™ BEH C18 (1.7 μm i.d. 2.1×50 mm) (Waters)
Flow rate: 0.8 mL/min
UV detection wavelength: 254 nm
Mobile phase: [A] is 10 mM ammonium carbonate in aqueous solution, and [B] is acetonitrile.
Gradient: Linear gradient of 5% to 100% solvent [B] for 3.5 minutes was performed, and 100% solvent [B] was maintained for 0.5 minute Hereinafter, MS (m/z) indicates the value observed in the mass spectrometry.

Example 1

Synthesis of Compound (I-11)

[Chemical Formula 64]

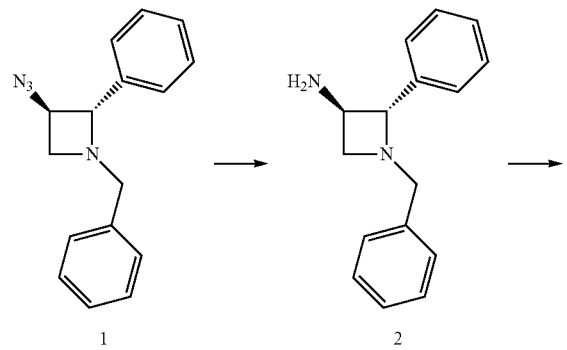

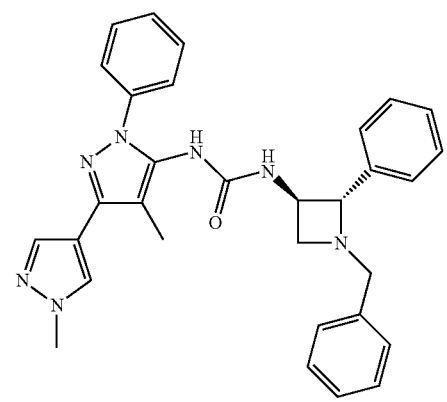

(I-11)

87
-continued

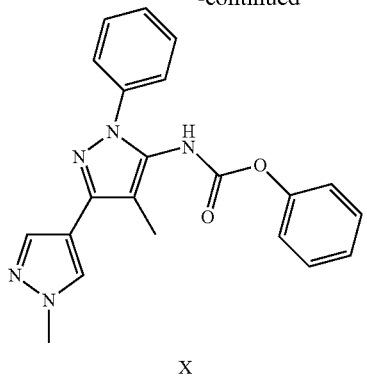

X

88
-continued

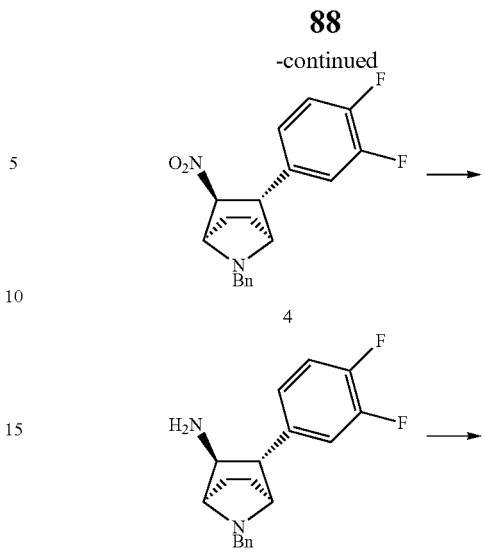

Step 1 Synthesis of Compound 2

Compound 1 (1.61 g, 6.07 mmol) which can be synthesized in according to the known method (Tetrahedron, 2006, 62, pp. 6882-6892) was dissolved in tetrahydrofuran (16 mL)-water (1.6 mL), and triphenylphosphine (1.91 g, 7.29 mmol) was added to the solution. The reaction mixture was stirred at room temperature for 30 minutes and at 60° C. for 15 hours. To the solution were added 1 mol/L hydrochloric acid and water, the aqueous layer was washed with ethylacetate. The aqueous layer was basified with saturated sodium bicarbonate aqueous solution and the generated solids were collected by filtration to give Compound 2 (962 mg, Yield 66.5%)

LC/MS (Method 1) RT=0.70, MS (m/z)=239.00

Step 2 Synthesis of Compound (I-11)

Compound 2 (300 mg, 1.26 mmol) was dissolved in 1,4-dioxane (6 mL), and triethylamine (0.262 mL, 1.89 mmol) and Compound X (564 mg, 1.51 mmol) which can be synthesized in according to the known method (WO2012158413) were added to the solution and the reaction mixture was stirred at room temperature for 90 minutes. To the mixture was added water and the generated solids were suspended in ethylacetate-chloroform and collected by filtration to give Compound (I-11) (racemate, 330 mg, Yield 50.6%).

$^1$H-NMR (DMSO-D$_6$) δ: 1.97 (s, 3H), 2.74 (t, J=7.0 Hz, 1H), 3.45 (s, 2H), 3.76 (d, J=13.1 Hz, 1H), 3.88 (s, 3H), 3.93-4.07 (m, 2H), 7.06 (d, J=8.3 Hz, 1H), 7.17-7.38 (m, 11H), 7.43 (t, J=7.8 Hz, 2H), 7.47-7.53 (m, 2H), 7.74 (s, 1H), 7.98 (s, 1H), 8.04 (s, 1H).

Example 2

Synthesis of Compound (I-30)

[Chemical Formula 65]

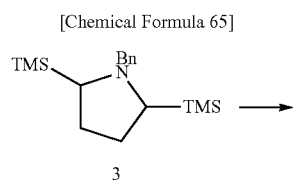

3

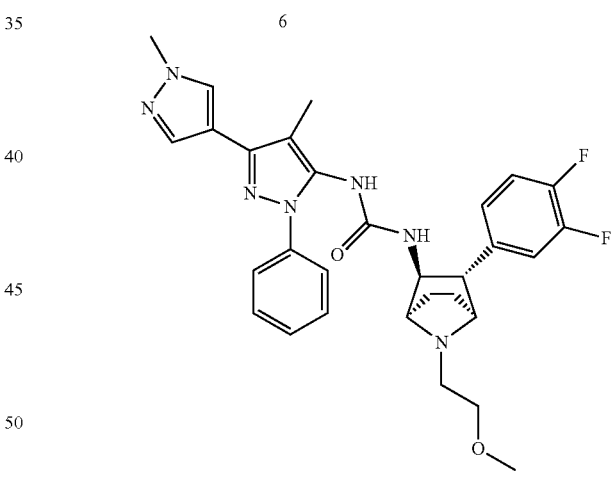

(I-30)

Step 1 Synthesis of Compound 4

(E)-1,2-difluoro-4-(2-nitrovinyl)benzene (88 mg, 0.48 mmol) was dissolved in dichloromethane (2 mL), and silver fluoride (193 mg, 1.52 mmol) was added to the solution. To this suspension was added dropwise 1 mL of dichloromethane solution of Compound 3 (133 mg, 0.46 mmol) which can be synthesized in accordance with the known method (J. Org. Chem. 1998, 63, 760-768) under nitrogen atmosphere, and the reaction mixture was stirred at room temperature for 15.5 hours. The reaction mixture was filtered through celite pad and the filtrate was concentrated under reduced pressure and the residue was purified by silicagel column chromatography (hexane-ethylacetate) to give Compound 4 (12 mg, Yield 7.9%).

$^1$H-NMR (CDCl$_3$) δ: 1.34-1.45 (m, 2H), 1.74 (m, 1H), 2.08 (m, 1H), 3.63 (m, 2H), 4.12 (d, J=5.2 Hz, 1H), 4.16 (m, 1H), 4.43 (d, J=4.8 Hz, 1H), 6.90 (m, 1H), 7.00 (ddd, J=10.4, 7.2, 2.0 Hz, 1H), 7.14 (dd, J=18.4, 8.4 Hz, 1H), 7.29 (m, 1H), 7.30-7.37 (m, 5H)

Step 2 Synthesis of Compound 5

Compound 4 (16 mg, 0.045 mmol) was dissolved in methanol (1.5 mL) under nitrogen atmosphere, and concentrated hydrochloric acid (0.095 mL, 1.1 mmol) and zinc (59 mg, 0.90 mmol) were added to the solution and the reaction mixture was stirred vigorously at room temperature for 1.5 hours.

Sodium hydrogen carbonate aqueous solution was added to the mixture. The mixture was extracted with ethylacetate. The organic layer was washed with water and dried over anhydrous sodium sulfate. The solvent was removed under reduced pressure and the residue was purified by silicagel column chromatography (chloroform-methanol) to give Compound 5 (6.1 mg, Yield 43%).

$^1$H-NMR (CDCl$_3$) δ: 1.21-1.33 (m, 2H), 1.63 (m, 1H), 1.91 (ddd, J=16.0, 5.6, 4.4 Hz, 1H), 2.87-2.93 (m, 2H), 3.04 (d, J=4.8 Hz, 2H), 3.41 (t, J=4.4 Hz, 1H), 3.57 (d, J=13.6 Hz, 1H), 3.64 (d, J=13.6 Hz, 1H), 6.87 (m, 1H), 7.06 (dd, J=18.4, 8.4 Hz, 1H), 7.28 (t, J=7.2 Hz, 1H), 7.35 (t, J=7.6 Hz, 1H), 7.42 (t, J=7.2 Hz, 1H)

Step 3 Synthesis of Compound 6

Compound 5 (6.1 mg, 0.019 mmol) was dissolved in tetrahydrofuran (1 mL) under nitrogen atmosphere, and DIEA (0.017 mL, 0.097 mmol) and Compound X (8.7 mg, 0.023 mmol) were added to the solution and the reaction mixture was heated to reflux for 1 hour. After the solution was allowed to cool to room temperature, water was added to the mixture. The mixture was extracted with chloroform. The organic layer was washed with water and dried over anhydrous sodium sulfate. The solvent was removed under reduced pressure and the obtained residue was purified by silicagel column chromatography (hexane-ethylacetate) to give Compound 6 (7.5 mg, Yield 65%).

$^1$H-NMR (CDCl$_3$) δ: 1.24-1.37 (m, 2H), 1.64 (m, 1H), 1.89 (m, 1H), 2.09 (s, 3H), 2.82 (m, 1H), 3.05 (m, 1H), 3.39-3.54 (m, 2H), 3.52 (m, 1H), 3.97 (m, 1H), 3.99 (s, 3H), 5.20 (d, J=6.8 Hz, 1H), 5.84 (br s, 1H), 6.88 (m, 1H), 6.95 (m, 1H), 7.07 (dd, J=18.4, 8.4 Hz, 1H), 7.12-7.21 (m, 5H), 7.27 (m, 1H), 7.34 (t, J=7.6 Hz, 2H), 7.44 (d, J=7.6 Hz, 2H), 7.78 (s, 1H), 7.91 (s, 1H)

Step 4 Synthesis of Compound (I-30)

Compound 6 (7.5 mg, 0.013 mmol) was dissolved in methanol (3 mL), and 2 mol/L hydrochloric acid aqueous solution (0.0076 mL, 0.015 mmol) and palladium hydroxide (10 mg, 0.071 mmol) were added to the solution. The reaction mixture was stirred at room temperature for 5.5 hours under hydrogen atmosphere. The mixture was filtered through celite pad and the filtrate was concentrated. The obtained residue was dissolved in DMF (1.5 mL), and DIEA (0.027 mL, 0.16 mmol) and 1-bromo-2-methoxyethane (0.024 mL, 0.26 mmol) were added to the solution and the reaction mixture was stirred at 70° C. for 1 day. After the mixture was allowed to cool to room temperature, water was added to the mixture. The mixture was extracted with ethylacetate. The organic layer was washed with water and dried over anhydrous sodium sulfate. The solvent was removed under reduced pressure and the obtained residue was purified by silicagel column chromatography (chloroform-methanol), and then purified by reverse phase HPLC (water-acetonitrile) to give Compound (I-30) (racemate, 3.2 mg, Yield 44%).

$^1$H-NMR (CDCl$_3$) δ: 1.20-1.34 (m, 2H), 1.50 (m, 1H), 1.72-1.85 (m, 3H), 2.16 (s, 3H), 2.47 (m, 1H), 2.53 (m, 1H), 3.05 (m, 1H), 3.21 (s, 3H), 3.32-3.43 (m, 2H), 3.47 (m, 1H), 3.85 (m, 1H), 3.96 (s, 3H), 5.50 (m, 1H), 6.92 (m, 1H), 6.94 (t, J=9.6 Hz, 1H), 7.07 (dd, J=18.4, 8.4 Hz, 1H), 7.29 (m, 1H), 7.37 (t, J=7.2 Hz, 2H), 7.52 (d, J=7.2 Hz, 2H), 7.75 (s, 1H), 7.86 (s, 1H)

Example 3

Synthesis of Compound (I-29)

[Chemical Formula 66]

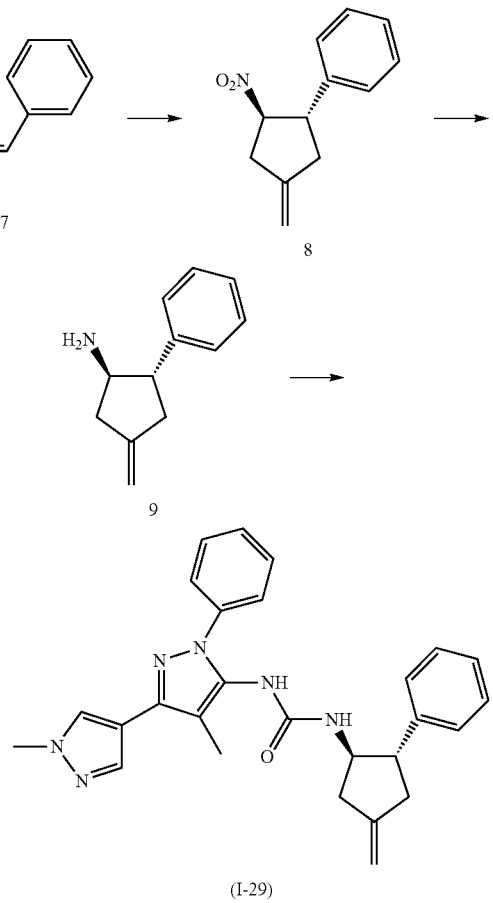

Step 1 Synthesis of Compound 8

Compound 7 (149 mg, 1.00 mmol) was dissolved in tetrahydrofuran (2 mL), and 2-((trimethylsilyl)methyl)allyl acetate (298 mg, 1.60 mmol), triisopropyl phosphite (69 μL, 0.30 mmol) and palladium acetate (23 mg, 0.10 mmol) were added to the solution and the mixture was stirred at 100° C. for 2 hours in a sealed tube.

After the reaction mixture was allowed to cool, generated solids were removed by filtration and water was added to the filtrate. The mixture was extracted with chloroform. The organic layer was dried over anhydrous sodium sulfate and the solvent was removed under reduced pressure. The obtained residue was purified by silicagel column chromatography (hexane-ethylacetate) to give known Compound 8 (110 mg, Yield 54%).

Step 2 Synthesis of Compound (I-29)

Compound 8 (68 mg, 0.335 mmol) was dissolved in ethanol (1 mL), and concentrated hydrochloric acid (0.7 mL) and zinc (438 mg, 6.69 mmol) were added to the solution under ice-cooling bath and the reaction mixture was stirred at room temperature for 30 minutes.

After generated solids were removed by filtration, 2 mol/L sodium hydroxide aqueous solution was added to the filtrate. The mixture was extracted with chloroform. The organic layer was dried over sodium sulfate and the solvent was removed under reduced pressure to give Compound 9 as crude product.

The obtained crude 9 (0.335 mmol) was dissolved in tetrahydrofuran (1 mL), and triethylamine (93 µL, 0.67 mmol) and Compound X (125 mg, 0.335 mmol) were added to the mixture and the reaction mixture was stirred at room temperature for 2 hours.

After adding water to the mixture, it was extracted with ethylacetate. The organic layer was washed with water and brine, and dried over anhydrous sodium sulfate. The solvent was removed under reduced pressure and the obtained residue was purified by amino silicagel column chromatography (hexane-ethylacetate) to give Compound (I-29) (racemate, 58 mg, Yield 38%).

$^1$H-NMR (CDCl$_3$) δ: 1.91 (s, 3H), 2.14 (m, 1H), 2.46 (m, 1H), 2.75 (dd, J=7.2, 16.4 Hz, 1H), 2.88 (1H, m), 3.01 (dd, J=7.8, 16.4 Hz, 1H), 3.97 (s, 3H), 4.32 (m, 1H), 4.63 (d, J=7.8 Hz, 1H), 4.91 (s, 1H), 4.91 (s, 1H), 5.60 (s, 1H), 7.17-7.36 (m, 10H), 7.74 (s, 1H), 7.84 (s, 1H).

Example 4

Synthesis of Compound (I-36)

[Chemical Formula 67]

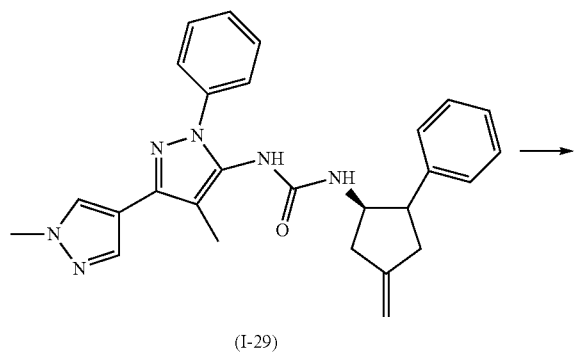

(I-29)

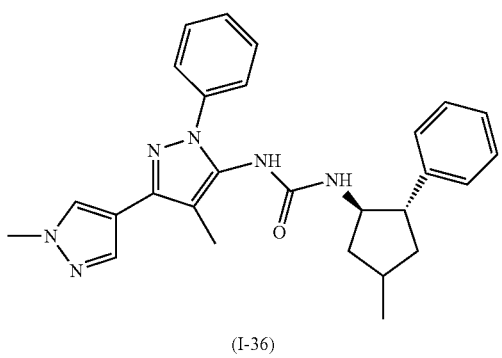

(I-36)

Step 1 Synthesis of Compound (I-36)

Compound (I-29) (30 mg, 0.066 mmol) was dissolved in methanol (1 mL), palladium hydroxide (93 mg, 0.133 mmol, 20% wt) was added to the solution, and the reaction mixture was stirred at room temperature for 1.5 hours under nitrogen atmosphere.

After the solids were removed by filtration and the filtrate was concentrated. The obtained residue was purified by amino silicagel column chromatography (hexane-ethylacetate) to give Compound (I-36) (trans, 7.5 mg, Yield 25%) as diastereoisomer mixture.

$^1$H-NMR (CDCl$_3$) δ: 1.04 (s, 1.2H), 1.06 (s, 1.8H), 1.24-1.37 (m, 1H), 1.65-1.77 (m, 1H), 1.92 (s, 1.8H), 1.95 (s, 1.2H), 2.10-2.30 (m, 1.4H), 2.38-2.48 (m, 0.6H), 2.68-2.83 (m, 1H), 3.97 (s, 3H), 4.19-4.32 (m, 1H), 4.56-4.67 (m, 1H), 5.67-5.85 (m, 1H), 7.14-7.39 (m, 10H), 7.74 (s, 1H), 7.84 (s, 1H).

Example 5

Synthesis of Compound (I-19)

[Chemical Formula 68]

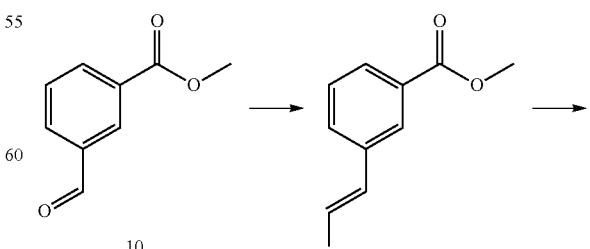

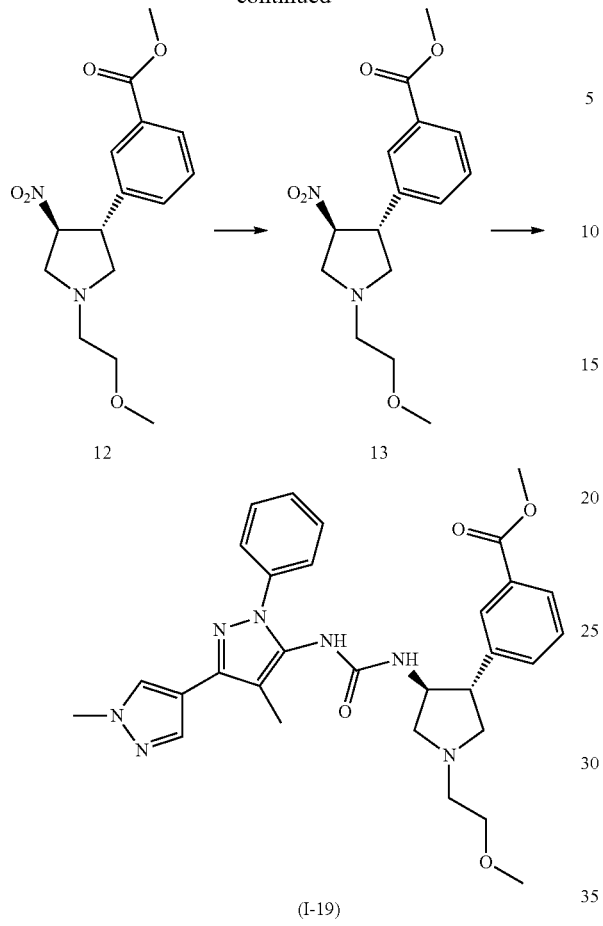

12    13

(I-19)

Step 1 Synthesis of Compound 11

Compound 10 (829 mg, 5.05 mmol) was dissolved in acetic acid (10 mL), ammonium acetate (894 mg, 11.61 mmol) and nitromethane (1 mL, 18.68 mmol) were added to the solution, and the reaction mixture was stirred at 100° C. overnight.

After the solvent was removed under reduced pressure, the obtained residue was purified by silicagel column chromatography (hexane-ethylacetate) to give Compound 11 (510 mg, Yield 49%).

LC/MS (Method 3): 1.99 min, MS (m/z)=208

Step 2 Synthesis of Compound (I-19)

Compound 11 (89 mg, 0.43 mmol) was dissolved in dichloromethane (2 mL) under ice-cooling bath, 2-methyloxy-N-methyloxymethyl-N-((trimethylsilyl)methyl)ethane-1-amine (150 mg, 0.73 mmol) which can be synthesized in accordance with the method described in WO2012158413 and TFA (3.3 µL, 0.0043 mmol) were added to the solution, and the reaction mixture was stirred at room temperature for 2 hours.

Saturated sodium hydrogen carbonate aqueous solution was added to the reaction mixture. The mixture was extracted with chloroform. The organic layer was dried over anhydrous sodium sulfate, and then the solvent was removed under reduced pressure to give Compound 12 as crude product.

Compound 12 (0.43 mmol) was dissolved in methanol (4 mL), concentrated hydrochloric acid (0.9 mL) and zinc (562 mg, 8.6 mmol) were added to the solution under ice-cooling bath, and the reaction mixture was stirred at room temperature for 30 minutes. After the solids were removed by filtration, 2 mol/L aqueous sodium hydroxide solution (5.4 mL) was added to the filtrate. The mixture was extracted with chloroform. The organic layer was dried over sodium sulfate and the solvent was removed under reduced pressure to give Compound 13 as crude product.

Compound 13 (0.1 mmol) was dissolved in tetrahydrofuran (2 mL), triethylamine (28 µL, 0.2 mmol) and Compound X (45 mg, 0.12 mmol) were added to the solution, and the reaction mixture was stirred at room temperature for 2 hours.

After the solvent was concentrated under reduced pressure, the obtained residue was purified by reverse phase chromatography to give Compound (I-19) (racemate, 16.9 mg, Yield 7.1%).

$^1$H-NMR (CDCl$_3$) δ: 2.13 (s, 3H), 2.36 (t, J=9.2 Hz, 1H), 2.33-2.38 (m, 2H), 2.82 (m, 2H), 3.10 (1H, m), 3.27 (m, 1H), 3.27 (s, 3H), 3.42 (m, 2H), 3.91 (s, 3H), 3.98 (s, 3H), 4.33 (s, 1H), 5.20 (d, J=8.4 Hz, 1H), 5.89 (s, 1H), 7.28-7.43 (m, 5H), 7.50 (m, 2H), 7.77 (s, 1H), 7.82-7.94 (m, 3H).

Example 6

Synthesis of Compound (I-1)

[Chemical Formula 69]

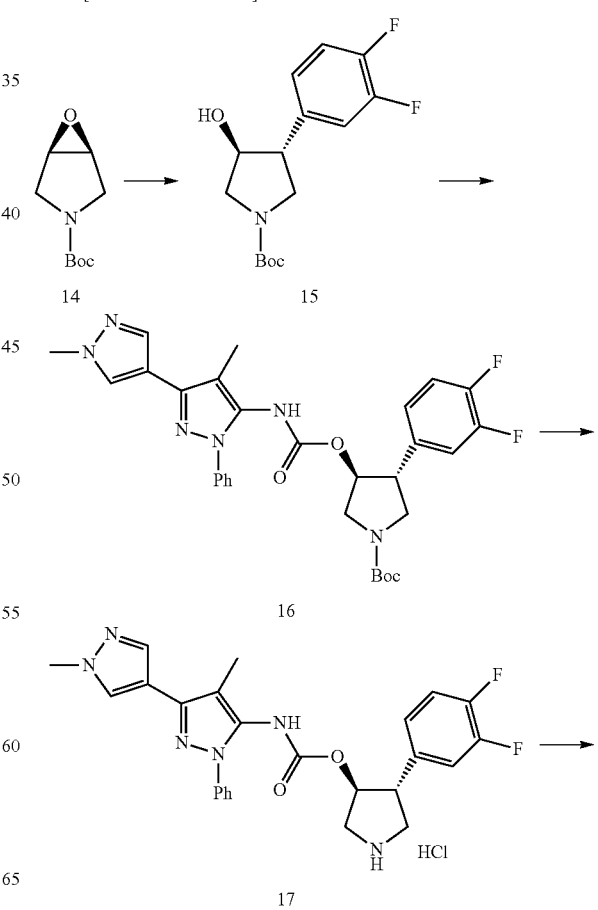

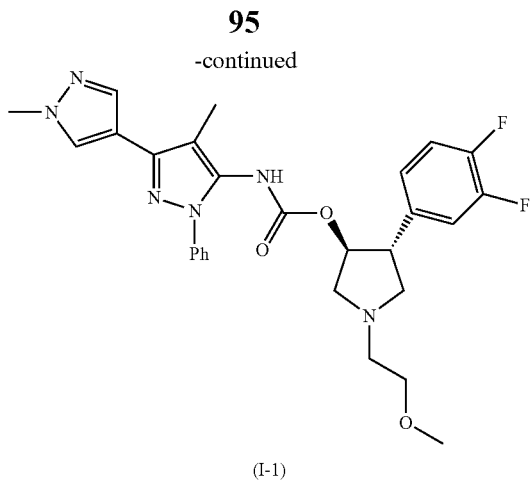

(I-1)

Step 1 Synthesis of Compound 15

To compound 14 (500 mg, 2.70 mmol) were added copper iodide (51.4 mg, 0.27 mmol) and tetrahydrofuran (5 mL) under nitrogen atmosphere, and the reaction mixture was cooled under ice-cooling bath. 3,4-Difluorophenylmagnesium bromide (8.1 mL, 4.05 mmol) was added dropwise to the mixture. After the mixture was stirred under ice-cooling bath for 3 hours, ethylacetate was added to the mixture. The organic layer was washed once with diluted hydrochloric acid and brine, respectively and dried over anhydrous sodium sulfate. The solvent was removed under reduced pressure and the obtained residue was purified by silicagel column chromatography (ethylacetate-hexane) to give Compound 15 (615 mg, Yield 76%) as a yellow oil.

Step 2 Synthesis of Compound 16

To Compound 15 (216 mg, 0.722 mmol) was added Compound X (296 mg, 0.794 mmol) and the mixture was dissolved in tetrahydrofuran (2.2 mL). To the solution were added DIEA (315 μL, 1.80 mmol), DMAP (17.6 mg, 0.144 mmol), and the reaction mixture was left to stand for 2 days. Additional Compound X (242 mg, 0.649 mmol) was added to the mixture and the mixture was stirred at 60° C. for 9 hours. Ethylacetate was added to the mixture. The organic layer was washed once with saturated sodium hydrogen carbonate aqueous solution, water, diluted hydrochloric acid aqueous solution and brine, respectively and dried over anhydrous sodium sulfate. The solvent was removed under reduced pressure and the obtained residue was purified by silicagel column chromatography (ethylacetate-hexane) to give Compound 16 (140 mg, Yield 34%) as a colorless amorphous.

1H-NMR (CDCl$_3$) δ: 1.49 (s, 9H), 2.13 (s, 3H), 2.96-3.83 (m, 5H), 3.96 (s, 3H), 5.07 (s, 1H), 6.26 (s, 1H), 6.78-7.17 (m, 3H), 7.33-7.50 (m, 5H), 7.74 (s, 1H), 7.85 (s, 1H).

Step 3 Synthesis of Compound 17

To Compound 16 (135 mg, 0.233 mmol) was added 4 mol/L hydrochloric acid-ethylacetate solution (1.35 mL), and the reaction mixture was stirred at room temperature for 3 hours. After the reaction solvent was removed under reduced pressure, the residue was solidified with ether to give Compound 17 (121 mg).

1H-NMR (DMSO-D$_6$) δ: 1.98 (s, 3H), 3.16-3.25 (m, 1H), 3.65-3.74 (m, 2H), 3.89 (s, 3H), 5.16-5.28 (m, 1H), 6.95-7.27 (m, 1H), 7.32-7.58 (m, 7H), 7.75 (s, 1H), 8.06 (s, 1H), 9.28-9.70 (m, 2H), 9.85 (s, 1H).

Step 4 Synthesis of Compound (I-1)

Compound 4 (50.0 mg, 0.097 mmol) was dissolved in DMF (1 mL). To the solution were added methoxyethyl bromide (16.2 mg, 0.117 mmol) and DIEA (40.7 μL, 0.233 mmol), and the reaction mixture was stirred at room temperature for 17 hours and at 65° C. for 16 hours. Ethylacetate was added to the mixture. The organic layer was washed once with saturated sodium hydrogen carbonate aqueous solution and brine, respectively and dried over anhydrous sodium sulfate. After the solvent was removed under reduced pressure, the obtained residue was purified by amino silicagel column chromatography (ethylacetate-hexane) to give Compound (I-1) (racemate, 28.8 mg, Yield 55%) as a colorless amorphous.

1H-NMR (CDCl$_3$) δ: 2.12 (s, 3H), 2.45 (s, 1H), 2.57-3.41 (m, 9H), 3.52 (s, 2H), 3.95 (s, 3H), 5.08 (s, 1H), 6.24 (s, 1H), 6.93 (s, 1H), 6.99-7.12 (m, 2H), 7.31-7.53 (m, 5H), 7.73 (s, 1H), 7.84 (s, 1H).

Example 7

Synthesis of Compound (I-6)

[Chemical Formula 70]

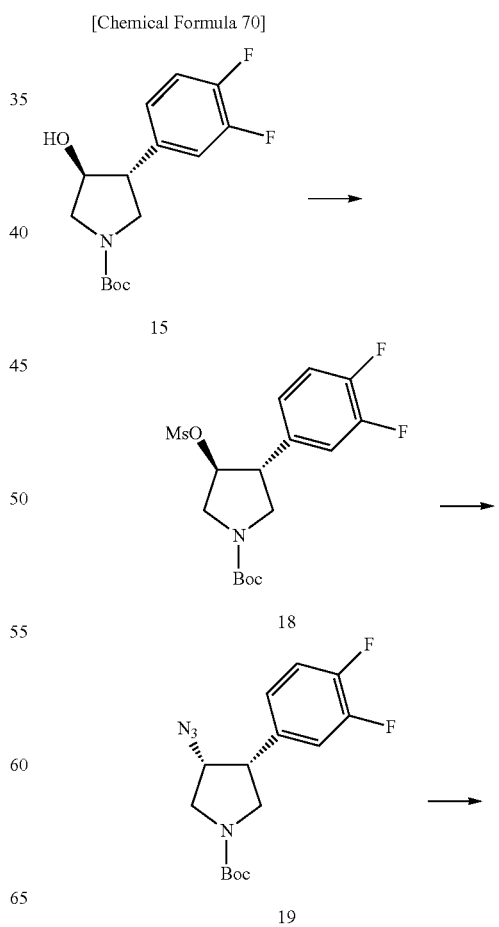

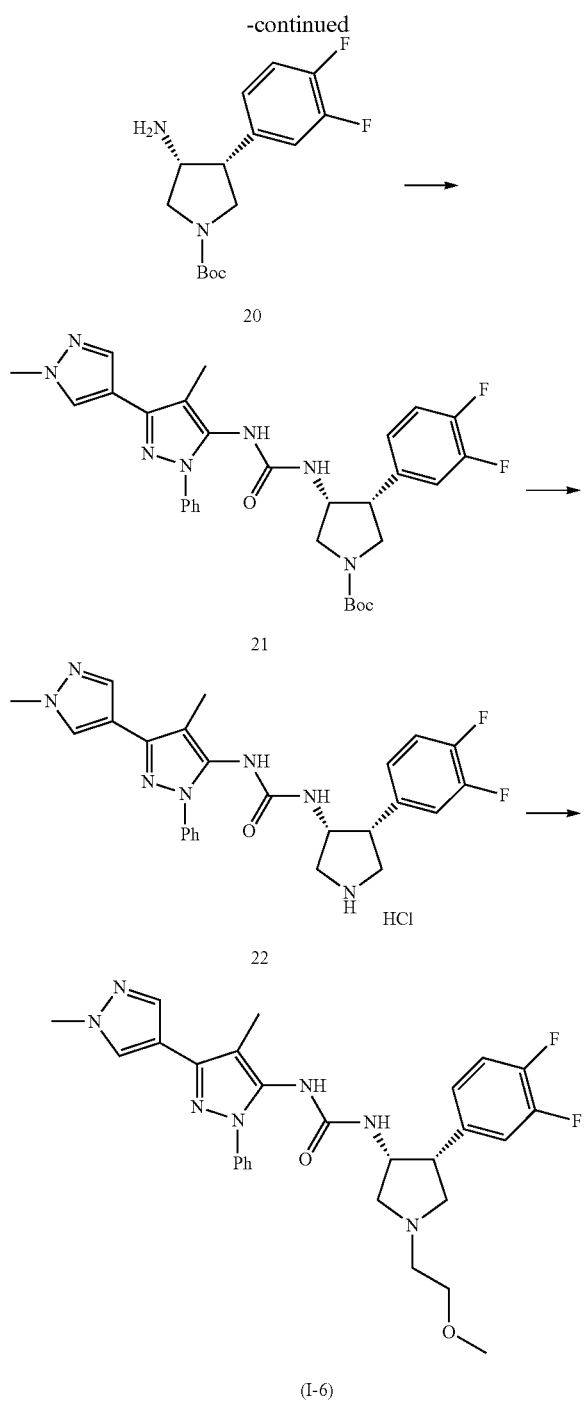

Step 1 Synthesis of Compound 18

Compound 15 (250 mg, 0.835 mmol) was dissolved in dichloromethane (5 mL) under nitrogen atmosphere. To the solution were added mesyl chloride (78 μL, 1.00 mmol) and triethylamine (174 μL, 1.25 mmol) under ice-cooling bath, and the reaction mixture was allowed to warm up to room temperature. After stirring for 2 hours, ethylacetate was added to the mixture. The organic layer was washed once with saturated sodium hydrogen carbonate aqueous solution and brine, respectively and dried over anhydrous sodium sulfate. After the solvent was removed under reduced pressure, the obtained residue was purified by silicagel column chromatography (ethylacetate-hexane) to give Compound 18 (273 mg, Yield 87%) as a colorless oil.

1H-NMR (CDCl$_3$) δ: 1.50 (s, 9H), 2.98 (d, J=9.0 Hz, 3H), 3.54-3.73 (m, 3H), 3.78 (dd, J=12.9, 5.5 Hz, 1H), 3.82-3.93 (m, 1H), 5.00 (d, J=4.1 Hz, 1H), 6.96-7.03 (m, 1H), 7.08 (t, J=8.5 Hz, 1H), 7.16 (dd, J=17.9, 8.6 Hz, 1H).

Step 2 Synthesis of Compound 19

Compound 18 (270 mg, 0.715 mmol) was dissolved in DMSO (2.7 mL), to the solution was added sodium azide (69.8 mg, 1.07 mmol), and the reaction mixture was stirred at 80° C. for 6 hours. Ethylacetate was added to the reaction mixture. The organic layer was washed once with saturated sodium hydrogen carbonate aqueous solution and brine, respectively and dried over anhydrous sodium sulfate. After the solvent was removed under reduced pressure, the obtained residue was purified by silicagel column chromatography (ethylacetate-hexane) to give Compound 19 (205 mg, Yield 88%) as a colorless oil.

1H-NMR (CDCl$_3$) δ: 1.49 (s, 9H), 3.41-3.52 (m, 1H), 3.54-3.87 (m, 4H), 4.21 (s, 1H), 6.99-7.06 (m, 1H), 7.10-7.21 (m, 2H).

Step 3 Synthesis of Compound 20

Compound 19 (200 mg, 0.617 mmol) was dissolved in methanol (4 mL), the solution was added palladium carbon (60 mg), and the reaction mixture was stirred for 2 hours under hydrogen atmosphere. The reaction mixture was filtered through a celite pad and the obtained filtrate was concentrated under reduced pressure to give Compound 20 (171 mg, Yield 93%) as a crude product.

Step 4 Synthesis of Compound 21

To Compound 20 (170 mg, 0.570 mmol) was added compound X (213 mg, 0.570 mmol), and the mixture was dissolved in tetrahydrofuran (1.7 mL). To the reaction mixture was added triethylamine (95 μL, 0.684 mmol) and left to stand overnight at room temperature. Ethylacetate was added to the mixture. The organic layer was washed once with saturated sodium hydrogen carbonate aqueous solution, water, diluted hydrochloric acid solution and brine, respectively and dried over anhydrous sodium sulfate. After the solvent was removed under reduced pressure, the residue was purified by silicagel column chromatography (ethylacetate-hexane) to give Compound 21 (311 mg, Yield 95%) as a pale yellow amorphous.

1H-NMR (CDCl$_3$) δ: 1.47 (s, 9H), 1.90 (s, 3H), 2.87-3.05 (m, 1H), 3.41-3.57 (m, 2H), 3.64-3.81 (m, 2H), 3.98 (s, 3H), 4.22-4.37 (m, 1H), 4.49-4.66 (m, 1H), 5.95 (s, 1H), 6.62-6.78 (m, 1H), 6.82-7.02 (m, 2H), 7.30-7.38 (m, 3H), 7.39-7.46 (m, 2H), 7.71 (s, 1H), 7.83 (s, 1H).

Step 4 Synthesis of Compound 22

Compound 22 (268 mg) was obtained as amorphous in the same manner as described in the step 3 of Example 6 by using Compound 21 (299 mg, 0.518 mmol) as the starting material.

1H-NMR (DMSO-D$_6$) δ: 1.79 (s, 3H), 3.05-3.16 (m, 1H), 3.61-3.69 (m, 3H), 3.88 (s, 3H), 4.60-4.69 (m, 1H), 6.85 (brs, 1H), 7.08-7.16 (m, 1H), 7.29-7.49 (m, 7H), 7.71 (d, J=0.5 Hz, 1H), 8.02 (s, 1H), 8.05 (s, 1H), 9.46 (brs, 2H).

Step 5 Synthesis of Compound (I-6)

Compound (I-6) (racemate, 23.5 mg, Yield 44%) was obtained as a pale yellow amorphous in the same manner as described in the step 4 of Example 6 by using Compound 22 (50.9 mg, 0.099 mmol) as the starting material.

1H-NMR (CDCl$_3$) δ: 1.89 (s, 3H), 2.52 (d, J=8.7 Hz, 1H), 2.66 (q, J=5.8 Hz, 2H), 2.78-2.95 (m, 3H), 3.33 (s, 3H), 3.43-3.56 (m, 3H), 3.98 (s, 3H), 4.48-4.59 (m, 1H), 4.74 (brs, 1H), 5.89 (s, 1H), 6.81-6.94 (m, 2H), 7.02-7.10 (m, 1H), 7.30-7.37 (m, 3H), 7.37-7.44 (m, 2H), 7.73 (s, 1H), 7.85 (s, 1H).

Example 8

Synthesis of Compound (I-18)

[Chemical Formula 71]

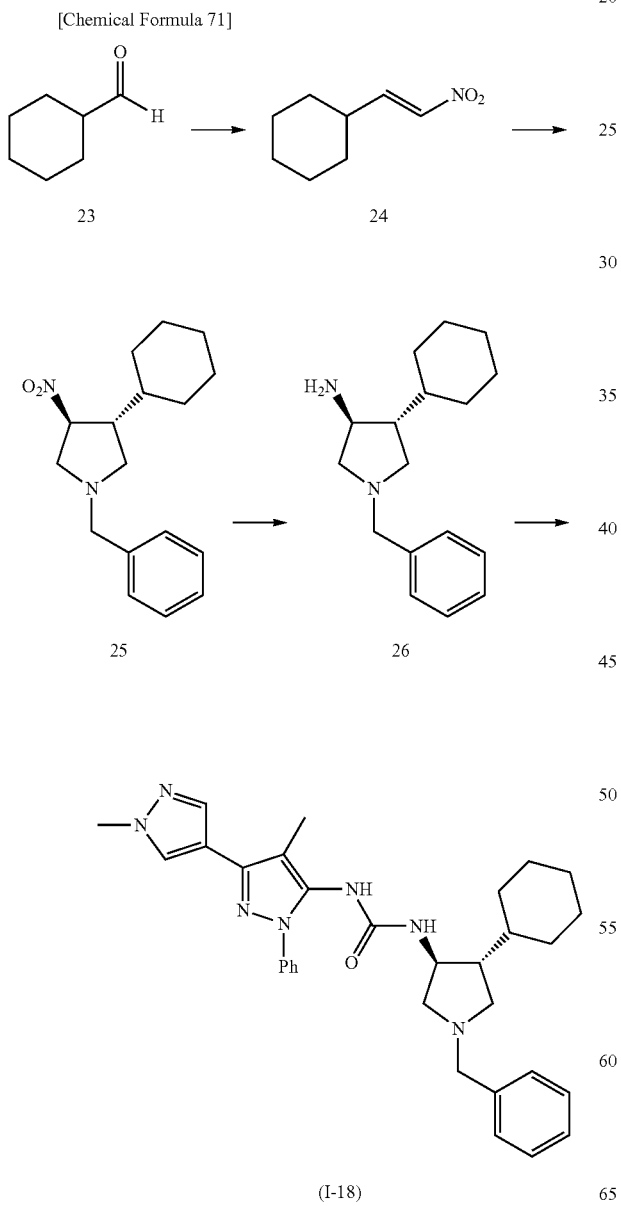

Step 1 Synthesis of Compound 24

To Compound 23 (2.00 g, 17.8 mmol) were added nitromethane (6.53 g, 107 mmol), piperidine (0.177 mL, 1.78 mmol), iron (III) chloride (289 mg, 1.78 mmol) and toluene (20 mL), and the reaction mixture was heated to reflux for 4 hours. After the solvent was removed under reduced pressure, the obtained residue was purified by silicagel column chromatography (ethylacetate-hexane) to give Compound 24 (2.77 g) as a yellow oil.

1H-NMR (CDCl$_3$) δ: 1.12-1.42 (m, 5H), 1.62-1.95 (m, 5H), 2.20-2.31 (m, 1H), 6.93 (d, J=13.4 Hz, 1H), 7.23 (dd, J=13.5, 7.2 Hz, 1H).

Step 2 Synthesis of Compound 25

To Compound 24 (1.00 g, 6.44 mmol) were added dichloromethane (10 mL) and TFA (124 μL, 1.61 mmol). To the reaction mixture was added dropwise N-benzyl-1-methoxy-((trimethyl silyl)methyl)methanamine (1.61 g, 6.77 mmol) under ice-cooling bath. The mixture was stirred at room temperature for 19 hours, and then the solvent was removed under reduced pressure. Ethylacetate was added to the obtained residue. The organic layer was washed once with saturated sodium hydrogen carbonate aqueous solution and brine, respectively and dried over anhydrous sodium sulfate. After the solvent was removed, the obtained residue was purified by silicagel column chromatography (ethylacetate-hexane) to give Compound 25 (1.23 g, Yield 66%) as yellow oil.

1H-NMR (CDCl$_3$) δ: 0.91-1.07 (m, 2H), 1.08-1.28 (m, 3H), 1.34 (dd, J=20.5, 11.1 Hz, 1H), 1.60-1.83 (m, 5H), 2.15 (t, J=8.7 Hz, 1H), 2.61-2.75 (m, 2H), 3.09 (t, J=8.4 Hz, 1H), 3.34 (d, J=9.9 Hz, 1H), 3.56 (d, J=13.2 Hz, 1H), 3.67 (d, J=13.1 Hz, 1H), 4.62-4.72 (m, 1H), 7.26-7.36 (m, 5H).

Step 3 Synthesis of Compound 26

Compound 25 (1.15 g, 3.99 mmol) was dissolved in acetonitrile (23 mL). To the solution was added tin chloride dihydrate (6.30 g, 27.9 mmol) and the mixture was heated to reflux overnight. After the reaction mixture was allowed to cool, 2 mol/L sodium hydroxide aqueous solution (28 mL) was added to the mixture. The mixture was extracted twice with ethylacetate and washed once with brine. The organic layer was dried over anhydrous sodium sulfate and the solvent was removed under reduced pressure to give Compound 26 (1.09 g) as a crude product.

Step 4 Synthesis of Compound (I-18)

Compound (I-18) (racemate, 207 mg, Yield 66%) was obtained as a pale yellow oil in the same manner as described in the step 4 of Example 6 by using Compound 26 (150 mg, 0.580 mmol) as the starting material.

1H-NMR (CDCl$_3$) δ: 0.70-0.90 (m, 2H), 1.03-1.26 (m, 4H), 1.33-1.88 (m, 9H), 2.09 (s, 3H), 2.33 (dd, J=10.2, 7.2 Hz, 1H), 2.89 (s, 1H), 3.23-3.58 (m, 2H), 3.98 (s, 3H), 5.11 (d, J=8.8 Hz, 1H), 7.06-7.25 (m, 5H), 7.31 (t, J=7.4 Hz, 1H), 7.38 (t, J=7.5 Hz, 2H), 7.49 (d, J=7.8 Hz, 2H), 7.77 (s, 1H), 7.89 (s, 1H).

Example 9

Synthesis of Compound (I-9)

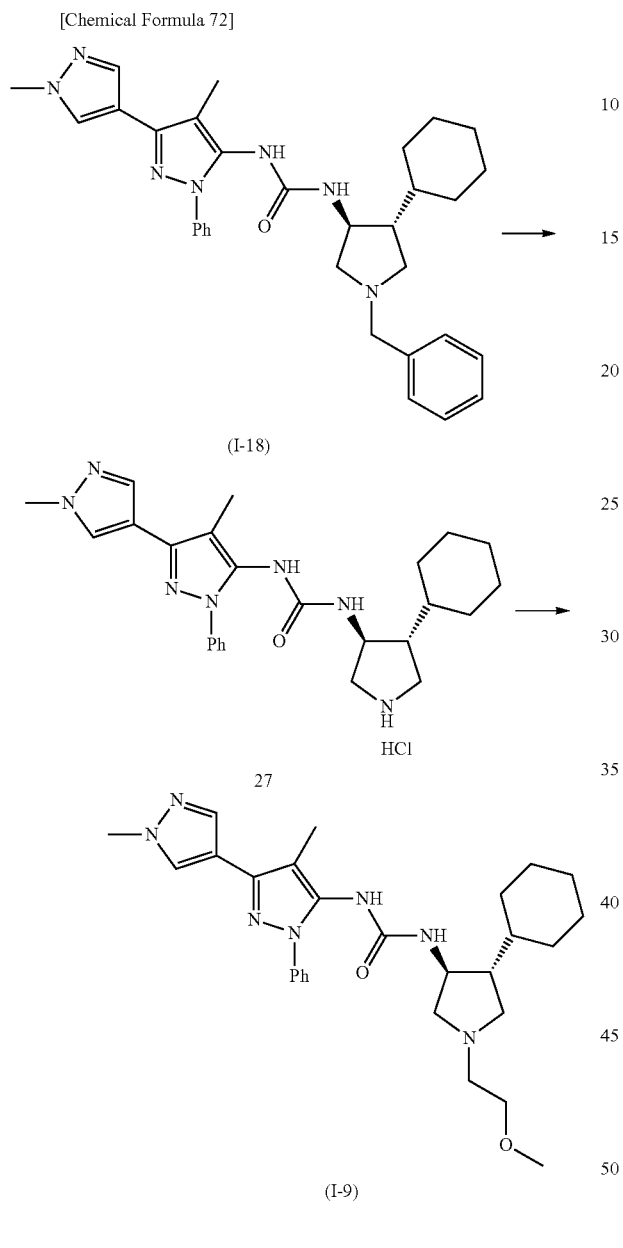

(I-9)

Step 1 Synthesis of Compound 27

Compound (I-18) (175 mg, 0.325 mmol) was dissolved in methanol (3.5 mL), and 2 mol/L hydrochloric acid-methanol solution (195 μL, 0.391 mmol) and palladium hydroxide (52.5 mg) were added to the solution. The reaction mixture was stirred for 12 hours under hydrogen atmosphere and filtered through celite pad. The filtrate was concentrated under reduced pressure to give Compound 27 (148 mg, Yield 94%) as a crude product.

Step 2 Synthesis of Compound (I-9)

Compound (I-9) (racemate, 33.9 mg, Yield 24%) was obtained as white solids in the same manner as described in the step 4 of Example 6 by using Compound 27 (134 mg, 0.277 mmol) as the starting material.

1H-NMR (CDCl$_3$) δ: 0.67-0.94 (m, 2H), 1.05-1.25 (m, 4H), 1.54 (d, J=13.1 Hz, 2H), 1.62-1.70 (m, overlapped with H2O signal, 4H), 1.75 (t, J=9.4 Hz, 2H), 2.15 (s, 3H), 2.33 (dd, J=10.2, 7.7 Hz, 1H), 2.38-2.59 (m, 2H), 2.62-2.89 (m, 1H), 2.95-3.06 (m, 1H), 3.11-3.47 (m, 5H), 3.96 (s, 3H), 5.20 (d, J=8.5 Hz, 1H), 5.92 (brs, 1H), 7.33 (t, J=7.4 Hz, 1H), 7.42 (t, J=7.8 Hz, 2H), 7.55 (d, J=8.0 Hz, 2H), 7.75 (s, 1H), 7.86 (s, 1H).

Example 10

Synthesis of Compound (I-14)

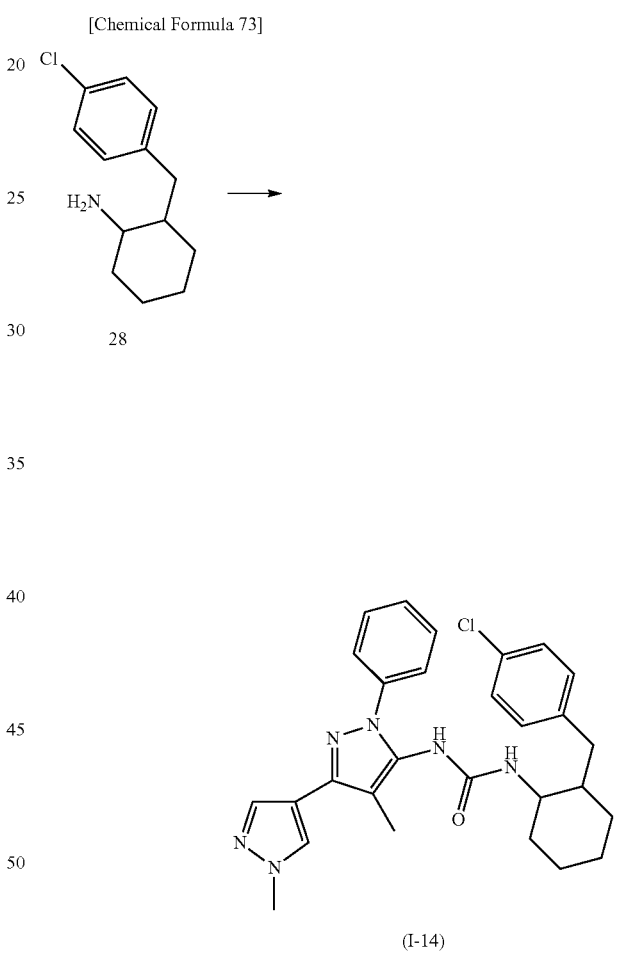

Compound 28 (11 mg, 0.05 mmol) was dissolved in tetrahydrofuran (1.5 mL) and Compound X (19 mg, 0.05 mmol) was added to the solution. After the reaction mixture was stirred at room temperature for 4 hours, the mixture was concentrated by using Genevac. The residue was dissolved in DMSO (1 mL) and purified by reverse phase HPLC (basic mobile phase) to give Compound (I-14) (19.8 mg, Yield 79%) as diastereoisomer mixtures.

$^1$H-NMR (CDCl$_3$) δ: 0.68-1.80 (m, 9H), 2.07-2.24 (m, 4H), 2.36 (dd, J=13.6, 6.3 Hz, 1H), 3.90-4.00 (m, 1H), 3.98 (s, 3H), 4.41 (d, J=9.3 Hz, 0.15H), 4.70 (d, J=9.0 Hz, 0.85H), 5.91 (s, 0.15H), 5.95 (s, 0.85H), 6.87-6.94 (m, 2H), 7.15-

7.21 (m, 2H), 7.29-7.48 (m, 3H), 7.58 (d, J=7.5 Hz, 0.3H), 7.62 (d, J=7.5 Hz, 1.7H), 7.80 (s, 1H), 7.91 (s, 1H).

Example 11

Synthesis of Compound (I-8)

[Chemical Formula 74]

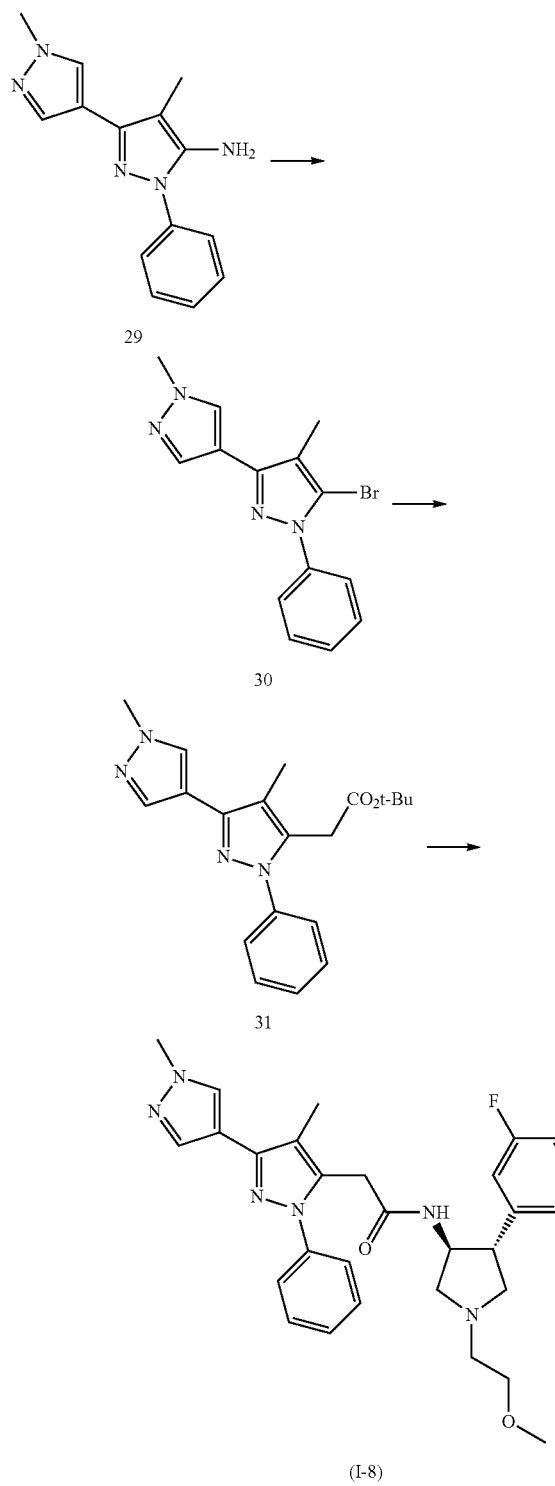

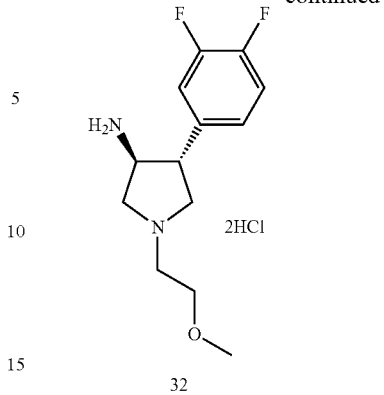

Step 1 Synthesis of Compound 30

Copper (II) bromide (229 mg, 1.03 mmol) was dissolved in acetonitrile (4 mL) under nitrogen atmosphere, and tert-butyl nitrite (0.142 mL, 1.18 mmol) was added to the solution under ice-cooling bath and the reaction mixture was stirred for 5 minutes. Compound 29 (200 mg, 0.79 mmol), which can be synthesized in accordance with the known method (WO2012158413), was added little by little to the mixture and stirred at room temperature for 1 hour.

Saturated ammonium chloride aqueous solution and saturated sodium hydrogen carbonate aqueous solution were added to the reaction mixture. The mixture was extracted with ethylacetate. The organic layer was washed with water and brine, and dried over sodium sulfate. The solvent was removed under reduced pressure and the obtained residue was purified by silicagel column chromatography (hexane-ethylacetate) to give Compound 30 (130 mg, Yield<52%) including an impurity.

LC/MS (Method 1) RT=1.99, MS (m/z)=317.15

Step 2 Synthesis of Compound 31

Compound 30 (120 mg, 0.378 mmol) obtained in the step 1 was dissolved in tetrahydrofuran (4 mL), bis(dibenzylideneacetone)palladium (0) (21.8 mg, 0.038 mmol), 1,2,3,4,5-pentaphenyl-1'-(di-tert-butylphosphino)ferrocene (26.9 mg, 0.038 mmol) and 0.5 mol/L diethyl ether solution of (2-tert-butoxy-2-oxoethyl)zinc chloride (3.41 mL, 1.70 mmol) were added to the solution, and the reaction mixture was stirred at room temperature for 20 hours. Water was added to the mixture. The mixture was extracted with ethylacetate. The organic layer was washed with water and brine, dried over anhydrous sodium sulfate. The solvent was removed under reduced pressure and the obtained residue was purified by silicagel column chromatography (hexane-ethylacetate) to give Compound 31 (54 mg, Yield 41%).

LC/MS (Method 3) RT=2.10, MS (m/z)=353.05

Step 3 Synthesis of Compound (I-8)

Compound 31 (54 mg, 0.153 mmol) was dissolved in dichloromethane (2 mL), TFA (1 mL, 12.98 mmol) was added to the solution and the reaction mixture was stirred at room temperature for 4 hours. The solvent was removed under reduced pressure. To the obtained residue was added dichloromethane (2 mL), followed by addition of HATU (70 mg, 0.184 mmol), Compound 32 (60.5 mg, 0.184 mmol) which can be synthesized in accordance with the known method (WO2012158413) and triethylamine (0.212 mL, 1.53 mmol) under ice-cooling bath, and the reaction mixture was stirred at room temperature for 30 minutes. Saturated sodium hydrogen carbonate aqueous solution was added to the mixture. The mixture was extracted with ethylacetate. The organic layer was washed with saturated sodium hydrogen carbonate aqueous solution and brine, and dried over sodium sulfate. The solvent was removed under reduced pressure and the obtained residue was purified by amino silicagel column chromatography (hexane-ethylacetate) to give Compound (I-8) (41 mg, Yield 50%).

$^1$H-NMR (CDCl$_3$) δ: 2.17 (s, 3H), 2.35-2.40 (m, 1H), 2.61-2.73 (m, 3H), 2.83-2.87 (m, 1H), 2.93-2.99 (m, 1H), 3.24-3.28 (m, 1H), 3.34 (s, 3H), 3.46-3.48 (m, 2H), 3.58 (s, 2H), 3.97 (s, 3H), 4.45-4.52 (m, 1H), 5.92 (d, J=8.4 Hz, 1H), 6.90-6.93 (br m, 1H), 7.00-7.09 (m, 2H), 7.35-7.43 (m, 5H), 7.76 (s, 1H), 7.87 (s, 1H).

Example 12

Synthesis of Compound I-44

[Chemical Formula 75]

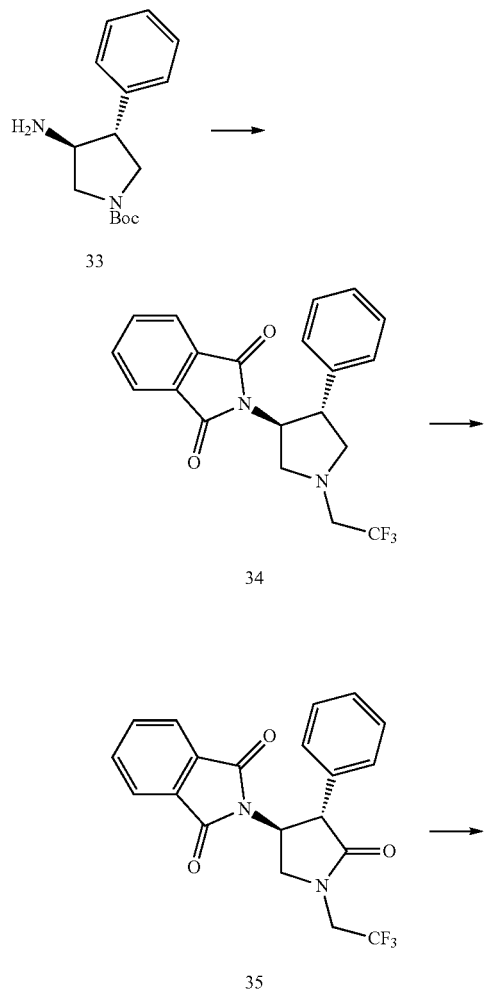

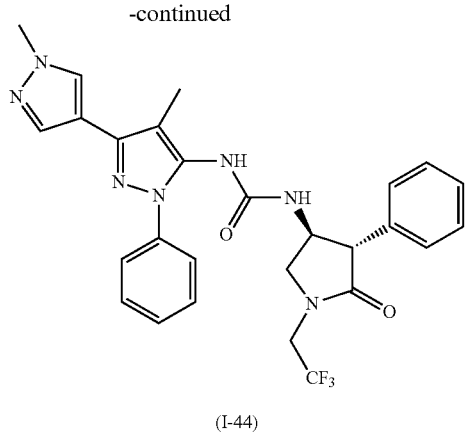

(I-44)

Step 1 Synthesis of Compound 34

To a solution of phthaloyl chloride (0.086 mL, 0.60 mmol) in dichloromethane (2 mL) were added dropwise 2 mL of dichloromethane solution of Compound 33 (150 mg, 0.572 mmol) and triethylamine (0.277 mL, 2.00 mmol) under ice-cooling bath, and the reaction mixture was stirred at room temperature for 2 hours under nitrogen atmosphere. Sodium hydrogen carbonate aqueous solution was added to the mixture. The mixture was extracted with ethylacetate. The organic layer was washed with aqueous citric acid solution, saturated sodium hydrogen carbonate aqueous solution and brine, and dried over anhydrous sodium sulfate. The solvent was removed under reduced pressure, the obtained residue was dissolved in dichloromethane (2 mL). TFA (0.5 mL) was added to the solution and the mixture was stirred at room temperature for 1 hour. After the solvent was removed under reduced pressure, 4 mol/L hydrochloric acid in dioxane was added and the solvent was removed under reduced pressure. The obtained residue was dissolved in DMF (3 mL), triethylamine (0.476 mL, 3.43 mmol) and 2,2,2-trifluoroethyl trifluoromethanesulfonate (0.099 mL, 0.686 mmol) were added to the solution and the reaction mixture was stirred at room temperature for 2 hours. EDC hydrochloride (110 mg, 0.572 mmol) was added to the mixture, and the mixture was stirred at room temperature for 5 hours. Sodium hydrogen carbonate aqueous solution was added to the mixture. The mixture was extracted with ethylacetate. The organic layer was washed with water and brine, and dried over sodium sulfate. The solvent was removed under reduced pressure and the obtained residue was purified by silicagel column chromatography (hexane-ethylacetate) to give Compound 34 (107 mg, Yield<50%) including an impurity.

LC/MS (Method 3) RT=2.45, MS (m/z)=375.00

Step 2 Synthesis of Compound 35

Compound b-2 (50 mg, 0.134 mmol) obtained in step 1 was dissolved in ethylacetate (1.5 mL), 10% sodium periodate aqueous solution (1.43 mL, 0.668 mmol) and ruthenium dioxide hydrate (1.0 mg) were added to the solution, and the reaction mixture was stirred at room temperature for 4 hours. 2-Propanol (0.041 mL, 0.534 mmol) was added to the mixture. The mixture was stirred at room temperature for additional 10 minutes. Water was added to the mixture, and the mixture was extracted with ethylacetate. The organic layer was washed with brine and dried over sodium sulfate.

The solvent was removed under reduced pressure to give Compound 35 (46 mg) as mixtures with 2-oxo isomer.

LC/MS (Method 3) RT=2.06, MS (m/z)=389.00, RT=2.15, MS (m/z)=389.00

Step 3 Synthesis of Compound I-44

Compound 35 (46 mg) obtained in step 2 was dissolved in ethanol (0.75 mL), hydrazine hydrate (7.2 μL, 0.148 mmol) was added to the solution, and the reaction mixture was stirred at room temperature for 49 hours. The solvent was removed under reduced pressure. Tetrahydrofuran (2 mL), triethylamine (0.033 mL, 0.237 mmol) and Compound X (66.3 mg, 0.178 mmol) were added to the residue, and the mixture was stirred at room temperature for 45 minutes. 0.1 mol/L hydrochloric acid was added to the mixture. The mixture was extracted with ethylacetate. The organic layer was washed with 1 mol/L hydrochloric acid, saturated sodium hydrogen carbonate aqueous solution and brine, and dried over sodium sulfate. The solvent was removed under reduced pressure and the residue was purified by diol silicagel column chromatography (hexane-ethylacetate), and then purified by reverse phase HPLC to give Compound (I-44) (racemate, 12.5 mg, Yield 20%).

$^1$H-NMR (CDCl$_3$) δ: 2.02 (s, 3H), 3.21-3.25 (m, 1H), 3.48 (d, J=8.5 Hz, 1H), 3.78-4.01 (m, 6H), 4.38-4.46 (m, 1H), 5.13 (d, J=6.5 Hz, 1H), 6.26 (s, 1H), 7.07-7.10 (br m, 2H), 7.26-7.43 (m, 8H), 7.73 (s, 1H), 7.83 (s, 1H).

Example 13

Synthesis of Compound (I-26)

[Chemical Formula 76]

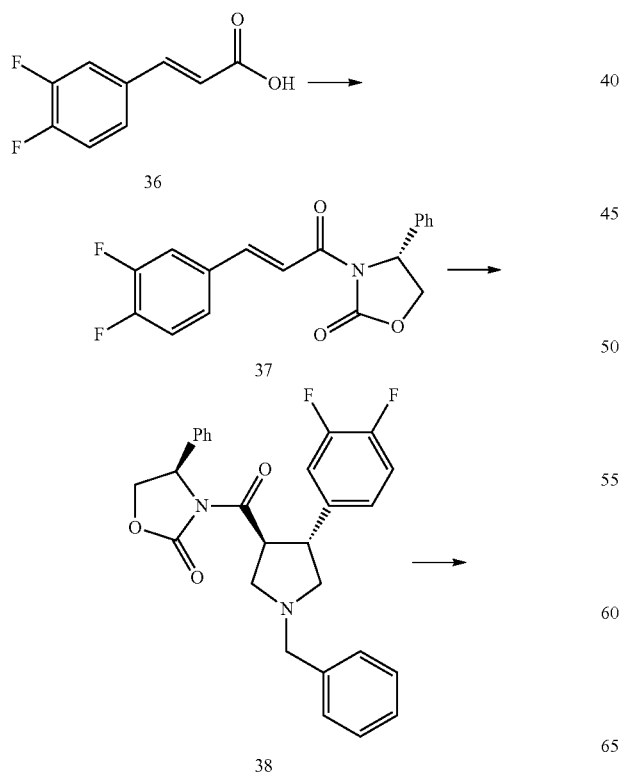

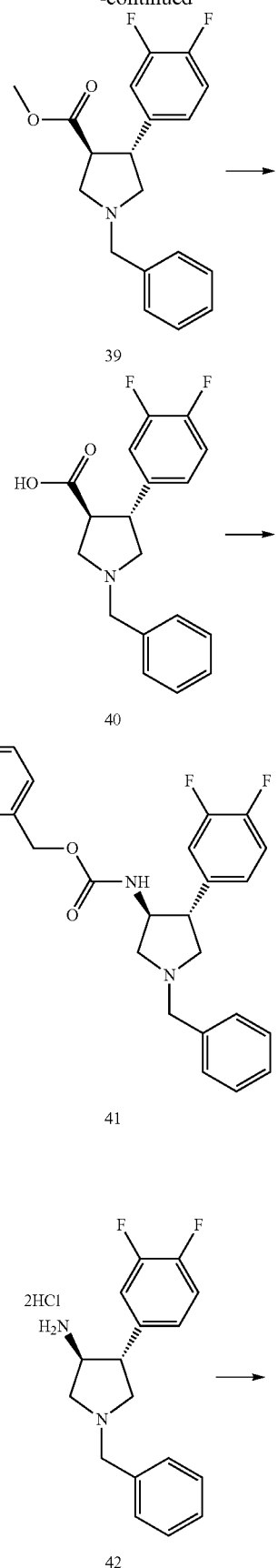

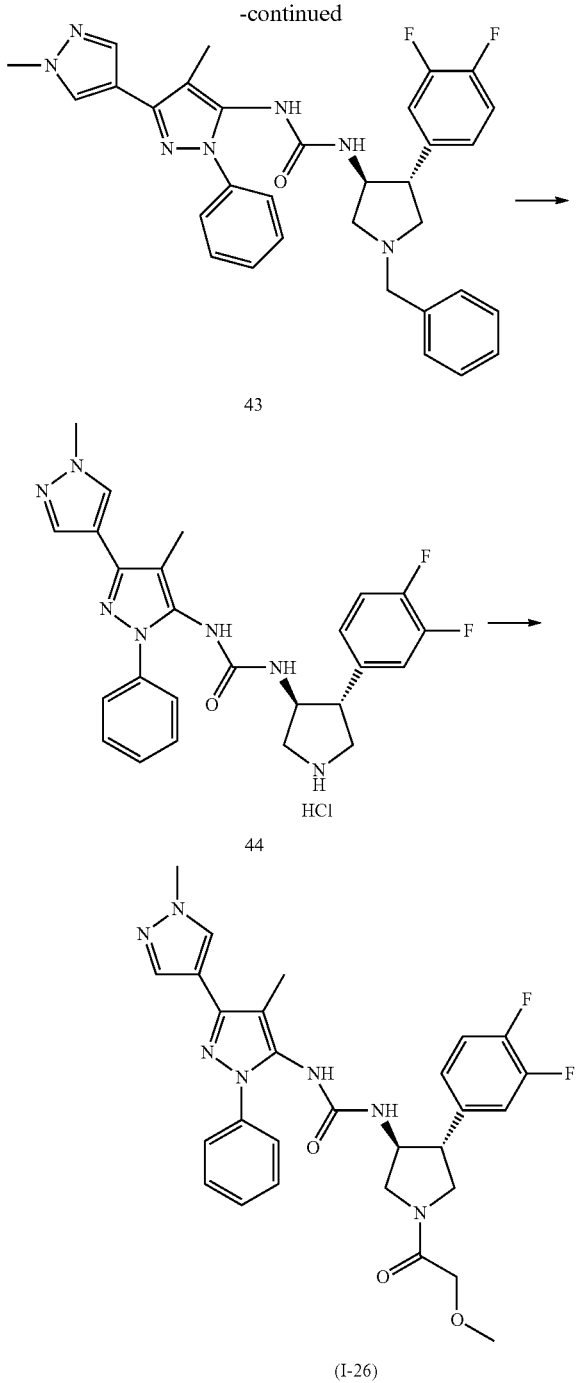

43

44

(I-26)

Step 1 Synthesis of Compound 37

In accordance with the method described in WO2012/158413 Preparation D (p81), Compound 37 was obtained (4.42 g, Yield 82%).

1H-NMR (CDCl3) δ: 4.34-4.35 (m, 1H), 4.76 (t, J=8.8 Hz, 1H), 5.55-5.56 (m, 1H), 7.17 (q, J=8.6 Hz, 1H), 7.32-7.39 (m, 7H), 7.66 (d, J=15.6 Hz, 1H), 7.85 (d, J=15.6 Hz, 1H).

Step 2 Synthesis of Compound 38

To Compound 37 (4.42 g, 13.4 mmol) were added toluene (33 mL), N-benzyl-1-methoxy-N-((trimethylsilyl)methyl) methanamine (4.12 mL, 16.10 mmol) and TFA (0.103 mL, 1.34 mmol), and the reaction mixture was stirred at room temperature for 3 hours. Water was added to the mixture, and the mixture was extracted with ethylacetate. The organic layer was washed with saturated sodium bicarbonate aqueous solution and brine, and dried over anhydrous sodium sulfate. The solvent was removed under reduced pressure and the obtained residue was purified by silicagel column chromatography (hexane-ethylacetate) to give Compound 38 (3.86 g, Yield 62%).

$^1$H-NMR (CDCl$_3$) δ: 2.63 (t, J=8.2 Hz, 2H), 3.00 (t, J=8.0 Hz, 1H), 3.32 (t, J=9.4 Hz, 1H), 3.54 (d, J=13.1 Hz, 1H), 3.70 (d, J=13.3 Hz, 1H), 3.93-3.91 (m, 1H), 4.21-4.24 (m, 1H), 4.65 (t, J=9.2 Hz, 1H), 5.38-5.41 (m, 1H), 7.02-7.05 (m, 2H), 7.13-7.15 (m, 1H), 7.25-7.29 (m, 16H), 7.38-7.39 (m, 3H).

Step 3 Synthesis of Compound 39

To Compound 38 (14.6 g, 31.6 mmol) were added methanol (146 mL) and samarium (III) trifluoromethanesulfonate (1.89 g, 3.16 mmol), and the reaction mixture was stirred at 60° C. for 10 minutes. Water was added to the mixture, and the mixture was extracted with ethylacetate. The organic layer was washed with saturated sodium bicarbonate aqueous solution and brine, and dried over anhydrous sodium sulfate. The solvent was removed under reduced pressure and the obtained residue was purified by silicagel column chromatography (hexane-ethylacetate) to give Compound 39 (9.13 g, Yield 87%).

$^1$H-NMR (CDCl$_3$) δ: 0.87-0.89 (m, 1H), 1.24-1.26 (m, 2H), 1.56 (s, 5H), 2.74-2.77 (m, 2H), 2.92 (t, J=8.8 Hz, 1H), 2.99-3.03 (m, 1H), 3.11 (t, J=8.7 Hz, 1H), 3.59-3.62 (m, 1H), 3.64-3.67 (m, 4H), 6.96-7.12 (m, 2H), 7.12-7.23 (m, 1H), 7.29-7.41 (m, 4H).

Step 4 Synthesis of Compound 40

To Compound 39 (5.95 g, 18.0 mmol) were added methanol (60 mL), tetrahydrofuran (60 mL) and sodium hydroxide (2 mol/L aqueous solution, 26.9 mL, 53.9 mmol), and the reaction mixture was stirred at room temperature for 3 hours. After the mixture was adjusted to pH4 with hydrochloric acid (2 mol/L aqueous solution), water was added to the mixture. The mixture was extracted with chloroform, and dried over anhydrous sodium sulfate. The solvent was removed under reduced pressure to give Compound 40 (5.0 g, Yield 88%).

LC/MS (Method 2) RT=1.36, MS (m/z)=318.00

Step 5 Synthesis of Compound 41

To Compound 40 (4.39 g, 13.8 mmol) were added toluene (43.9 mL), DPPA (4.16 mL, 19.4 mmol) and triethylamine (4.79 mL, 34.6 mmol), and the reaction mixture was stirred at 90° C. for 5 hours. Benzyl alcohol (2.88 mL, 27.7 mmol) was added to the mixture, and the mixture was stirred at 90° C. overnight. Water was added to the mixture. The mixture was extracted with ethylacetate. The organic layer was washed with saturated sodium bicarbonate aqueous solution and brine, and dried over anhydrous sodium sulfate. The solvent was removed under reduced pressure and the obtained residue was purified by silicagel column chromatography (hexane-ethylacetate) to give Compound 41 (2.76 g, Yield 47%).

$^1$H-NMR (CDCl$_3$) δ: 2.45-2.47 (m, 1H), 2.65-2.66 (m, 1H), 2.93-2.95 (m, 1H), 3.12 (t, J=12.7 Hz, 2H), 3.64-3.67 (m, 2H), 4.21 (s, 1H), 5.07-5.09 (m, 3H), 7.00-7.12 (m, 3H), 7.28-7.42 (m, 7H).

Step 6 Synthesis of Compound 42

To Compound 41 (2.62 g, 6.20 mmol) was added TFA (26 mL), and the reaction mixture was stirred at 90° C. for 5 hours. Toluene (10 mL) was added to the mixture, and the solvent was removed under reduced pressure twice by azeotropy. Hydrochloric acid (4 mol/L in dioxane, 6.20 mL, 24.8 mmol) was added to the residue, and the solvent was removed under reduced pressure to give Compound 42 (2.75 g).
LC/MS (Method 1) RT=0.78, MS (m/z)=289.00

Step 7 Synthesis of Compound 43

To Compound 42 (2.24 g, 6.20 mmol) were added tetrahydrofuran (22.4 mL), Compound X (2.43 g, 6.51 mmol) and DIEA (4.33 mL, 24.8 mmol), and the reaction mixture was stirred at room temperature for 1 hour. Water was added to the mixture. The mixture was extracted with ethylacetate. The organic layer was washed with saturated sodium bicarbonate aqueous solution and brine, and dried over anhydrous sodium sulfate. The solvent was removed under reduced pressure and the obtained residue was purified by silicagel column chromatography (hexane-ethylacetate) to give Compound 43 (4.76 g, Yield 96%).
$^1$H-NMR (CDCl$_3$) δ: 2.09 (s, 3H), 2.31 (t, J=8.9 Hz, 1H), 2.57 (s, 1H), 2.77 (t, J=8.7 Hz, 1H), 2.88 (br s, 1H), 3.05 (t, J=8.6 Hz, 1H), 3.55 (s, 2H), 3.98 (s, 3H), 5.11 (br s, 1H), 6.84 (br s, 1H), 6.91-7.08 (m, 2H), 7.13-7.23 (m, 1H), 7.23-7.28 (m, 4H), 7.28-7.33 (m, 1H), 7.36 (t, J=7.5 Hz, 2H), 7.47 (d, J=7.8 Hz, 2H), 7.77 (s, 1H), 7.89 (s, 1H).

Step 8 Synthesis of Compound 44

To Compound 43 (3.34 g, 5.88 mmol) were added methanol (20 mL), tetrahydrofuran (5 mL), palladium hydroxide (1.03 g, 3.67 mmol) and hydrochloric acid (2 mol/L aqueous solution, 3.53 mL, 7.06 mmol), and the reaction mixture was stirred at room temperature for 5 hours under hydrogen atmosphere. The mixture was filtered through celite pad, and the solvent was removed under reduced pressure to give Compound 44 (3.01 g, Yield 100%).
$^1$H-NMR (DMSO-D$_6$) δ: 1.90 (s, 3H), 2.98-3.00 (m, 1H), 3.19-3.22 (m, 2H), 3.63-3.66 (m, 1H), 3.89 (s, 3H), 4.09-4.11 (m, 1H), 4.41 (t, J=8.9 Hz, 1H), 6.95 (br s, 1H), 7.17 (s, 1H), 7.36-7.43 (m, 6H), 7.74 (s, 1H), 8.04 (s, 1H), 8.22 (s, 1H), 9.15-9.32 (br m, 2H).

Step 9 Synthesis of Compound (I-26)

To Compound 9 (20 mg, 0.039 mmol) were added dichloromethane (200 μL), 2-methoxyacetyl chloride (4.46 mg, 0.041 mmol) and DIEA (27.2 μL, 0.156 mmol), and the mixture was stirred at room temperature for 30 minutes. The solvent was removed under reduced pressure and the obtained residue was purified by reverse phase HPLC (basic mobile phase) to give Compound (I-26) (18.1 mg, Yield 84%).
$^1$H-NMR (CDCl$_3$) δ: 2.03 (d, J=4.8 Hz, 3H), 3.16-3.24 (m, 2H), 3.37 (d, J=5.5 Hz, 3H), 3.44-3.46 (m, 1H), 3.82-3.92 (m, 1H), 3.94-3.99 (m, 5H), 4.38-4.41 (br m, 1H), 5.08 (br s, 1H), 6.23-6.26 (br m, 1H), 6.95-7.07 (m, 3H), 7.32-7.42 (m, 5H), 7.73 (s, 1H), 7.85 (s, 1H).

Example 14

Synthesis of Compound (I-31)

[Chemical Formula 77]

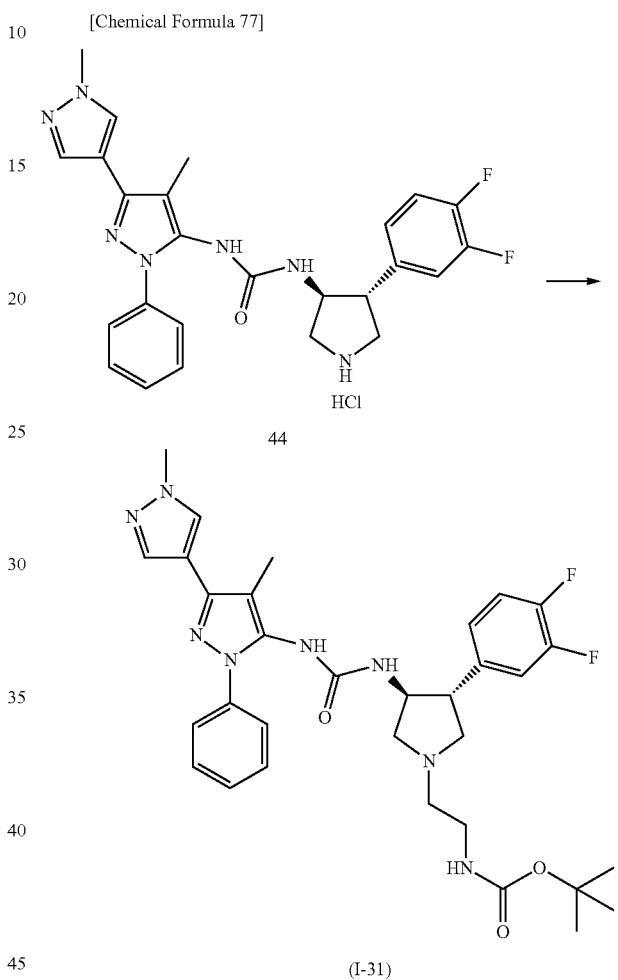

Step 1 Synthesis of Compound (I-31)

To Compound 44 (120 mg, 0.233 mmol) were added DMF (1.2 mL), tert-butyl(2-bromoethyl)carbamate (54.9 mg, 0.245 mmol), sodium iodide (7.00 mg, 0.047 mmol) and DIEA (163 μL, 0.934 mmol), and the reaction mixture was stirred at 70° C. for 7 hours. Water was added to the mixture. The mixture was extracted with ethylacetate. The organic layer was washed with saturated sodium bicarbonate aqueous solution and brine, and dried over anhydrous sodium sulfate. The solvent was removed under reduced pressure and the obtained residue was purified by silicagel column chromatography (hexane-ethylacetate) to give Compound (I-31) (94.3 mg, Yield 65%).
$^1$H-NMR (CDCl$_3$) δ: 1.26 (t, J=7.2 Hz, 1H), 1.44 (s, 9H), 2.14 (s, 3H), 2.41-2.44 (br m, 1H), 2.53-2.55 (br m, 3H), 2.87 (s, 2H), 3.09 (s, 1H), 3.18 (s, 2H), 3.98 (s, 3H), 4.30 (br s, 1H), 4.79 (br s, 1H), 4.90 (br s, 1H), 6.86-6.89 (br m, 1H), 6.97-7.05 (m, 2H), 7.34-7.36 (m, 1H), 7.42 (t, J=7.7 Hz, 2H), 7.51 (d, J=7.8 Hz, 2H), 7.78 (s, 1H), 7.89 (s, 1H).

Example 15

Synthesis of Compound (I-42)

[Chemical Formula 78]

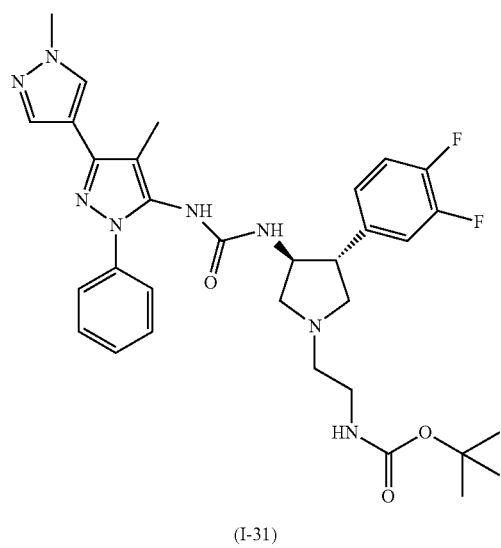

(I-31)

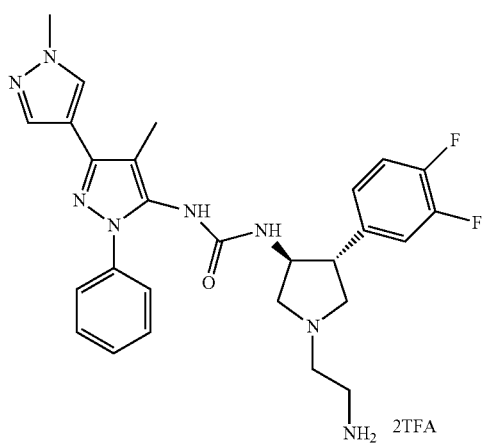

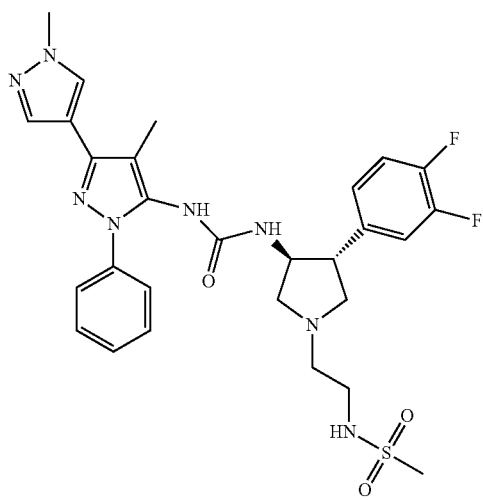

(I-42)

Step 1 Synthesis of Compound 45

To Compound (I-31) (88 mg, 0.142 mmol) were added dichloromethane (600 μL) and TFA (260 μL, 3.37 mmol), and the reaction mixture was stirred under ice-cooling bath for 3 hours. Toluene (1 mL) was added to the mixture, and the solvent was removed under reduced pressure twice by azeotropy to give Compound 45 (183.3 mg).

$^1$H-NMR (DMSO-D$_6$) δ: 1.96 (s, 3H), 2.63-2.66 (m, 2H), 2.85 (t, J=8.4 Hz, 1H), 2.98-3.09 (m, 3H), 3.89 (s, 3H), 4.06-4.08 (m, 1H), 6.86-6.89 (br m, 1H), 7.07-7.09 (br m, 1H), 7.29-7.34 (m, 3H), 7.43 (t, J=7.8 Hz, 2H), 7.50 (d, J=8.0 Hz, 2H), 7.74 (s, 1H), 8.00 (br s, 1H), 8.04 (s, 1H).

Step 2 Synthesis of Compound (I-42)

To Compound 45 (25 mg, 0.033 mmol) were added DMF (250 μL), methanesulfonyl chloride (2.84 μL, 0.037 mmol) and DIEA (23.3 μL, 0.134 mmol), and the reaction mixture was stirred at room temperature for 30 minutes. The solvent was removed under reduced pressure and the obtained residue was purified by reverse phase HPLC (basic mobile phase) to give Compound (I-42) (11.7 mg, Yield 59%).

$^1$H-NMR (CDCl$_3$) δ: 2.14 (s, 3H), 2.45 (t, J=8.7 Hz, 1H), 2.65-2.67 (m, 3H), 2.86-2.88 (m, 1H), 2.93 (s, 4H), 3.10-3.18 (m, 3H), 3.98 (s, 3H), 4.31-4.34 (br m, 1H), 4.74-4.76 (br m, 1H), 4.97-4.99 (br m, 1H), 5.84-5.86 (br m, 1H), 6.87-6.90 (br m, 1H), 6.95-7.10 (m, 2H), 7.28-7.33 (m, 2H), 7.42 (t, J=7.7 Hz, 2H), 7.49-7.51 (m, 2H), 7.79 (s, 1H), 7.89 (s, 1H).

Example 16

Synthesis of Compound (I-3)

[Chemical Formula 79]

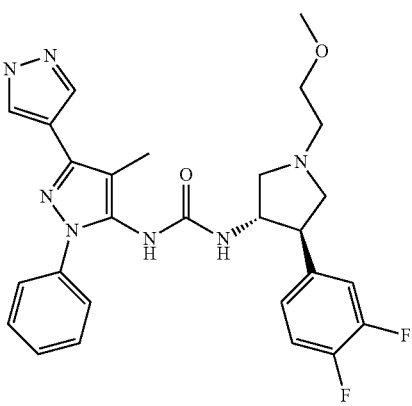

46

115

-continued

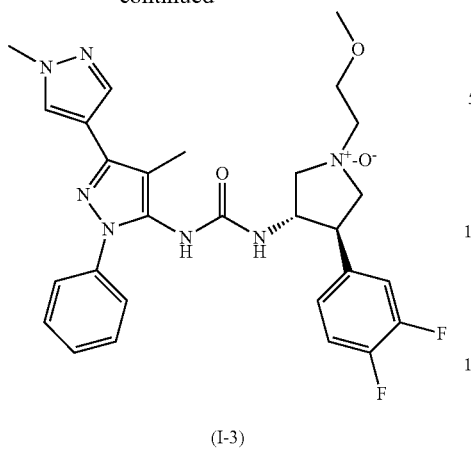

(I-3)

[Seed Cultivation]

The seed medium which was composed of 5 g/L glucose, 1.5 g/L pinedex TK-16 (Matsutani chemical industry), 10 g/L yeast extract, 0.6 g/L $K_2HPO_4$, 0.3 g/L $KH_2PO_4$, 0.1 g/L $MgSO_4 \cdot 7H_2O$, 0.1 g/L $CaCl_2 \cdot 2H_2O$, 0.05 g/L NaCl, and 1 ml/L metal mixture (0.01% $H_3BO_3$, 0.5% $FeSO_4 \cdot 7H_2O$, 0.005% KI, 0.2% $CoCl_2 \cdot 2H_2O$, 0.02% $CuSO_4 \cdot 5H_2O$, 0.2% $MnCl_2 \cdot 4H_2O$, 0.4% $ZnSO_4 \cdot 7H_2O$, 0.1% $H_2SO_4$) was prepared and autoclaved.

The actinomycetes growing on an agar medium which was containing 2 g/L yeast extract, 10 g/L starch, and 15 g/L agar was inoculated into 100 mL of seed culture in 500 mL wide-mouthed erlenmyer flask.

The seed culture was shaken at 180 rpm at 28° C. for 4 days.

[Growing Cell Reaction]

The contents of conversion medium were same as the seed medium. 0.36 g/mL of Compound 46 (synthesis method was described in WO2012158413) dissolved in 12.5 µl DMSO was added into 40 mL conversion medium in 500 mL wide-mouthed erlenmyer flasks (9 flasks each). 2 mL of seed was inoculated and cultivated with shaking at 180 rpm at 28° C. for 3 days. The supernatant of the centrifuged culture was analyzed by UPLC using reverse phase column and calculated the conversion rate. After 3 days, Compound (I-3) was obtained in 80% conversion rate.

[Extraction and Purification]

The supernatant and the cell pellet were separated from 360 mL of culture by centrifugation. 200 mL of ethyl acetate was added to the supernatant for extraction. Extraction works repeated 3 times. Ethyl acetate layer was collected, evaporated, and then prepared 500 µl of DMSO solution. 30-50% acetonitril gradient separation with 0.05% TFA was done using ODS-HG-5 column (Develosil, 20×150 mm). After lyophilization of fractions, 27 mg of Compound (I-3) was obtained (75% yield, 99% purity).

$^1$H-NMR (CDCl$_3$) δ: 2.05 (s, 3H), 3.38 (s, 3H), 3.54 (t, J=10 Hz, 1H), 3.70 (br, s, 2H), 3.76-3.82 (m, 1H), 3.85 (m, 2H), 3.90 (s, 3H), 4.02-4.29 (m, 2H), 4.56-4.76 (m, 1H), 6.83 (m, 1H), 7.01 (m, 2H), 7.28 (t, J=7.3 Hz, 1H), 7.35 (t, J=7.9 Hz, 2H), 7.48 (d, J=7.3 Hz, 2H), 7.65 (s, 1H), 7.81 (s, 1H).

116

Example 17

Synthesis of Compound (I-15)

[Chemical Formula 80]

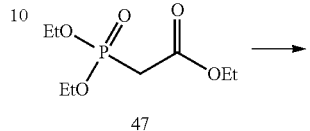

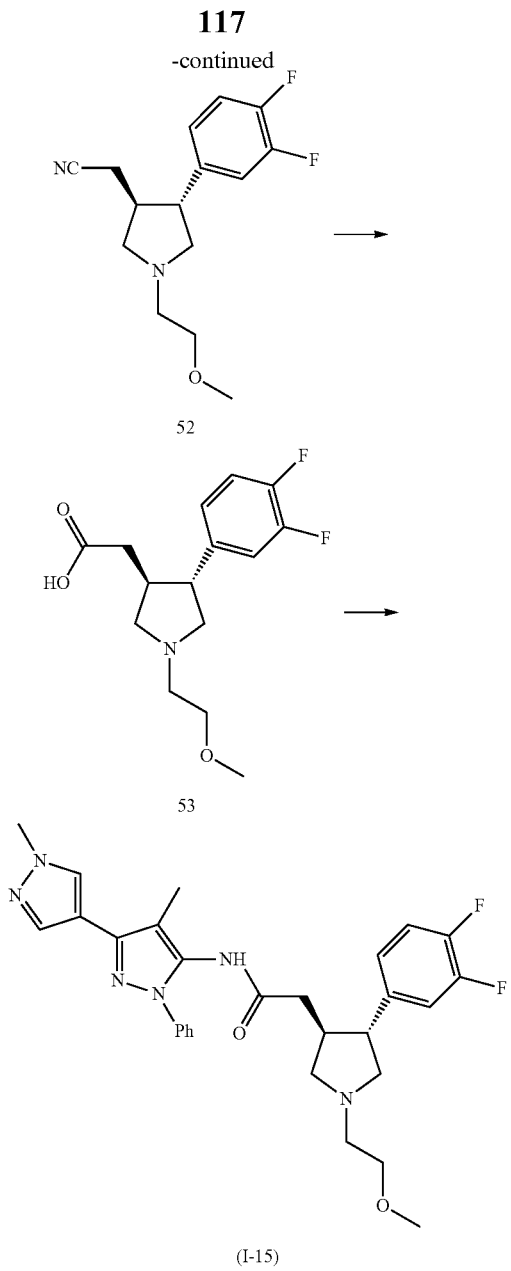

Step 1 Synthesis of Compound 48

Compound 47 (1.58 g, 7.04 mmol) was dissolved in tetrahydrofuran (30 mL) under nitrogen atmosphere, sodium hydride (366 mg, 9.15 mmol) was added to the solution under ice-cooling bath and the mixture was stirred at room temperature for 30 minutes. Then, 3,4-difluorobenzaldehyde (1 g, 7.04 mmol) was added to the reaction mixture and the mixture was stirred at room temperature for 1 hour. Saturated ammonium chloride aqueous solution was added to the mixture. The mixture was extracted with ethylacetate. The organic layer was washed with water and dried over anhydrous magnesium sulfate. The solvent was removed under reduced pressure to give Compound 48 (1.74 g, Yield 117%).

$^1$H-NMR (CDCl$_3$) δ: 1.34 (t, J=6.4 Hz, 3H), 4.27 (q, J=7.1 Hz, 2H), 6.35 (d, J=16.1 Hz, 1H), 7.18 (dd, J=17.3, 8.7 Hz, 1H), 7.24-7.27 (m, 1H), 7.33-7.35 (m, 1H), 7.58 (d, J=16.1 Hz, 1H).

LC/MS (Method 1) RT=2.14, MS (m/z)=212.95.

Step 2 Synthesis of Compound 49

Compound 48 (555 mg, 2.62 mmol) was dissolved in dichloromethane (4 mL), 2-methoxy-N-(methoxymethyl)-N-((trimethyl silyl)methyl)ethaneamine (913 mg, 4.45 mmol) and TFA (0.020 ml, 0.262 mmol) were added to the solution, and the reaction mixture was stirred at room temperature for 2 hours. The solvent was removed under reduced pressure to give Compound 49 (940 mg, Yield 114%) as a crude product.

Step 3 Synthesis of Compound 50

The crude Compound 49 (940 mg) was dissolved in tetrahydrofuran (8 mL) under nitrogen atmosphere, lithium aluminum hydride (99 mg, 2.62 mmol) was added to the solution under ice-cooling bath, and the reaction mixture was stirred at room temperature for 2 hours. 2 mol/L Hydrochloric acid aqueous solution was added to the mixture. The mixture was stirred for a while, and then adjusted to pH7 with 2 mol/L sodium hydroxide aqueous solution. The obtained mixture was purified by ion exchange resin (ISOLUTE™ SCX-2, eluted with 20% triethylamine-methanol solution) to give Compound 50 (450 mg, Yield 63%).

LC/MS (Method 1) RT=0.78, MS (m/z)=272.45.

Step 4 Synthesis of Compound 51

Compound 50 (410 mg) was dissolved in dichloromethane (8 mL) under nitrogen atmosphere, triethylamine (0.251 ml, 1.813 mmol) and methanesulfonyl chloride (0.130 ml, 1.662 mmol) were added to the solution under ice-cooling bath, and the reaction mixture was stirred at room temperature for 2 hours. The solvent was removed under reduced pressure to give Compound 51 (528 mg, Yield 100%) as a crude product.

LC/MS (Method 1) RT=0.87, MS (m/z)=350.35.

Step 5 Synthesis of Compound 52

Compound 51 (528 mg, 1.51 mmol) was dissolved in DMSO (8 ml), sodium cyanide (592 mg, 12.1 mmol) was added to the solution under ice-cooling bath and the mixture was stirred at 80° C. for 1 hour. Water was added to the mixture. The mixture was extracted with ethylacetate. The organic layer was washed with water and dried over anhydrous magnesium sulfate. The solvent was removed under reduced pressure to give Compound 52 (424 mg, Yield 100%) as a crude product.

LC/MS (Method 1) RT=0.84, MS (m/z)=281.00.

Step 6 Synthesis of Compound 53

Compound 52 (424 mg, 1.51 mmol) was dissolved in methanol (8 ml), 2 mol/L sodium hydroxide aqueous solution (6 ml, 12 mmol) was added to the solution and the mixture was stirred at 100° C. for 14 hours. 2 mol/L Hydrochloric acid aqueous solution was added to the reaction mixture, and the mixture was adjusted to pH7. The obtained solution was purified by reverse phase chromatography (DIAION™ HP20, eluted with acetonitrile-water) to give Compound 53 (370 mg, Yield 82%).

$^1$H-NMR (MeOD) δ: 2.06 (dd, J=15.7, 9.2 Hz, 1H), 2.19 (dd, J=15.6, 4.0 Hz, 1H), 2.52 (td, J=9.2, 3.8 Hz, 1H), 3.17-3.20 (m, 5H), 3.18 (s, 3H), 3.49 (t, J=5.1 Hz, 2H), 3.56 (ddd, J=12.6, 6.6, 4.7 Hz, 2H), 6.94-7.09 (m, 2H), 7.15 (ddd, J=11.7, 7.6, 2.1 Hz, 1H).

LC/MS (Method 1) RT=0.82, MS (m/z)=300.00.

Step 7 Synthesis of Compound (I-15)

To Compound 53 (119 mg, 0.398 mmol) were added tetrahydrofuran (4 mL), 1'-4-dimethyl-1-phenyl-1H, 1'H-[3,4'-bipyrazol]-5-amine (111 mg, 0.437 mmol), triethylamine (0.110 ml, 0.795 mmol) and HATU (181 mg, 0.477 mmol), the reaction mixture was stirred at 80° C. for 6 hours. The solvent was removed under reduced pressure and the residue was purified by reverse phase HPLC (acetonitrile-water) to give Compound (I-15) (racemate, 8.5 mg, Yield 4%).

$^1$H-NMR (CDCl$_3$) δ: 2.09 (s, 3H), 2.37 (t, J=9.0 Hz, 1H), 2.47-2.59 (m, 3H), 2.60-2.71 (m, 2H), 2.78 (t, J=9.0 Hz, 1H), 2.82-2.90 (m, 1H), 2.91-3.00 (m, 1H), 3.00-3.06 (m, 1H), 3.16 (s, 3H), 3.34-3.39 (m, 2H), 3.94 (s, 3H), 6.86-6.91 (m, 1H), 6.97-7.04 (m, 2H), 7.04-7.12 (m, 1H), 7.32-7.39 (m, 1H), 7.40-7.52 (m, 4H), 7.72 (s, 1H), 7.83 (s, 1H), 9.57 (s, 1H).

Example 18

Synthesis of Compound (I-16)

[Chemical Formula 81]

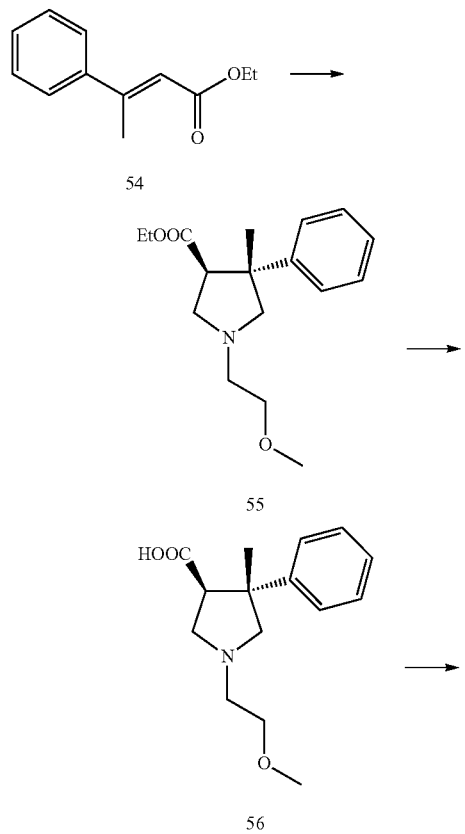

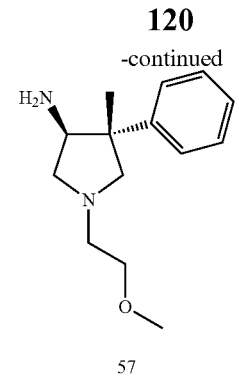

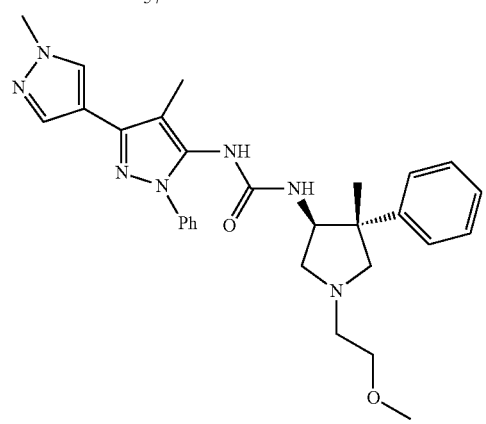

Step 1 Synthesis of Compound 55

Compound 54 (555 mg, 2.62 mmol) was dissolved in dichloromethane (4 mL), and 2-methoxy-N-(methoxymethyl)-N-((trimethylsilyl)methyl)ethaneamine (913 mg, 4.45 mmol) and TFA (0.020 ml, 0.262 mmol) were added to the solution. The mixture was stirred at room temperature for 2 hours. The solvent was removed under reduced pressure and the residue was purified by amino silicagel column chromatography (hexane-ethylacetate, followed by ethylacetate-methanol) to give Compound 55 (110 mg, Yield 36%).

$^1$H-NMR (CDCl$_3$) δ: 1.25 (t, J=7.2 Hz, 3H), 1.38 (s, 3H), 2.59-2.72 (m, 2H), 2.75-2.86 (m, 1H), 3.00 (t, J=8.8 Hz, 1H), 3.08 (t, J=8.7 Hz, 1H), 3.24 (d, J=9.5 Hz, 2H), 3.32 (t, J=8.0 Hz, 1H), 3.38 (s, 3H), 3.55 (t, J=5.8 Hz, 2H), 4.05-4.27 (m, 2H), 7.20 (t, J=7.3 Hz, 1H), 7.32 (t, J=7.8 Hz, 2H), 7.52 (d, J=7.5 Hz, 2H).

Step 2 Synthesis of Compound 56

Compound 55 (110 mg, 0.377 mmol) was dissolved in tetrahydrofuran (2 mL) and ethanol (1 mL), 2 mol/L sodium hydroxide aqueous solution (1.0 mL, 2.0 mmol) was added to the solution, and the mixture was heated to reflux for 8 hours. The solution was adjusted to pH7 by the addition of 2 mol/L hydrochloric acid aqueous solution. The solvent was removed under reduced pressure and the obtained solution was purified by reverse phase chromatography (HP-20, acetonitrile-water) to give Compound 56 (52 mg, Yield 52%).

$^1$H-NMR (MeOD) δ: 1.49 (s, 3H), 3.38 (s, 3H), 3.40-3.47 (m, 3H), 3.50 (dd, J=7.0, 5.0 Hz, 1H), 3.58 (d, J=11.8 Hz, 1H), 3.65-3.74 (m, 3H), 3.93 (d, J=11.8 Hz, 1H), 7.25 (t, J=7.3 Hz, 1H), 7.37 (t, J=7.8 Hz, 2H), 7.58 (d, J=7.5 Hz, 2H).

LC/MS (Method 1) RT=0.71, MS (m/z)=264.50

Step 3 Synthesis of Compound 57

To Compound 56 (51 mg, 0.194 mmol) were added toluene (2 ml), DPPA (0.058 ml, 0.271 mmol) and triethylamine (0.040 ml, 0.291 mmol), and the reaction mixture was stirred at 100° C. for 2 hours. After the mixture was allowed to cool to room temperature, 2 mol/L sodium hydroxide aqueous solution (2.0 mL, 4.0 mmol) was added to the mixture. The mixture was stirred for 3 hours. The solution was adjusted to pH7 by the addition of 2 mol/L hydrochloric acid aqueous solution. The aqueous layer was purified by ion exchange resin (Varian bond elut scx, eluted with 20% triethylamine-methanol) to give Compound 57 (50 mg, Yield 110%).

$^1$H-NMR (MeOD) δ: 1.34 (s, 1H), 1.37 (s, 2H), 1.89 (s, 2H), 2.59 (dd, J=9.8, 8.0 Hz, 1H), 2.65-2.78 (m, 3H), 2.80 (d, J=10.0 Hz, 1H), 3.02-3.17 (m, 1H), 3.19 (d, J=9.8 Hz, 1H), 3.35 (s, 3H), 3.53 (t, J=5.6 Hz, 2H), 3.66 (t, J=10.0 Hz, 1H), 7.13-7.21 (m, 1H), 7.23-7.37 (m, 2H), 7.39-7.47 (m, 2H).

LC/MS (Method 1) RT=0.49, MS (m/z)=235.10.

Step 4 Synthesis of Compound (I-16)

Compound 57 (50 mg, 0.123 mmol) and Compound X (80 mg, 0.123 mmol) were dissolved in DMF (1 ml) under nitrogen atmosphere, diisopropylethylamine (0.056 ml, 0.32 mmol) was added to the solution under ice-cooling bath. The reaction mixture was stirred at room temperature overnight. Water was added to the mixture. The mixture was extracted with chloroform. The organic layer was washed with water and dried over anhydrous magnesium sulfate. The solvent was removed under reduced pressure and the residue was purified by amino silicagel column chromatography (hexane-ethylacetate) to give Compound (I-16) (racemate, 60 mg, Yield 55%).

$^1$H-NMR (CDCl$_3$) δ: 1.16 (s, 3H), 2.16 (s, 3H), 2.47-2.66 (m, 3H), 2.78-2.86 (m, 3H), 3.29 (s, 3H), 3.42 (t, J=5.6 Hz, 2H), 3.96 (s, 3H), 4.61 (br s, 1H), 5.23 (d, J=8.9 Hz, 1H), 6.36 (br s, 1H), 7.16 (t, J=7.2 Hz, 1H), 7.22-7.36 (m, 5H), 7.40 (t, J=7.7 Hz, 2H), 7.53 (d, J=7.9 Hz, 2H), 7.76 (s, 1H), 7.87 (s, 1H).

Example 19

Synthesis of Compound (I-25)

[Chemical Formula 82]

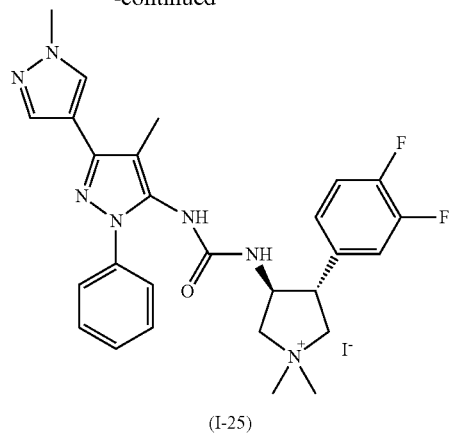

Step 1 Synthesis of Compound (I-25)

To Compound 44 (20 mg, 0.039 mmol) were added DMF (0.2 mL), methyl iodide (6.63 mg, 0.047 mmol), sodium iodide (1.17 mg, 0.0078 mmol) and DIEA (27.2 μL, 0.156 mmol), and the reaction mixture was stirred at 45° C. for 2 hours. Water was added to the mixture. The mixture was extracted with ethylacetate. The organic layer was washed with saturated sodium bicarbonate aqueous solution and brine, and dried over anhydrous sodium sulfate. The solvent was removed under reduced pressure and the obtained residue was purified by reverse phase HPLC (basic mobile phase) to give Compound (I-25) (14.4 mg, Yield 72%).

$^1$H-NMR (DMSO-D$_6$) δ: 1.90 (s, 3H), 3.25 (s, 2H), 3.68-3.71 (m, 1H), 3.91-3.95 (m, 6H), 4.54-4.72 (m, 1H), 7.23 (s, 1H), 7.30-7.31 (m, 1H), 7.36-7.38 (m, 2H), 7.46-7.51 (m, 3H), 7.73 (s, 1H), 8.03 (s, 1H), 8.48 (s, 1H).

Example 20

Synthesis of Compound I-47

[Chemical Formula 83]

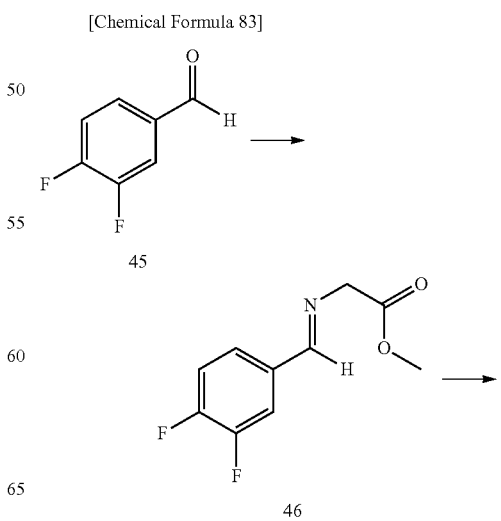

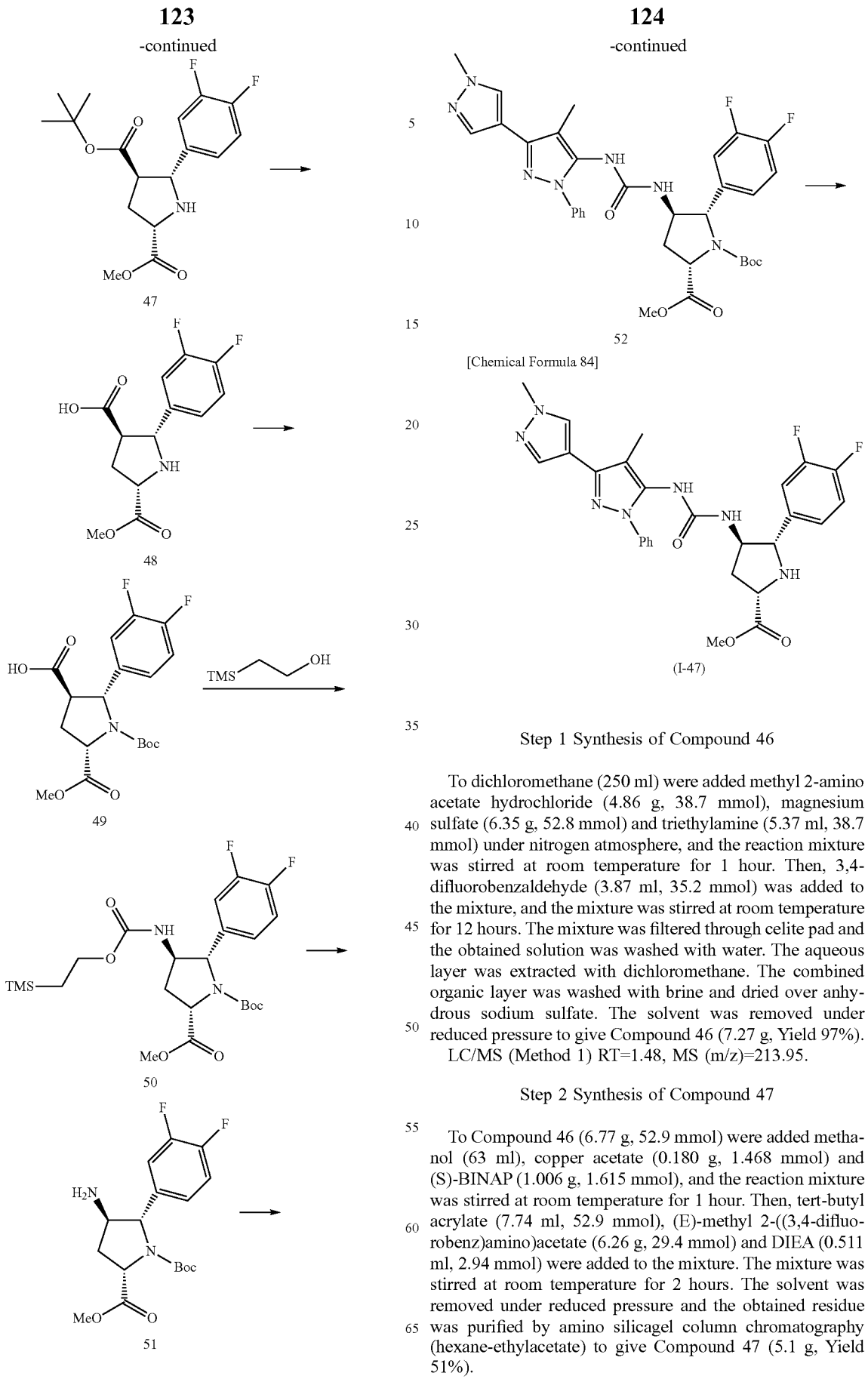

Step 1 Synthesis of Compound 46

To dichloromethane (250 ml) were added methyl 2-amino acetate hydrochloride (4.86 g, 38.7 mmol), magnesium sulfate (6.35 g, 52.8 mmol) and triethylamine (5.37 ml, 38.7 mmol) under nitrogen atmosphere, and the reaction mixture was stirred at room temperature for 1 hour. Then, 3,4-difluorobenzaldehyde (3.87 ml, 35.2 mmol) was added to the mixture, and the mixture was stirred at room temperature for 12 hours. The mixture was filtered through celite pad and the obtained solution was washed with water. The aqueous layer was extracted with dichloromethane. The combined organic layer was washed with brine and dried over anhydrous sodium sulfate. The solvent was removed under reduced pressure to give Compound 46 (7.27 g, Yield 97%).

LC/MS (Method 1) RT=1.48, MS (m/z)=213.95.

Step 2 Synthesis of Compound 47

To Compound 46 (6.77 g, 52.9 mmol) were added methanol (63 ml), copper acetate (0.180 g, 1.468 mmol) and (S)-BINAP (1.006 g, 1.615 mmol), and the reaction mixture was stirred at room temperature for 1 hour. Then, tert-butyl acrylate (7.74 ml, 52.9 mmol), (E)-methyl 2-((3,4-difluorobenz)amino)acetate (6.26 g, 29.4 mmol) and DIEA (0.511 ml, 2.94 mmol) were added to the mixture. The mixture was stirred at room temperature for 2 hours. The solvent was removed under reduced pressure and the obtained residue was purified by amino silicagel column chromatography (hexane-ethylacetate) to give Compound 47 (5.1 g, Yield 51%).

$^1$H-NMR (CDCl$_3$) δ: 1.38 (s, 9H), 2.33 (ddd, 1H, J=5.2, 8.4, 13.6 Hz), 2.38-2.48 (m, 1H), 2.45 (ddd, 1H, J=8.4, 8.8, 12.8 Hz), 2.73 (q, J=8.5 Hz, 1H), 3.78 (s, 3H), 4.02 (dd, J=8.9, 5.4 Hz, 1H), 4.33 (d, J=8.5 Hz, 1H), 7.06-7.15 (m, 1H), 7.16-7.18 (br m, 1H), 7.35 (ddd, J=11.5, 7.7, 2.2 Hz, 1H).

LC/MS (Method 1) RT=1.58, MS (m/z)=342.50.

Step 3 Synthesis of Compound 48

To a solution of Compound 47 (440 mg, 1.29 mmol) in dichloromethane (2.2 ml) was added TFA (2 ml, 26 mmol) under nitrogen atmosphere, and the reaction mixture was stirred at room temperature for 2 hours. The solvent was removed under reduced pressure to give Compound 48 (368 mg, Yield 100%) as a crude product.

LC/MS (Method 1) RT=0.69, MS (m/z)=286.30.

Step 4 Synthesis of Compound 49

To a solution of the crude compound 48 (4.33 g, 15.2 mmol) in tetrahydrofuran (43 ml) was added trietylamine (6.31 ml, 45.5 mmol) under nitrogen atmosphere, followed by dropwise addition of di-tert-butyl dicarbonate (4.58 ml, 19.73 mmol), and the reaction mixture was stirred at room temperature for 2 hours. Water was added to the mixture, and the mixture was extracted with ethylacetate. The organic layer was washed with brine and dried over sodium sulfate. The solvent was removed under reduced pressure and the obtained residue was purified by amino silicagel column chromatography (hexane-ethylacetate) to give Compound 49 (3.44 g, Yield 59%).

LC/MS (Method 1) RT=1.92, MS (m/z)=286.00.

Step 5 Synthesis of Compound 50

To Compound 49 (3.16 g, 8.2 mmol) in toluene (35 ml) were added DPPA (2.47 ml, 11.48 mmol) and triethylamine (1.71 ml, 12.3 mmol), and the reaction mixture was stirred at 100° C. for 2 hours. 2-(trimethylsilyl)ethanol (5.13 ml, 41.0 mmol) was added to the mixture, and the mixture was stirred at 70° C. for 5 hours. The solvent was removed under reduced pressure and dichloromethane was added to the residue to give solids, which were filtered. The filtrate was purified by amino silicagel column chromatography (hexane-ethylacetate) to give Compound 50 (1.42 g, Yield 35%).

LC/MS (Method 1) RT=2.68, MS (m/z)=401.10.

Step 6 Synthesis of Compound 51

To Compound 50 (1.05 g, 2.10 mmol) in tetrahydrofuran (10 ml) was added a 1 mol/L tetrahydrofuran solution of TBAF (4.19 ml, 4.19 mmol), and the reaction mixture was stirred at room temperature for 12 hours. Brine was added to the mixture, and the mixture was extracted with ethylacetate. The organic layer was dried over sodium sulfate and the solvent was removed under reduced pressure to give Compound 51 (0.747 g, 2.097 mmol, Yield 100%).

LC/MS (Method 1) RT=1.20, MS (m/z)=257.30.

Step 7 Synthesis of Compound 52

Compound 51 (256 mg, 0.718 mmol) and Compound X were dissolved in DMF (1 ml) under nitrogen atmosphere, diisopropylethylamine (0.056 ml, 0.32 mmol) was added to the solution under ice-cooling bath, and the reaction mixture was stirred at room temperature overnight. Water was added to the mixture, and the mixture was extracted with ethylacetate. The organic layer was washed with water and dried over anhydrous magnesium sulfate. The solvent was removed under reduced pressure and the obtained residue was purified by silicagel column chromatography (hexane-ethylacetate) to give Compound 52 (240 mg, Yield 53%).

$^1$H-NMR (CDCl$_3$) δ: 1.18 (s, 5H), 1.38 (s, 4H), 2.07-2.15 (br m, 4H), 3.77 (s, 3H), 3.94 (s, 3H), 4.06-4.17 (m, 1H), 4.18-4.27 (m, OH), 4.30-4.40 (m, OH), 4.56 (br s, OH), 4.73 (br s, OH), 5.13 (br s, 1H), 6.62-6.76 (br m, 1H), 7.07 (dd, J=18.2, 8.4 Hz, 1H), 7.24-7.31 (m, 1H), 7.31-7.37 (m, 1H), 7.38-7.54 (m, 5H), 7.74 (s, 1H), 7.84 (s, 1H).

LC/MS (Method 1) RT=2.04, MS (m/z)=636.25.

Step 8 Synthesis of Compound (I-47)

To a solution of Compound 52 (9.5 mg, 0.015 mmol) in dichloromethane (1 ml) was added TFA (0.5 ml, 26 mmol) under nitrogen atmosphere, and the reaction mixture was stirred at room temperature for 2 hours. The solvent was removed under reduced pressure and the obtained residue was dissolved in dichloromethane. The solution was washed with saturated sodium hydrogen carbonate aqueous solution and concentrated to give Compound (I-47) (racemate, 8 mg, Yield 100%).

$^1$H-NMR (MeOD) δ: 2.01-2.10 (m, 1H), 2.07 (s, 3H), 2.25-2.36 (m, 1H), 3.79 (s, 3H), 3.95-3.99 (m, 1H), 3.97 (s, 3H), 4.02 (dd, J=8.5, 5.7 Hz, 1H), 4.10 (q, J=7.8 Hz, 1H), 4.60 (br s, 2H), 7.15-7.25 (m, 2H), 7.38-7.50 (m, 6H), 7.85 (s, 1H), 7.97 (s, 1H).

Example 21

Synthesis of Compound (I-2)

[Chemical Formula 85]

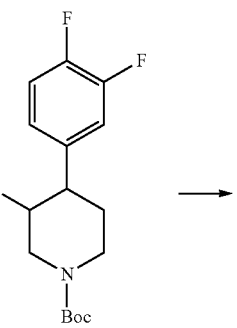

53

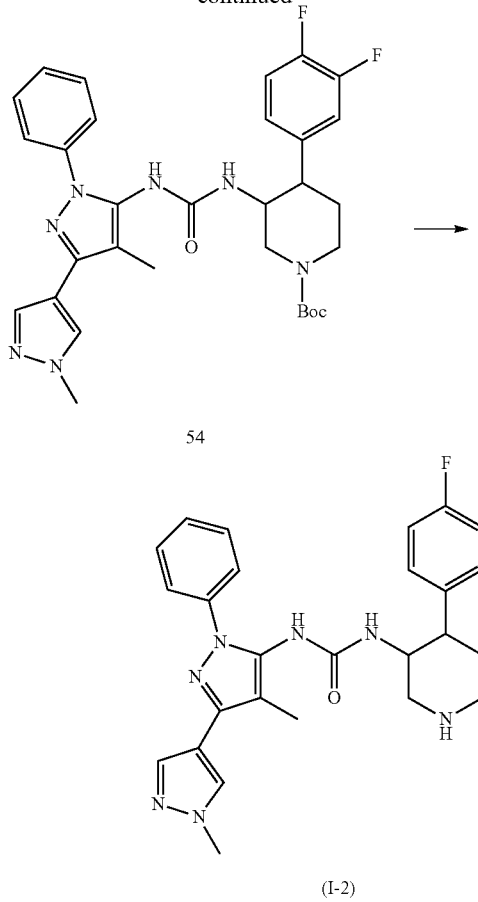

Step 1 Synthesis of Compound 54

Compound 54 (152 mg, Yield 80.0%) was obtained in the same manner as described in the step 4 of Example 7 by using Compound 53 (100 mg, 0.320 mmol) as the starting material.

LC/MS (Method 1) RT=2.01, MS (m/z)=592.25

Step 2 Synthesis of Compound (I-2)

To compound 54 (128 mg, 0.216 mmol) was added 4 mol/L hydrogen chloride in dioxane (1.50 mL) and methanol (0.5 mL), and the reaction mixture was stirred at room temperature for 1 hour. Water and saturated sodium bicarbonate aqueous solution were added to the mixture to give solids, which were collected by filtration to give Compound (I-2) (58 mg, 54.5%).

$^1$H-NMR (DMSO-D$_6$) δ: 1.56 (d, J=10.5 Hz, 1H), 1.73-1.87 (m, 1H), 1.80 (s, 3H), 2.58 (t, J=12.4 Hz, 1H), 2.77 (s, 2H), 2.87 (d, J=12.5 Hz, 1H), 3.03 (d, J=11.3 Hz, 1H), 3.87 (s, 3H), 3.98 (d, J=9.0 Hz, 1H), 6.51-6.68 (m, 1H), 6.99-7.07 (m, 1H), 7.16-7.28 (m, 2H), 7.29-7.37 (m, 1H), 7.38-7.47 (m, 4H), 7.70 (s, 1H), 7.89 (s, 1H), 8.01 (s, 1H).

The following Compounds were obtained in accordance with the general synthetic methods and Examples. The chemical structures and the physical properties (LC/MS data) of Compounds are described below.

In the following tables, Compound with "HCl" in the chemical structure means that Compound forms "HCl" salt. Compound with plural "HCl" in the chemical structure means that Compound forms plural "HCl salt".

In addition, "wedged bond" and "hashed wedged bond" in the chemical structure means configuration. Specifically Compound with "racemate" in item of "configuration" means racemic compound whose relative configuration was determined. Compound with "racemate 2" in item of "configuration" means racemic compound which has a bond whose relative configuration to the group of "—Z-L-Z$^A$-(Ring C)" was not entirely determined. Compound with "trans" in item of "configuration" means compound whose relative configuration between the group of "—Z-L-Z$^A$-(Ring C)" and the group of "—Y—B" was trans, and other configuration were not determined. Compound whose item of "configuration" is blank means Compound in which absolute configurations at the carbon atom binding to the group of "—Z-L-Z$^A$-(Ring C)" and the carbon atom binding to the group of "—Y—B" were as described in the chemical structure.

Moreover, the bond which binds to the asymmetric carbon or N—O bond in N-oxide group is indicated as solid line when their configurations were not determined.

TABLE 2

| No. | Structure | LCMS method No | RT | MS (m/z) | Configuration |
|---|---|---|---|---|---|
| I-1 | 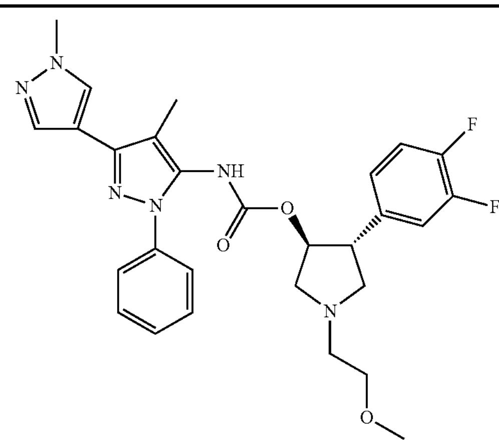 | 1 | 1.24 | 537.00 | racemate |

TABLE 2-continued

| No. | Structure | LCMS method No | RT | MS (m/z) | Configuration |
|---|---|---|---|---|---|
| I-2 | 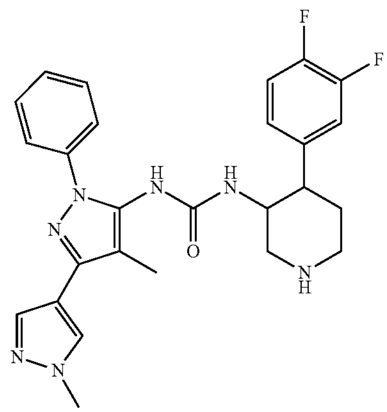 [SMILES: Cc1c(-c2cnn(C)c2)nn(-c2ccccc2)c1NC(=O)NC1CNCCC1c1ccc(F)c(F)c1] | 1 | 1.2 | 492.20 | |
| I-3 | 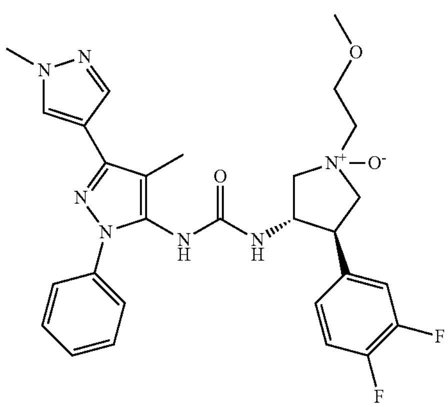 [SMILES: COCC[N+]1([O-])C[C@@H](NC(=O)Nc2c(C)c(-c3cnn(C)c3)nn2-c2ccccc2)[C@H](c2ccc(F)c(F)c2)C1] | 1 | 1.29 | 552.20 | |
| I-4 | 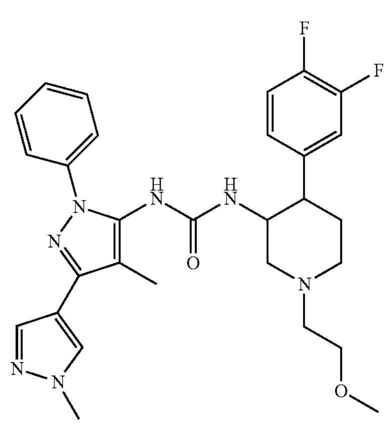 [SMILES: COCCN1CCC(c2ccc(F)c(F)c2)C(NC(=O)Nc2c(C)c(-c3cnn(C)c3)nn2-c2ccccc2)C1] | 1 | 1.26 | 550.25 | |

TABLE 3

| No. | Structure | LCMS method No | RT | MS (m/z) | Configuration |
|---|---|---|---|---|---|
| I-5 | 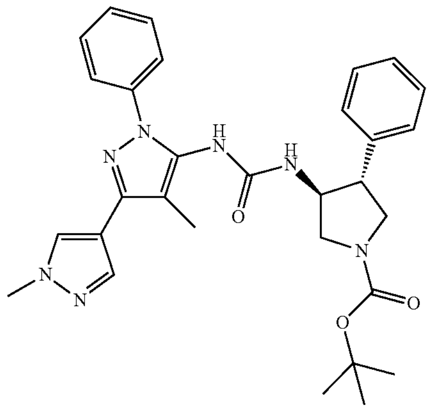 [SMILES: Cc1c(-c2cnn(C)c2)nn(-c2ccccc2)c1NC(=O)N[C@@H]1CN(C(=O)OC(C)(C)C)C[C@H]1c1ccccc1] | 1 | 1.96 | 542.30 | racemate |
| I-6 | 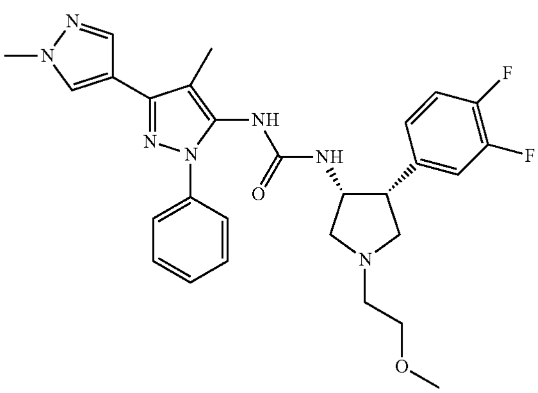 [SMILES: COCCN1C[C@H](NC(=O)Nc2c(C)c(-c3cnn(C)c3)nn2-c2ccccc2)[C@H](c2ccc(F)c(F)c2)C1] | 1 | 1.18 | 536.00 | racemate |
| I-7 | 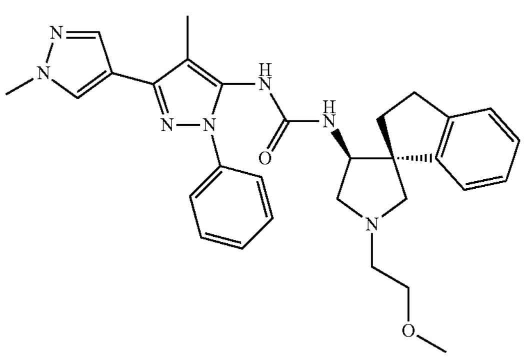 [SMILES: COCCN1C[C@@H](NC(=O)Nc2c(C)c(-c3cnn(C)c3)nn2-c2ccccc2)[C@@]2(CCc3ccccc32)C1] | 1 | 1.14 | 526.25 | racemate |

TABLE 3-continued

| No. | Structure | LCMS method No | RT | MS (m/z) | Configuration |
|---|---|---|---|---|---|
| I-8 | 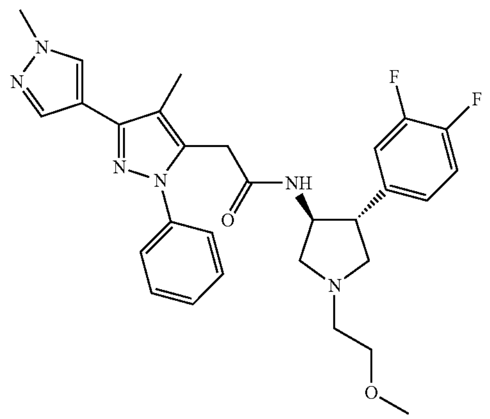 [SMILES: COCCN1C[C@@H](NC(=O)Cc2c(C)c(-c3cnn(C)c3)nn2-c2ccccc2)[C@H](c2ccc(F)c(F)c2)C1] | 1 | 1.18 | 535.25 | |

TABLE 4

| No. | Structure | LCMS method No | RT | MS (m/z) | Configuration |
|---|---|---|---|---|---|
| I-9 | 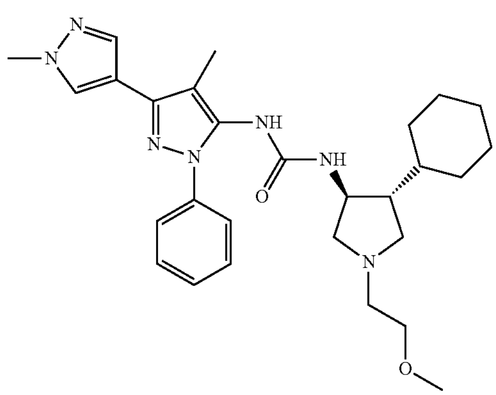 [SMILES: COCCN1C[C@@H](NC(=O)Nc2c(C)c(-c3cnn(C)c3)nn2-c2ccccc2)[C@H](C2CCCCC2)C1] | 1 | 1.24 | 506.00 | racemate |
| I-10 | 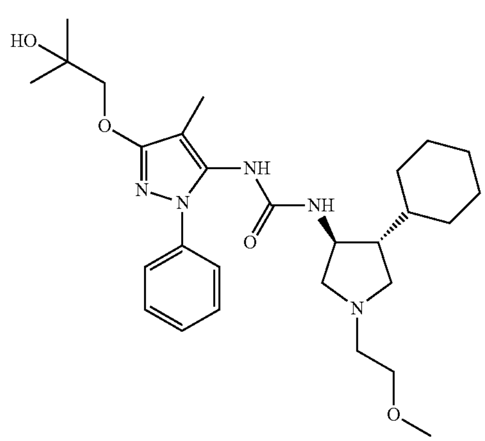 [SMILES: COCCN1C[C@@H](NC(=O)Nc2c(C)c(OCC(C)(C)O)nn2-c2ccccc2)[C@H](C2CCCCC2)C1] | 1 | 1.33 | 514.00 | racemate |

TABLE 4-continued
| No. | Structure | LCMS method No | RT | MS (m/z) | Configuration |
|---|---|---|---|---|---|
| I-11 | 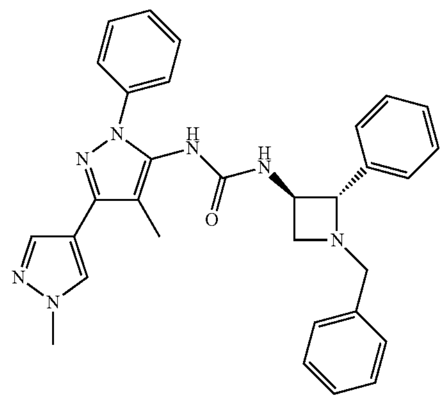 [SMILES: Cc1c(-c2cnn(C)c2)nn(-c2ccccc2)c1NC(=O)N[C@@H]1CN(Cc2ccccc2)[C@H]1c1ccccc1] | 1 | 1.28 | 518.20 | racemate |
| I-12 | 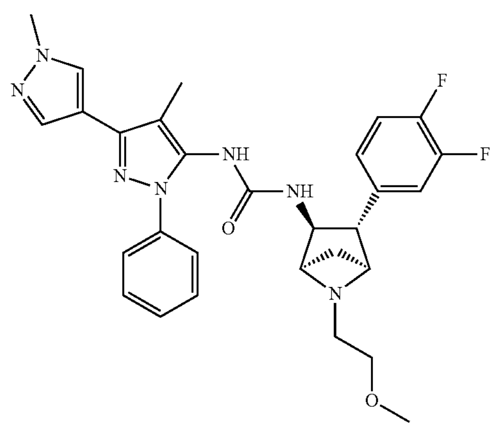 [SMILES: COCCN1[C@@H]2C[C@H]1[C@@H](c1ccc(F)c(F)c1)[C@@H]2NC(=O)Nc1c(C)c(-c2cnn(C)c2)nn1-c1ccccc1] | 1 | 1.32 | 576.25 | racemate |
TABLE 5
| No. | Structure | LCMS method No | RT | MS (m/z) | Configuration |
|---|---|---|---|---|---|
| I-13 | 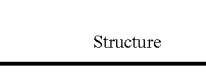 | 2 | 2 | 441.23 | racemate |

TABLE 5-continued

| No. | Structure | LCMS method No | RT | MS (m/z) | Configuration |
|---|---|---|---|---|---|
| I-14 | 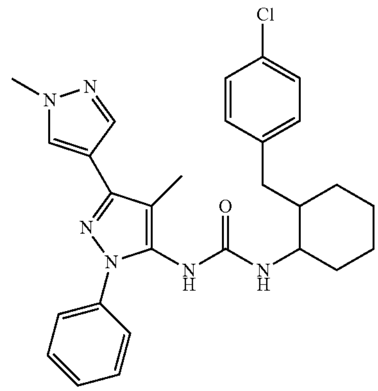 [SMILES: Cc1c(-c2cnn(C)c2)nn(-c2ccccc2)c1NC(=O)NC1CCCCC1Cc1ccc(Cl)cc1] | 2 | 2.49 | 503.22 | |
| I-15 | 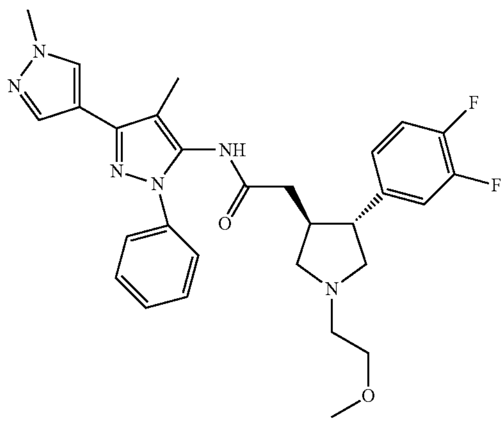 [SMILES: COCCN1C[C@@H](CC(=O)Nc2c(C)c(-c3cnn(C)c3)nn2-c2ccccc2)[C@H](c2ccc(F)c(F)c2)C1] | 2 | 1.41 | 535.00 | racemate |
| I-16 | | 1 | 1.16 | 514.00 | racemate |

TABLE 6

| No. | Structure | LCMS method No | RT | MS (m/z) | Configuration |
|---|---|---|---|---|---|
| I-17 | 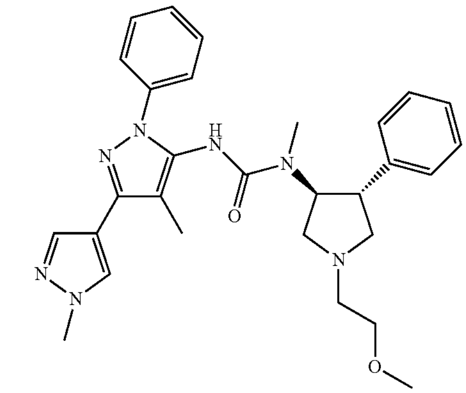 [SMILES: COCCN1C[C@@H](N(C)C(=O)Nc2c(C)c(-c3cnn(C)c3)nn2-c2ccccc2)[C@H](c2ccccc2)C1] | 2 | 1.28 | 514.29 | racemate |
| I-18 | 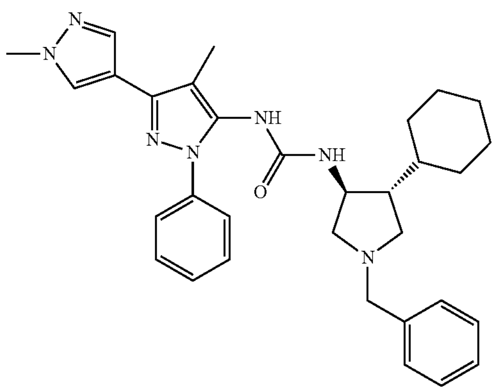 [SMILES: Cc1c(-c2cnn(C)c2)nn(-c2ccccc2)c1NC(=O)N[C@@H]1CN(Cc2ccccc2)C[C@H]1C1CCCCC1] | 1 | 1.48 | 538.00 | racemate |
| I-19 | 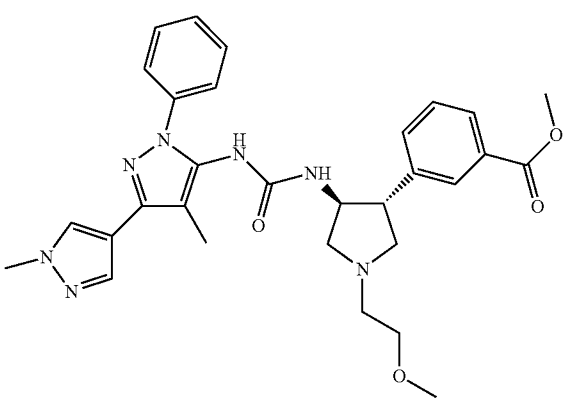 [SMILES: COCCN1C[C@@H](NC(=O)Nc2c(C)c(-c3cnn(C)c3)nn2-c2ccccc2)[C@H](c2cccc(C(=O)OC)c2)C1] | 2 | 1.24 | 558.28 | racemate |

TABLE 6-continued

| No. | Structure | LCMS method No | RT | MS (m/z) | Configuration |
|---|---|---|---|---|---|
| I-20 | 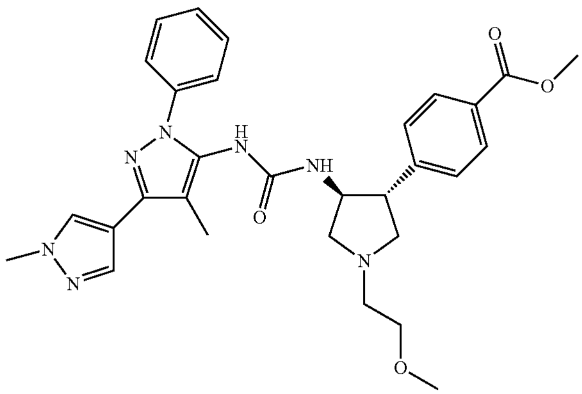 | 2 | 1.22 | 558.28 | racemate |

TABLE 7

| No. | Structure | LCMS method No | RT | MS (m/z) | Configuration |
|---|---|---|---|---|---|
| I-21 | 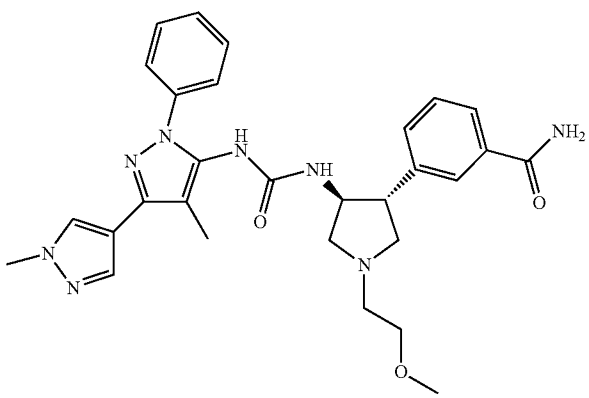 [SMILES: COCCN1C[C@@H](NC(=O)Nc2c(C)c(-c3cnn(C)c3)nn2-c2ccccc2)[C@H](c2cccc(C(N)=O)c2)C1] | 2 | 1.51 | 543.28 | racemate |
| I-22 | 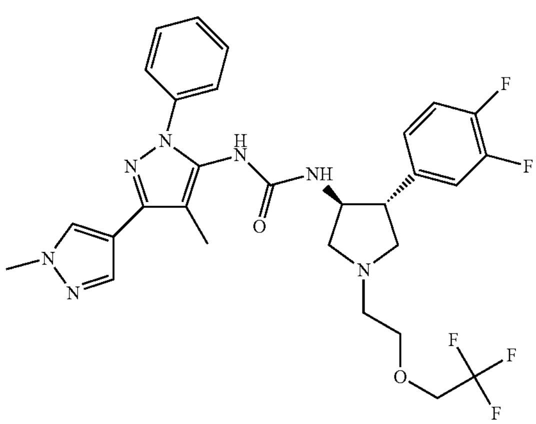 [SMILES: Cc1c(-c2cnn(C)c2)nn(-c2ccccc2)c1NC(=O)N[C@@H]1CN(CCOCC(F)(F)F)C[C@H]1c1ccc(F)c(F)c1] | 2 | 1.78 | 604.00 | |

TABLE 7-continued

| No. | Structure | LCMS method No | RT | MS (m/z) | Configuration |
|---|---|---|---|---|---|
| I-23 | 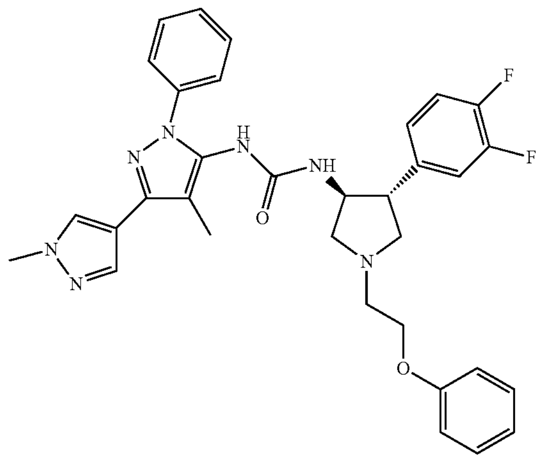 [SMILES: Cc1c(-c2cnn(C)c2)nn(-c2ccccc2)c1NC(=O)N[C@@H]1CN(CCOc2ccccc2)C[C@H]1c1ccc(F)c(F)c1] | 2 | 1.92 | 598.00 | |
| I-24 | 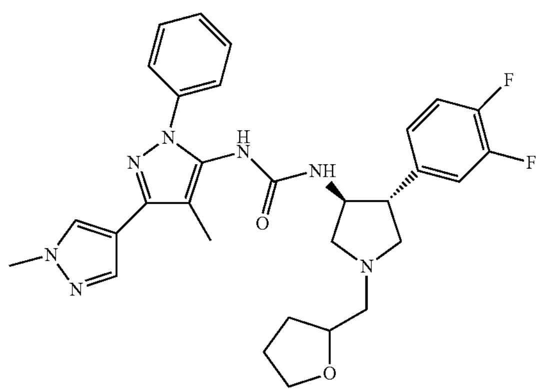 [SMILES: Cc1c(-c2cnn(C)c2)nn(-c2ccccc2)c1NC(=O)N[C@@H]1CN(CC2CCCO2)C[C@H]1c1ccc(F)c(F)c1] | 2 | 1.59 | 562.00 | |

TABLE 8

| No. | Structure | LCMS method No | RT | MS (m/z) | Configuration |
|---|---|---|---|---|---|
| I-25 | 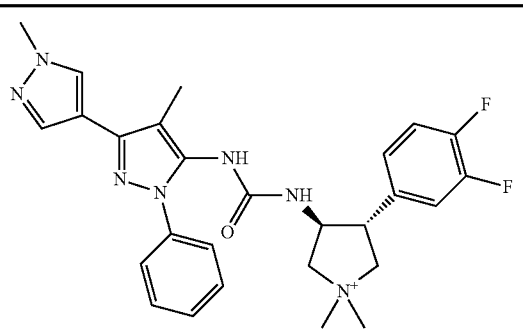 | 2 | 1.25 | 507.00 | |

TABLE 8-continued

| No. | Structure | LCMS method No | RT | MS (m/z) | Configuration |
|---|---|---|---|---|---|
| I-26 | 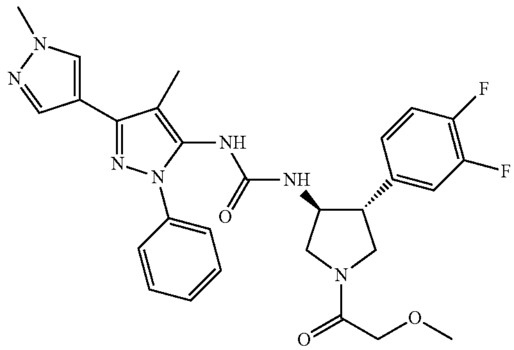 [SMILES: COCC(=O)N1C[C@@H](NC(=O)Nc2c(C)c(-c3cnn(C)c3)nn2-c2ccccc2)[C@H](c2ccc(F)c(F)c2)C1] | 2 | 1.58 | 550.23 | |
| I-27 | 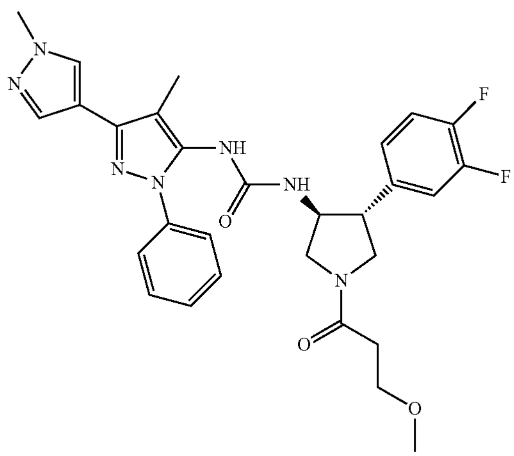 [SMILES: COCCC(=O)N1C[C@@H](NC(=O)Nc2c(C)c(-c3cnn(C)c3)nn2-c2ccccc2)[C@H](c2ccc(F)c(F)c2)C1] | 2 | 1.66 | 564.25 | |
| I-28 | 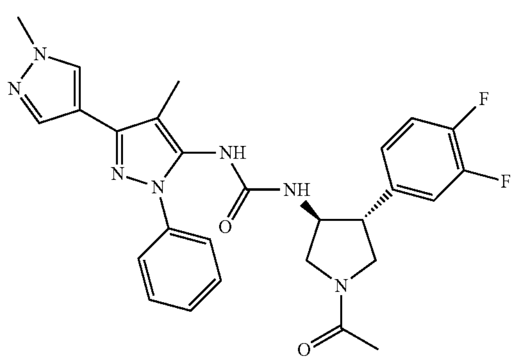 [SMILES: CC(=O)N1C[C@@H](NC(=O)Nc2c(C)c(-c3cnn(C)c3)nn2-c2ccccc2)[C@H](c2ccc(F)c(F)c2)C1] | 2 | 1.59 | 520.22 | |

TABLE 9
| No. | Structure | LCMS method No | RT | MS (m/z) | Configuration |
|---|---|---|---|---|---|
| I-29 | 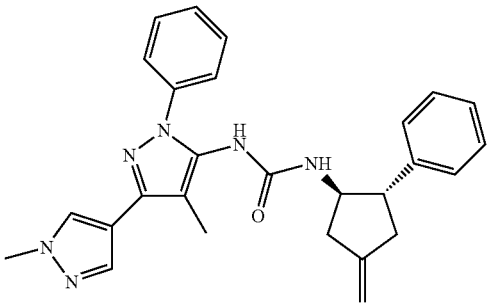 [SMILES: C=C1C[C@@H](NC(=O)Nc2c(C)c(-c3cnn(C)c3)nn2-c2ccccc2)[C@H](c2ccccc2)C1] | 2 | 2.08 | 453.00 | racemate |
| I-30 | 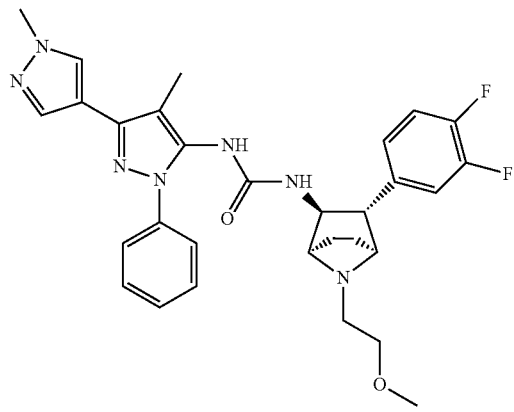 [SMILES: COCCN1[C@@H]2CC[C@H]1[C@@H](c1ccc(F)c(F)c1)[C@@H]2NC(=O)Nc1c(C)c(-c2cnn(C)c2)nn1-c1ccccc1] | 1 | 1.32 | 562.00 | racemate |
| I-31 | 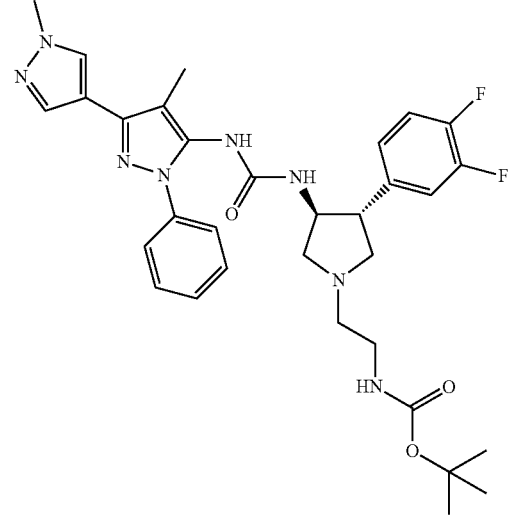 [SMILES: Cc1c(-c2cnn(C)c2)nn(-c2ccccc2)c1NC(=O)N[C@@H]1CN(CCNC(=O)OC(C)(C)C)C[C@H]1c1ccc(F)c(F)c1] | 2 | 1.83 | 621.00 | |

TABLE 9-continued

| No. | Structure | LCMS method No | RT | MS (m/z) | Configuration |
|---|---|---|---|---|---|
| I-32 | 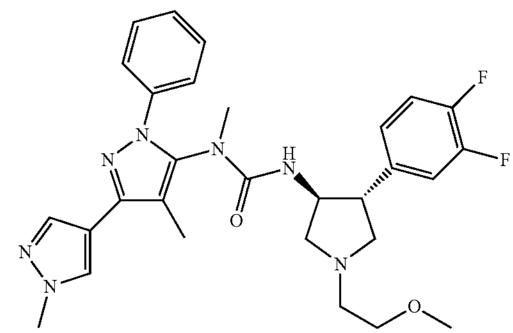 [SMILES: COCCN1C[C@@H](NC(=O)N(C)c2c(C)c(-c3cnn(C)c3)nn2-c2ccccc2)[C@H](c2ccc(F)c(F)c2)C1] | 2 | 1.48 | 550.00 | |

20

TABLE 10

| No. | Structure | LCMS method No | RT | MS (m/z) | Configuration |
|---|---|---|---|---|---|
| I-33 | 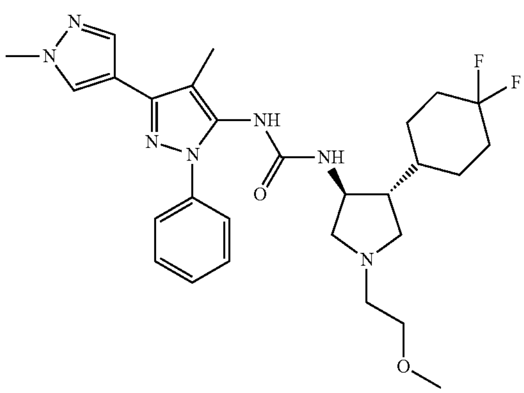 [SMILES: COCCN1C[C@@H](NC(=O)Nc2c(C)c(-c3cnn(C)c3)nn2-c2ccccc2)[C@H](C2CCC(F)(F)CC2)C1] | 1 | 1.19 | 542.00 | racemate |
| I-34 | 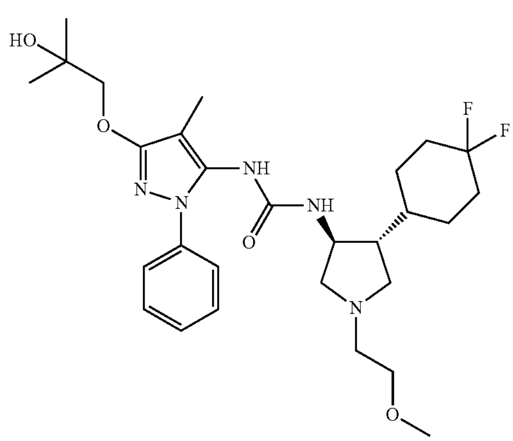 [SMILES: COCCN1C[C@@H](NC(=O)Nc2c(C)c(OCC(C)(C)O)nn2-c2ccccc2)[C@H](C2CCC(F)(F)CC2)C1] | 1 | 1.29 | 550.00 | racemate |

TABLE 10-continued

| No. | Structure | LCMS method No | RT | MS (m/z) | Configuration |
|---|---|---|---|---|---|
| I-35 | 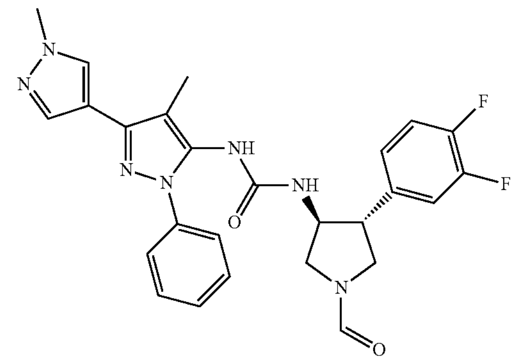 [SMILES: Cc1c(-c2cnn(C)c2)nn(-c2ccccc2)c1NC(=O)N[C@@H]1CN(C=O)C[C@H]1c1ccc(F)c(F)c1] | 2 | 1.56 | 506.00 | |
| I-36 | 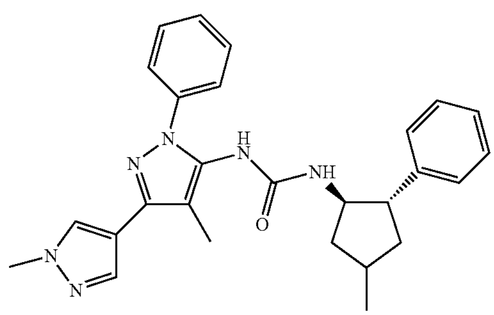 [SMILES: Cc1c(-c2cnn(C)c2)nn(-c2ccccc2)c1NC(=O)N[C@@H]1CC(C)C[C@H]1c1ccccc1] | 2 | 2.14 | 455.00 | trans |

TABLE 11

| No. | Structure | LCMS method No | RT | MS (m/z) | Configuration |
|---|---|---|---|---|---|
| I-37 | 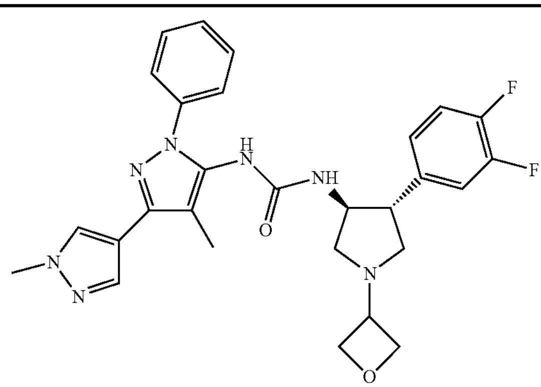 | 2 | 2.03 | 534.00 | |

TABLE 11-continued

| No. | Structure | LCMS method No | RT | MS (m/z) | Configuration |
|---|---|---|---|---|---|
| I-38 | 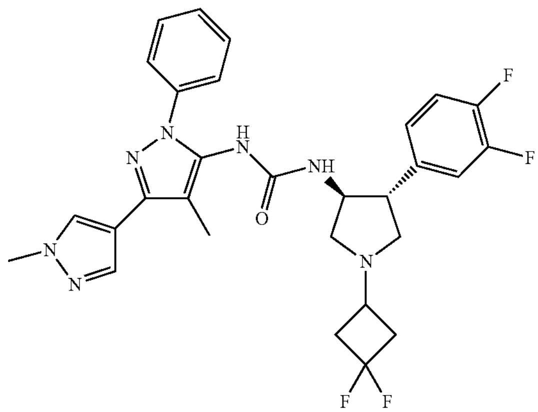 [SMILES: Cc1c(-c2cnn(C)c2)nn(-c2ccccc2)c1NC(=O)N[C@@H]1CN(C2CC(F)(F)C2)C[C@H]1c1ccc(F)c(F)c1] | 2 | 2.45 | 568.00 | |
| I-39 | 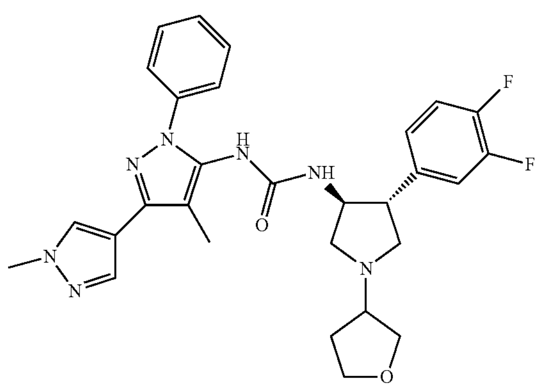 [SMILES: Cc1c(-c2cnn(C)c2)nn(-c2ccccc2)c1NC(=O)N[C@@H]1CN(C2CCOC2)C[C@H]1c1ccc(F)c(F)c1] | 2 | 2.13 | 548.00 | trans |
| I-40 | 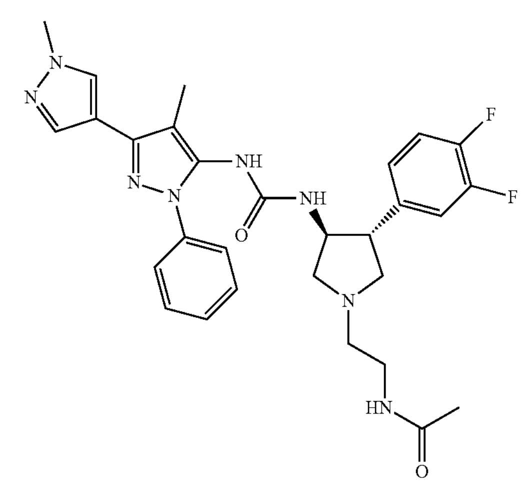 [SMILES: CC(=O)NCCN1C[C@@H](NC(=O)Nc2c(C)c(-c3cnn(C)c3)nn2-c2ccccc2)[C@H](c2ccc(F)c(F)c2)C1] | 2 | 1.25 | 563.00 | |

TABLE 12

| No. | Structure | LCMS method No | RT | MS (m/z) | Configuration |
|---|---|---|---|---|---|
| I-41 | 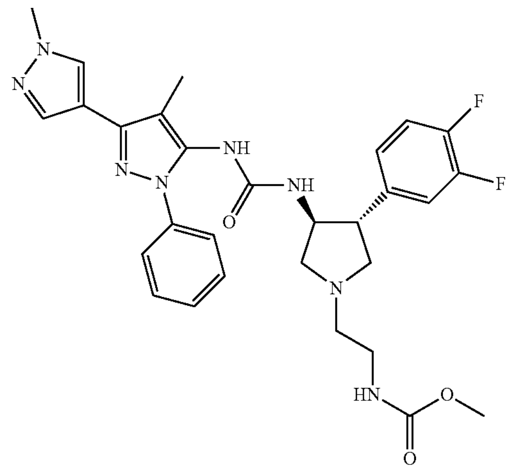 [SMILES: COC(=O)NCCN1C[C@@H](NC(=O)Nc2c(C)c(-c3cnn(C)c3)nn2-c2ccccc2)[C@H](c2ccc(F)c(F)c2)C1] | 2 | 1.3 | 579.00 | |
| I-42 | 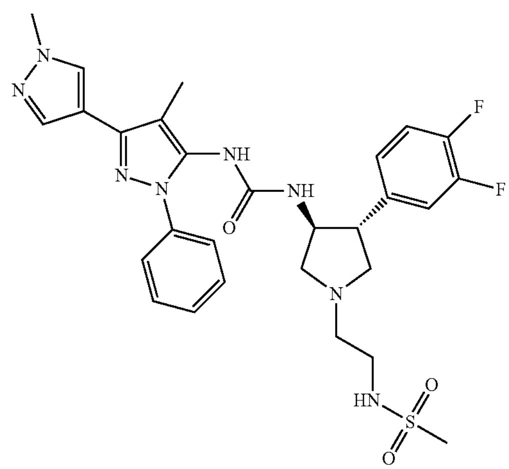 [SMILES: Cc1c(-c2cnn(C)c2)nn(-c2ccccc2)c1NC(=O)N[C@@H]1CN(CCNS(C)(=O)=O)C[C@H]1c1ccc(F)c(F)c1] | 2 | 1.3 | 599.00 | |
| I-43 | 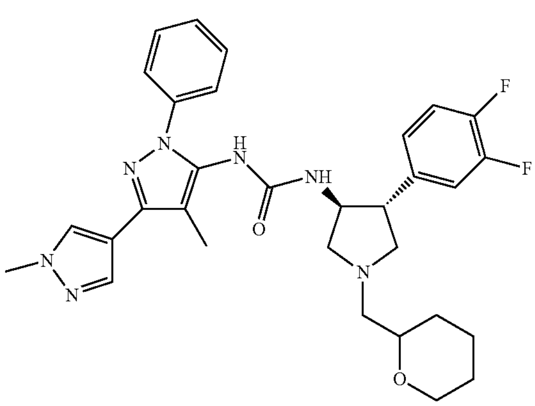 [SMILES: Cc1c(-c2cnn(C)c2)nn(-c2ccccc2)c1NC(=O)N[C@@H]1CN(CC2CCCCO2)C[C@H]1c1ccc(F)c(F)c1] | 2 | 1.68 | 576.00 | |

TABLE 12-continued

| No. | Structure | LCMS method No | RT | MS (m/z) | Configuration |
|---|---|---|---|---|---|
| I-44 | | 1 | 1.67 | 538.20 | racemate |

TABLE 13

| No. | Structure | LCMS method No | RT | MS (m/z) | Configuration |
|---|---|---|---|---|---|
| I-45 | 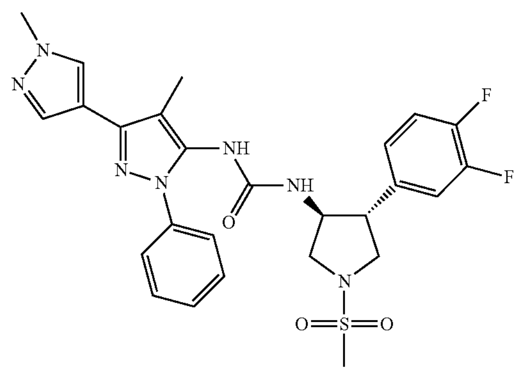 [SMILES: Cc1c(-c2cnn(C)c2)nn(-c2ccccc2)c1NC(=O)N[C@@H]1CN(S(C)(=O)=O)C[C@H]1c1ccc(F)c(F)c1] | 2 | 1.76 | 556.00 | |
| I-46 | 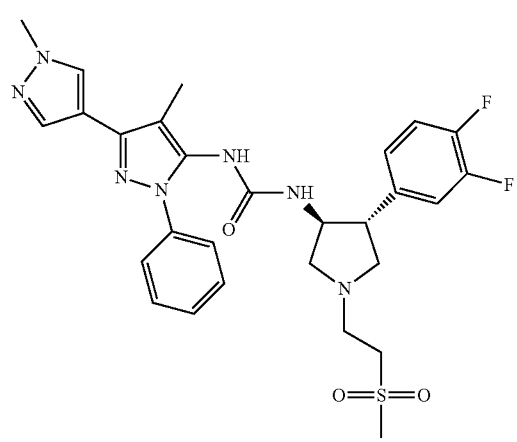 [SMILES: Cc1c(-c2cnn(C)c2)nn(-c2ccccc2)c1NC(=O)N[C@@H]1CN(CCS(C)(=O)=O)C[C@H]1c1ccc(F)c(F)c1] | 2 | 1.31 | 584.00 | |

TABLE 13-continued

| No. | Structure | LCMS method No | RT | MS (m/z) | Configuration |
|---|---|---|---|---|---|
| I-47 | 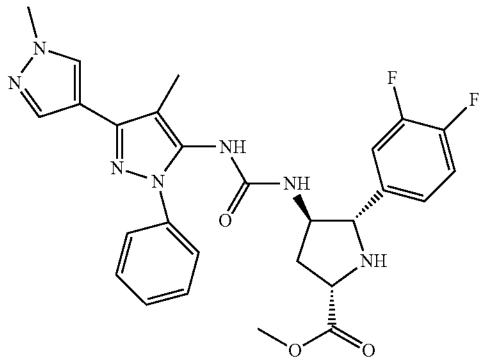 [SMILES: COC(=O)[C@@H]1C[C@@H](NC(=O)Nc2c(C)c(-c3cnn(C)c3)nn2-c2ccccc2)[C@H](c2ccc(F)c(F)c2)N1] | 1 | 1.15 | 536.20 | racemate |
| I-48 | 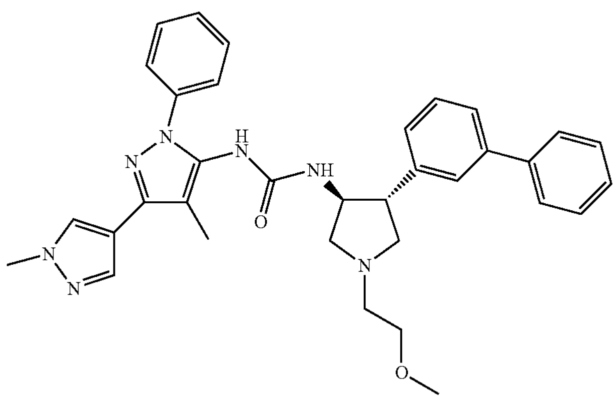 [SMILES: COCCN1C[C@@H](NC(=O)Nc2c(C)c(-c3cnn(C)c3)nn2-c2ccccc2)[C@H](c2cccc(-c3ccccc3)c2)C1] | 2 | 1.63 | 576.00 | racemate |

TABLE 14

| No. | Structure | LCMS method No | RT | MS (m/z) | Configuration |
|---|---|---|---|---|---|
| I-49 | 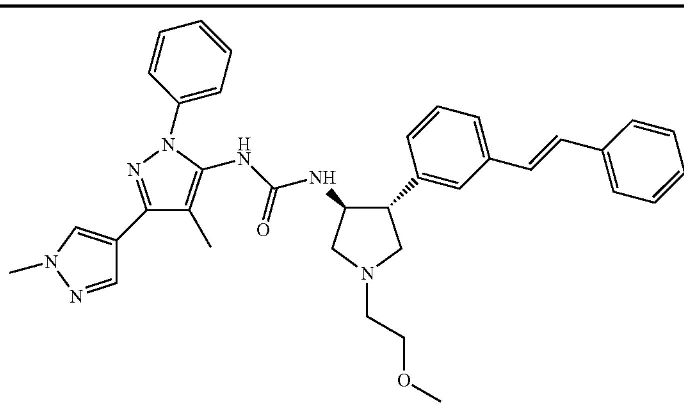 | 1 | 1.8 | 602.00 | racemate |

TABLE 14-continued

| No. | Structure | LCMS method No | RT | MS (m/z) | Configuration |
|---|---|---|---|---|---|
| I-50 | 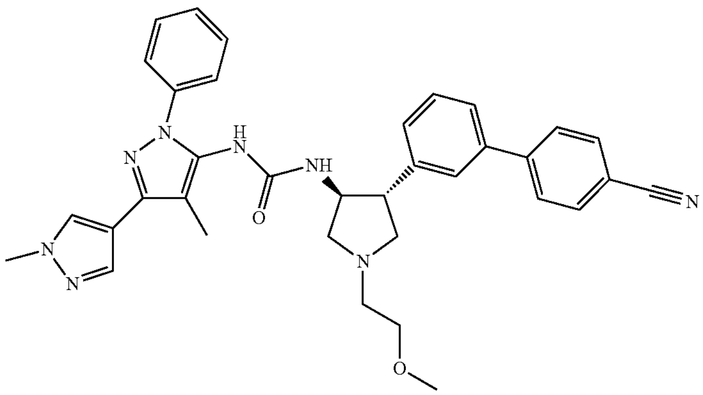 [SMILES: COCCN1C[C@@H](NC(=O)Nc2c(C)c(-c3cnn(C)c3)nn2-c2ccccc2)[C@H](c2cccc(-c3ccc(C#N)cc3)c2)C1] | 2 | 1.53 | 601.00 | racemate |
| I-51 | 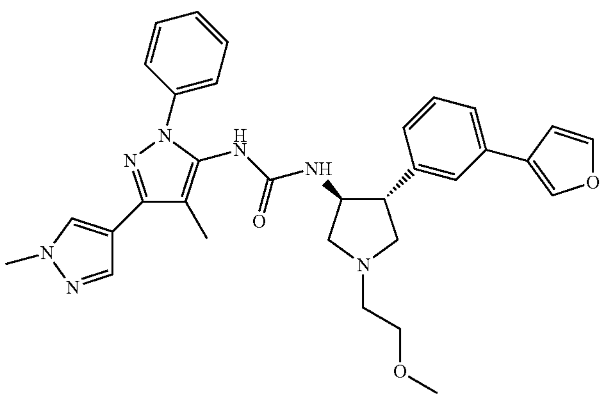 [SMILES: COCCN1C[C@@H](NC(=O)Nc2c(C)c(-c3cnn(C)c3)nn2-c2ccccc2)[C@H](c2cccc(-c3ccoc3)c2)C1] | 2 | 1.47 | 566.00 | racemate |
| I-52 | 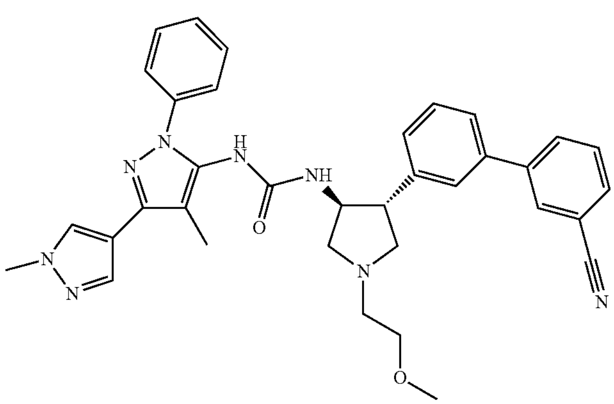 [SMILES: COCCN1C[C@@H](NC(=O)Nc2c(C)c(-c3cnn(C)c3)nn2-c2ccccc2)[C@H](c2cccc(-c3cccc(C#N)c3)c2)C1] | 2 | 1.54 | 601.00 | racemate |

TABLE 15

| No. | Structure | LCMS method No | RT | MS (m/z) | Configuration |
|---|---|---|---|---|---|
| I-53 | 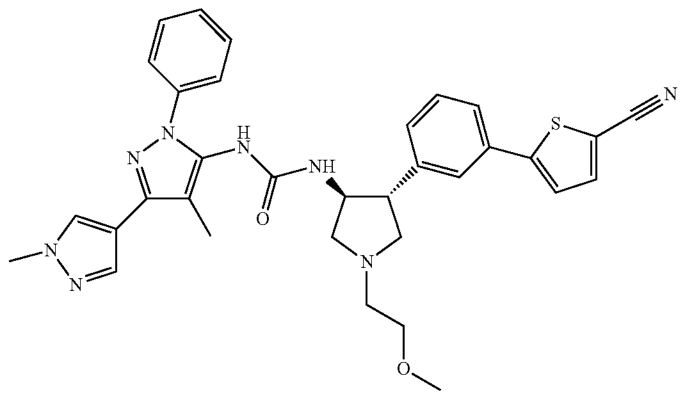 [SMILES: COCCN1C[C@@H](NC(=O)Nc2c(C)c(-c3cnn(C)c3)nn2-c2ccccc2)[C@H](c2cccc(-c3ccc(C#N)s3)c2)C1] | 2 | 1.52 | 607.00 | racemate |
| I-54 | 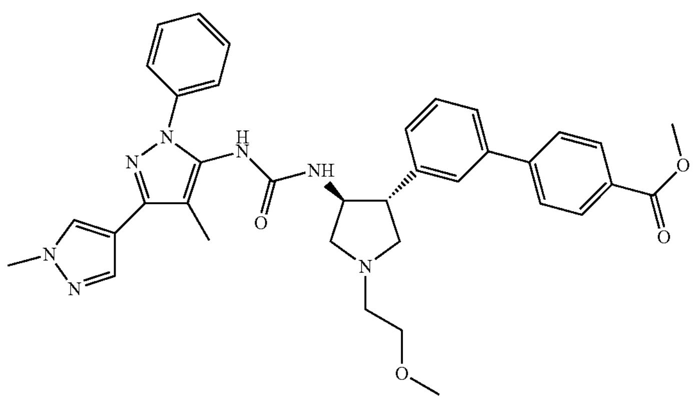 [SMILES: COCCN1C[C@@H](NC(=O)Nc2c(C)c(-c3cnn(C)c3)nn2-c2ccccc2)[C@H](c2cccc(-c3ccc(C(=O)OC)cc3)c2)C1] | 2 | 1.6 | 634.00 | racemate |
| I-55 | 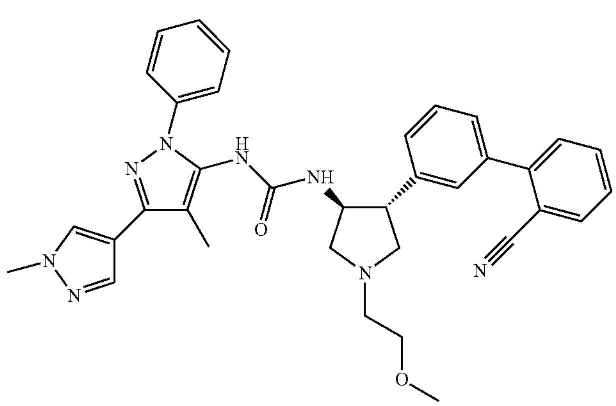 [SMILES: COCCN1C[C@@H](NC(=O)Nc2c(C)c(-c3cnn(C)c3)nn2-c2ccccc2)[C@H](c2cccc(-c3ccccc3C#N)c2)C1] | 2 | 1.52 | 601.00 | racemate |

TABLE 15-continued

| No. | Structure | LCMS method No | RT | MS (m/z) | Configuration |
|---|---|---|---|---|---|
| I-56 | 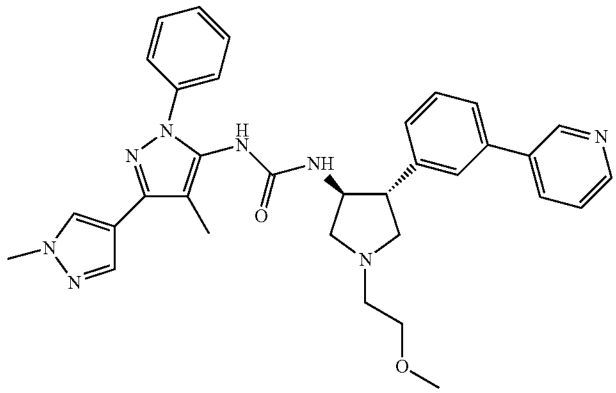 [SMILES: COCCN1C[C@@H](NC(=O)Nc2c(C)c(-c3cnn(C)c3)nn2-c2ccccc2)[C@H](c2cccc(-c3cccnc3)c2)C1] | 2 | 0.96 | 577.00 | racemate |

TABLE 16

| No. | Structure | LCMS method No | RT | MS (m/z) | Configuration |
|---|---|---|---|---|---|
| I-57 | 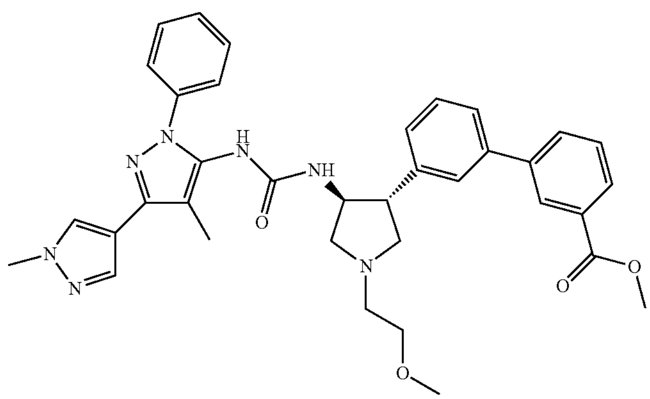 | 2 | 1.62 | 634.00 | racemate |
| I-58 | 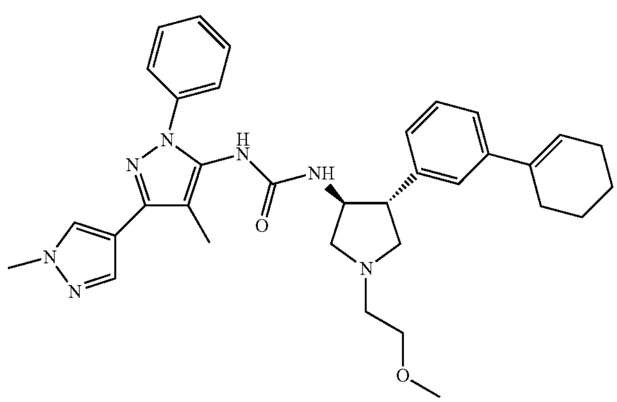 [SMILES: COCCN1C[C@@H](NC(=O)Nc2c(C)c(-c3cnn(C)c3)nn2-c2ccccc2)[C@H](c2cccc(C3=CCCCC3)c2)C1] | 2 | 1.78 | 580.00 | racemate |

TABLE 16-continued

| No. | Structure | LCMS method No | RT | MS (m/z) | Configuration |
|---|---|---|---|---|---|
| I-59 | 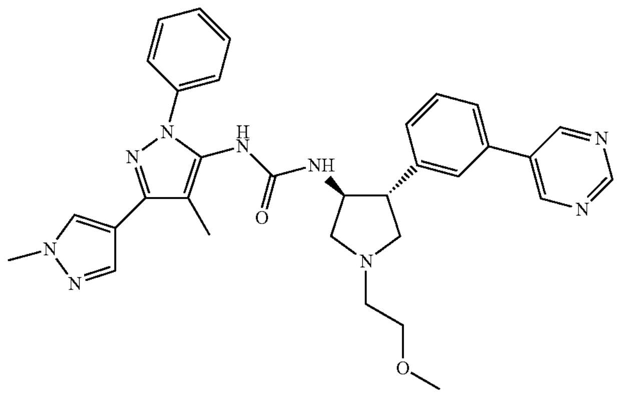 [SMILES: COCCN1C[C@@H](NC(=O)Nc2c(C)c(-c3cnn(C)c3)nn2-c2ccccc2)[C@H](c2cccc(-c3cncnc3)c2)C1] | 2 | 1.12 | 578.00 | racemate |
| I-60 | 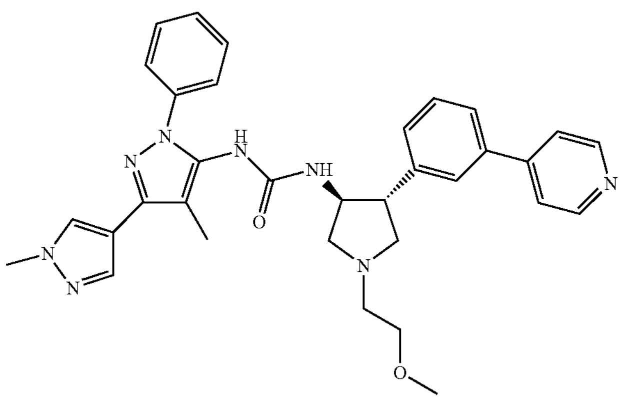 [SMILES: COCCN1C[C@@H](NC(=O)Nc2c(C)c(-c3cnn(C)c3)nn2-c2ccccc2)[C@H](c2cccc(-c3ccncc3)c2)C1] | 2 | 0.85 | 577.00 | racemate |

TABLE 17

| No. | Structure | LCMS method No | RT | MS (m/z) | Configuration |
|---|---|---|---|---|---|
| I-61 | 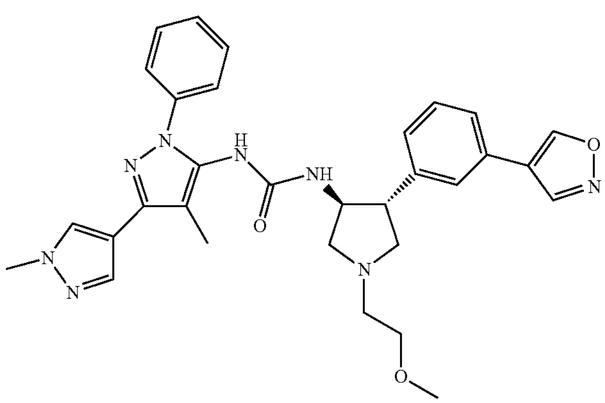 [SMILES: COCCN1C[C@@H](NC(=O)Nc2c(C)c(-c3cnn(C)c3)nn2-c2ccccc2)[C@H](c2cccc(-c3cnoc3)c2)C1] | 2 | 1.23 | 567.00 | racemate |

TABLE 17-continued

| No. | Structure | LCMS method No | RT | MS (m/z) | Configuration |
|---|---|---|---|---|---|
| I-62 | 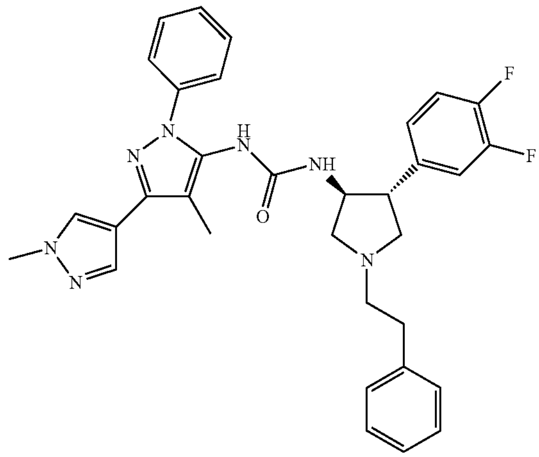 [SMILES: Cc1c(-c2cnn(C)c2)nn(-c2ccccc2)c1NC(=O)N[C@@H]1CN(CCc2ccccc2)C[C@H]1c1ccc(F)c(F)c1] | 2 | 1.8 | 582.00 | |
| I-63 | 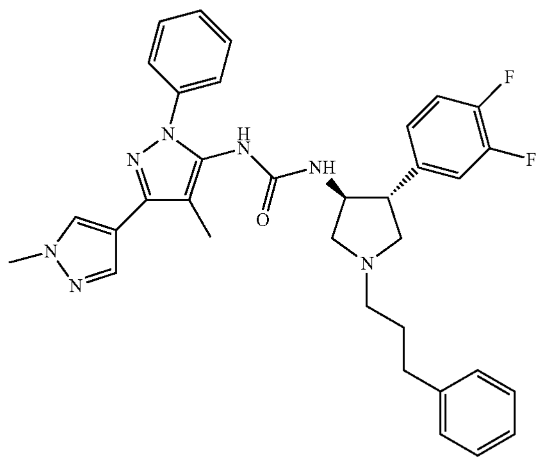 [SMILES: Cc1c(-c2cnn(C)c2)nn(-c2ccccc2)c1NC(=O)N[C@@H]1CN(CCCc2ccccc2)C[C@H]1c1ccc(F)c(F)c1] | 2 | 1.96 | 596.00 | |

TABLE 18

| No. | Structure | LCMS method No | RT | MS (m/z) | Configuration |
|---|---|---|---|---|---|
| I-64 | 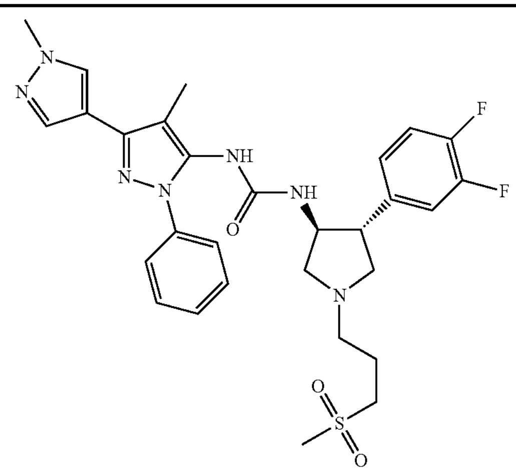 | 2 | 1.3 | 598.00 | |

TABLE 18-continued
| No. | Structure | LCMS method No | RT | MS (m/z) | Configuration |
|---|---|---|---|---|---|
| I-65 | 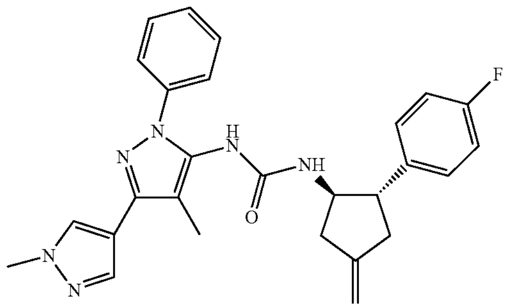 [SMILES: C=C1C[C@@H](NC(=O)Nc2c(C)c(-c3cnn(C)c3)nn2-c2ccccc2)[C@H](c2ccc(F)cc2)C1] | 2 | 2.09 | 471.00 | racemate |
| I-66 | 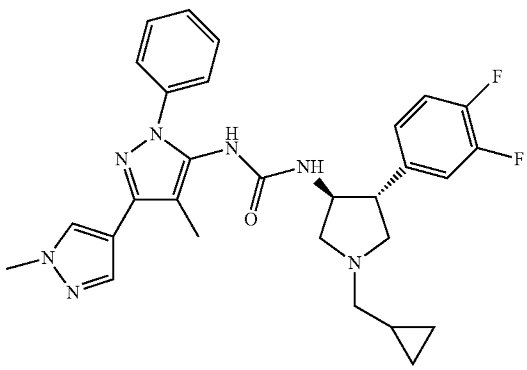 [SMILES: Cc1c(-c2cnn(C)c2)nn(-c2ccccc2)c1NC(=O)N[C@@H]1CN(CC2CC2)C[C@H]1c1ccc(F)c(F)c1] | 2 | 1.57 | 532.00 | |
| I-67 | 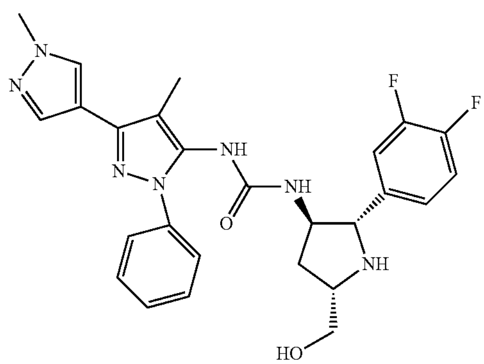 [SMILES: Cc1c(-c2cnn(C)c2)nn(-c2ccccc2)c1NC(=O)N[C@@H]1C[C@@H](CO)N[C@H]1c1ccc(F)c(F)c1] | 1 | 0.95 | 508.25 | racemate |
TABLE 19
| No. | Structure | LCMS method No | RT | MS (m/z) | Configuration |
|---|---|---|---|---|---|
| I-68 | 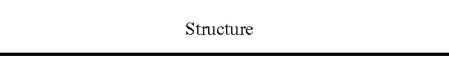 | 2 | 1.59 | 504.40 | racemate |

TABLE 19-continued

| No. | Structure | LCMS method No | RT | MS (m/z) | Configuration |
|---|---|---|---|---|---|
| I-69 | 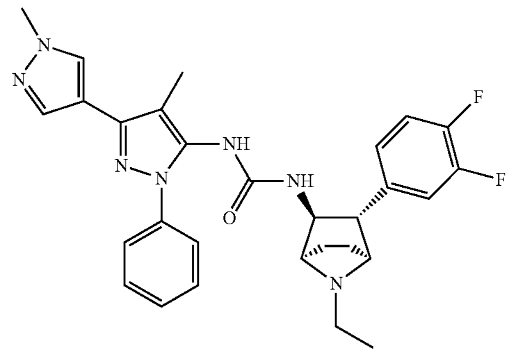 [SMILES: CCN1[C@@H]2CC[C@H]1[C@@H](c1ccc(F)c(F)c1)[C@@H]2NC(=O)Nc1c(C)c(-c2cnn(C)c2)nn1-c1ccccc1] | 1 | 1.32 | 532.00 | racemate |
| I-70 | 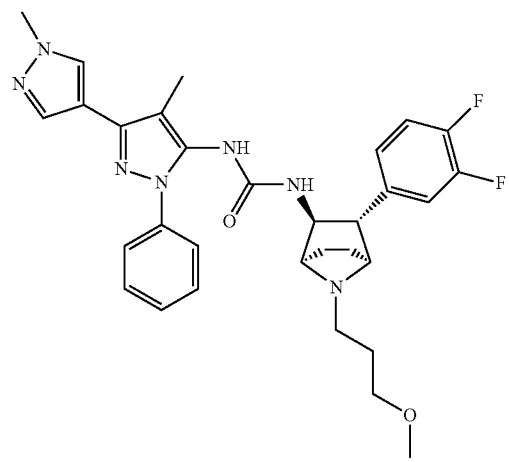 [SMILES: COCCCN1[C@@H]2CC[C@H]1[C@@H](c1ccc(F)c(F)c1)[C@@H]2NC(=O)Nc1c(C)c(-c2cnn(C)c2)nn1-c1ccccc1] | 1 | 1.37 | 576.00 | racemate |
| I-71 | 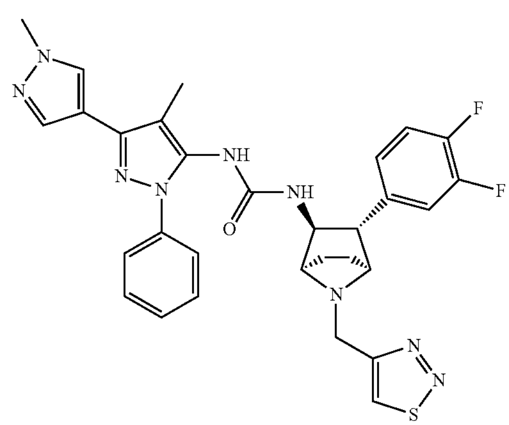 [SMILES: Cc1c(-c2cnn(C)c2)nn(-c2ccccc2)c1NC(=O)N[C@H]1[C@H](c2ccc(F)c(F)c2)[C@@H]2CC[C@H]1N2Cc1csnn1] | 1 | 1.32 | 602.00 | racemate |

TABLE 20

| No. | Structure | LCMS method No | RT | MS (m/z) | Configuration |
|---|---|---|---|---|---|
| I-72 | 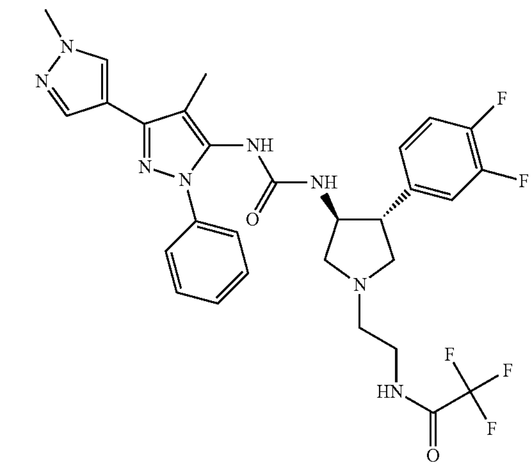 [SMILES: Cc1c(-c2cnn(C)c2)nn(-c2ccccc2)c1NC(=O)N[C@@H]1CN(CCNC(=O)C(F)(F)F)C[C@H]1c1ccc(F)c(F)c1] | 2 | 1.46 | 617.00 | |
| I-73 | 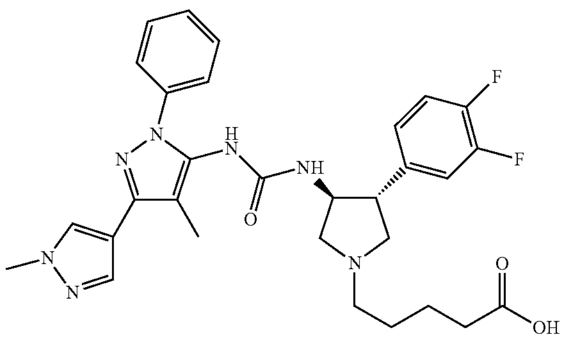 [SMILES: Cc1c(-c2cnn(C)c2)nn(-c2ccccc2)c1NC(=O)N[C@@H]1CN(CCCCC(=O)O)C[C@H]1c1ccc(F)c(F)c1] | 2 | 1.42 | 578.00 | |
| I-74 | 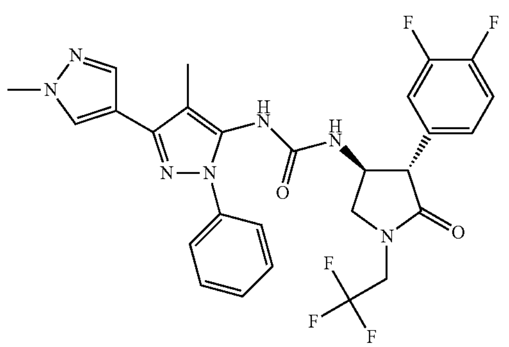 [SMILES: Cc1c(-c2cnn(C)c2)nn(-c2ccccc2)c1NC(=O)N[C@@H]1CN(CC(F)(F)F)C(=O)[C@H]1c1ccc(F)c(F)c1] | 1 | 1.77 | 574.15 | |
| I-75 | 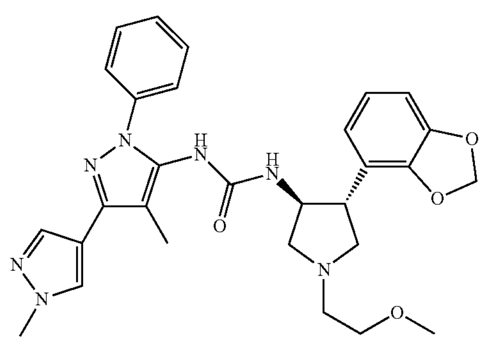 [SMILES: COCCN1C[C@@H](NC(=O)Nc2c(C)c(-c3cnn(C)c3)nn2-c2ccccc2)[C@H](c2cccc3c2OCO3)C1] | 2 | 1.21 | 544.00 | racemate |

TABLE 21

| No. | Structure | LCMS method No | RT | MS (m/z) | Configuration |
|---|---|---|---|---|---|
| I-76 | 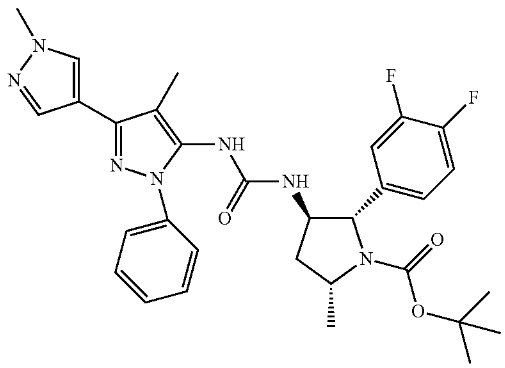 [SMILES: Cc1c(-c2cnn(C)c2)nn(-c2ccccc2)c1NC(=O)N[C@@H]1C[C@@H](C)N(C(=O)OC(C)(C)C)[C@H]1c1ccc(F)c(F)c1] | 1 | 2.13 | 592.25 | racemate |
| I-77 | 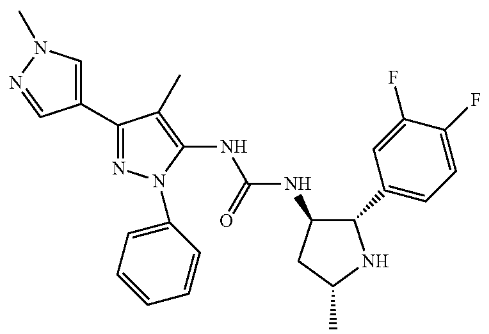 [SMILES: Cc1c(-c2cnn(C)c2)nn(-c2ccccc2)c1NC(=O)N[C@@H]1C[C@@H](C)N[C@H]1c1ccc(F)c(F)c1] | 1 | 1.03 | 492.20 | racemate |
| I-78 | 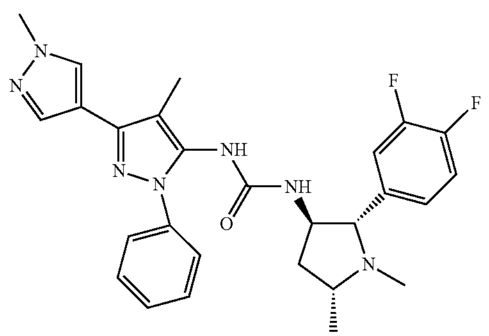 [SMILES: Cc1c(-c2cnn(C)c2)nn(-c2ccccc2)c1NC(=O)N[C@@H]1C[C@@H](C)N(C)[C@H]1c1ccc(F)c(F)c1] | 1 | 1.08 | 506.25 | racemate |
| I-79 | 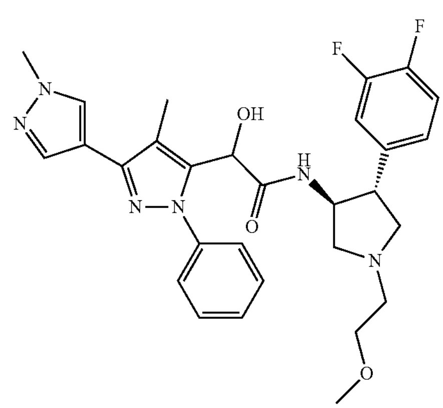 [SMILES: COCCN1C[C@@H](NC(=O)C(O)c2c(C)c(-c3cnn(C)c3)nn2-c2ccccc2)[C@H](c2ccc(F)c(F)c2)C1] | 1 | 1.07 | 551.20 | |

TABLE 22

| No. | Structure | LCMS method No | RT | MS (m/z) | Configuration |
|---|---|---|---|---|---|
| I-80 | 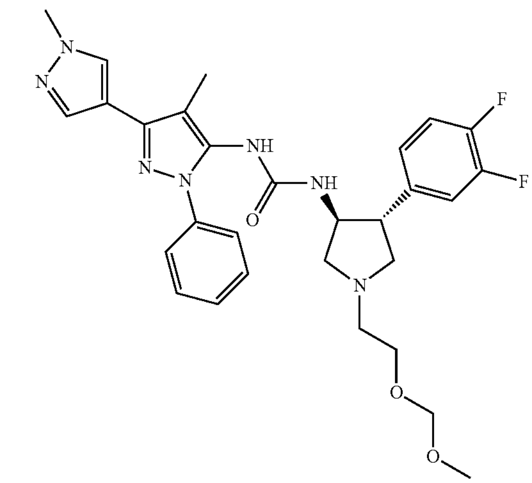 [SMILES: COCOCCN1C[C@@H](NC(=O)Nc2c(C)c(-c3cnn(C)c3)nn2-c2ccccc2)[C@H](c2ccc(F)c(F)c2)C1] | 2 | 2 | 566.26 | |
| I-81 | 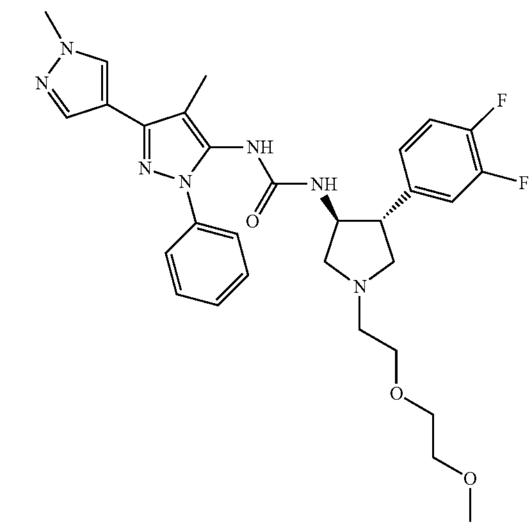 [SMILES: COCCOCCN1C[C@@H](NC(=O)Nc2c(C)c(-c3cnn(C)c3)nn2-c2ccccc2)[C@H](c2ccc(F)c(F)c2)C1] | 2 | 2.5 | 580.28 | |
| I-82 | 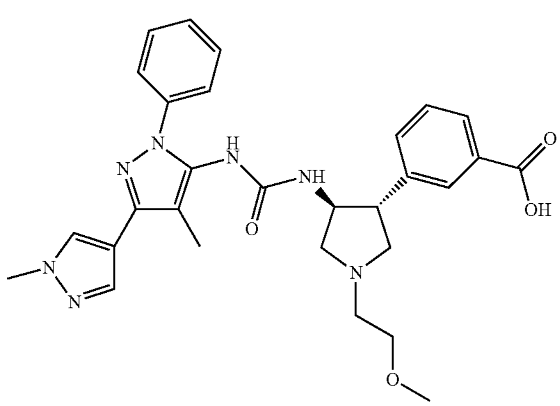 [SMILES: COCCN1C[C@@H](NC(=O)Nc2c(C)c(-c3cnn(C)c3)nn2-c2ccccc2)[C@H](c2cccc(C(=O)O)c2)C1] | 2 | 1.08 | 544.00 | racemate |

TABLE 23

| No. | Structure | LCMS method No | RT | MS (m/z) | Configuration |
|---|---|---|---|---|---|
| I-83 | 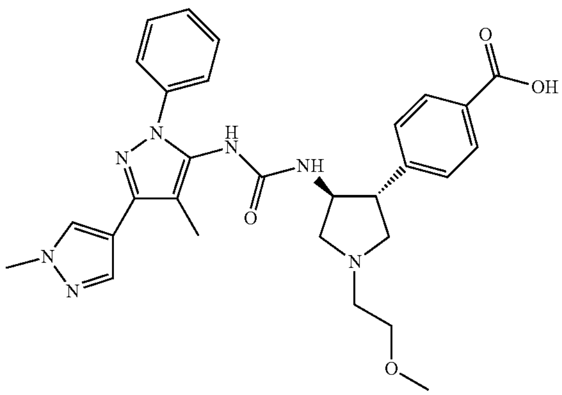 [SMILES: COCCN1C[C@@H](NC(=O)Nc2c(C)c(-c3cnn(C)c3)nn2-c2ccccc2)[C@H](c2ccc(C(=O)O)cc2)C1] | 2 | 0.98 | 544.00 | racemate |

TABLE 24

| No. | Structure | LCMS method No | RT | MS (m/z) | Configuration |
|---|---|---|---|---|---|
| I-84 | 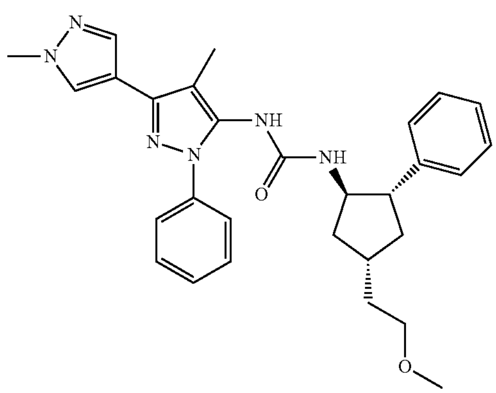 [SMILES: COCC[C@@H]1C[C@@H](NC(=O)Nc2c(C)c(-c3cnn(C)c3)nn2-c2ccccc2)[C@H](c2ccccc2)C1] | 2 | 1.94 | 499 | |
| I-85 | 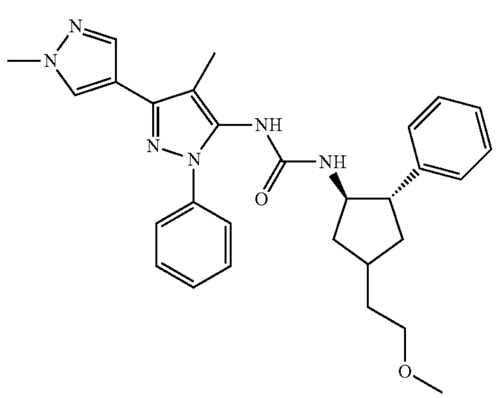 | 1 | 1.88 | 499 | |

TABLE 24-continued

| No. | Structure | LCMS method No | RT | MS (m/z) | Configuration |
|-----|-----------|----------------|-----|----------|---------------|
| I-86 | 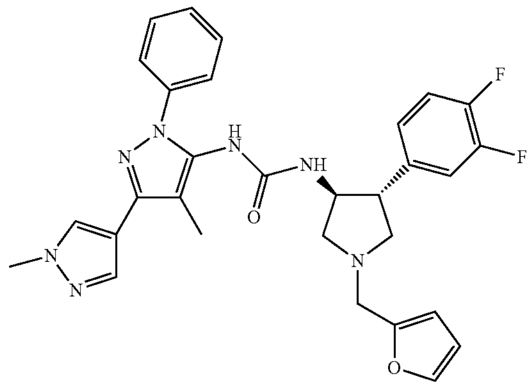 [SMILES: Cc1c(-c2cnn(C)c2)nn(-c2ccccc2)c1NC(=O)N[C@@H]1CN(Cc2ccco2)C[C@H]1c1ccc(F)c(F)c1] | 2 | 1.38 | 558 | |
| I-87 | 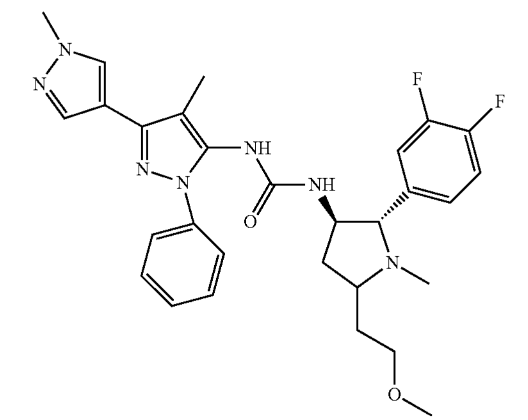 [SMILES: COCCC1C[C@@H](NC(=O)Nc2c(C)c(-c3cnn(C)c3)nn2-c2ccccc2)[C@H](c2ccc(F)c(F)c2)N1C] | 1 | 1.1 | 550.3 | trans |

TABLE 25

| No. | Structure | LCMS method No | RT | MS (m/z) | Configuration |
|-----|-----------|----------------|-----|----------|---------------|
| I-88 | 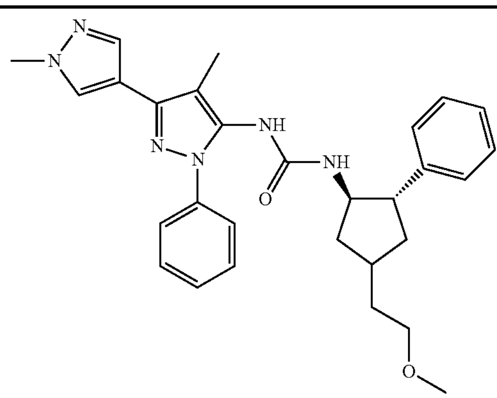 | 1 | 1.87 | 499 | trans |

TABLE 25-continued

| No. | Structure | LCMS method No | RT | MS (m/z) | Configuration |
|---|---|---|---|---|---|
| I-89 | 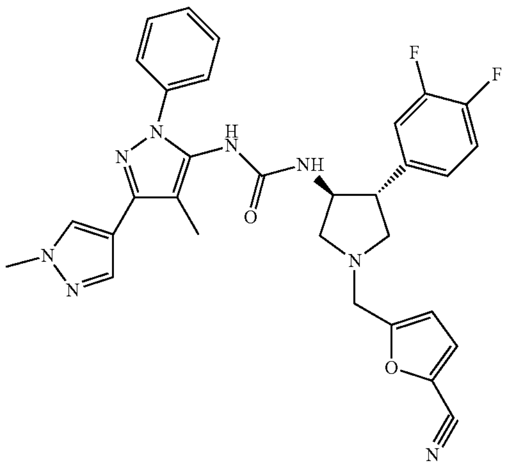 [SMILES: Cc1c(-c2cnn(C)c2)nn(-c2ccccc2)c1NC(=O)N[C@@H]1CN(Cc2ccc(C#N)o2)C[C@H]1c1ccc(F)c(F)c1] | 2 | 1.4 | 583 | |
| I-90 | 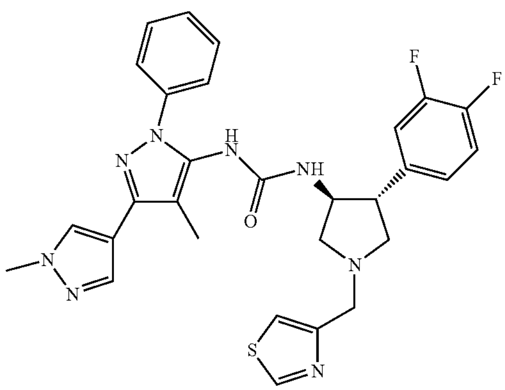 [SMILES: Cc1c(-c2cnn(C)c2)nn(-c2ccccc2)c1NC(=O)N[C@@H]1CN(Cc2cscn2)C[C@H]1c1ccc(F)c(F)c1] | 2 | 1.39 | 575.21 | |

TABLE 26

| No. | Structure | LCMS method No | RT | MS (m/z) | Configuration |
|---|---|---|---|---|---|
| I-91 | 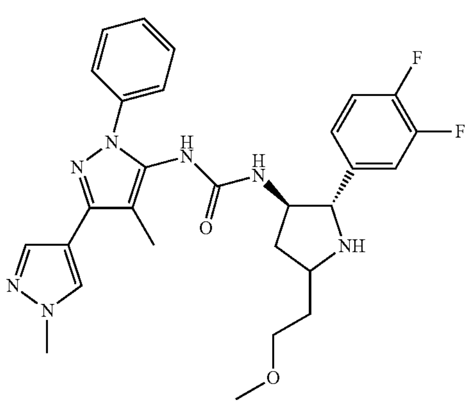 [SMILES: COCCC1C[C@@H](NC(=O)Nc2c(C)c(-c3cnn(C)c3)nn2-c2ccccc2)[C@H](c2ccc(F)c(F)c2)N1] | 1 | 1.21 | 536.25 | trans |

TABLE 26-continued
| No. | Structure | LCMS method No | RT | MS (m/z) | Configuration |
|---|---|---|---|---|---|
| I-92 | 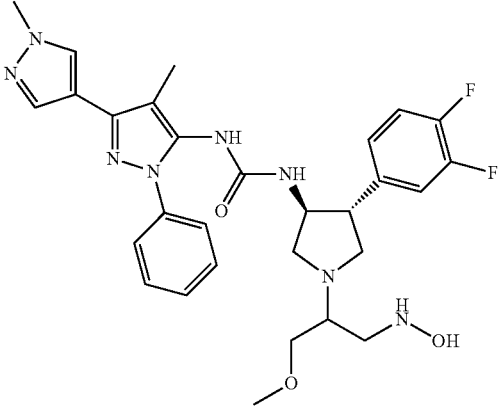 [SMILES: COCC(CNO)N1C[C@@H](NC(=O)Nc2c(C)c(-c3cnn(C)c3)nn2-c2ccccc2)[C@H](c2ccc(F)c(F)c2)C1] | 2 | 1.36 | 581.27 | |
| I-93 | 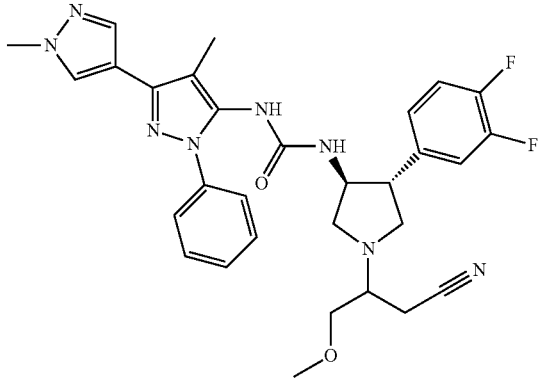 [SMILES: COCC(CC#N)N1C[C@@H](NC(=O)Nc2c(C)c(-c3cnn(C)c3)nn2-c2ccccc2)[C@H](c2ccc(F)c(F)c2)C1] | 2 | 1.48 | 575.26 | |
TABLE 27
| No. | Structure | LCMS method No | RT | MS (m/z) | Configuration |
|---|---|---|---|---|---|
| I-94 | 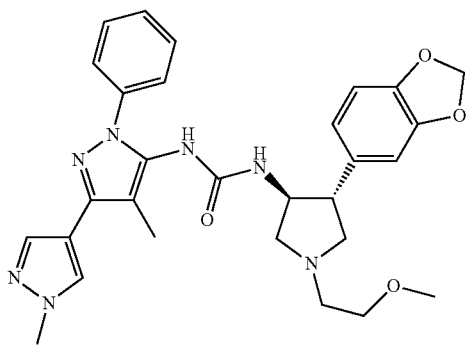 [SMILES: COCCN1C[C@@H](NC(=O)Nc2c(C)c(-c3cnn(C)c3)nn2-c2ccccc2)[C@H](c2ccc3c(c2)OCO3)C1] | 2 | 1.19 | 544 | racemate |

TABLE 27-continued

| No. | Structure | LCMS method No | RT | MS (m/z) | Configuration |
|---|---|---|---|---|---|
| I-95 | 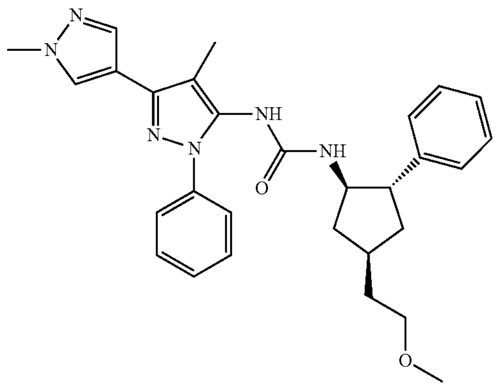 [SMILES: COCC[C@H]1C[C@@H](NC(=O)Nc2c(C)c(-c3cnn(C)c3)nn2-c2ccccc2)[C@H](c2ccccc2)C1] | 2 | 1.93 | 499 | |
| I-96 | 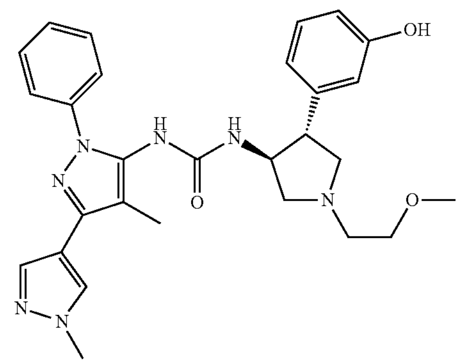 [SMILES: COCCN1C[C@@H](NC(=O)Nc2c(C)c(-c3cnn(C)c3)nn2-c2ccccc2)[C@H](c2cccc(O)c2)C1] | 1 | 1.07 | 516.26 | racemate |

TABLE 28

| No. | Structure | LCMS method No | RT | MS (m/z) | Configuration |
|---|---|---|---|---|---|
| I-97 | 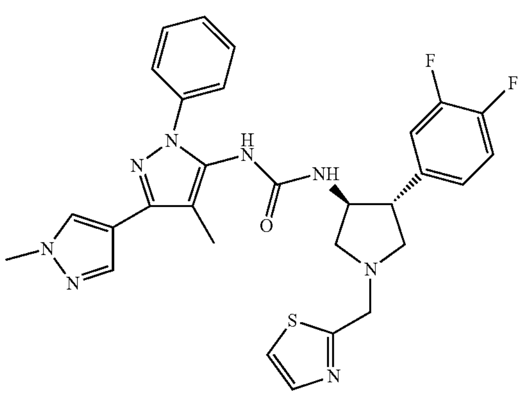 [SMILES: Cc1c(-c2cnn(C)c2)nn(-c2ccccc2)c1NC(=O)N[C@@H]1CN(Cc2nccs2)C[C@H]1c1ccc(F)c(F)c1] | 2 | 1.42 | 575.21 | |

TABLE 28-continued

| No. | Structure | LCMS method No | RT | MS (m/z) | Configuration |
|---|---|---|---|---|---|
| I-98 | 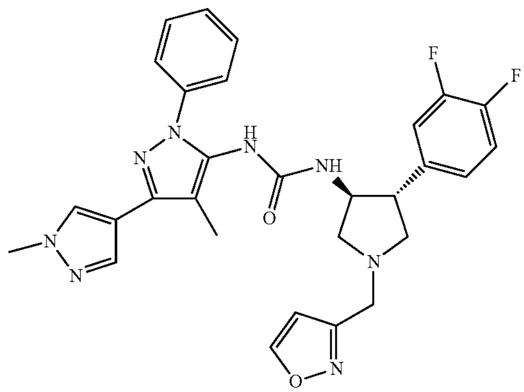 [SMILES: Cc1c(-c2cnn(C)c2)nn(-c2ccccc2)c1NC(=O)N[C@@H]1CN(Cc2ccon2)C[C@H]1c1ccc(F)c(F)c1] | 2 | 1.4 | 559.23 | |
| I-99 | 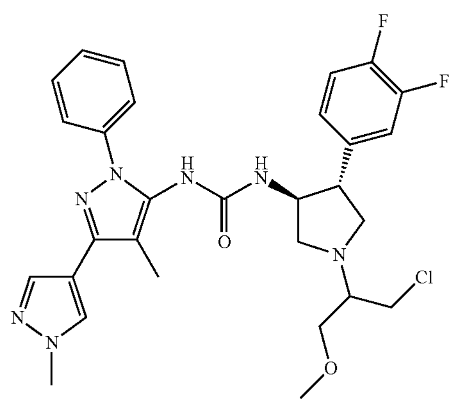 [SMILES: COCC(CCl)N1C[C@@H](NC(=O)Nc2c(C)c(-c3cnn(C)c3)nn2-c2ccccc2)[C@H](c2ccc(F)c(F)c2)C1] | 1 | 1.32 | 584.2 | |

TABLE 29

| No. | Structure | LCMS method No | RT | MS (m/z) | Configuration |
|---|---|---|---|---|---|
| I-100 | 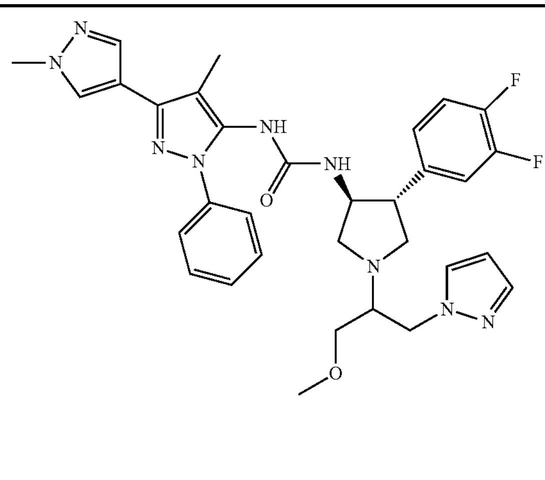 | 2 | 1.51 | 616.29 | |

TABLE 29-continued

| No. | Structure | LCMS method No | RT | MS (m/z) | Configuration |
|---|---|---|---|---|---|
| I-101 | 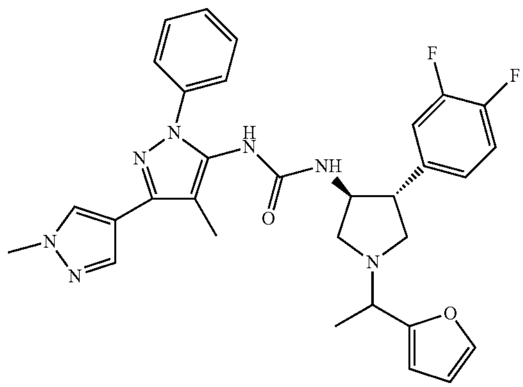 [SMILES: Cc1c(-c2cnn(C)c2)nn(-c2ccccc2)c1NC(=O)N[C@@H]1CN(C(C)c2ccco2)C[C@H]1c1ccc(F)c(F)c1] | 2 | 1.47 | 572 | |
| I-102 | 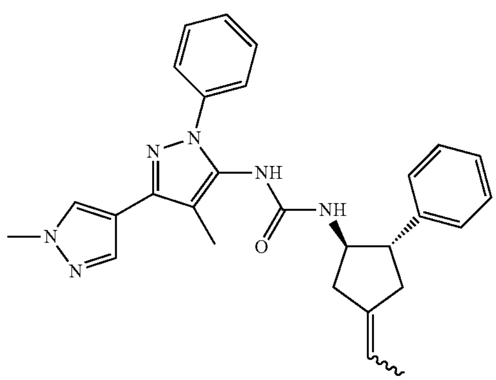 | 1 | 2.07 | 467 | trans |

TABLE 30

| No. | Structure | LCMS method No | RT | MS (m/z) | Configuration |
|---|---|---|---|---|---|
| I-103 | 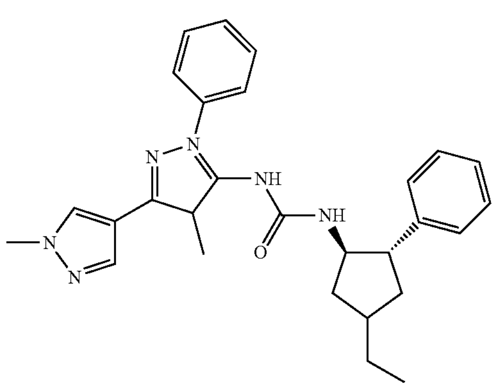 | 1 | 2.15 | 469 | trans |

TABLE 30-continued
| No. | Structure | LCMS method No | RT | MS (m/z) | Configuration |
|---|---|---|---|---|---|
| I-104 | 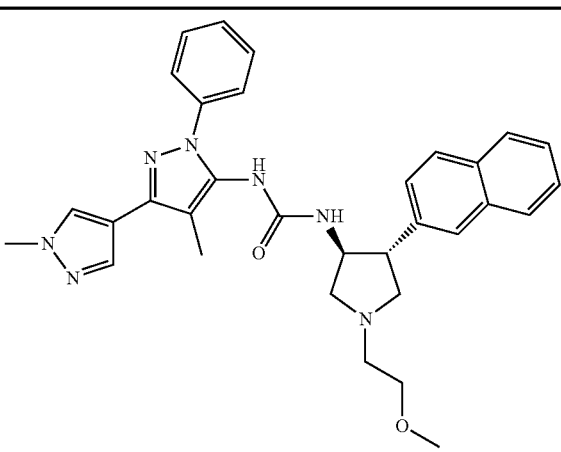 | 2 | 1.46 | 550 | racemate |
| I-105 | 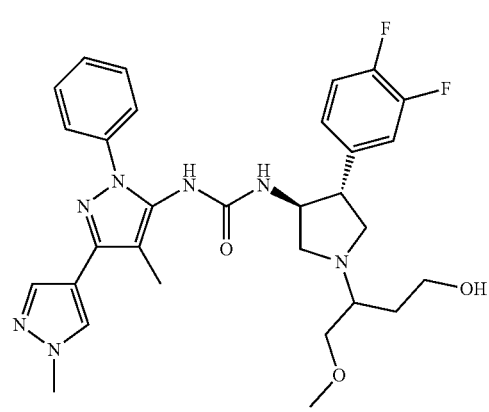 [SMILES: COCC(CCO)N1C[C@@H](NC(=O)Nc2c(C)c(-c3cnn(C)c3)nn2-c2ccccc2)[C@H](c2ccc(F)c(F)c2)C1] | 1 | 1.19 | 580.25 | |
TABLE 31
| No. | Structure | LCMS method No | RT | MS (m/z) | Configuration |
|---|---|---|---|---|---|
| I-106 | 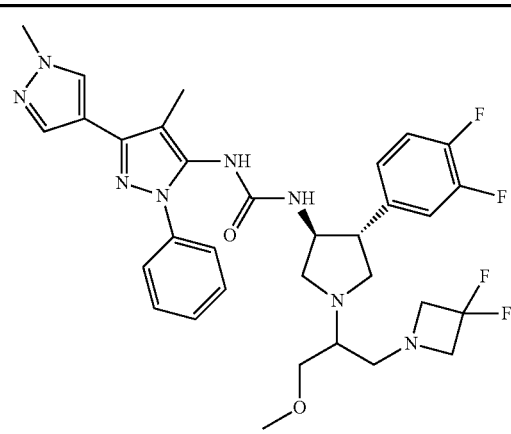 | 2 | 1.64 | 641.29 | |

TABLE 31-continued

| No. | Structure | LCMS method No | RT | MS (m/z) | Configuration |
|---|---|---|---|---|---|
| I-107 | 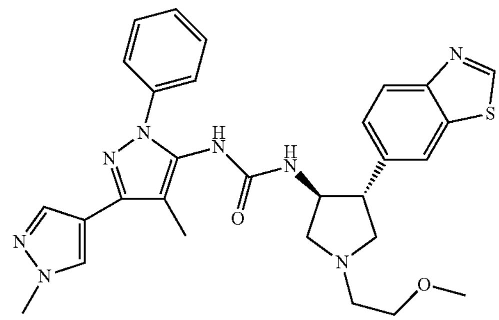 [SMILES: COCCN1C[C@@H](NC(=O)Nc2c(C)c(-c3cnn(C)c3)nn2-c2ccccc2)[C@H](c2ccc3ncsc3c2)C1] | 2 | 1.11 | 557 | racemate |
| I-108 | 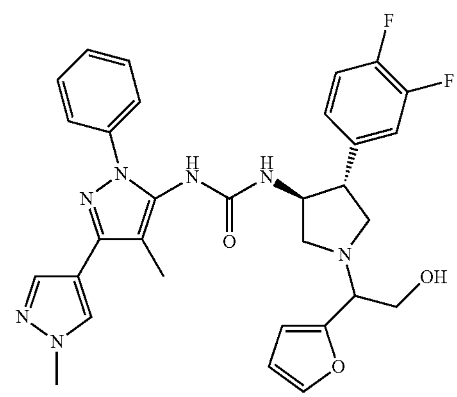 [SMILES: Cc1c(-c2cnn(C)c2)nn(-c2ccccc2)c1NC(=O)N[C@@H]1CN(C(CO)c2ccco2)C[C@H]1c1ccc(F)c(F)c1] | 1 | 1.25 | 588.25 | |

TABLE 32

| No. | Structure | LCMS method No | RT | MS (m/z) | Configuration |
|---|---|---|---|---|---|
| I-109 | 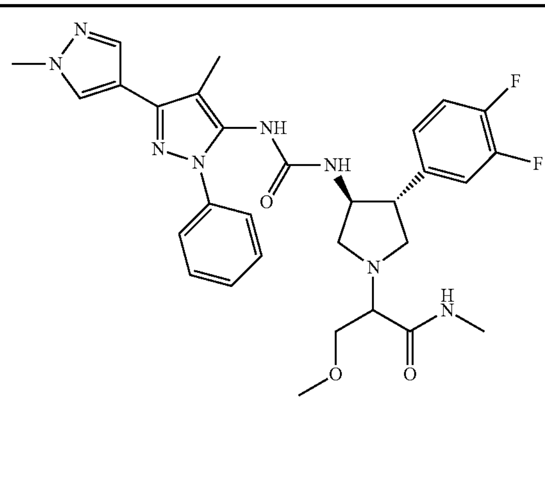 | 3 | 1.64 | 593 | |

TABLE 32-continued

| No. | Structure | LCMS method No | RT | MS (m/z) | Configuration |
|---|---|---|---|---|---|
| I-110 | 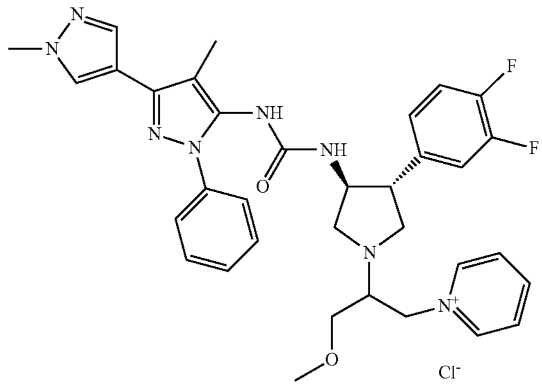 [SMILES: COCC(C[n+]1ccccc1)N1C[C@@H](NC(=O)Nc2c(C)c(-c3cnn(C)c3)nn2-c2ccccc2)[C@H](c2ccc(F)c(F)c2)C1 ; [Cl-]] | 1 | 1.32 | 627.35 | |
| I-111 | 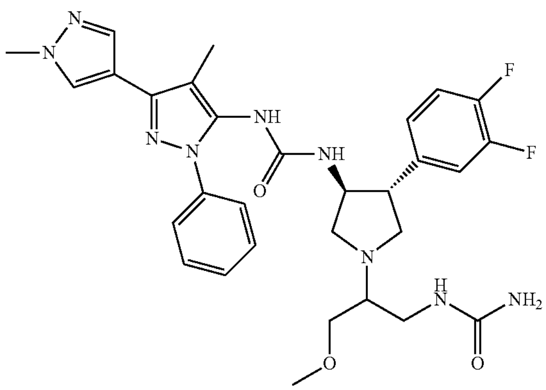 [SMILES: COCC(CNC(N)=O)N1C[C@@H](NC(=O)Nc2c(C)c(-c3cnn(C)c3)nn2-c2ccccc2)[C@H](c2ccc(F)c(F)c2)C1] | 4 | 1.3 | 608.28 | |

TABLE 33

| No. | Structure | LCMS method No | RT | MS (m/z) | Configuration |
|---|---|---|---|---|---|
| I-112 | 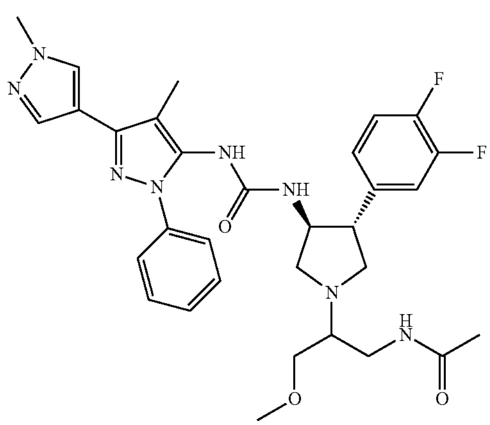 [SMILES: COCC(CNC(C)=O)N1C[C@@H](NC(=O)Nc2c(C)c(-c3cnn(C)c3)nn2-c2ccccc2)[C@H](c2ccc(F)c(F)c2)C1] | 4 | 1.61 | 607 | |

TABLE 33-continued

| No. | Structure | LCMS method No | RT | MS (m/z) | Configuration |
|---|---|---|---|---|---|
| I-113 | 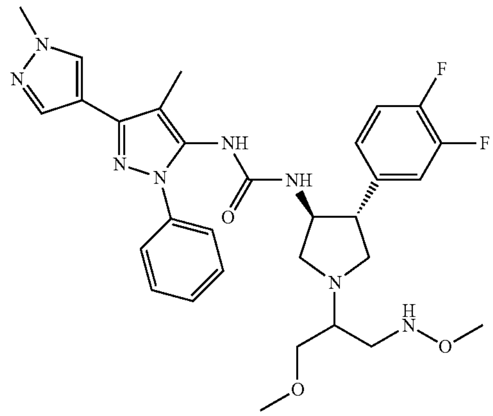 [SMILES: COCC(CNOC)N1C[C@@H](NC(=O)Nc2c(C)c(-c3cnn(C)c3)nn2-c2ccccc2)[C@H](c2ccc(F)c(F)c2)C1] | 2 | 1.44 | 595.29 | |
| I-114 | 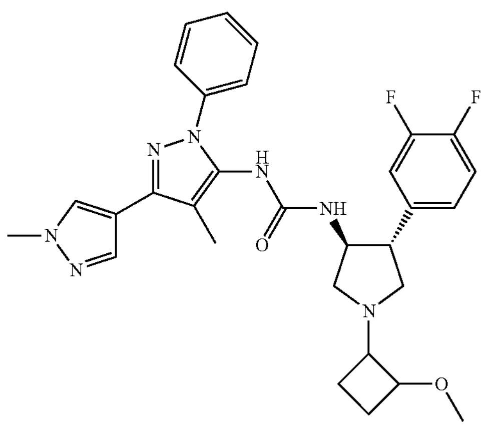 [SMILES: COC1CCC1N1C[C@@H](NC(=O)Nc2c(C)c(-c3cnn(C)c3)nn2-c2ccccc2)[C@H](c2ccc(F)c(F)c2)C1] | 2 | 1.38 | 562 | |

TABLE 34

| No. | Structure | LCMS method No | RT | MS (m/z) | Configuration |
|---|---|---|---|---|---|
| I-115 | 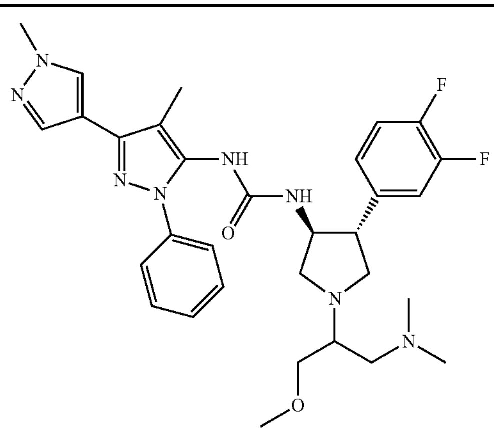 | 1 | 1.29 | 593.3 | |

TABLE 34-continued

| No. | Structure | LCMS method No | RT | MS (m/z) | Configuration |
|---|---|---|---|---|---|
| I-116 | 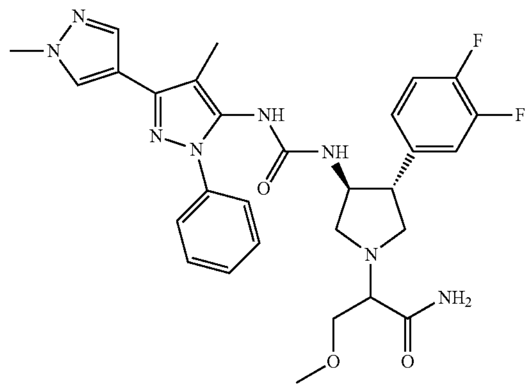 [SMILES: COCC(C(N)=O)N1C[C@@H](NC(=O)Nc2c(C)c(-c3cnn(C)c3)nn2-c2ccccc2)[C@H](c2ccc(F)c(F)c2)C1] | 3 | 1.59 | 579 | |
| I-117 | 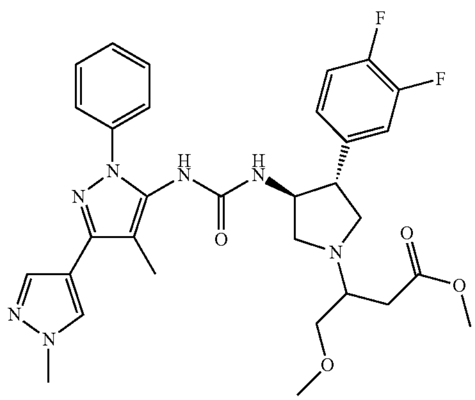 [SMILES: COCC(CC(=O)OC)N1C[C@@H](NC(=O)Nc2c(C)c(-c3cnn(C)c3)nn2-c2ccccc2)[C@H](c2ccc(F)c(F)c2)C1] | 1 | 1.3 | 608.3 | |

TABLE 35

| No. | Structure | LCMS method No | RT | MS (m/z) | Configuration |
|---|---|---|---|---|---|
| I-118 | 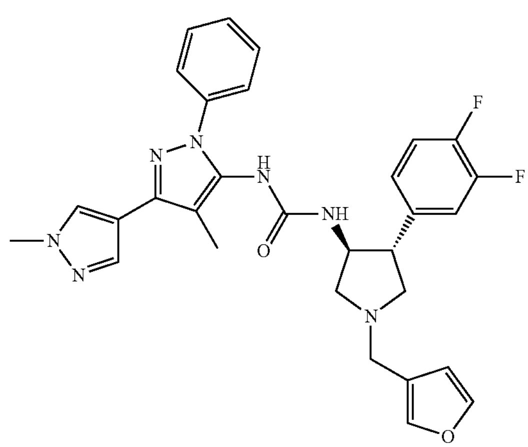 [SMILES: Cc1c(-c2cnn(C)c2)nn(-c2ccccc2)c1NC(=O)N[C@@H]1CN(Cc2ccoc2)C[C@H]1c1ccc(F)c(F)c1] | 2 | 1.4 | 558 | |

TABLE 35-continued
| No. | Structure | LCMS method No | RT | MS (m/z) | Configuration |
|---|---|---|---|---|---|
| I-119 | 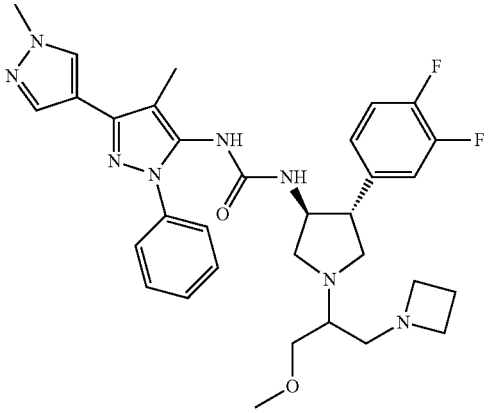 [SMILES: COCC(CN1CCC1)N1C[C@@H](NC(=O)Nc2c(C)c(-c3cnn(C)c3)nn2-c2ccccc2)[C@H](c2ccc(F)c(F)c2)C1] | 2 | 1.38 | 605.31 | |
| I-120 | 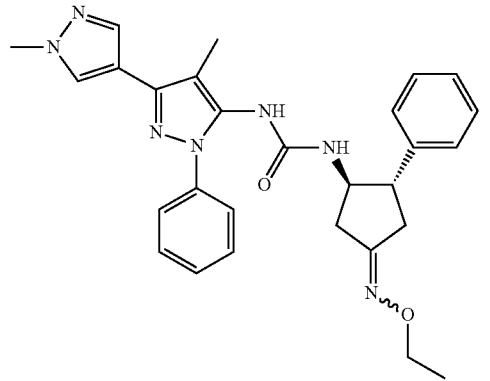 [SMILES: CCON=C1C[C@@H](NC(=O)Nc2c(C)c(-c3cnn(C)c3)nn2-c2ccccc2)[C@H](c2ccccc2)C1] | 1 | 1.78 | 498 | trans either E or Z form |
TABLE 36
| No. | Structure | LCMS method No | RT | MS (m/z) | Configuration |
|---|---|---|---|---|---|
| I-121 | 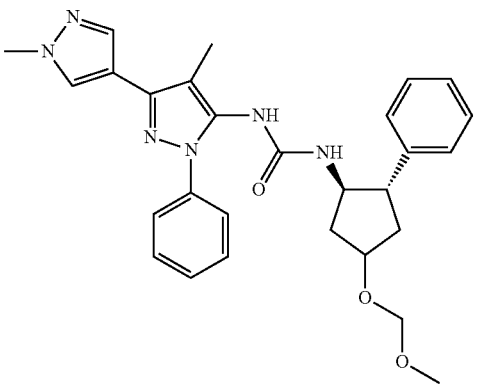 [SMILES: COCOC1C[C@@H](NC(=O)Nc2c(C)c(-c3cnn(C)c3)nn2-c2ccccc2)[C@H](c2ccccc2)C1] | 2 | 1.8 | 501 | trans |

TABLE 36-continued
| No. | Structure | LCMS method No | RT | MS (m/z) | Configuration |
|---|---|---|---|---|---|
| I-122 | 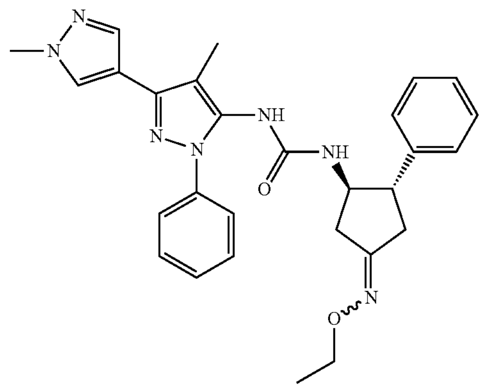 [SMILES: CCON=C1C[C@@H](NC(=O)Nc2c(C)c(-c3cnn(C)c3)nn2-c2ccccc2)[C@H](c2ccccc2)C1] | 1 | 1.85 | 498 | trans either E or Z form |
| I-123 | 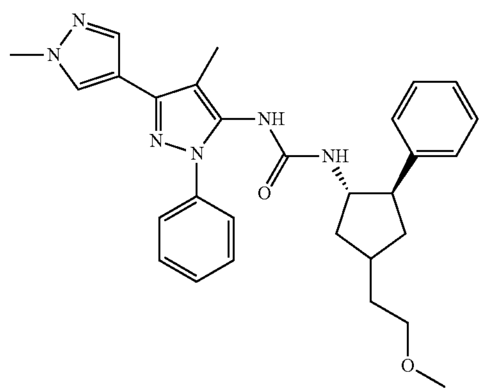 [SMILES: COCCC1C[C@H](NC(=O)Nc2c(C)c(-c3cnn(C)c3)nn2-c2ccccc2)[C@@H](c2ccccc2)C1] | 1 | 1.88 | 499 | |
TABLE 37
| No. | Structure | LCMS method No | RT | MS (m/z) | Configuration |
|---|---|---|---|---|---|
| I-124 | 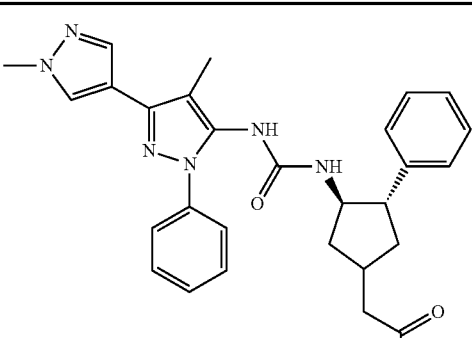 | 2 | 2.02 | 527 | trans |

TABLE 37-continued

| No. | Structure | LCMS method No | RT | MS (m/z) | Configuration |
|---|---|---|---|---|---|
| I-125 | 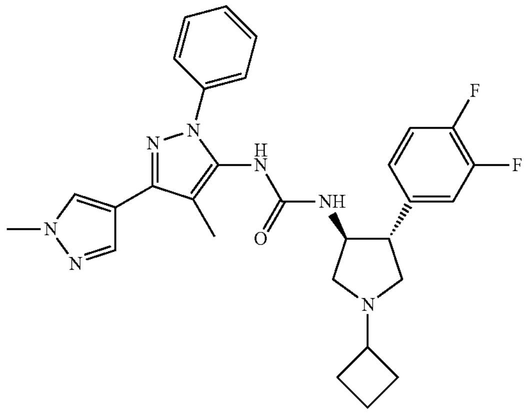 [SMILES: Cc1c(-c2cnn(C)c2)nn(-c2ccccc2)c1NC(=O)N[C@@H]1CN(C2CCC2)C[C@H]1c1ccc(F)c(F)c1] | 2 | 1.4 | 532 | |
| I-126 | 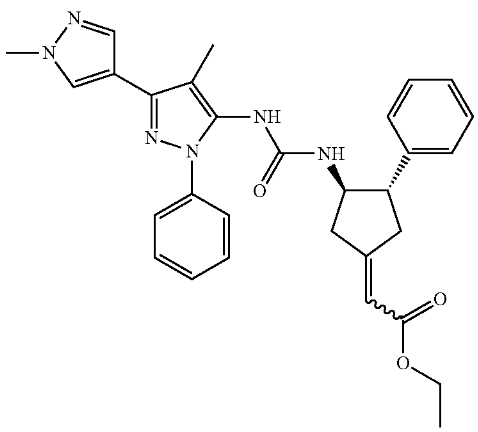 [SMILES: CCOC(=O)C=C1C[C@@H](NC(=O)Nc2c(C)c(-c3cnn(C)c3)nn2-c2ccccc2)[C@H](c2ccccc2)C1] | 2 | 2.02 | 525 | trans |

TABLE 38

| No. | Structure | LCMS method No | RT | MS (m/z) | Configuration |
|---|---|---|---|---|---|
| I-127 | 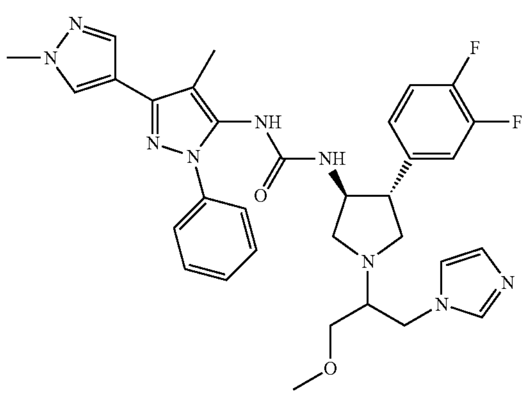 [SMILES: COCC(Cn1ccnc1)N1C[C@@H](NC(=O)Nc2c(C)c(-c3cnn(C)c3)nn2-c2ccccc2)[C@H](c2ccc(F)c(F)c2)C1] | 2 | 1.25 | 616.29 | |

TABLE 38-continued

| No. | Structure | LCMS method No | RT | MS (m/z) | Configuration |
|---|---|---|---|---|---|
| I-128 | 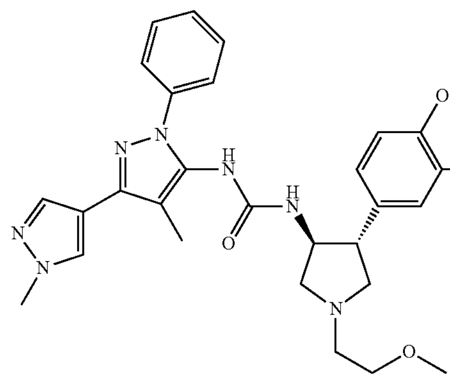 | 2 | 1.23 | 558 | racemate |
| I-129 | 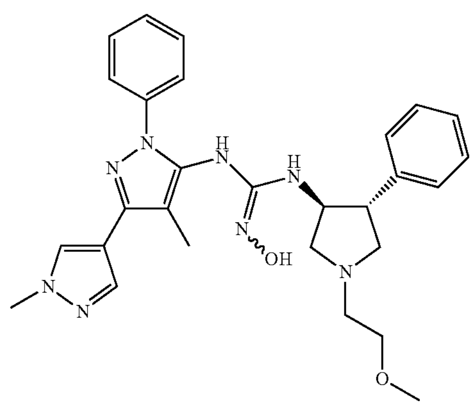 [SMILES: COCCN1C[C@@H](NC(=NO)Nc2c(C)c(-c3cnn(C)c3)nn2-c2ccccc2)[C@H](c2ccccc2)C1] | 1 | 1 | 515.3 | trans |

TABLE 39

| No. | Structure | LCMS method No | RT | MS (m/z) | Configuration |
|---|---|---|---|---|---|
| I-130 | 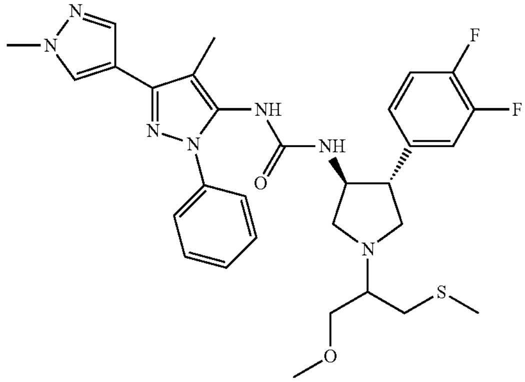 [SMILES: COCC(CSC)N1C[C@@H](NC(=O)Nc2c(C)c(-c3cnn(C)c3)nn2-c2ccccc2)[C@H](c2ccc(F)c(F)c2)C1] | 2 | 1.43 | 596.25 | |

TABLE 39-continued

| No. | Structure | LCMS method No | RT | MS (m/z) | Configuration |
|---|---|---|---|---|---|
| I-131 | 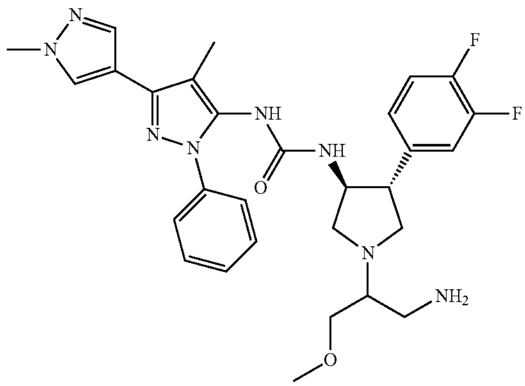 [SMILES: COCC(CN)N1C[C@@H](NC(=O)Nc2c(C)c(-c3cnn(C)c3)nn2-c2ccccc2)[C@H](c2ccc(F)c(F)c2)C1] | 2 | 1.23 | 565.28 | |
| I-132 | 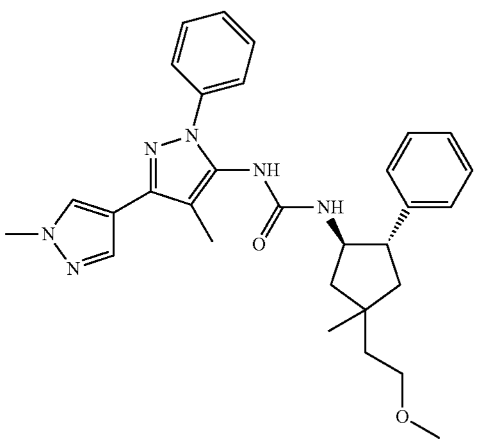 [SMILES: COCCC1(C)C[C@@H](NC(=O)Nc2c(C)c(-c3cnn(C)c3)nn2-c2ccccc2)[C@H](c2ccccc2)C1] | 1 | 1.97 | 513 | trans |

TABLE 40

| No. | Structure | LCMS method No | RT | MS (m/z) | Configuration |
|---|---|---|---|---|---|
| I-133 | 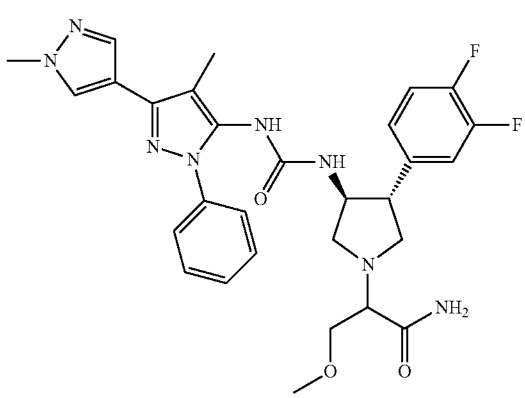 [SMILES: COCC(C(N)=O)N1C[C@@H](NC(=O)Nc2c(C)c(-c3cnn(C)c3)nn2-c2ccccc2)[C@H](c2ccc(F)c(F)c2)C1] | 3 | 1.59 | 579 | |

TABLE 40-continued

| No. | Structure | LCMS method No | RT | MS (m/z) | Configuration |
|---|---|---|---|---|---|
| I-134 | 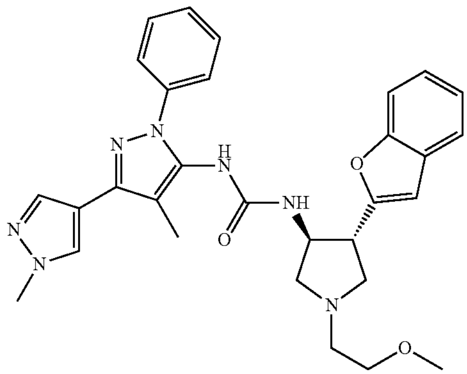 [SMILES: COCCN1C[C@@H](NC(=O)Nc2c(C)c(-c3cnn(C)c3)nn2-c2ccccc2)[C@H](c2cc3ccccc3o2)C1] | 2 | 1.39 | 540 | racemate |
| I-135 | 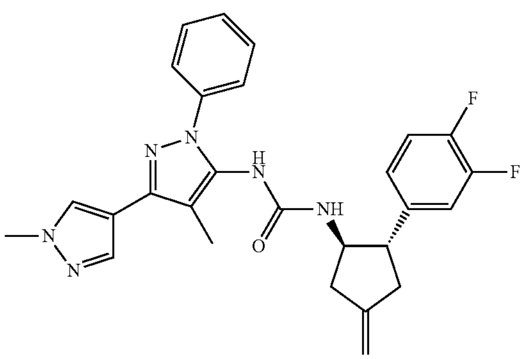 [SMILES: C=C1C[C@@H](NC(=O)Nc2c(C)c(-c3cnn(C)c3)nn2-c2ccccc2)[C@H](c2ccc(F)c(F)c2)C1] | 2 | 2.1 | 489 | racemate |

TABLE 41

| No. | Structure | LCMS method No | RT | MS (m/z) | Configuration |
|---|---|---|---|---|---|
| I-136 | 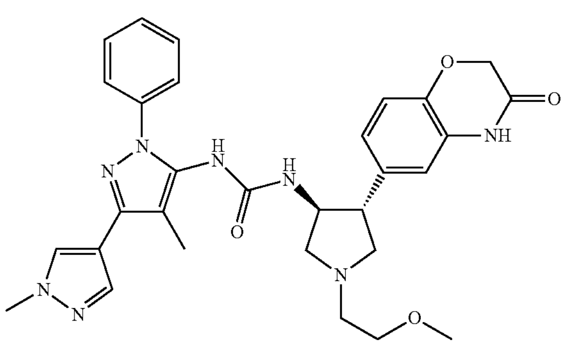 [SMILES: COCCN1C[C@@H](NC(=O)Nc2c(C)c(-c3cnn(C)c3)nn2-c2ccccc2)[C@H](c2ccc3c(c2)NC(=O)CO3)C1] | 2 | 0.99 | 571 | racemate |

TABLE 41-continued

| No. | Structure | LCMS method No | RT | MS (m/z) | Configuration |
|---|---|---|---|---|---|
| I-137 | 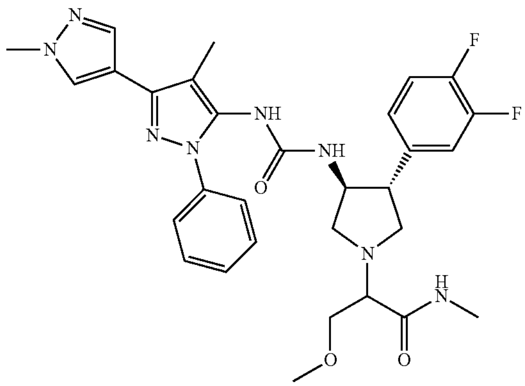 [SMILES: CNC(=O)C(COC)N1C[C@@H](NC(=O)Nc2c(C)c(-c3cnn(C)c3)nn2-c2ccccc2)[C@H](c2ccc(F)c(F)c2)C1] | 3 | 1.65 | 593 | |
| I-138 | 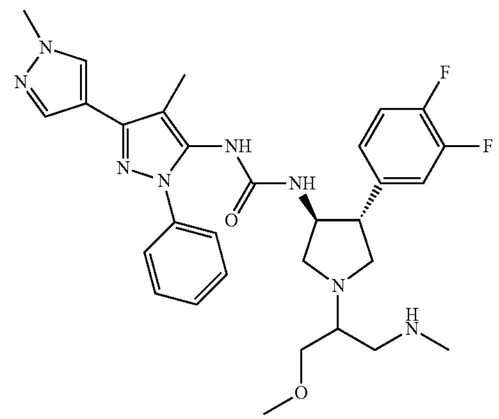 [SMILES: CNCC(COC)N1C[C@@H](NC(=O)Nc2c(C)c(-c3cnn(C)c3)nn2-c2ccccc2)[C@H](c2ccc(F)c(F)c2)C1] | 1 | 1.23 | 579.3 | |

TABLE 42

| No. | Structure | LCMS method No | RT | MS (m/z) | Configuration |
|---|---|---|---|---|---|
| I-139 | 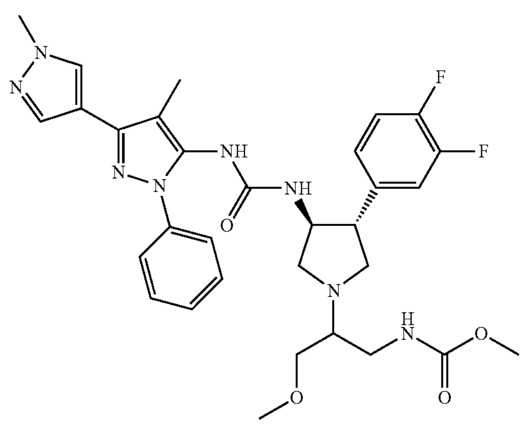 [SMILES: COCC(CNC(=O)OC)N1C[C@@H](NC(=O)Nc2c(C)c(-c3cnn(C)c3)nn2-c2ccccc2)[C@H](c2ccc(F)c(F)c2)C1] | 4 | 1.79 | 623 | |

TABLE 42-continued

| No. | Structure | LCMS method No | RT | MS (m/z) | Configuration |
|---|---|---|---|---|---|
| I-140 | 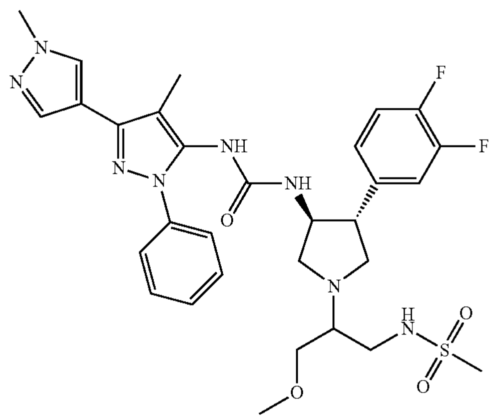 [SMILES: COCC(CNS(C)(=O)=O)N1C[C@@H](NC(=O)Nc2c(C)c(-c3cnn(C)c3)nn2-c2ccccc2)[C@H](c2ccc(F)c(F)c2)C1] | 4 | 1.75 | 643 | |
| I-141 | 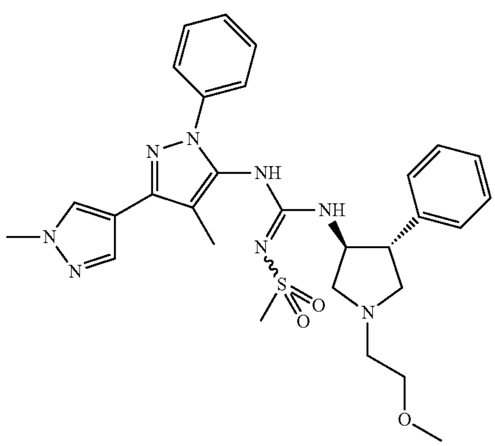 [SMILES: COCCN1C[C@@H](NC(=NS(C)(=O)=O)Nc2c(C)c(-c3cnn(C)c3)nn2-c2ccccc2)[C@H](c2ccccc2)C1] | 1 | 1.2 | 577.25 | trans |

TABLE 43

| No. | Structure | LCMS method No | RT | MS (m/z) | Configuration |
|---|---|---|---|---|---|
| I-142 | 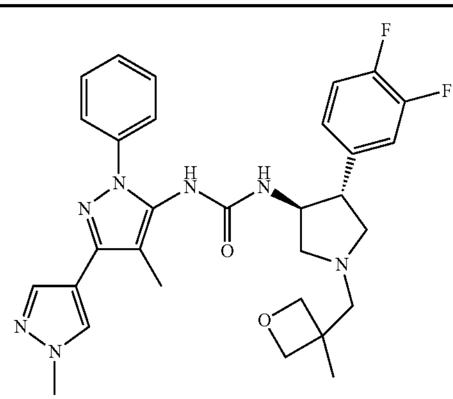 | 1 | 1.18 | 562.25 | |

TABLE 43-continued
| No. | Structure | LCMS method No | RT | MS (m/z) | Configuration |
|---|---|---|---|---|---|
| I-143 | 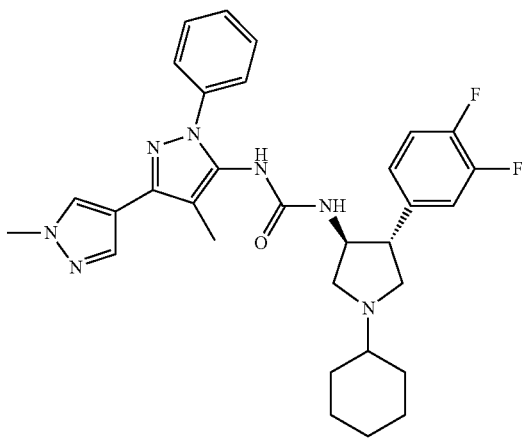 [SMILES: Cc1c(-c2cnn(C)c2)nn(-c2ccccc2)c1NC(=O)N[C@@H]1CN(C2CCCCC2)C[C@H]1c1ccc(F)c(F)c1] | 2 | 1.54 | 560 | |
| I-144 | 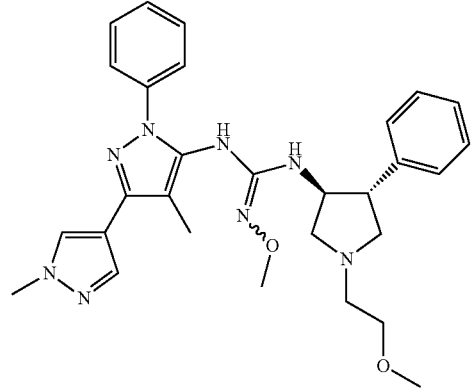 [SMILES: COCCN1C[C@@H](NC(=NOC)Nc2c(C)c(-c3cnn(C)c3)nn2-c2ccccc2)[C@H](c2ccccc2)C1] | 1 | 1.24 | 529.3 | trans |
TABLE 44
| No. | Structure | LCMS method No | RT | MS (m/z) | Configuration |
|---|---|---|---|---|---|
| I-145 | 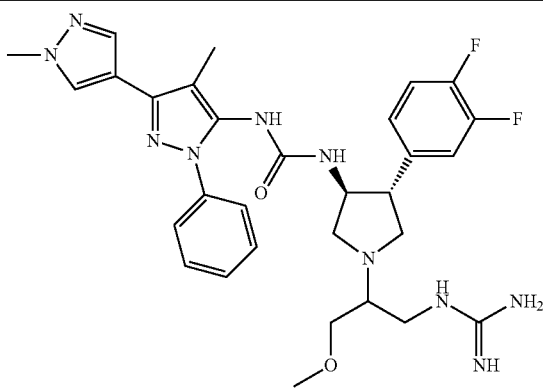 | 4 | 1.51 | 607 | |

TABLE 44-continued
| No. | Structure | LCMS method No | RT | MS (m/z) | Configuration |
|---|---|---|---|---|---|
| I-146 | 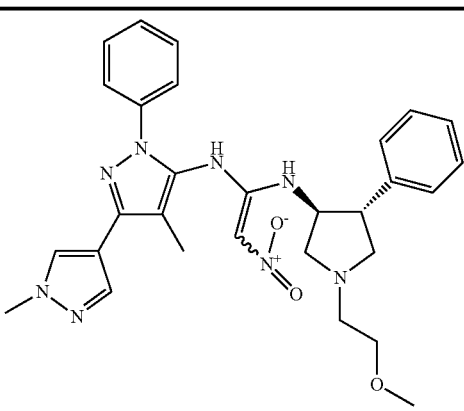 | 1 | 1.32 | 543.3 | trans |
| I-147 | 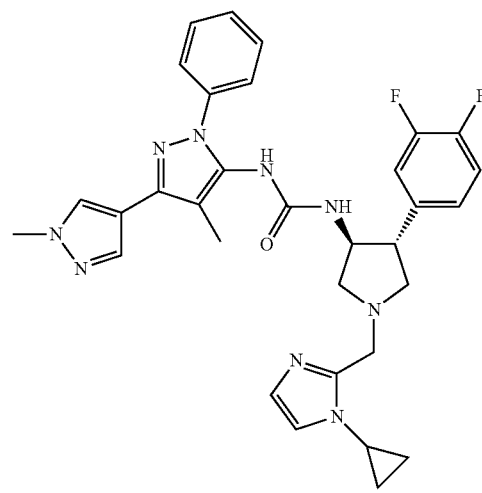 [SMILES: Cc1c(-c2cnn(C)c2)nn(-c2ccccc2)c1NC(=O)N[C@@H]1CN(Cc2nccn2C2CC2)C[C@H]1c1ccc(F)c(F)c1] | 2 | 1.51 | 598.28 | |
TABLE 45
| No. | Structure | LCMS method No | RT | MS (m/z) | Configuration |
|---|---|---|---|---|---|
| I-148 | 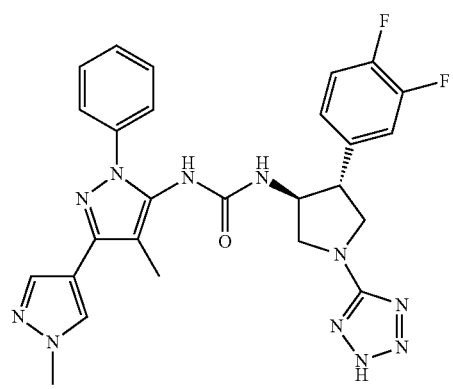 [SMILES: Cc1c(-c2cnn(C)c2)nn(-c2ccccc2)c1NC(=O)N[C@@H]1CN(c2nn[nH]n2)C[C@H]1c1ccc(F)c(F)c1] | 1 | 1.44 | 546.2 | |

TABLE 45-continued

| No. | Structure | LCMS method No | RT | MS (m/z) | Configuration |
|---|---|---|---|---|---|
| I-149 | 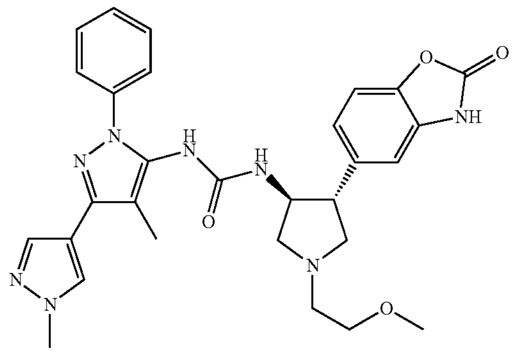 [SMILES: COCCN1C[C@@H](NC(=O)Nc2c(C)c(-c3cnn(C)c3)nn2-c2ccccc2)[C@H](c2ccc3oc(=O)[nH]c3c2)C1] | 2 | 1.03 | 557 | racemate |
| I-150 | 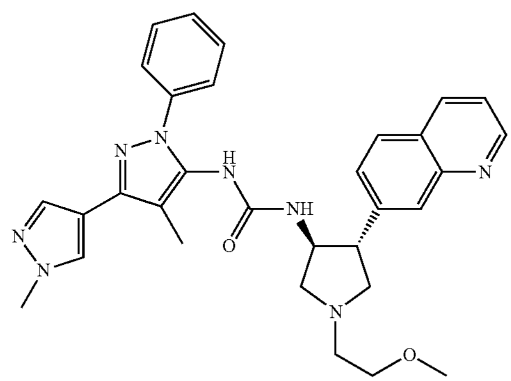 [SMILES: COCCN1C[C@@H](NC(=O)Nc2c(C)c(-c3cnn(C)c3)nn2-c2ccccc2)[C@H](c2ccc3cccnc3c2)C1] | 2 | 0.92 | 551 | racemate |

TABLE 46

| No. | Structure | LCMS method No | RT | MS (m/z) | Configuration |
|---|---|---|---|---|---|
| I-151 | 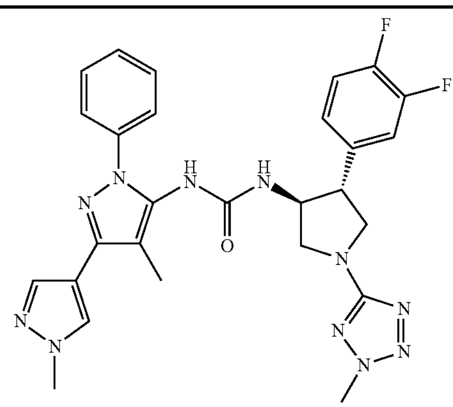 | 1 | 1.68 | 560.2 | |

TABLE 46-continued

| No. | Structure | LCMS method No | RT | MS (m/z) | Configuration |
|---|---|---|---|---|---|
| I-152 | 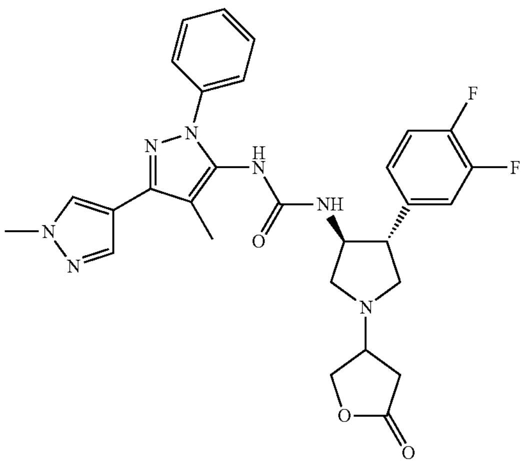 [SMILES: Cc1c(-c2cnn(C)c2)nn(-c2ccccc2)c1NC(=O)N[C@@H]1CN(C2COC(=O)C2)C[C@H]1c1ccc(F)c(F)c1] | 2 | 1.34 | 562.23 | |
| I-153 | 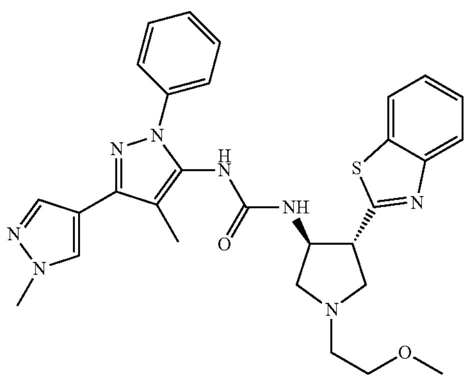 [SMILES: COCCN1C[C@@H](NC(=O)Nc2c(C)c(-c3cnn(C)c3)nn2-c2ccccc2)[C@H](c2nc3ccccc3s2)C1] | 2 | 1.28 | 557 | racemate |
| I-154 | 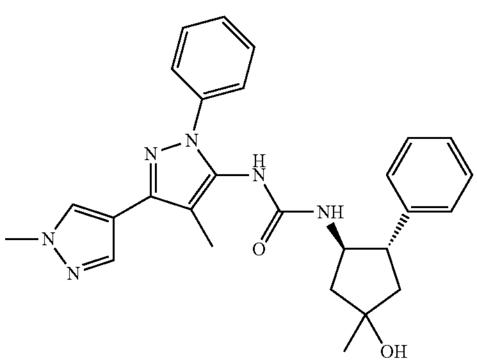 [SMILES: Cc1c(-c2cnn(C)c2)nn(-c2ccccc2)c1NC(=O)N[C@@H]1CC(C)(O)C[C@H]1c1ccccc1] | 2 | 1.57 | 471 | trans |

TABLE 47

| No. | Structure | LCMS method No | RT | MS (m/z) | Configuration |
|---|---|---|---|---|---|
| I-155 | 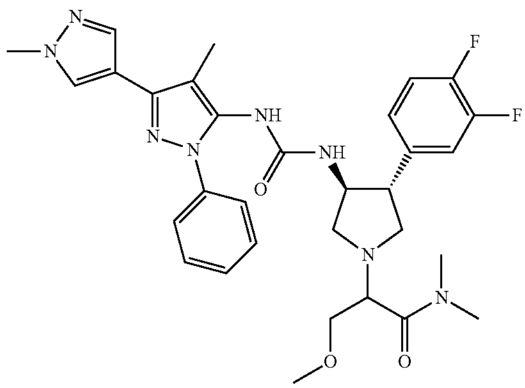 [SMILES: COCC(C(=O)N(C)C)N1C[C@@H](NC(=O)Nc2c(C)c(-c3cnn(C)c3)nn2-c2ccccc2)[C@H](c2ccc(F)c(F)c2)C1] | 3 | 1.72 | 607 | |
| I-156 | 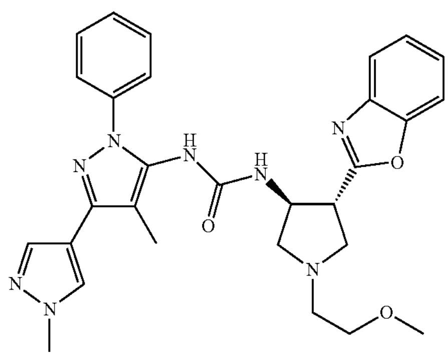 [SMILES: COCCN1C[C@@H](NC(=O)Nc2c(C)c(-c3cnn(C)c3)nn2-c2ccccc2)[C@H](c2nc3ccccc3o2)C1] | 2 | 1.22 | 541 | racemate |
| I-157 | 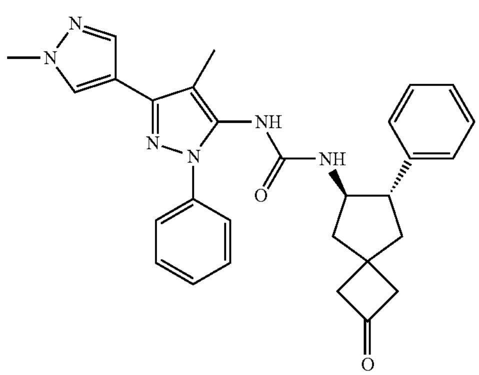 [SMILES: Cc1c(-c2cnn(C)c2)nn(-c2ccccc2)c1NC(=O)N[C@@H]1CC2(CC(=O)C2)C[C@H]1c1ccccc1] | 1 | 1.68 | 495 | racemate |
| I-158 | 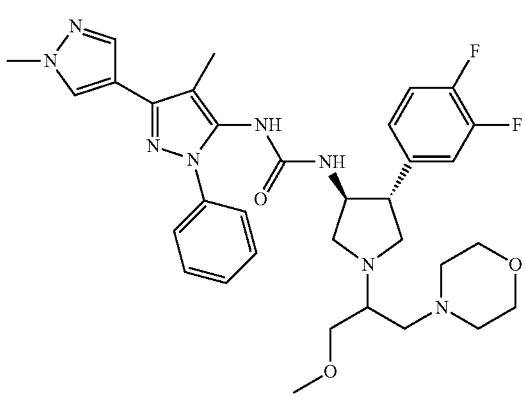 [SMILES: COCC(CN1CCOCC1)N1C[C@@H](NC(=O)Nc2c(C)c(-c3cnn(C)c3)nn2-c2ccccc2)[C@H](c2ccc(F)c(F)c2)C1] | 2 | 1.49 | 635.32 | |

TABLE 48

| No. | Structure | LCMS method No | RT | MS (m/z) | Configuration |
|---|---|---|---|---|---|
| I-159 | 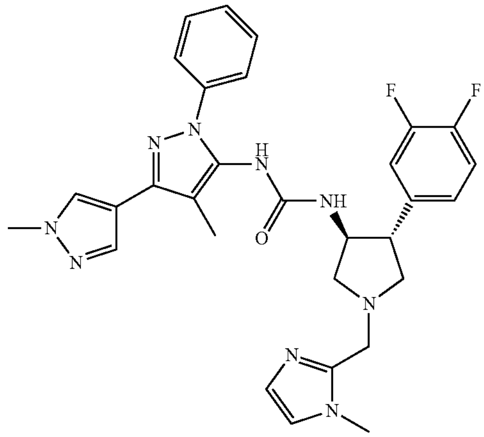 [SMILES: Cc1c(-c2cnn(C)c2)nn(-c2ccccc2)c1NC(=O)N[C@@H]1CN(Cc2nccn2C)C[C@H]1c1ccc(F)c(F)c1] | 2 | 1.41 | 572.26 | |
| I-160 | 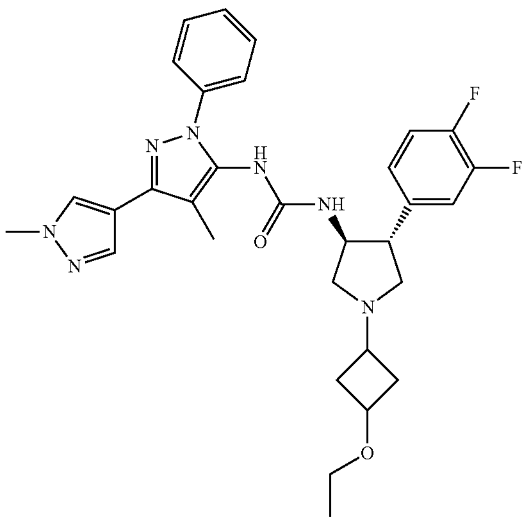 [SMILES: CCOC1CC(N2C[C@@H](NC(=O)Nc3c(C)c(-c4cnn(C)c4)nn3-c3ccccc3)[C@H](c3ccc(F)c(F)c3)C2)C1] | 2 | 1.4 | 576 | |
| I-161 | 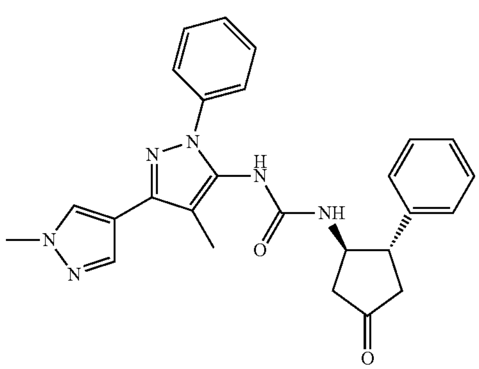 [SMILES: Cc1c(-c2cnn(C)c2)nn(-c2ccccc2)c1NC(=O)N[C@@H]1CC(=O)C[C@H]1c1ccccc1] | 2 | 1.55 | 455 | racemate |

TABLE 48-continued
| No. | Structure | LCMS method No | RT | MS (m/z) | Configuration |
|---|---|---|---|---|---|
| I-162 | 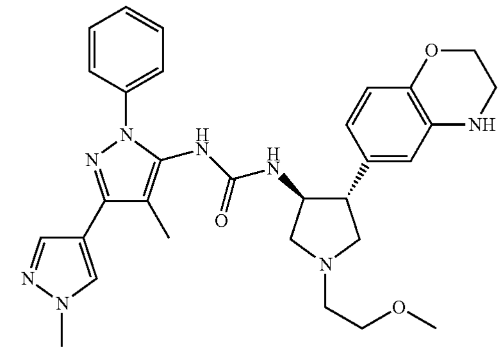 [SMILES: COCCN1C[C@@H](NC(=O)Nc2c(C)c(-c3cnn(C)c3)nn2-c2ccccc2)[C@H](c2ccc3c(c2)NCCO3)C1] | 2 | 1.11 | 557 | racemate |
TABLE 49
| No. | Structure | LCMS method No | RT | MS (m/z) | Configuration |
|---|---|---|---|---|---|
| I-163 | 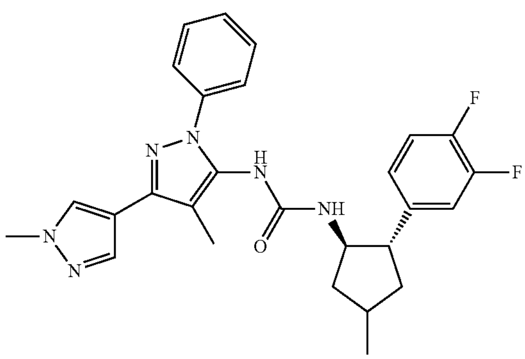 [SMILES: Cc1c(-c2cnn(C)c2)nn(-c2ccccc2)c1NC(=O)N[C@@H]1CC(C)C[C@H]1c1ccc(F)c(F)c1] | 2 | 2.18 | 491 | trans |
| I-164 | 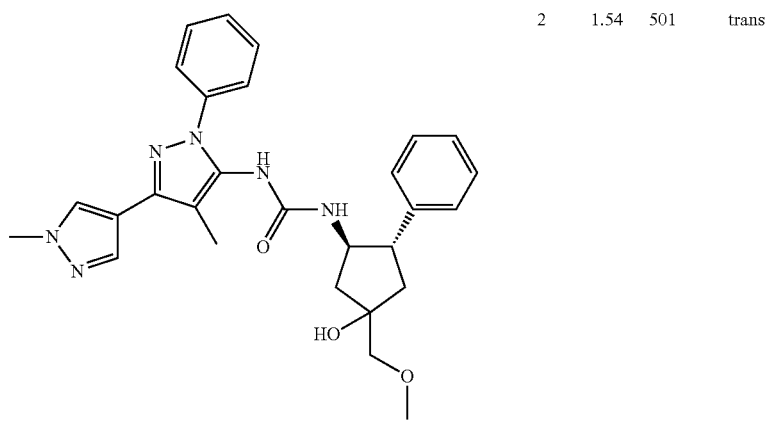 | 2 | 1.54 | 501 | trans |

TABLE 49-continued

| No. | Structure | LCMS method No | RT | MS (m/z) | Configuration |
|---|---|---|---|---|---|
| I-165 | 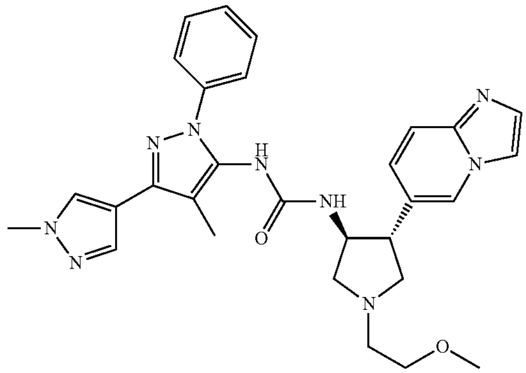 [SMILES: COCCN1C[C@@H](NC(=O)Nc2c(C)c(-c3cnn(C)c3)nn2-c2ccccc2)[C@H](c2ccc3nccn3c2)C1] | 2 | 0.66 | 540 | racemate |
| I-166 | 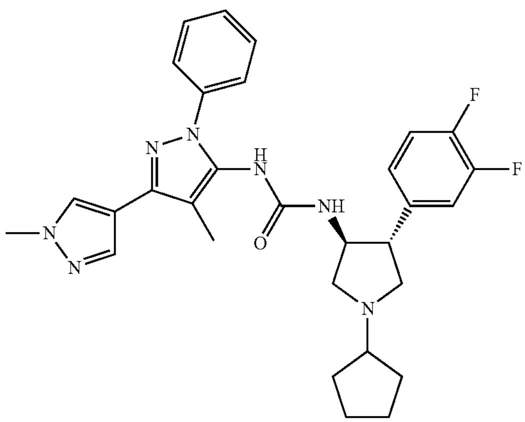 [SMILES: Cc1c(-c2cnn(C)c2)nn(-c2ccccc2)c1NC(=O)N[C@@H]1CN(C2CCCC2)C[C@H]1c1ccc(F)c(F)c1] | 2 | 1.46 | 546 | |

TABLE 50

| No. | Structure | LCMS method No | RT | MS (m/z) | Configuration |
|---|---|---|---|---|---|
| I-167 | 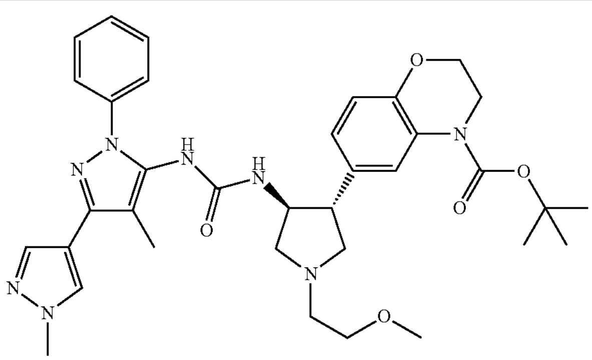 [SMILES: COCCN1C[C@@H](NC(=O)Nc2c(C)c(-c3cnn(C)c3)nn2-c2ccccc2)[C@H](c2ccc3c(c2)N(C(=O)OC(C)(C)C)CCO3)C1] | 2 | 1.72 | 657 | racemate |

TABLE 50-continued

| No. | Structure | LCMS method No | RT | MS (m/z) | Configuration |
|---|---|---|---|---|---|
| I-168 | 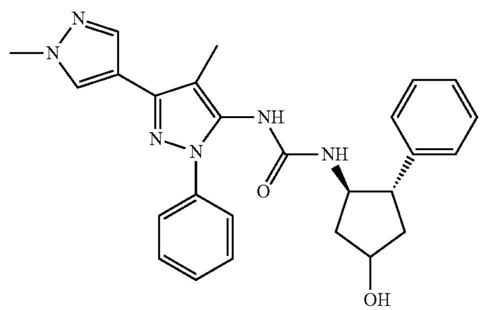 [SMILES: Cc1c(-c2cnn(C)c2)nn(-c2ccccc2)c1NC(=O)N[C@@H]1CC(O)C[C@H]1c1ccccc1] | 2 | 1.45 | 457 | trans |
| I-169 | 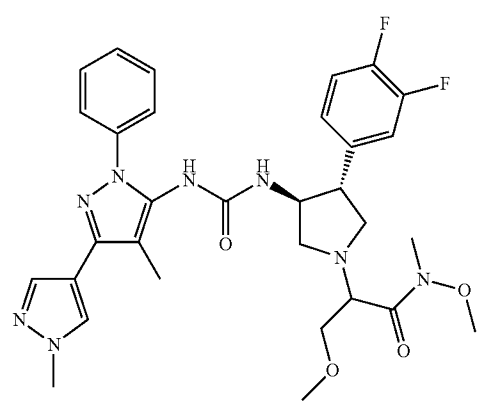 [SMILES: COCC(C(=O)N(C)OC)N1C[C@@H](NC(=O)Nc2c(C)c(-c3cnn(C)c3)nn2-c2ccccc2)[C@H](c2ccc(F)c(F)c2)C1] | 1 | 1.28 | 623.3 | |
| I-170 | 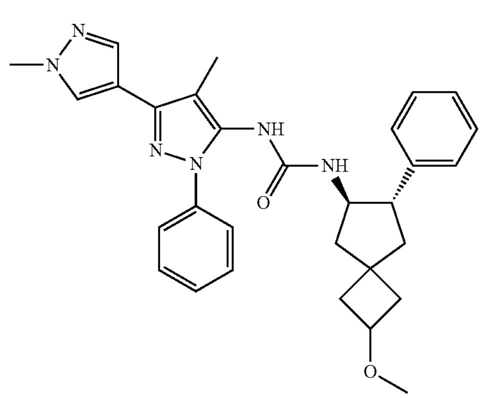 [SMILES: COC1CC2(C1)C[C@@H](NC(=O)Nc1c(C)c(-c3cnn(C)c3)nn1-c1ccccc1)[C@H](c1ccccc1)C2] | 1 | 1.9 | 511 | racemate |

TABLE 51

| No. | Structure | LCMS method No | RT | MS (m/z) | Configuration |
|---|---|---|---|---|---|
| I-171 | 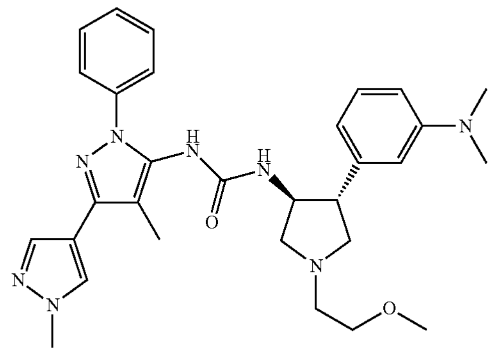 [SMILES: COCCN1C[C@@H](NC(=O)Nc2c(C)c(-c3cnn(C)c3)nn2-c2ccccc2)[C@H](c2cccc(N(C)C)c2)C1] | 2 | 1.03 | 543 | racemate |
| I-172 | 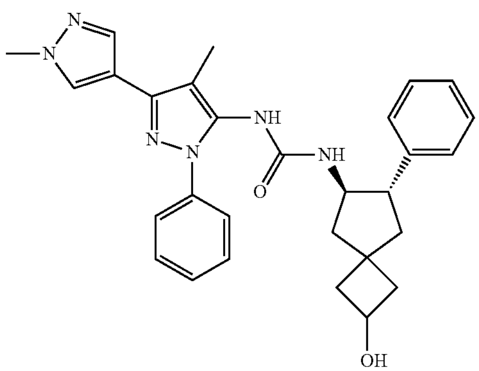 [SMILES: Cc1c(-c2cnn(C)c2)nn(-c2ccccc2)c1NC(=O)N[C@@H]1CC2(CC(O)C2)C[C@H]1c1ccccc1] | 1 | 1.56 | 497 | racemate |
| I-173 | 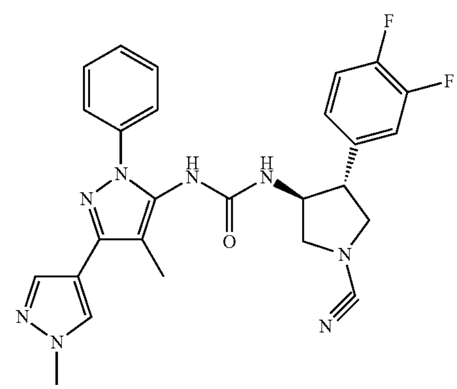 [SMILES: Cc1c(-c2cnn(C)c2)nn(-c2ccccc2)c1NC(=O)N[C@@H]1CN(C#N)C[C@H]1c1ccc(F)c(F)c1] | 1 | 1.92 | 503.2 | |
| I-174 | 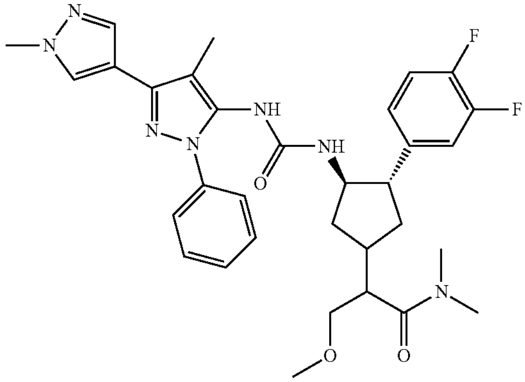 | 3 | 1.73 | 607 | |

TABLE 52

| No. | Structure | LCMS method No | RT | MS (m/z) | Configuration |
|---|---|---|---|---|---|
| I-175 | 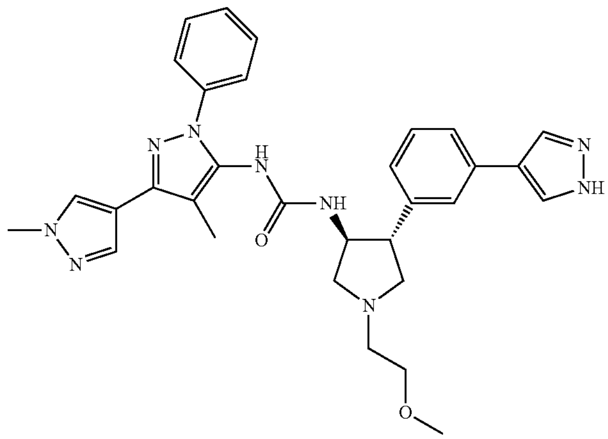 [SMILES: COCCN1C[C@@H](NC(=O)Nc2c(C)c(-c3cnn(C)c3)nn2-c2ccccc2)[C@H](c2cccc(-c3cn[nH]c3)c2)C1] | 2 | 1.24 | 566 | racemate |
| I-176 | 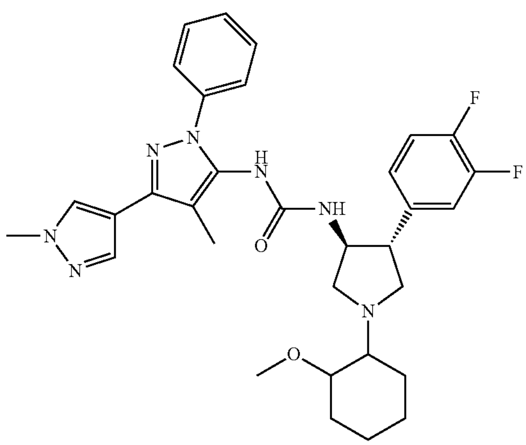 [SMILES: COC1CCCCC1N1C[C@@H](NC(=O)Nc2c(C)c(-c3cnn(C)c3)nn2-c2ccccc2)[C@H](c2ccc(F)c(F)c2)C1] | 2 | 1.45 | 590 | |
| I-177 | 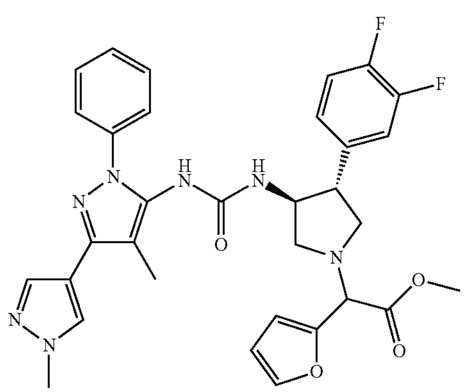 [SMILES: COC(=O)C(c1ccco1)N1C[C@@H](NC(=O)Nc2c(C)c(-c3cnn(C)c3)nn2-c2ccccc2)[C@H](c2ccc(F)c(F)c2)C1] | 1 | 1.63 | 616.25 | |

TABLE 52-continued

| No. | Structure | LCMS method No | RT | MS (m/z) | Configuration |
|---|---|---|---|---|---|
| I-178 | 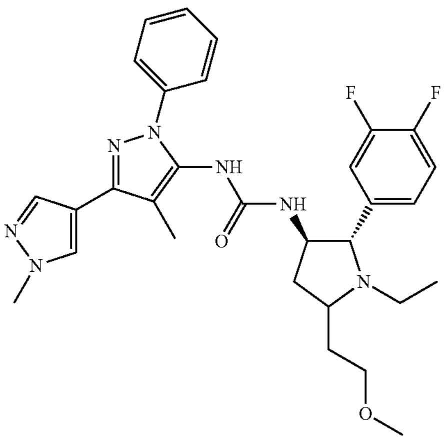 [SMILES: CCN1C(CCOC)C[C@@H](NC(=O)Nc2c(C)c(-c3cnn(C)c3)nn2-c2ccccc2)[C@@H]1c1ccc(F)c(F)c1] | 2 | 1.3 | 564.28 | trans |

TABLE 53

| No. | Structure | LCMS method No | RT | MS (m/z) | Configuration |
|---|---|---|---|---|---|
| I-179 | 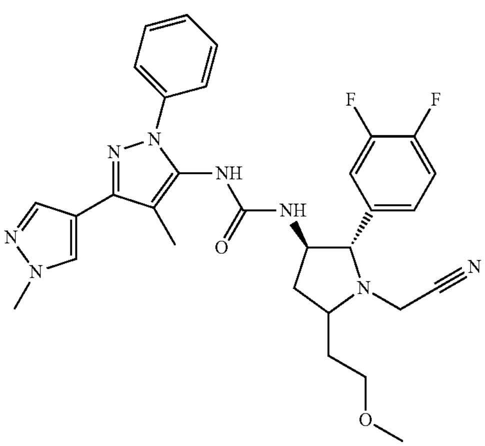 [SMILES: COCCC1C[C@@H](NC(=O)Nc2c(C)c(-c3cnn(C)c3)nn2-c2ccccc2)[C@H](c2ccc(F)c(F)c2)N1CC#N] | 2 | 1.95 | 575.26 | trans |
| I-180 | 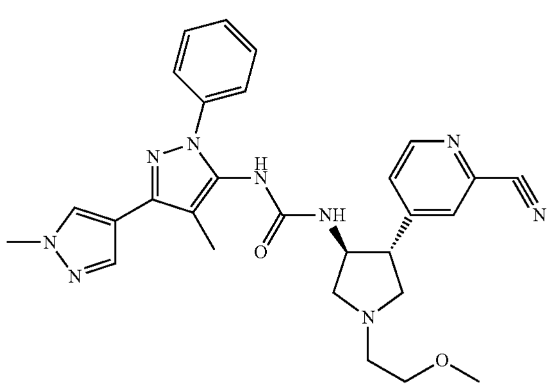 [SMILES: COCCN1C[C@@H](NC(=O)Nc2c(C)c(-c3cnn(C)c3)nn2-c2ccccc2)[C@H](c2ccnc(C#N)c2)C1] | 2 | 1 | 526 | racemate |

TABLE 53-continued

| No. | Structure | LCMS method No | RT | MS (m/z) | Configuration |
|---|---|---|---|---|---|
| I-181 | 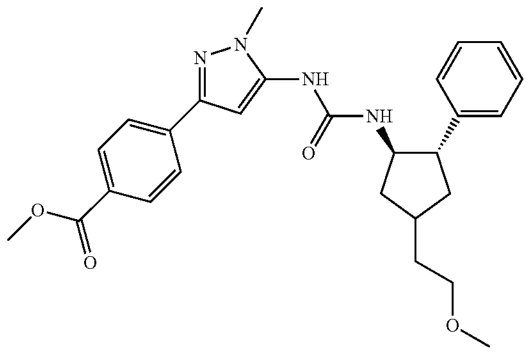 [SMILES: COCCC1C[C@@H](NC(=O)Nc2cc(-c3ccc(C(=O)OC)cc3)nn2C)[C@H](c2ccccc2)C1] | 2 | 2.16 | 477 | trans |
| I-182 | 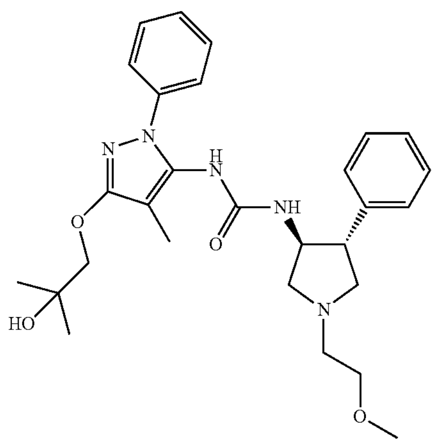 [SMILES: COCCN1C[C@@H](NC(=O)Nc2c(C)c(OCC(C)(C)O)nn2-c2ccccc2)[C@H](c2ccccc2)C1] | 2 | 2.08 | 507 | trans |

TABLE 54

| No. | Structure | LCMS method No | RT | MS (m/z) | Configuration |
|---|---|---|---|---|---|
| I-183 | 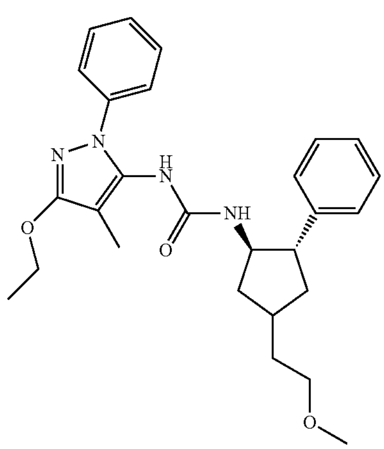 [SMILES: CCOc1nn(-c2ccccc2)c(NC(=O)N[C@@H]2CC(CCOC)C[C@H]2c2ccccc2)c1C] | 2 | 2.34 | 463 | trans |

TABLE 54-continued

| No. | Structure | LCMS method No | RT | MS (m/z) | Configuration |
|---|---|---|---|---|---|
| I-184 | 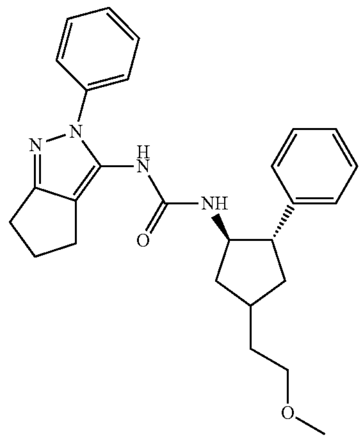 [SMILES: COCCC1C[C@@H](NC(=O)Nc2c3c(nn2-c2ccccc2)CCC3)[C@H](c2ccccc2)C1] | 2 | 2.11 | 445 | trans |
| I-185 | 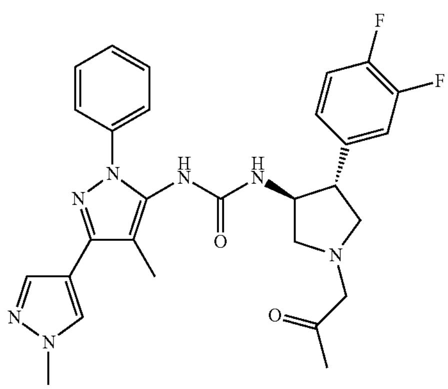 [SMILES: CC(=O)CN1C[C@@H](NC(=O)Nc2c(C)c(-c3cnn(C)c3)nn2-c2ccccc2)[C@H](c2ccc(F)c(F)c2)C1] | 1 | 1.17 | 534.24 | |
| I-186 | 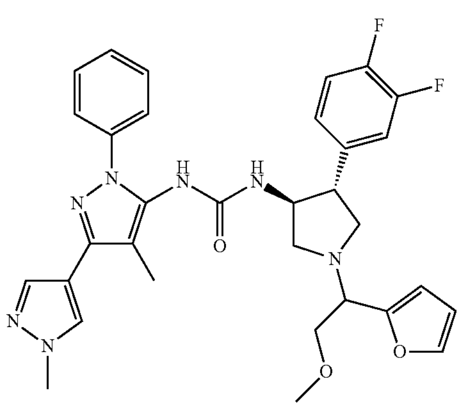 [SMILES: COCC(c1ccco1)N1C[C@@H](NC(=O)Nc2c(C)c(-c3cnn(C)c3)nn2-c2ccccc2)[C@H](c2ccc(F)c(F)c2)C1] | 1 | 1.39 | 602.25 | |

TABLE 55

| No. | Structure | LCMS method No | RT | MS (m/z) | Configuration |
|---|---|---|---|---|---|
| I-187 | 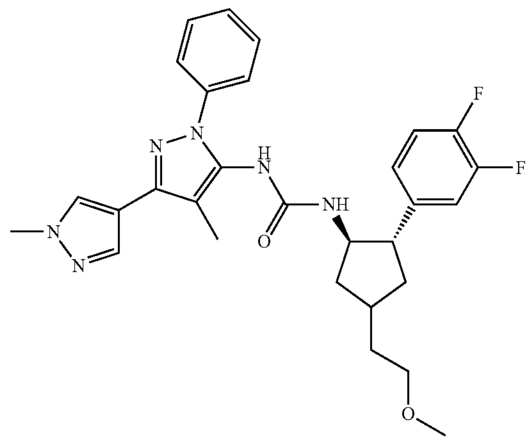 [SMILES: COCCC1C[C@@H](NC(=O)Nc2c(C)c(-c3cnn(C)c3)nn2-c2ccccc2)[C@H](c2ccc(F)c(F)c2)C1] | 1 | 2.02 | 535 | trans |
| I-188 | 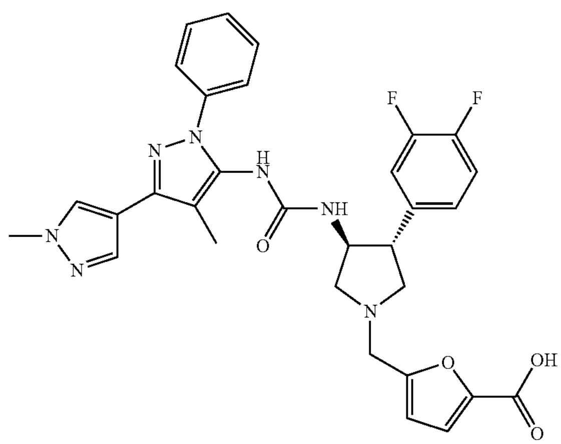 [SMILES: Cc1c(-c2cnn(C)c2)nn(-c2ccccc2)c1NC(=O)N[C@@H]1CN(Cc2ccc(C(=O)O)o2)C[C@H]1c1ccc(F)c(F)c1] | 2 | 1.26 | 602 | |
| I-189 | 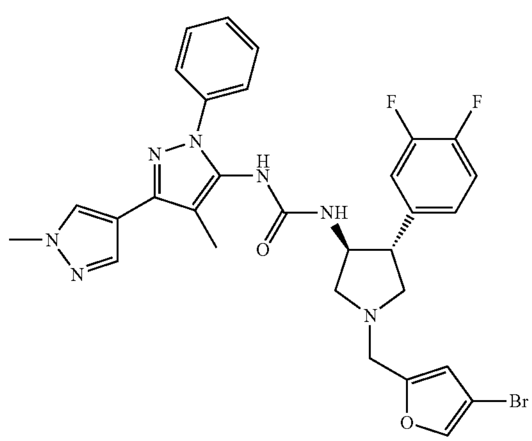 [SMILES: Cc1c(-c2cnn(C)c2)nn(-c2ccccc2)c1NC(=O)N[C@@H]1CN(Cc2cc(Br)co2)C[C@H]1c1ccc(F)c(F)c1] | 2 | 1.54 | 636 | |

TABLE 55-continued
| No. | Structure | LCMS method No | RT | MS (m/z) | Configuration |
|---|---|---|---|---|---|
| I-190 | 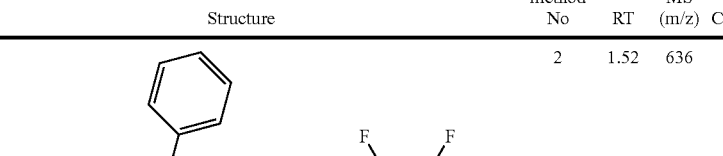 | 2 | 1.52 | 636 | |
TABLE 56
| No. | Structure | LCMS method No | RT | MS (m/z) | Configuration |
|---|---|---|---|---|---|
| I-191 | 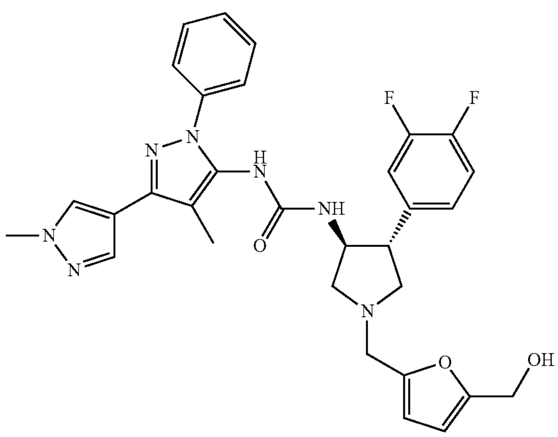 [SMILES: Cc1c(-c2cnn(C)c2)nn(-c2ccccc2)c1NC(=O)N[C@@H]1CN(Cc2ccc(CO)o2)C[C@H]1c1ccc(F)c(F)c1] | 2 | 1.26 | 588 | |
| I-192 | 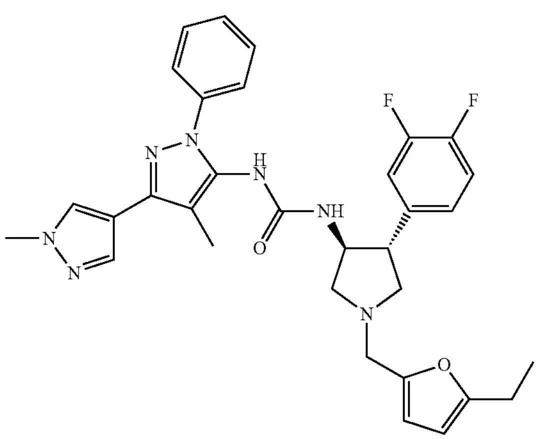 [SMILES: CCc1ccc(CN2C[C@@H](NC(=O)Nc3c(C)c(-c4cnn(C)c4)nn3-c3ccccc3)[C@H](c3ccc(F)c(F)c3)C2)o1] | 2 | 1.57 | 586 | |

TABLE 56-continued
| No. | Structure | LCMS method No | RT | MS (m/z) | Configuration |
|---|---|---|---|---|---|
| I-193 | 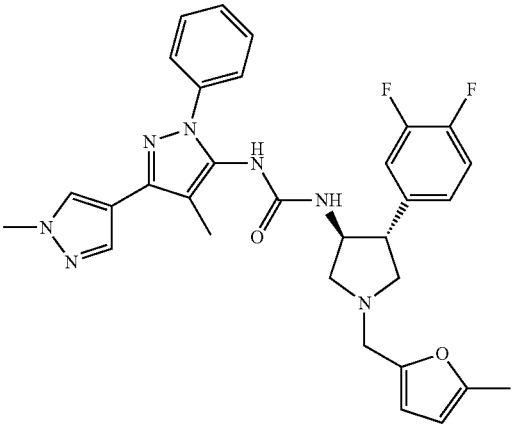 | 2 | 1.47 | 572 | |
| I-194 | 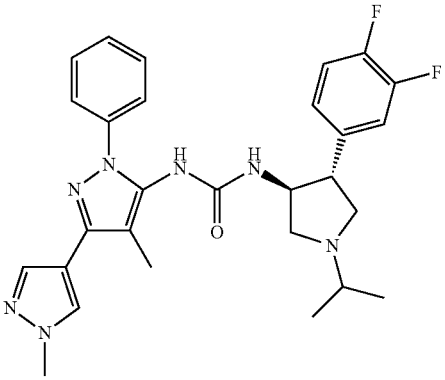 [SMILES: Cc1c(-c2cnn(C)c2)nn(-c2ccccc2)c1NC(=O)N[C@@H]1CN(C(C)C)C[C@H]1c1ccc(F)c(F)c1] | 1 | 1.21 | 520.25 | |
TABLE 57
| No. | Structure | LCMS method No | RT | MS (m/z) | Configuration |
|---|---|---|---|---|---|
| I-195 | 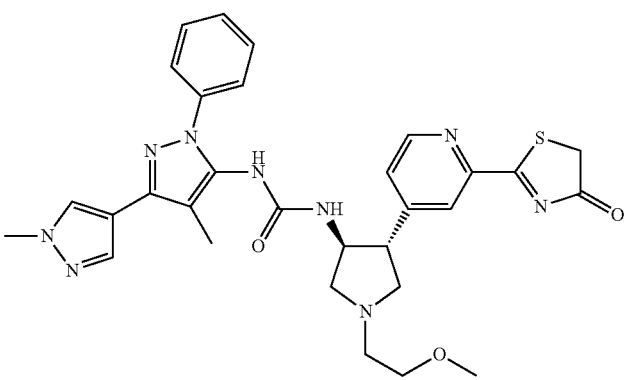 [SMILES: COCCN1C[C@@H](NC(=O)Nc2c(C)c(-c3cnn(C)c3)nn2-c2ccccc2)[C@H](c2ccnc(C3=NC(=O)CS3)c2)C1] | 2 | 1.1 | 600 | racemate |

TABLE 57-continued

| No. | Structure | LCMS method No | RT | MS (m/z) | Configuration |
|---|---|---|---|---|---|
| I-196 | 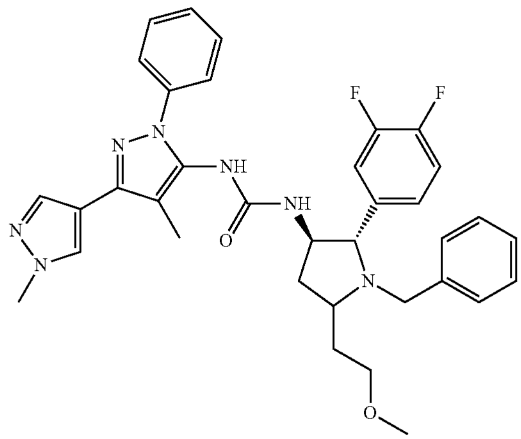 [SMILES: COCCC1C[C@@H](NC(=O)Nc2c(C)c(-c3cnn(C)c3)nn2-c2ccccc2)[C@H](c2ccc(F)c(F)c2)N1Cc1ccccc1] | 2 | 1.71 | 626.3 | trans |
| I-197 | 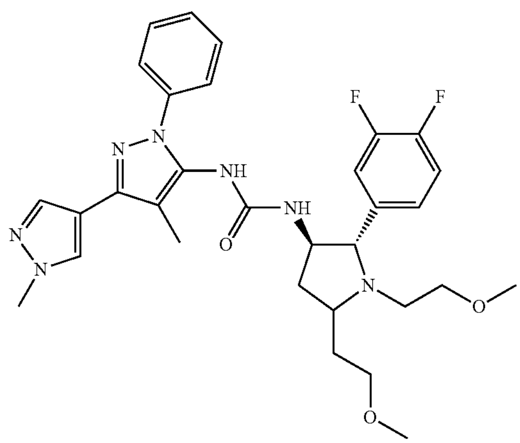 [SMILES: COCCC1C[C@@H](NC(=O)Nc2c(C)c(-c3cnn(C)c3)nn2-c2ccccc2)[C@H](c2ccc(F)c(F)c2)N1CCOC] | 2 | 1.4 | 594.29 | trans |
| I-198 | 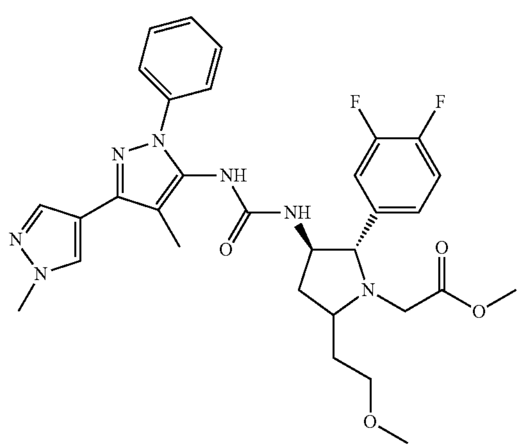 [SMILES: COCCC1C[C@@H](NC(=O)Nc2c(C)c(-c3cnn(C)c3)nn2-c2ccccc2)[C@H](c2ccc(F)c(F)c2)N1CC(=O)OC] | 2 | 2.01 | 608.27 | trans |

TABLE 58
| No. | Structure | LCMS method No. | RT | MS (m/z) | Configuration |
|---|---|---|---|---|---|
| I-199 | 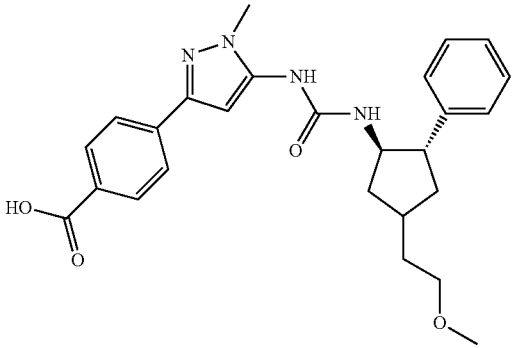 [SMILES: COCCC1C[C@@H](NC(=O)Nc2cc(-c3ccc(C(=O)O)cc3)nn2C)[C@H](c2ccccc2)C1] | 2 | 1.85 | 463 | trans |
| I-200 | 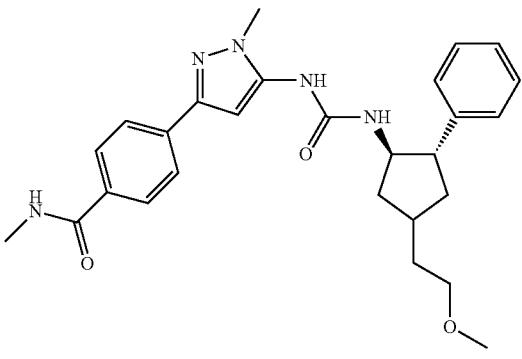 [SMILES: CNC(=O)c1ccc(-c2cc(NC(=O)N[C@@H]3CC(CCOC)C[C@H]3c3ccccc3)n(C)n2)cc1] | 2 | 1.71 | 476 | trans |
| I-201 | 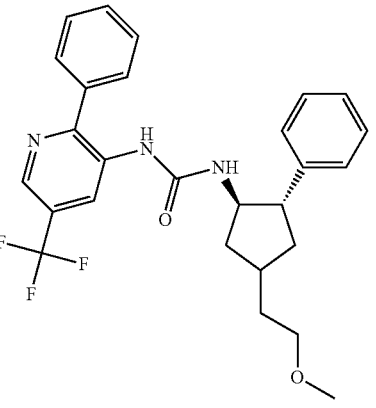 | 2 | 2.58 | 484 | trans |
| I-202 | 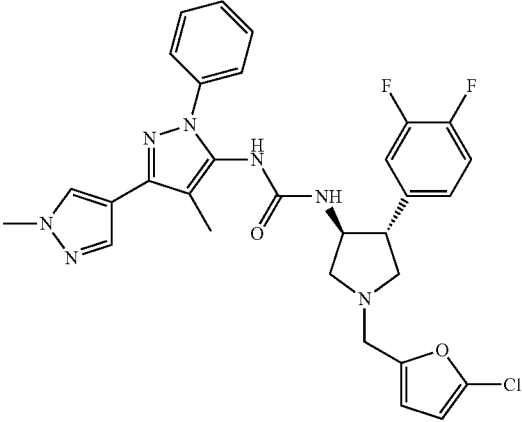 [SMILES: Cc1c(-c2cnn(C)c2)nn(-c2ccccc2)c1NC(=O)N[C@@H]1CN(Cc2ccc(Cl)o2)C[C@H]1c1ccc(F)c(F)c1] | 2 | 1.68 | 592 | |

TABLE 59

| No. | Structure | LCMS method No. | RT | MS (m/z) | Configuration |
|---|---|---|---|---|---|
| I-203 | 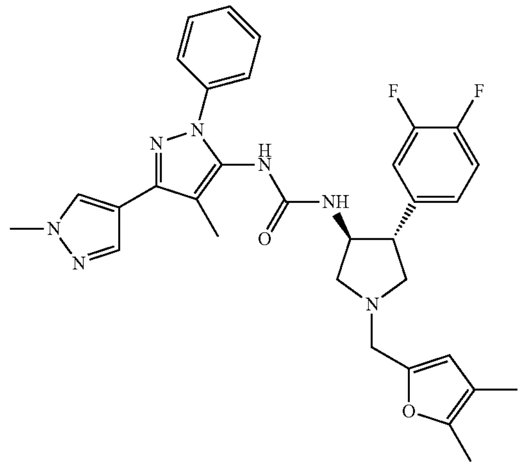 | 2 | 1.81 | 586 | |
| I-204 | 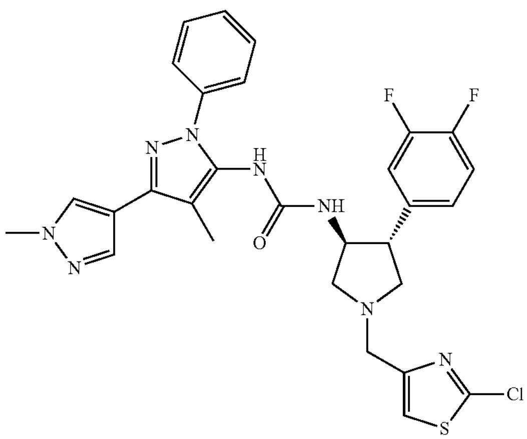 [SMILES: Cc1c(-c2cnn(C)c2)nn(-c2ccccc2)c1NC(=O)N[C@@H]1CN(Cc2csc(Cl)n2)C[C@H]1c1ccc(F)c(F)c1] | 2 | 1.64 | 609 | |
| I-205 | 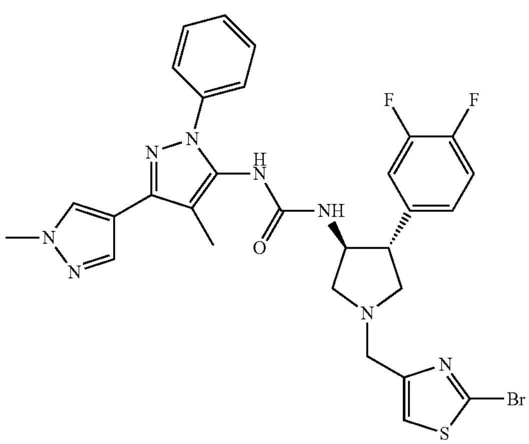 [SMILES: Cc1c(-c2cnn(C)c2)nn(-c2ccccc2)c1NC(=O)N[C@@H]1CN(Cc2csc(Br)n2)C[C@H]1c1ccc(F)c(F)c1] | 2 | 1.64 | 653 | |

TABLE 59-continued

| No. | Structure | LCMS method No. | RT | MS (m/z) | Configuration |
|---|---|---|---|---|---|
| I-206 | 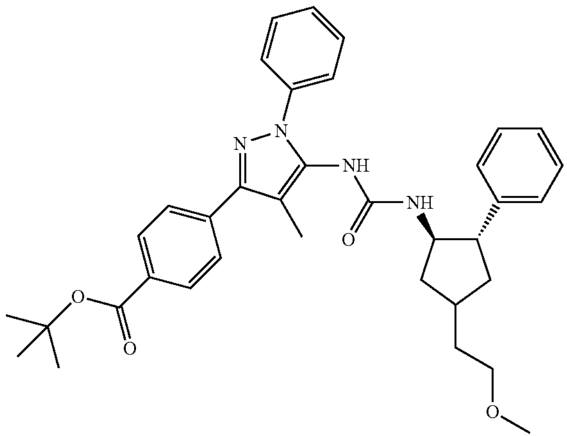 [SMILES: COCCC1C[C@@H](NC(=O)Nc2c(C)c(-c3ccc(C(=O)OC(C)(C)C)cc3)nn2-c2ccccc2)[C@H](c2ccccc2)C1] | 2 | 2.89 | 595 | trans |

TABLE 60

| No. | Structure | LCMS method No. | RT | MS (m/z) | Configuration |
|---|---|---|---|---|---|
| I-207 | 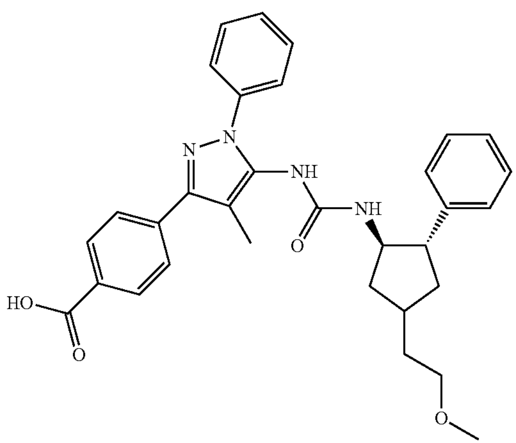 [SMILES: COCCC1C[C@@H](NC(=O)Nc2c(C)c(-c3ccc(C(=O)O)cc3)nn2-c2ccccc2)[C@H](c2ccccc2)C1] | 2 | 2.13 | 539 | trans |
| I-208 | 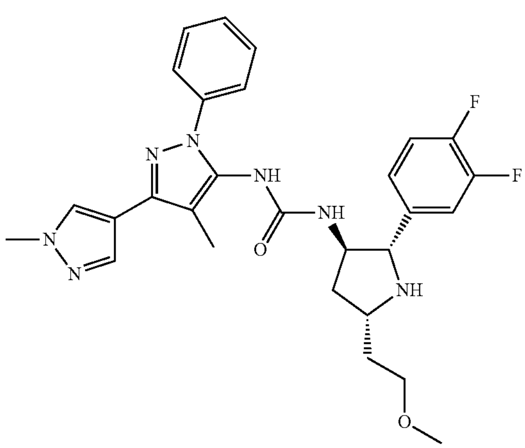 [SMILES: COCC[C@@H]1C[C@@H](NC(=O)Nc2c(C)c(-c3cnn(C)c3)nn2-c2ccccc2)[C@H](c2ccc(F)c(F)c2)N1] | 1 | 1.11 | 536.25 | |

TABLE 60-continued

| No. | Structure | LCMS method No. | RT | MS (m/z) | Configuration |
|---|---|---|---|---|---|
| I-209 | 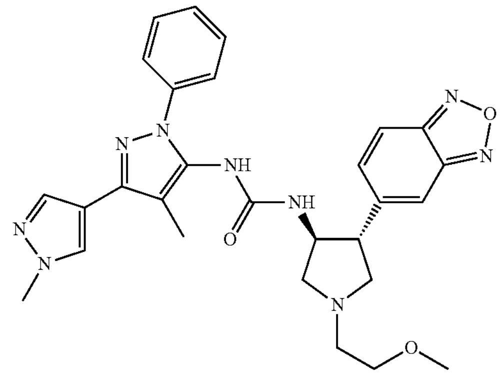 [SMILES: COCCN1C[C@@H](NC(=O)Nc2c(C)c(-c3cnn(C)c3)nn2-c2ccccc2)[C@H](c2ccc3nonc3c2)C1] | 2 | 1.21 | 542 | racemate |
| I-210 | 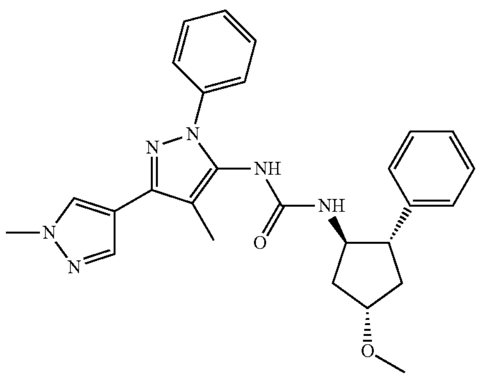 [SMILES: CO[C@@H]1C[C@@H](NC(=O)Nc2c(C)c(-c3cnn(C)c3)nn2-c2ccccc2)[C@H](c2ccccc2)C1] | 1 | 1.68 | 471 | racemate |

TABLE 61

| No. | Structure | LCMS method No. | RT | MS (m/z) | Configuration |
|---|---|---|---|---|---|
| I-211 | 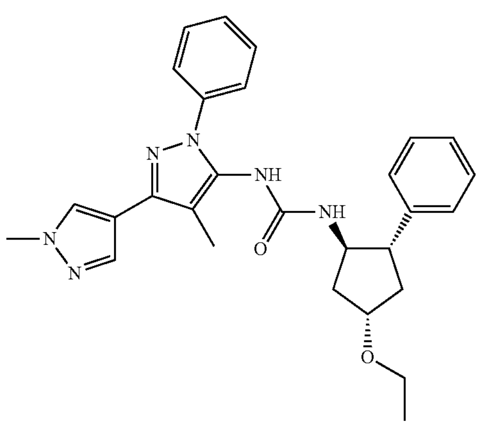 [SMILES: CCO[C@@H]1C[C@@H](NC(=O)Nc2c(C)c(-c3cnn(C)c3)nn2-c2ccccc2)[C@H](c2ccccc2)C1] | 1 | 1.82 | 485 | racemate |

TABLE 61-continued

| No. | Structure | LCMS method No. | RT | MS (m/z) | Configuration |
|---|---|---|---|---|---|
| I-212 | 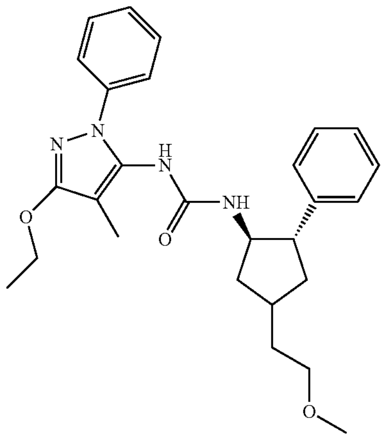 [SMILES: CCOc1nn(-c2ccccc2)c(NC(=O)N[C@@H]2CC(CCOC)C[C@H]2c2ccccc2)c1C] | 2 | 2.34 | 463 | trans |
| I-213 | 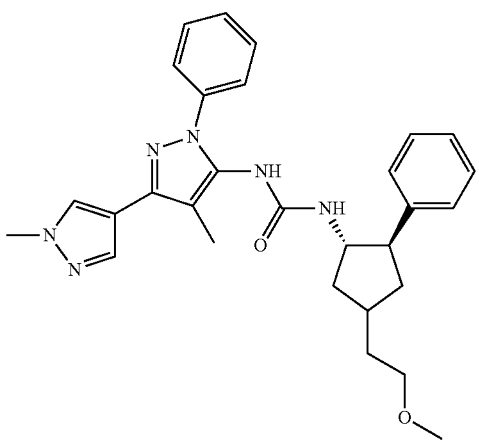 [SMILES: COCCC1C[C@H](NC(=O)Nc2c(C)c(-c3cnn(C)c3)nn2-c2ccccc2)[C@@H](c2ccccc2)C1] | 2 | 1.94 | 499 | |
| I-214 | 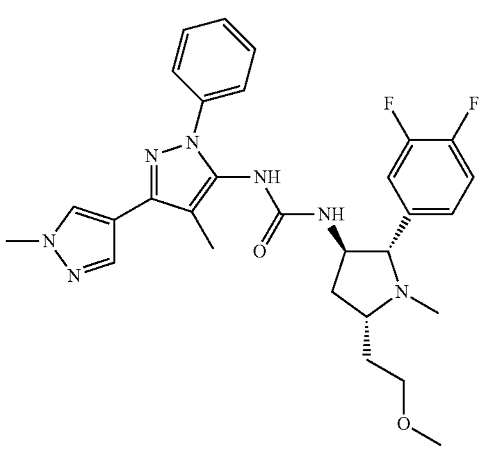 [SMILES: COCC[C@@H]1C[C@@H](NC(=O)Nc2c(C)c(-c3cnn(C)c3)nn2-c2ccccc2)[C@H](c2ccc(F)c(F)c2)N1C] | 1 | 1.12 | 550.15 | |

TABLE 62

| No. | Structure | LCMS method No. | RT | MS (m/z) | Configuration |
|---|---|---|---|---|---|
| I-215 | 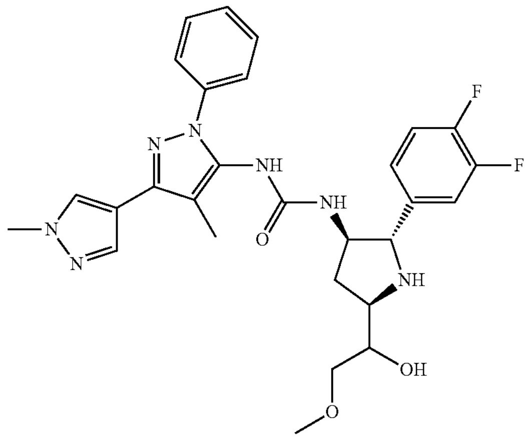 [SMILES: COCC(O)[C@H]1C[C@@H](NC(=O)Nc2c(C)c(-c3cnn(C)c3)nn2-c2ccccc2)[C@H](c2ccc(F)c(F)c2)N1] | 1 | 1.08 | 552.2 | |
| I-216 | 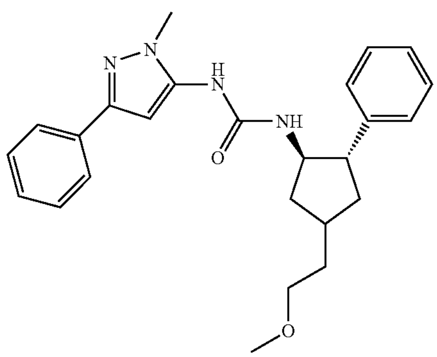 [SMILES: COCCC1C[C@@H](NC(=O)Nc2cc(-c3ccccc3)nn2C)[C@H](c2ccccc2)C1] | 2 | 2.11 | 419 | trans |
| I-217 | 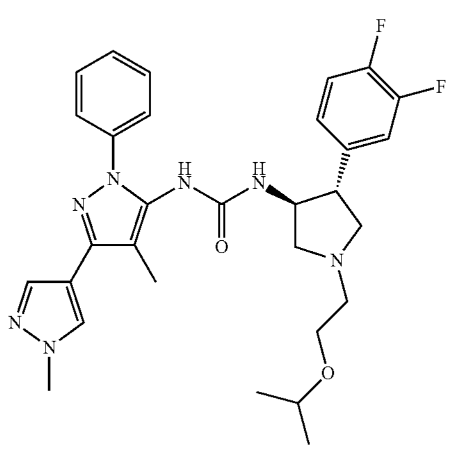 [SMILES: Cc1c(-c2cnn(C)c2)nn(-c2ccccc2)c1NC(=O)N[C@@H]1CN(CCOC(C)C)C[C@H]1c1ccc(F)c(F)c1] | 1 | 1.37 | 564.3 | |

TABLE 62-continued

| No. | Structure | LCMS method No. | RT | MS (m/z) | Configuration |
|---|---|---|---|---|---|
| I-218 | 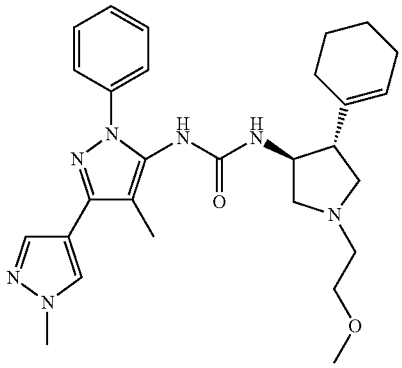 [SMILES: COCCN1C[C@@H](NC(=O)Nc2c(C)c(-c3cnn(C)c3)nn2-c2ccccc2)[C@H](C2=CCCCC2)C1] | 1 | 1.23 | 504.3 | racemate |

TABLE 63

| No. | Structure | LCMS method No. | RT | MS (m/z) | Configuration |
|---|---|---|---|---|---|
| I-219 | 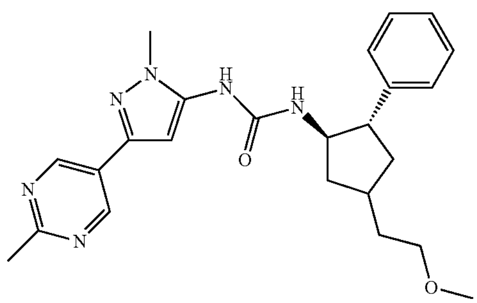 | 2 | 1.66 | 435 | trans |
| I-220 | 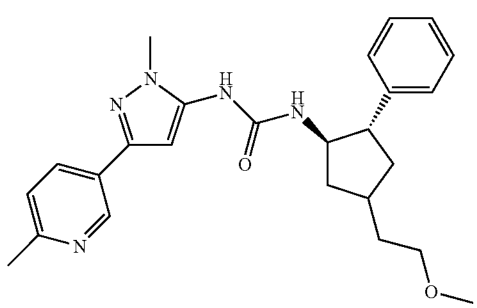 | 2 | 1.4 | 434 | trans |

TABLE 63-continued
| No. | Structure | LCMS method No. | RT | MS (m/z) | Configuration |
|---|---|---|---|---|---|
| I-221 | 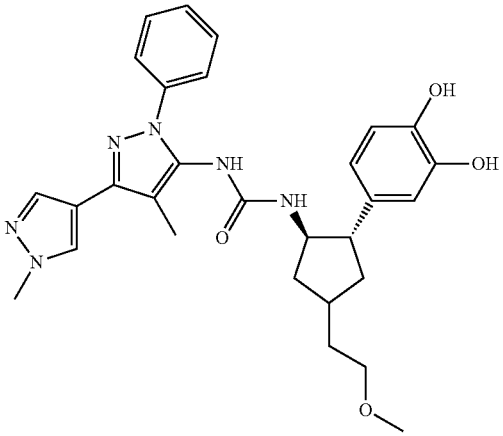 [SMILES: COCCC1C[C@@H](NC(=O)Nc2c(C)c(-c3cnn(C)c3)nn2-c2ccccc2)[C@H](c2ccc(O)c(O)c2)C1] | 1 | 1.46 | 531.3 | |
| I-222 | 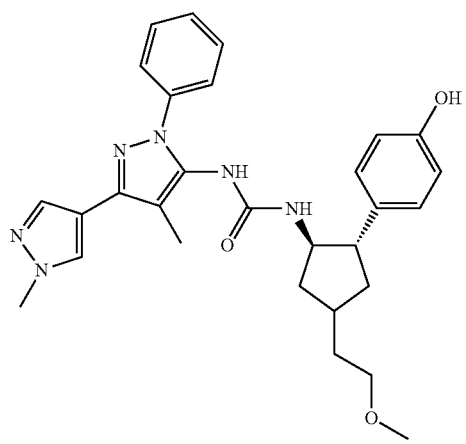 [SMILES: COCCC1C[C@@H](NC(=O)Nc2c(C)c(-c3cnn(C)c3)nn2-c2ccccc2)[C@H](c2ccc(O)cc2)C1] | 1 | 1.56 | 515.3 | |
TABLE 64
| No. | Structure | LCMS method No. | RT | MS (m/z) | Configuration |
|---|---|---|---|---|---|
| I-223 | 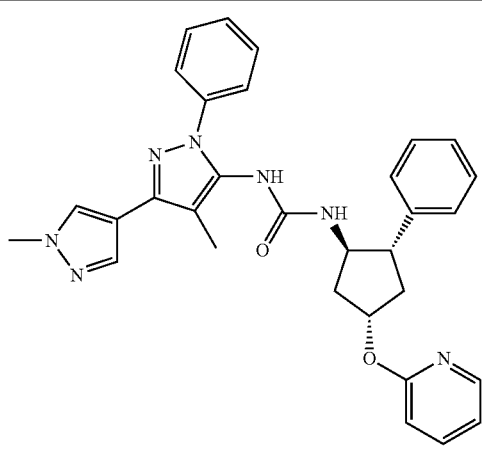 | 1 | 1.91 | 534 | racemate |

TABLE 64-continued

| No. | Structure | LCMS method No. | RT | MS (m/z) | Configuration |
|---|---|---|---|---|---|
| I-224 | 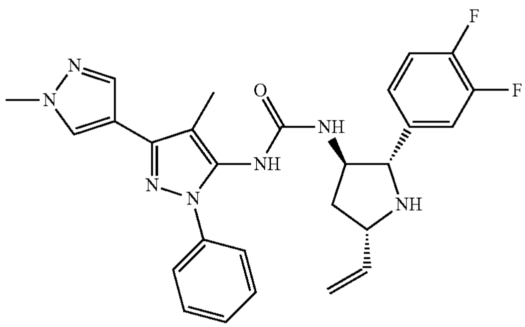 [SMILES: C=C[C@@H]1C[C@@H](NC(=O)Nc2c(C)c(-c3cnn(C)c3)nn2-c2ccccc2)[C@H](c2ccc(F)c(F)c2)N1] | 1 | 1.09 | 504.25 | |
| I-225 | 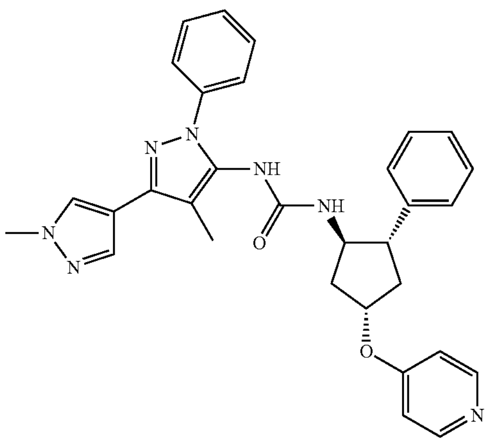 [SMILES: Cc1c(-c2cnn(C)c2)nn(-c2ccccc2)c1NC(=O)N[C@@H]1C[C@@H](Oc2ccncc2)C[C@H]1c1ccccc1] | 1 | 1.2 | 534 | racemate |
| I-226 | 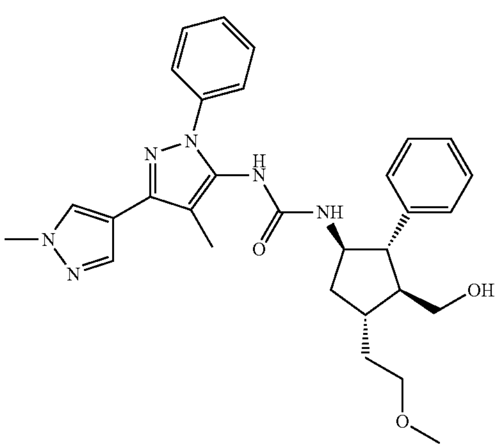 [SMILES: COCC[C@@H]1C[C@@H](NC(=O)Nc2c(C)c(-c3cnn(C)c3)nn2-c2ccccc2)[C@H](c2ccccc2)[C@H]1CO] | 2 | 1.54 | 529 | |

TABLE 65

| No. | Structure | LCMS method No. | RT | MS (m/z) | Configuration |
|---|---|---|---|---|---|
| I-227 | 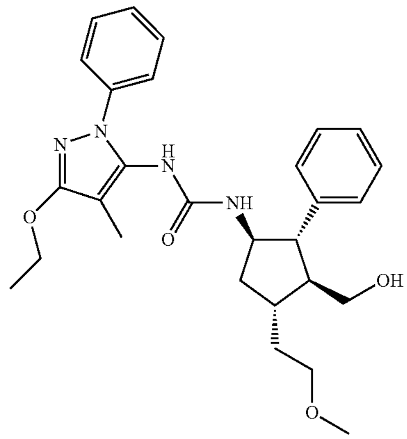 [SMILES: CCOc1nn(-c2ccccc2)c(NC(=O)N[C@@H]2C[C@@H](CCOC)[C@H](CO)[C@H]2c2ccccc2)c1C] | 2 | 1.88 | 493 | |
| I-228 | 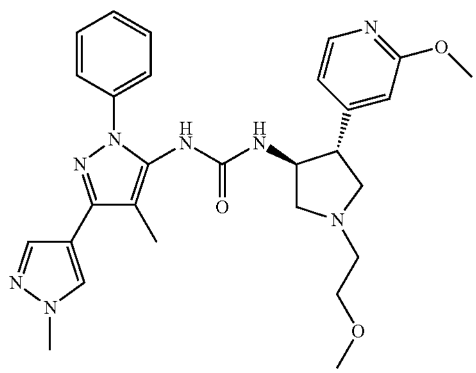 [SMILES: COCCN1C[C@@H](NC(=O)Nc2c(C)c(-c3cnn(C)c3)nn2-c2ccccc2)[C@H](c2ccnc(OC)c2)C1] | 1 | 0.96 | 531.35 | racemate |
| I-229 | 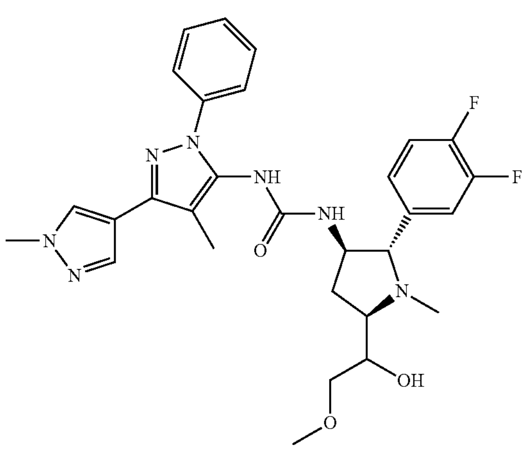 [SMILES: COCC(O)[C@H]1C[C@@H](NC(=O)Nc2c(C)c(-c3cnn(C)c3)nn2-c2ccccc2)[C@H](c2ccc(F)c(F)c2)N1C] | 1 | 1.14 | 566.3 | |

TABLE 65-continued
| No. | Structure | LCMS method No. | RT | MS (m/z) | Configuration |
|---|---|---|---|---|---|
| I-230 | 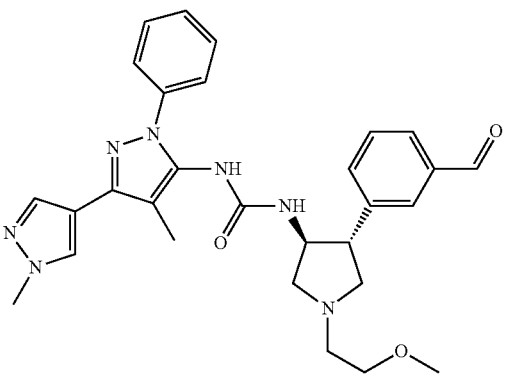 [SMILES: COCCN1C[C@@H](NC(=O)Nc2c(C)c(-c3cnn(C)c3)nn2-c2ccccc2)[C@H](c2cccc(C=O)c2)C1] | 2 | 1.11 | 528 | racemate |
TABLE 66
| No. | Structure | LCMS method No. | RT | MS (m/z) | Configuration |
|---|---|---|---|---|---|
| I-231 | 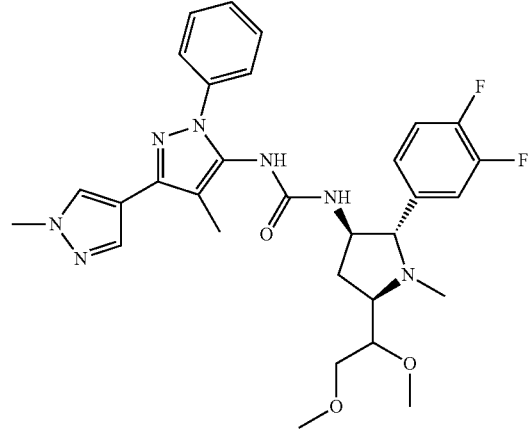 [SMILES: COCC(OC)[C@H]1C[C@@H](NC(=O)Nc2c(C)c(-c3cnn(C)c3)nn2-c2ccccc2)[C@H](c2ccc(F)c(F)c2)N1C] | 1 | 1.35 | 580.2 | |
| I-232 | 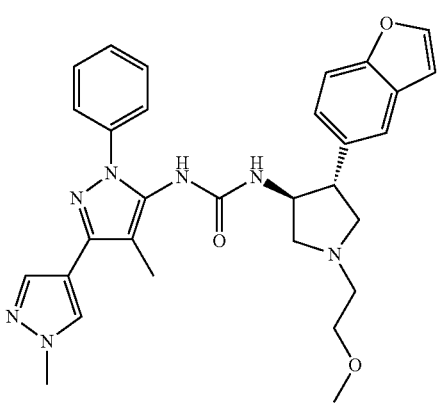 [SMILES: COCCN1C[C@@H](NC(=O)Nc2c(C)c(-c3cnn(C)c3)nn2-c2ccccc2)[C@H](c2ccc3occc3c2)C1] | 1 | 1.2 | 540.3 | racemate |

TABLE 66-continued

| No. | Structure | LCMS method No. | RT | MS (m/z) | Configuration |
|---|---|---|---|---|---|
| I-233 | 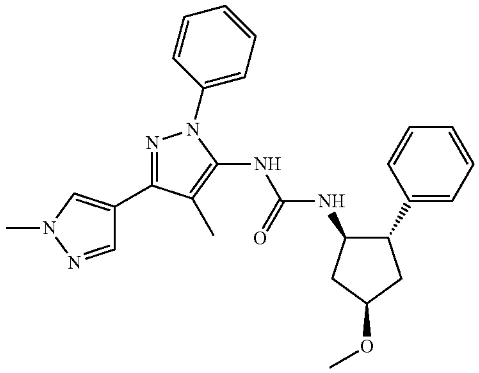 [SMILES: CO[C@H]1C[C@@H](NC(=O)Nc2c(C)c(-c3cnn(C)c3)nn2-c2ccccc2)[C@H](c2ccccc2)C1] | 1 | 1.71 | 471 | racemate |
| I-234 | 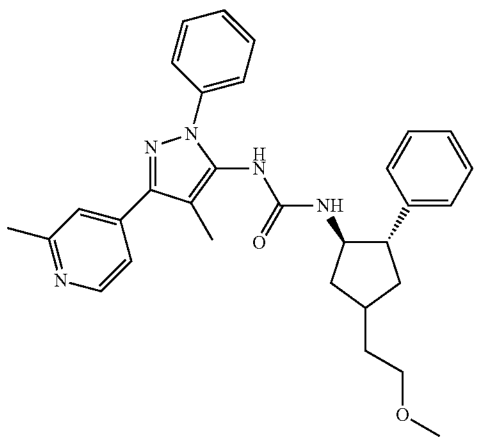 [SMILES: COCCC1C[C@@H](NC(=O)Nc2c(C)c(-c3ccnc(C)c3)nn2-c2ccccc2)[C@H](c2ccccc2)C1] | 2 | 1.71 | 510 | trans |

TABLE 67

| No. | Structure | LCMS method No. | RT | MS (m/z) | Configuration |
|---|---|---|---|---|---|
| I-235 | 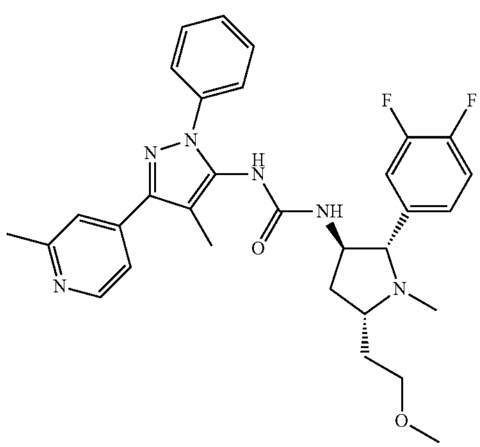 [SMILES: COCC[C@@H]1C[C@@H](NC(=O)Nc2c(C)c(-c3ccnc(C)c3)nn2-c2ccccc2)[C@H](c2ccc(F)c(F)c2)N1C] | 2 | 1.21 | 561 | |

TABLE 67-continued

| No. | Structure | LCMS method No. | RT | MS (m/z) | Configuration |
|---|---|---|---|---|---|
| I-236 | 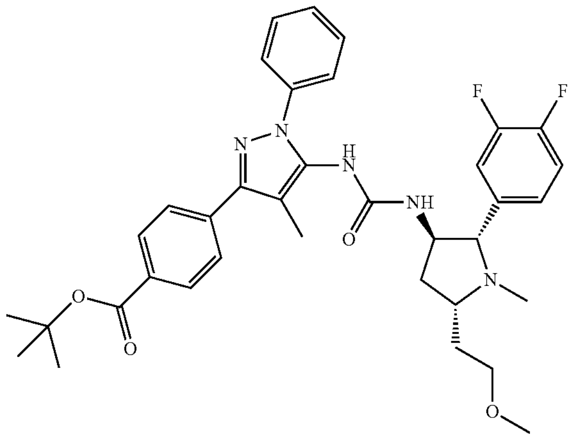 [SMILES: COCC[C@@H]1C[C@@H](NC(=O)Nc2c(C)c(-c3ccc(C(=O)OC(C)(C)C)cc3)nn2-c2ccccc2)[C@H](c2ccc(F)c(F)c2)N1C] | 2 | 2.37 | 646 | |
| I-237 | 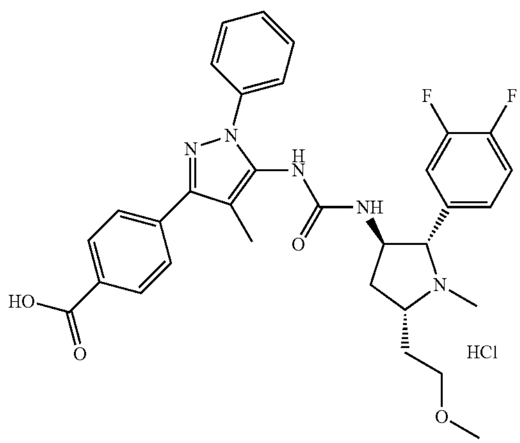 [SMILES: COCC[C@@H]1C[C@@H](NC(=O)Nc2c(C)c(-c3ccc(C(=O)O)cc3)nn2-c2ccccc2)[C@H](c2ccc(F)c(F)c2)N1C ; Cl] | 2 | 1.47 | 590 | |
| I-238 | 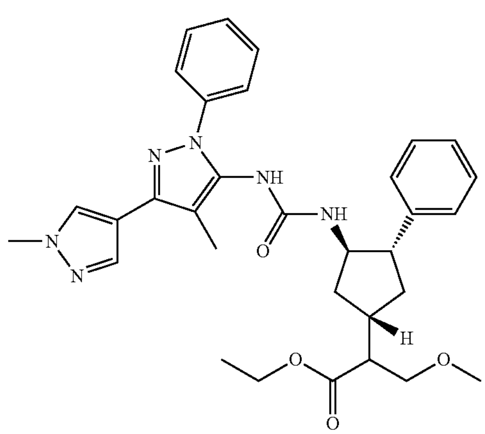 | 1 | 1.92 | 571 | racemate2 |

TABLE 68

| No. | Structure | LCMS method No. | RT | MS (m/z) | Configuration |
|---|---|---|---|---|---|
| I-239 | 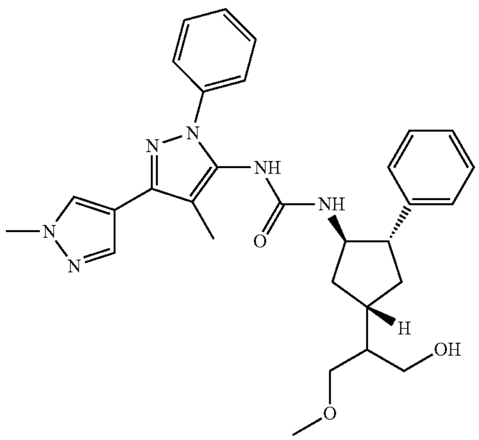 [SMILES: COCC(CO)[C@@H]1C[C@@H](NC(=O)Nc2c(C)c(-c3cnn(C)c3)nn2-c2ccccc2)[C@H](c2ccccc2)C1] | 1 | 1.56, 1.62 | 529 | mixture of 4 diastereomers |
| I-240 | 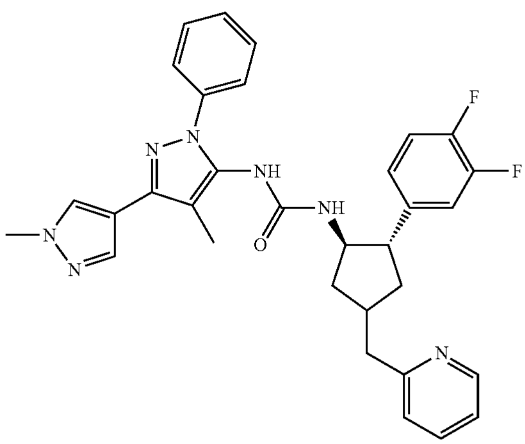 [SMILES: Cc1c(-c2cnn(C)c2)nn(-c2ccccc2)c1NC(=O)N[C@@H]1CC(Cc2ccccn2)C[C@H]1c1ccc(F)c(F)c1] | 1 | 1.3 | 569 | |
| I-241 | 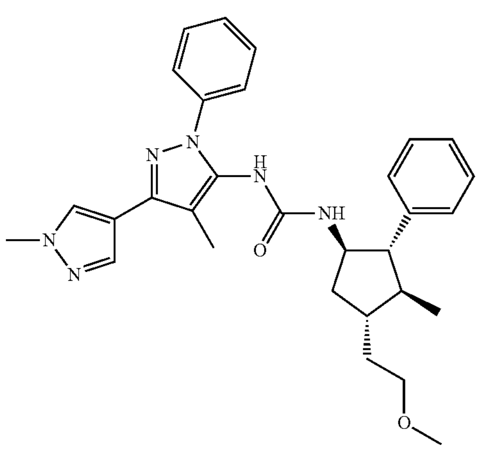 [SMILES: COCC[C@@H]1C[C@@H](NC(=O)Nc2c(C)c(-c3cnn(C)c3)nn2-c2ccccc2)[C@H](c2ccccc2)[C@H]1C] | 2 | 2.04 | 513 | |

TABLE 68-continued

| No. | Structure | LCMS method No. | RT | MS (m/z) | Configuration |
|---|---|---|---|---|---|
| I-242 | 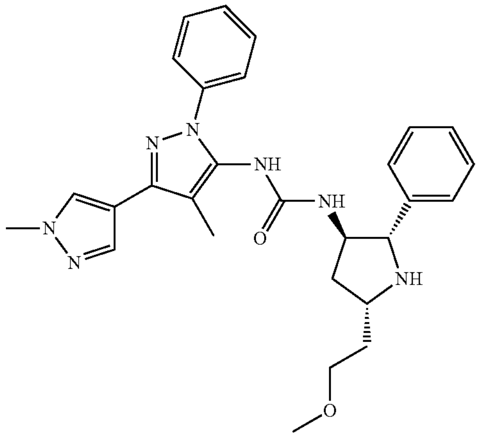 [SMILES: COCC[C@@H]1C[C@@H](NC(=O)Nc2c(C)c(-c3cnn(C)c3)nn2-c2ccccc2)[C@H](c2ccccc2)N1] | 1 | 1.03 | 500.25 | |

TABLE 69

| No. | Structure | LCMS method No. | RT | MS (m/z) | Configuration |
|---|---|---|---|---|---|
| I-243 | 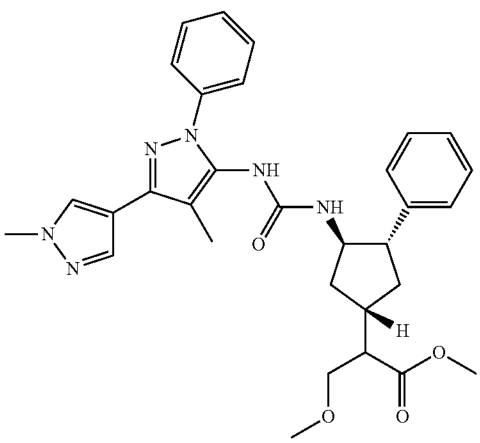 | 1 | 1.8 | 557 | racemate2 |
| I-244 | 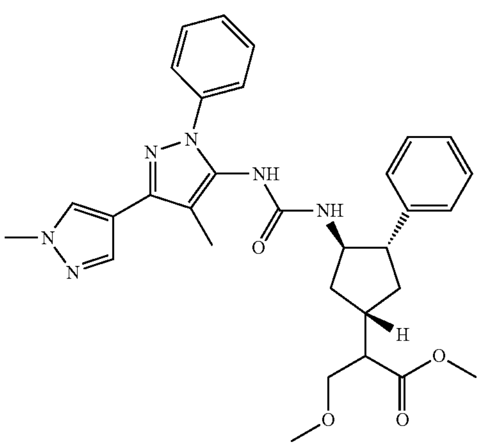 | 1 | 1.82 | 557 | racemate2 |

TABLE 69-continued

| No. | Structure | LCMS method No. | RT | MS (m/z) | Configuration |
|---|---|---|---|---|---|
| I-245 | 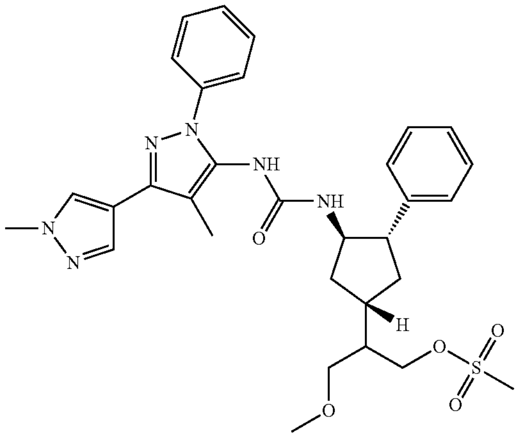 | 1 | 1.76, 1.82 | 607 | mixture of 4 diastereomers |
| I-246 | 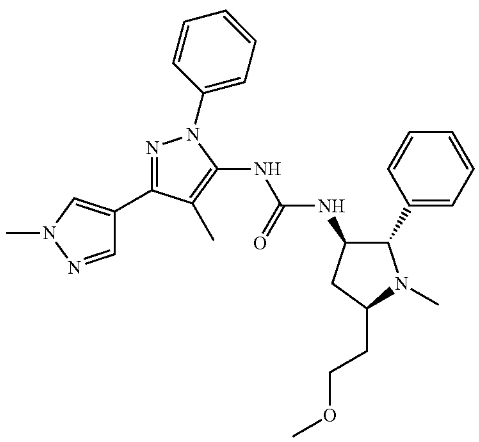 [SMILES: COCC[C@H]1C[C@@H](NC(=O)Nc2c(C)c(-c3cnn(C)c3)nn2-c2ccccc2)[C@H](c2ccccc2)N1C] | 1 | 1.08 | 514.35 | |

TABLE 70

| No. | Structure | LCMS method No. | RT | MS (m/z) | Configuration |
|---|---|---|---|---|---|
| I-247 | 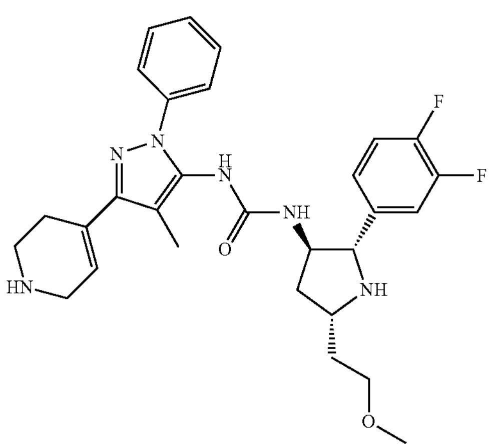 [SMILES: COCC[C@@H]1C[C@@H](NC(=O)Nc2c(C)c(C3=CCNCC3)nn2-c2ccccc2)[C@H](c2ccc(F)c(F)c2)N1] | 2 | 1.09 | 537 | |

TABLE 70-continued

| No. | Structure | LCMS method No. | RT | MS (m/z) | Configuration |
|---|---|---|---|---|---|
| I-248 | 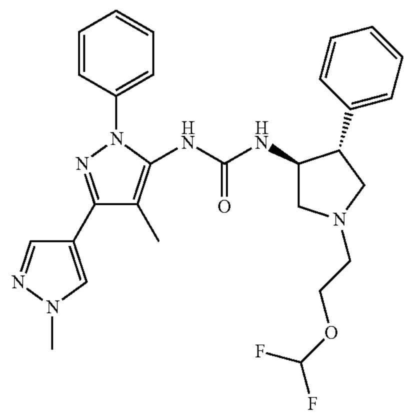 [SMILES: Cc1c(-c2cnn(C)c2)nn(-c2ccccc2)c1NC(=O)N[C@@H]1CN(CCOC(F)F)C[C@H]1c1ccccc1] | 1 | 1.23 | 536.3 | racemate |
| I-249 | 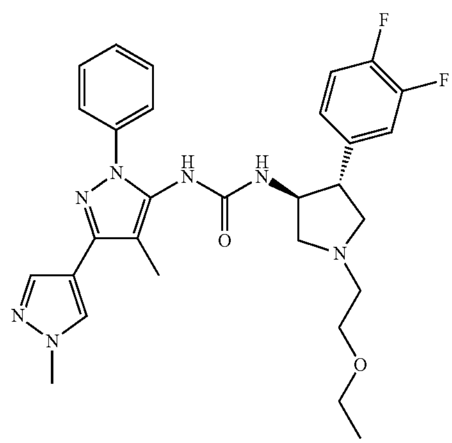 [SMILES: CCOCCN1C[C@@H](NC(=O)Nc2c(C)c(-c3cnn(C)c3)nn2-c2ccccc2)[C@H](c2ccc(F)c(F)c2)C1] | 1 | 1.32 | 550.3 | |
| I-250 | 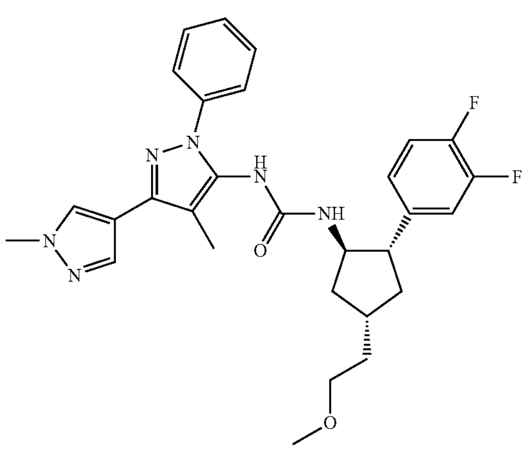 [SMILES: COCC[C@@H]1C[C@@H](NC(=O)Nc2c(C)c(-c3cnn(C)c3)nn2-c2ccccc2)[C@H](c2ccc(F)c(F)c2)C1] | 2 | 2.01 | 535 | |

TABLE 71

| No. | Structure | LCMS method No. | RT | MS (m/z) | Configuration |
|---|---|---|---|---|---|
| I-251 | 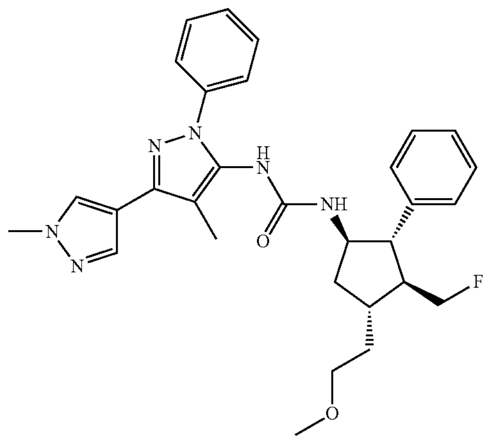 [SMILES: COCC[C@@H]1C[C@@H](NC(=O)Nc2c(C)c(-c3cnn(C)c3)nn2-c2ccccc2)[C@H](c2ccccc2)[C@H]1CF] | 2 | 1.87 | 531 | |
| I-252 | 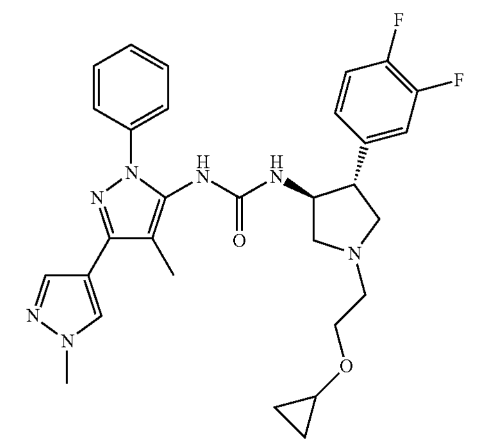 [SMILES: Cc1c(-c2cnn(C)c2)nn(-c2ccccc2)c1NC(=O)N[C@@H]1CN(CCOC2CC2)C[C@H]1c1ccc(F)c(F)c1] | 1 | 1.4 | 562.3 | |
| I-253 | 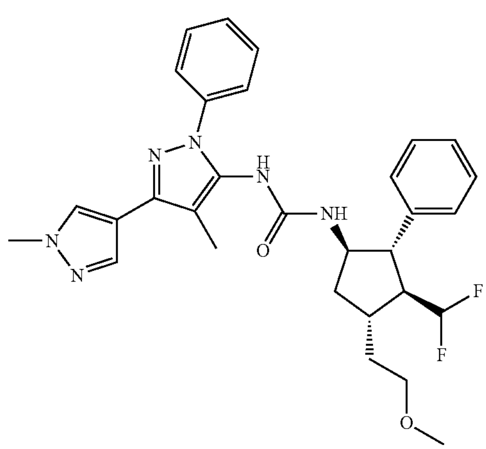 [SMILES: COCC[C@@H]1C[C@@H](NC(=O)Nc2c(C)c(-c3cnn(C)c3)nn2-c2ccccc2)[C@H](c2ccccc2)[C@H]1C(F)F] | 2 | 1.87 | 549 | |

TABLE 71-continued

| No. | Structure | LCMS method No. | RT | MS (m/z) | Configuration |
|---|---|---|---|---|---|
| I-254 | 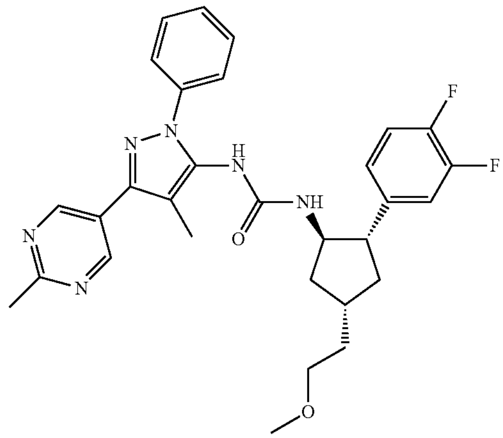 [SMILES: COCC[C@@H]1C[C@@H](NC(=O)Nc2c(C)c(-c3cnc(C)nc3)nn2-c2ccccc2)[C@H](c2ccc(F)c(F)c2)C1] | 2 | 1.95 | 547 | |

TABLE 72

| No. | Structure | LCMS method No. | RT | MS (m/z) | Configuration |
|---|---|---|---|---|---|
| I-255 | 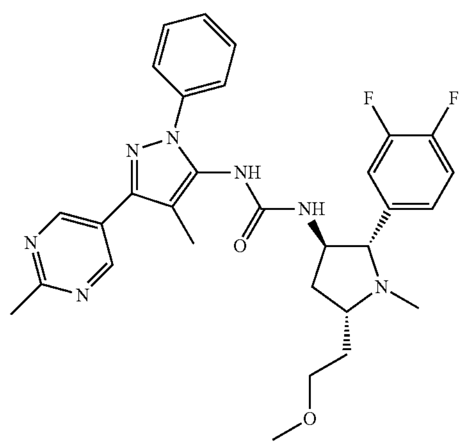 [SMILES: COCC[C@@H]1C[C@@H](NC(=O)Nc2c(C)c(-c3cnc(C)nc3)nn2-c2ccccc2)[C@H](c2ccc(F)c(F)c2)N1C] | 2 | 1.24 | 562 | |
| I-256 | 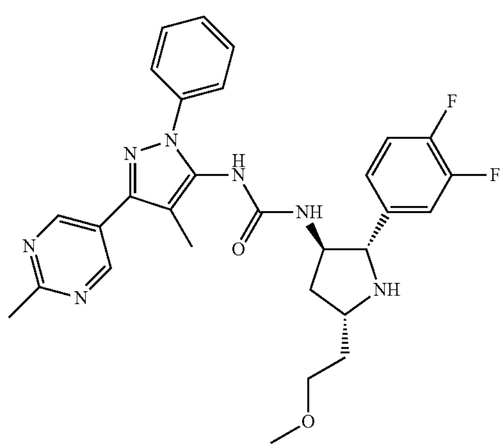 [SMILES: COCC[C@@H]1C[C@@H](NC(=O)Nc2c(C)c(-c3cnc(C)nc3)nn2-c2ccccc2)[C@H](c2ccc(F)c(F)c2)N1] | 2 | 1.36 | 548 | |

TABLE 72-continued

| No. | Structure | LCMS method No. | RT | MS (m/z) | Configuration |
|---|---|---|---|---|---|
| I-257 | 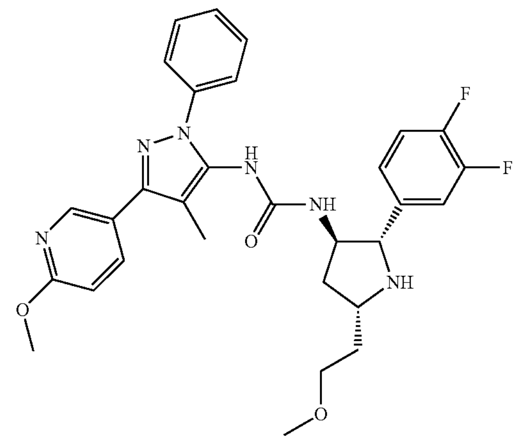 [SMILES: COCC[C@@H]1C[C@@H](NC(=O)Nc2c(C)c(-c3ccc(OC)nc3)nn2-c2ccccc2)[C@H](c2ccc(F)c(F)c2)N1] | 2 | 1.19 | 563 | |
| I-258 | 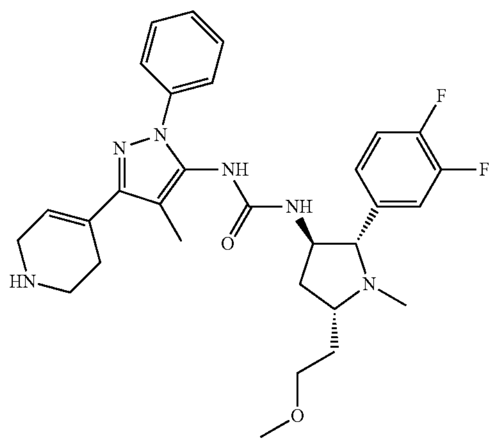 [SMILES: COCC[C@@H]1C[C@@H](NC(=O)Nc2c(C)c(C3=CCNCC3)nn2-c2ccccc2)[C@H](c2ccc(F)c(F)c2)N1C] | 1 | 0.84 | 551.25 | |

TABLE 73

| No. | Structure | LCMS method No. | RT | MS (m/z) | Configuration |
|---|---|---|---|---|---|
| I-259 | 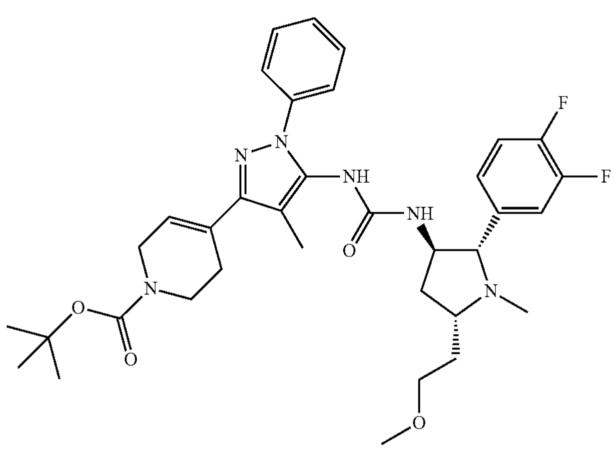 [SMILES: COCC[C@@H]1C[C@@H](NC(=O)Nc2c(C)c(C3=CCN(C(=O)OC(C)(C)C)CC3)nn2-c2ccccc2)[C@H](c2ccc(F)c(F)c2)N1C] | 1 | 1.69 | 651.45 | |

TABLE 73-continued

| No. | Structure | LCMS method No. | RT | MS (m/z) | Configuration |
|---|---|---|---|---|---|
| I-260 | 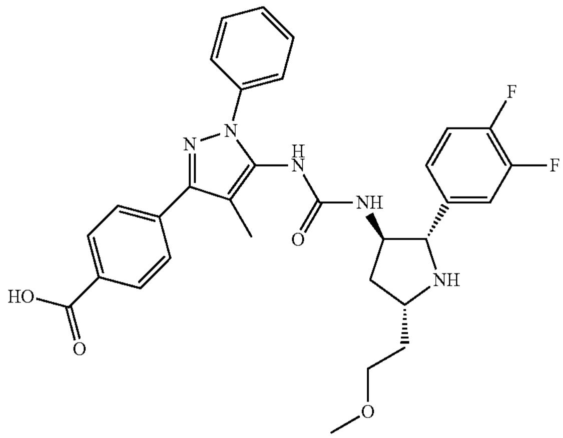 [SMILES: COCC[C@@H]1C[C@@H](NC(=O)Nc2c(C)c(-c3ccc(C(=O)O)cc3)nn2-c2ccccc2)[C@H](c2ccc(F)c(F)c2)N1] | 1 | 1.3 | 576 | |
| I-261 | 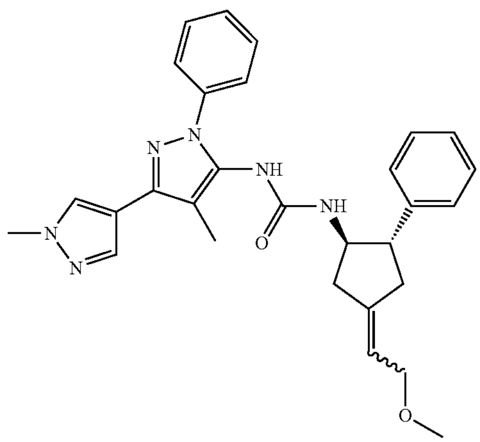 [SMILES: COCC=C1C[C@@H](NC(=O)Nc2c(C)c(-c3cnn(C)c3)nn2-c2ccccc2)[C@H](c2ccccc2)C1] | 1 | 1.81 | 497 | trans |
| I-262 | 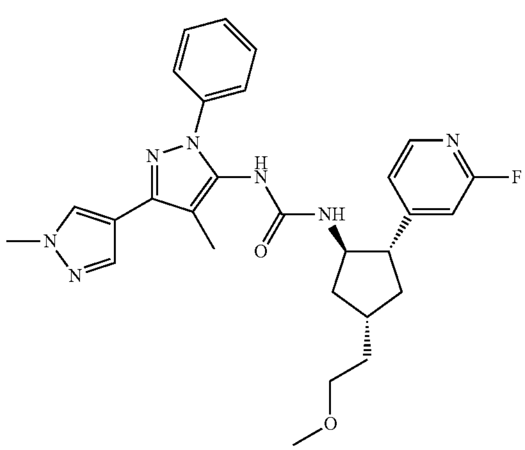 [SMILES: COCC[C@@H]1C[C@@H](NC(=O)Nc2c(C)c(-c3cnn(C)c3)nn2-c2ccccc2)[C@H](c2ccnc(F)c2)C1] | 1 | 1.59 | 518 | |

TABLE 74

| No. | Structure | LCMS method No. | RT | MS (m/z) | Configuration |
|---|---|---|---|---|---|
| I-263 | 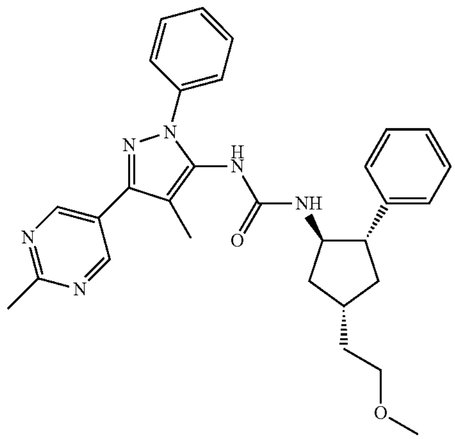 [SMILES: COCC[C@@H]1C[C@@H](NC(=O)Nc2c(C)c(-c3cnc(C)nc3)nn2-c2ccccc2)[C@H](c2ccccc2)C1] | 2 | 1.97 | 511 | |
| I-264 | 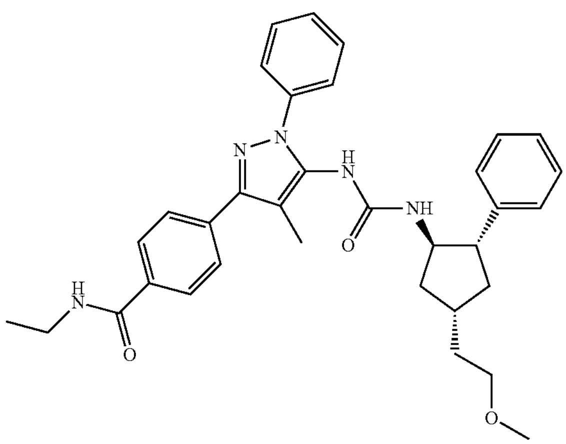 [SMILES: CCNC(=O)c1ccc(-c2nn(-c3ccccc3)c(NC(=O)N[C@@H]3C[C@@H](CCOC)C[C@H]3c3ccccc3)c2C)cc1] | 2 | 2.13 | 566 | |
| I-265 | 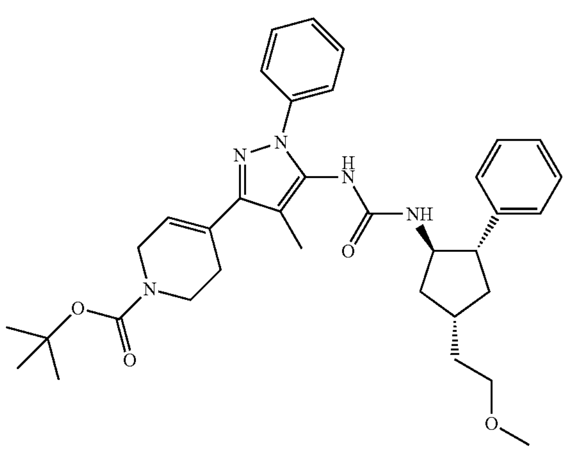 [SMILES: COCC[C@@H]1C[C@@H](NC(=O)Nc2c(C)c(C3=CCN(C(=O)OC(C)(C)C)CC3)nn2-c2ccccc2)[C@H](c2ccccc2)C1] | 2 | 2.63 | 600 | |

TABLE 74-continued

| No. | Structure | LCMS method No. | RT | MS (m/z) | Configuration |
|---|---|---|---|---|---|
| I-266 | 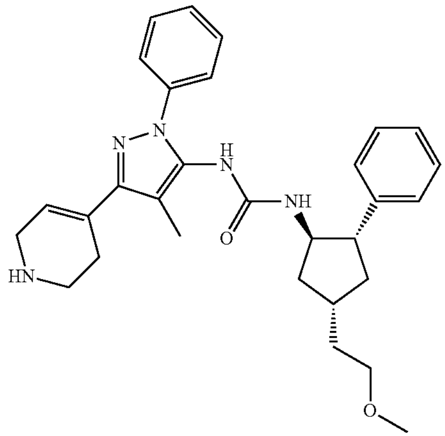 [SMILES: COCC[C@@H]1C[C@@H](NC(=O)Nc2c(C)c(C3=CCNCC3)nn2-c2ccccc2)[C@H](c2ccccc2)C1] | 2 | 1.61 | 500 | |

TABLE 75

| No. | Structure | LCMS method No. | RT | MS (m/z) | Configuration |
|---|---|---|---|---|---|
| I-267 | 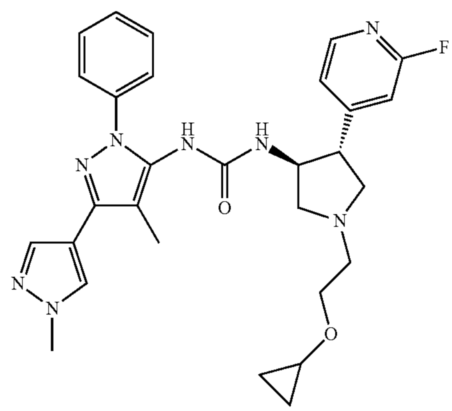 [SMILES: Cc1c(-c2cnn(C)c2)nn(-c2ccccc2)c1NC(=O)N[C@@H]1CN(CCOC2CC2)C[C@H]1c1ccnc(F)c1] | 1 | 1.09 | 545.25 | racemate |
| I-268 | 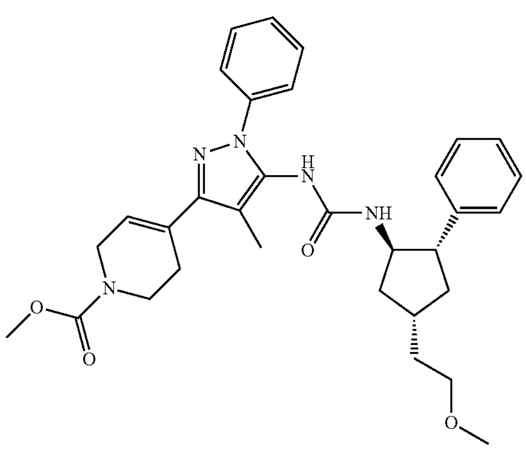 [SMILES: COCC[C@@H]1C[C@@H](NC(=O)Nc2c(C)c(C3=CCN(C(=O)OC)CC3)nn2-c2ccccc2)[C@H](c2ccccc2)C1] | 2 | 2.22 | 558 | |

TABLE 75-continued

| No. | Structure | LCMS method No. | RT | MS (m/z) | Configuration |
|---|---|---|---|---|---|
| I-269 | 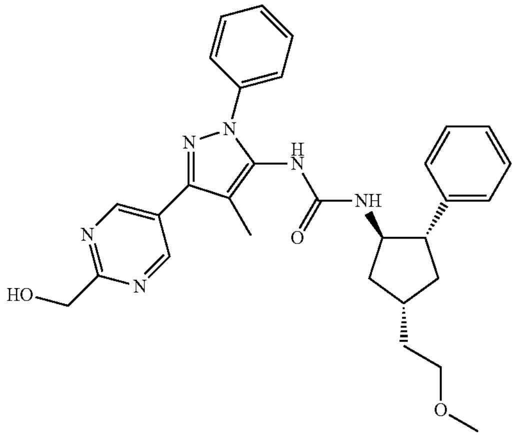 [SMILES: COCC[C@@H]1C[C@@H](NC(=O)Nc2c(C)c(-c3cnc(CO)nc3)nn2-c2ccccc2)[C@H](c2ccccc2)C1] | 2 | 1.81 | 527 | |
| I-270 | 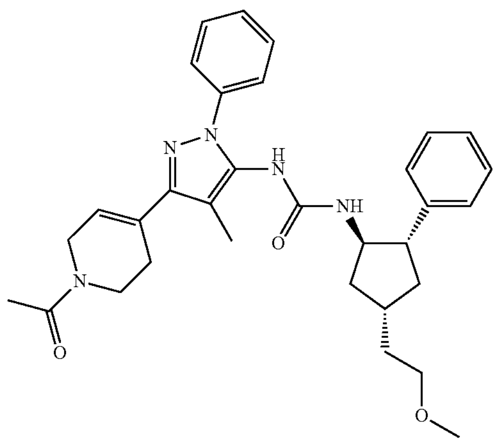 [SMILES: COCC[C@@H]1C[C@@H](NC(=O)Nc2c(C)c(C3=CCN(C(C)=O)CC3)nn2-c2ccccc2)[C@H](c2ccccc2)C1] | 2 | 1.97 | 542 | |

TABLE 76

| No. | Structure | LCMS method No. | RT | MS (m/z) | Configuration |
|---|---|---|---|---|---|
| I-271 | 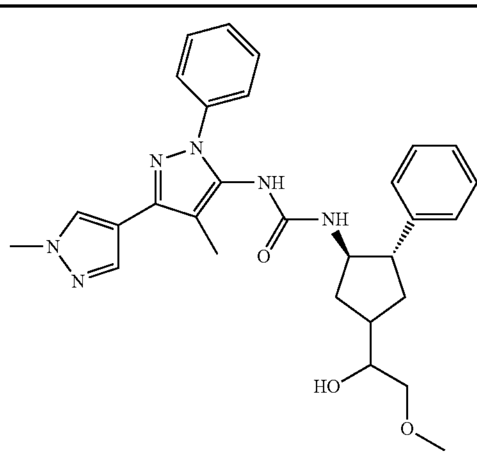 | 1 | 1.56 | 515 | mixture of 8 diastereomers |

TABLE 76-continued

| No. | Structure | LCMS method No. | RT | MS (m/z) | Configuration |
|---|---|---|---|---|---|
| I-272 | 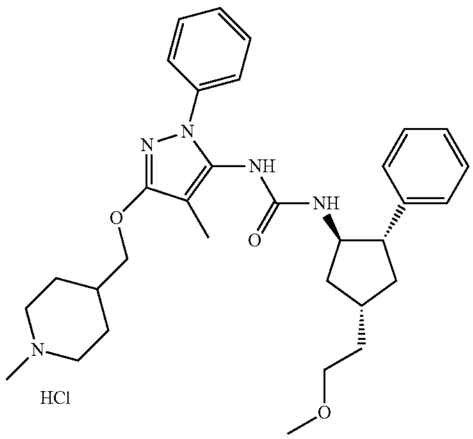 [SMILES: COCC[C@@H]1C[C@@H](NC(=O)Nc2c(C)c(OCC3CCN(C)CC3)nn2-c2ccccc2)[C@H](c2ccccc2)C1 ; Cl] | 1 | 1.42 | 546.2 | |
| I-273 | 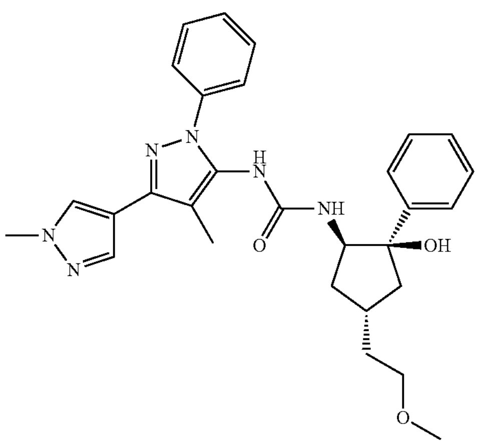 [SMILES: COCC[C@@H]1C[C@@H](NC(=O)Nc2c(C)c(-c3cnn(C)c3)nn2-c2ccccc2)[C@](O)(c2ccccc2)C1] | 2 | 1.45 | 515 | |
| I-274 | 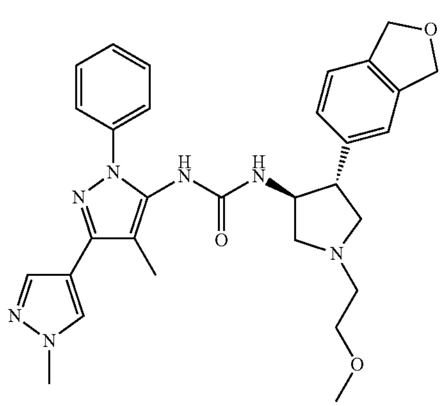 [SMILES: COCCN1C[C@@H](NC(=O)Nc2c(C)c(-c3cnn(C)c3)nn2-c2ccccc2)[C@H](c2ccc3c(c2)COC3)C1] | 1 | 0.96 | 542.3 | racemate |

TABLE 77
| No. | Structure | LCMS method No. | RT | MS (m/z) | Configuration |
|---|---|---|---|---|---|
| I-275 | 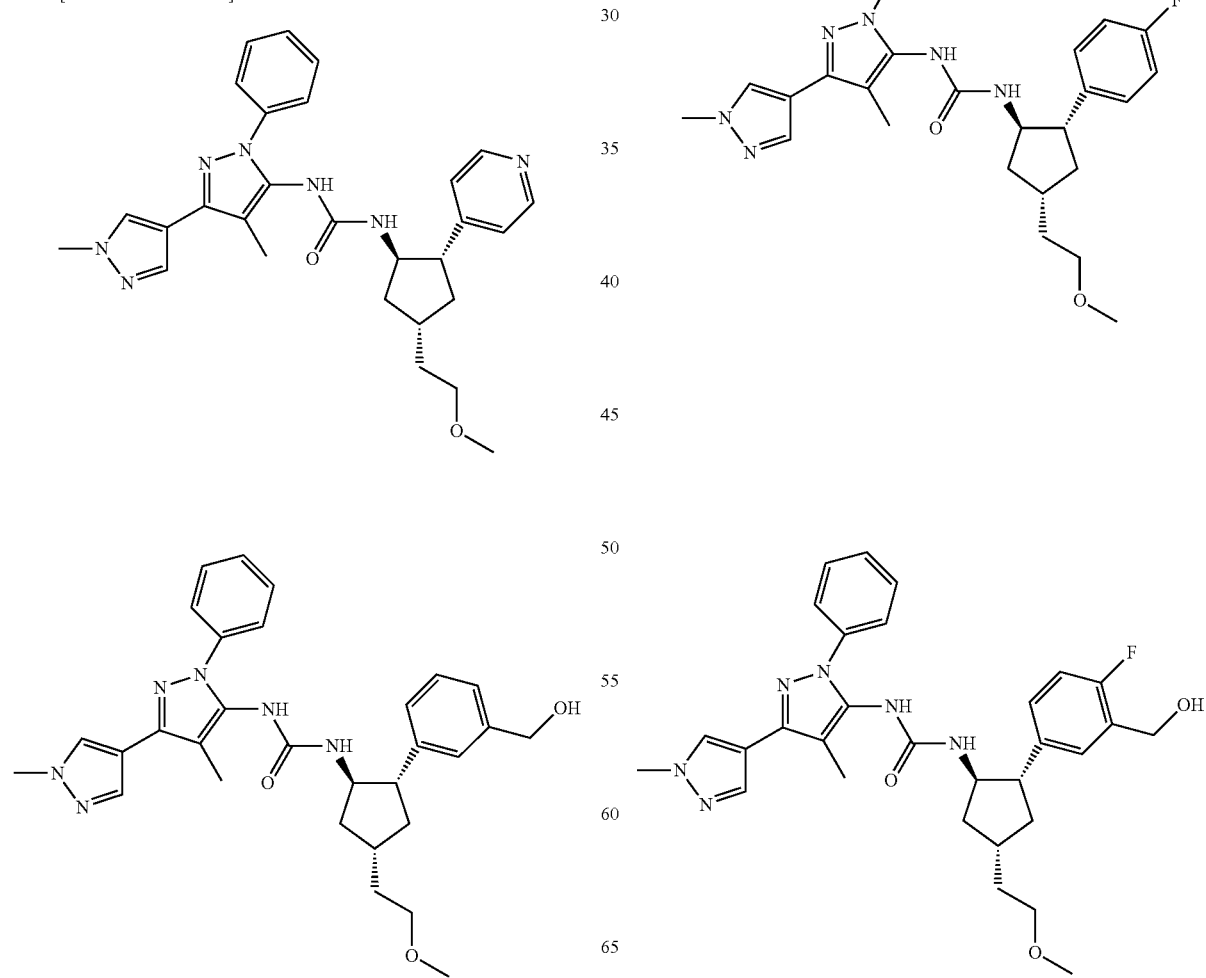 | 2 | 1.12 | 532 | |
The following compounds can be synthesized in accordance with the same manner as described above.
[Chemical Formula 86]

309
-continued
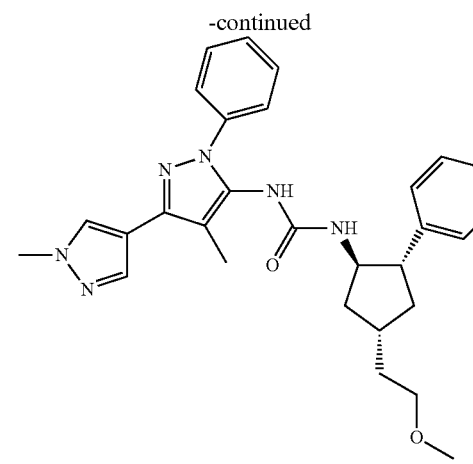
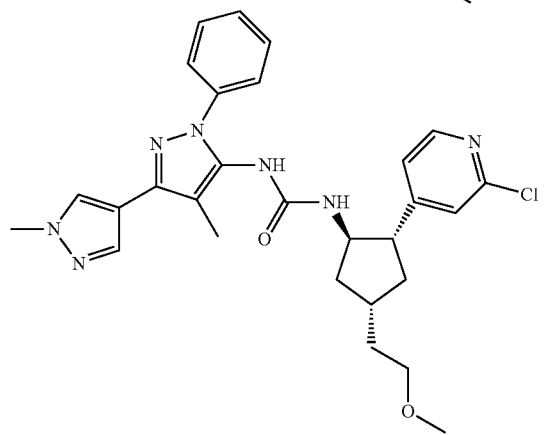
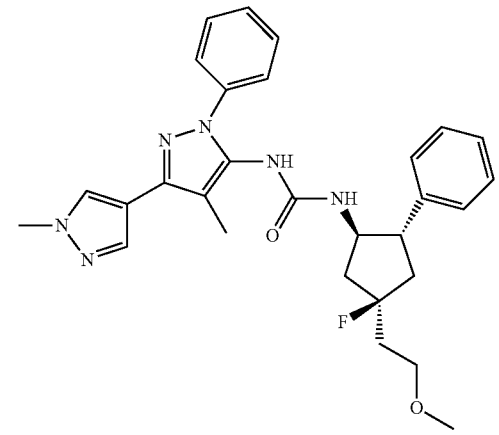
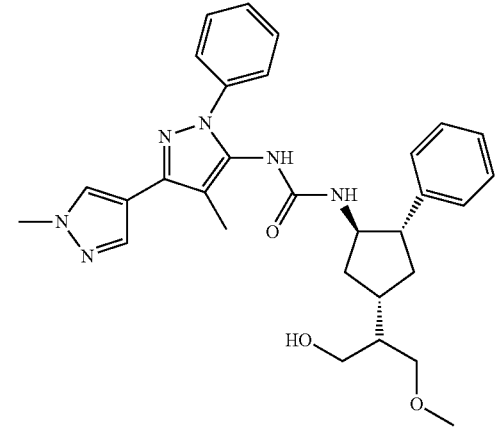
310
-continued
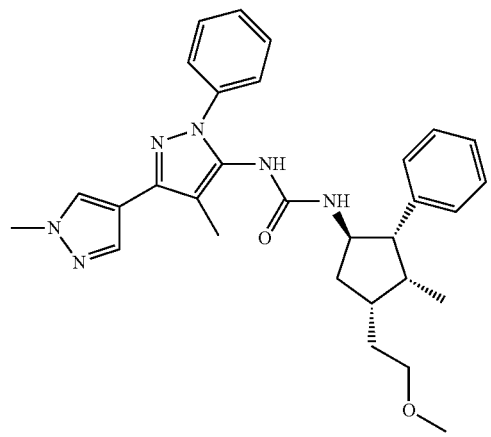
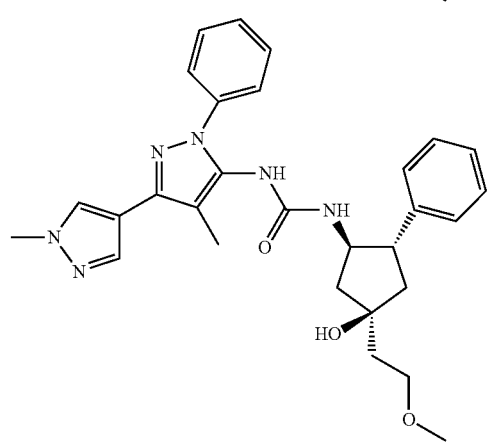
[Chemical Formula 87]
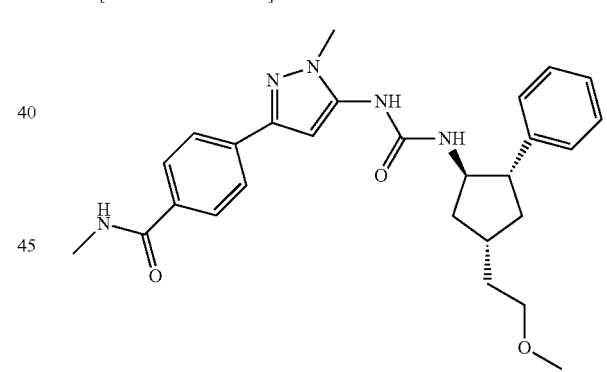
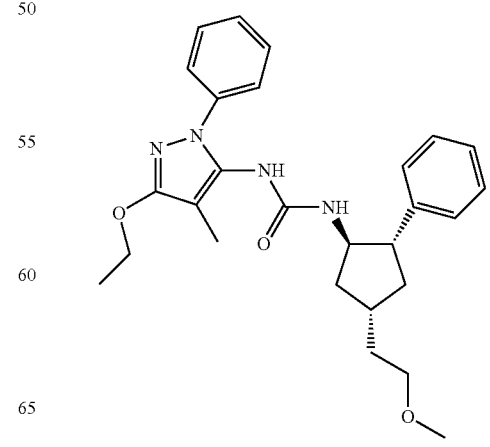

311
-continued
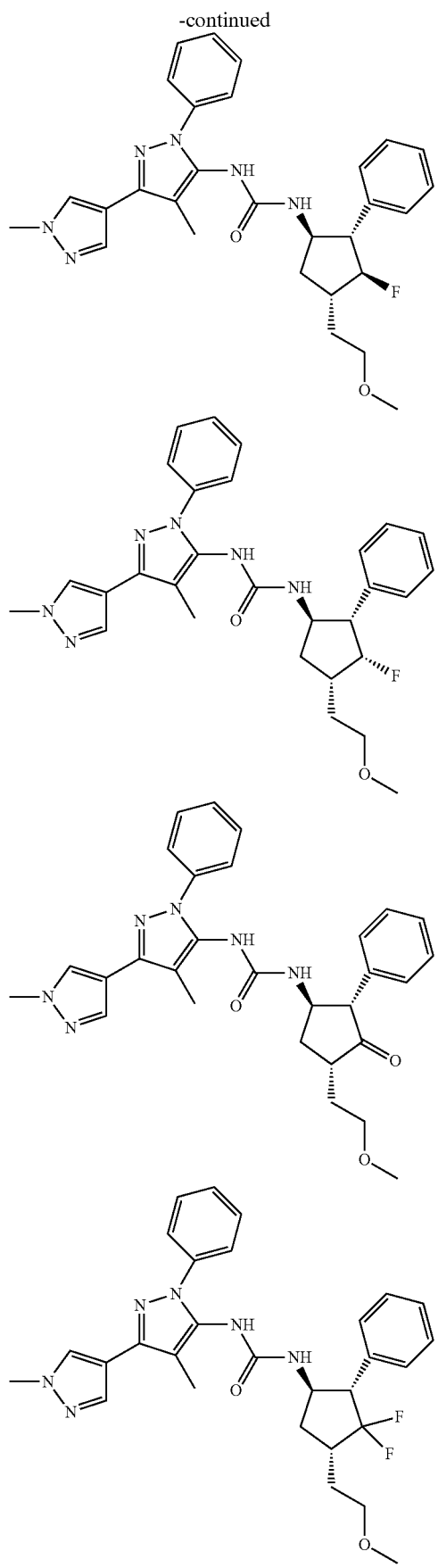
312
-continued
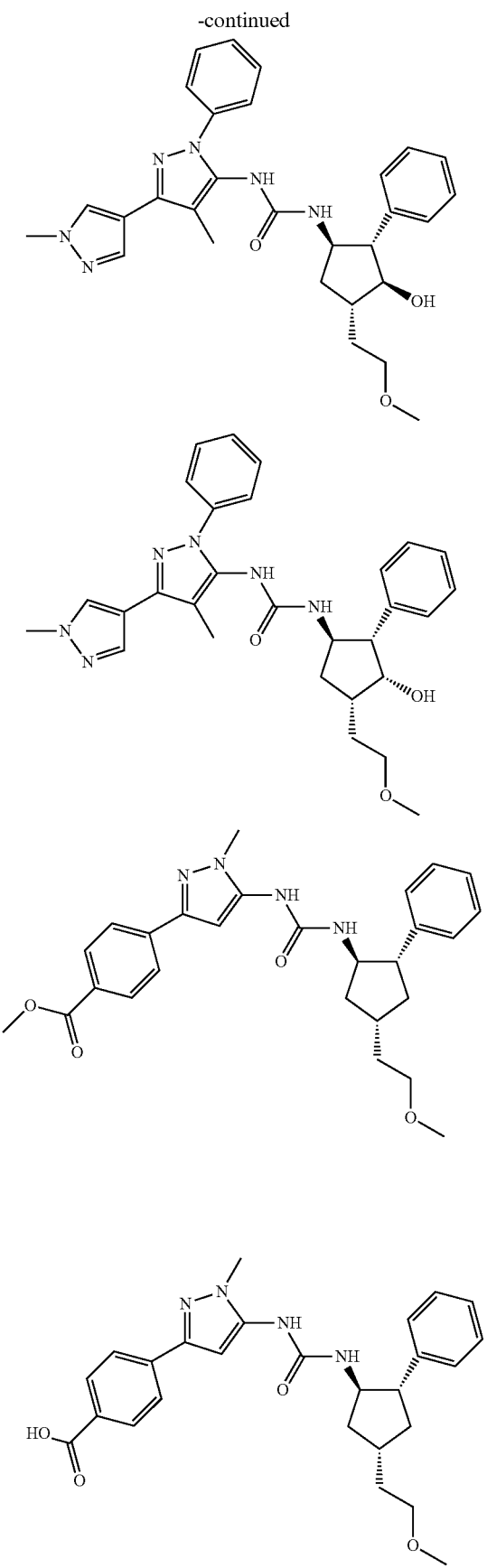

313
-continued
[Chemical Formula 88]
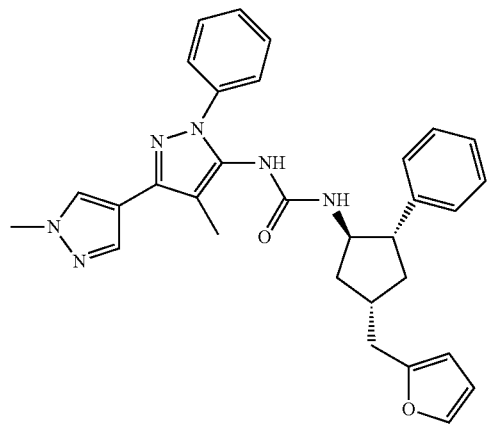
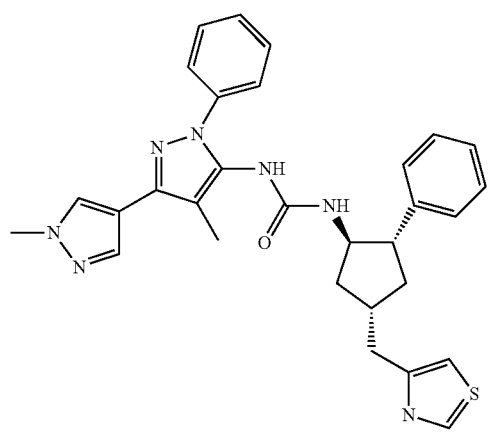
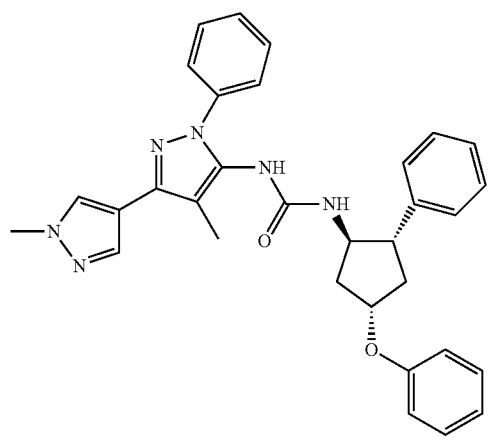
314
-continued
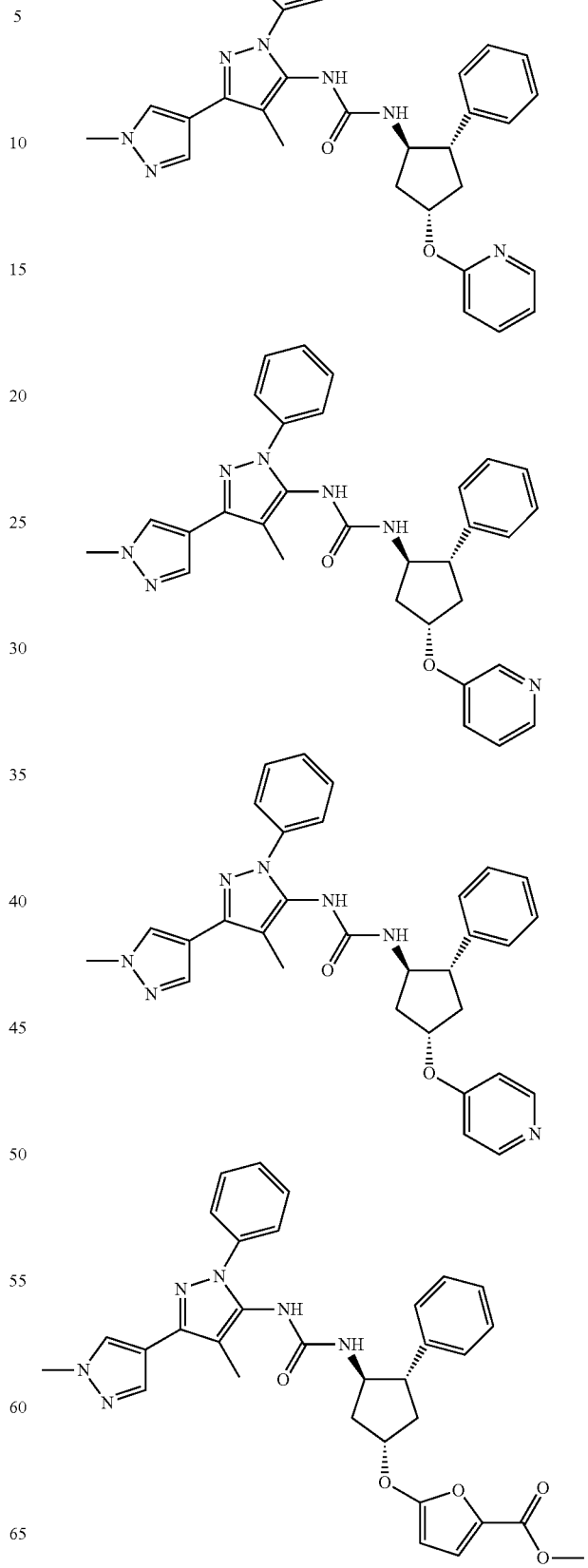

315
-continued
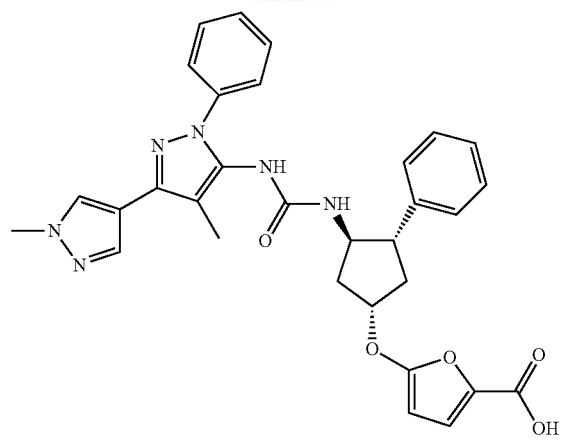
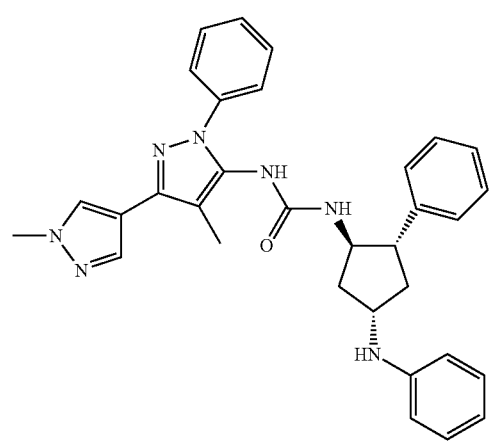
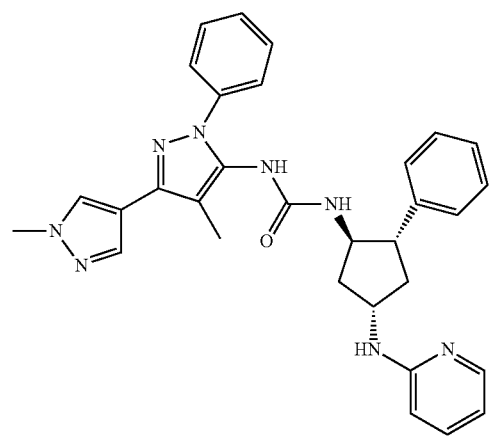
316
-continued
[Chemical Formula 89]
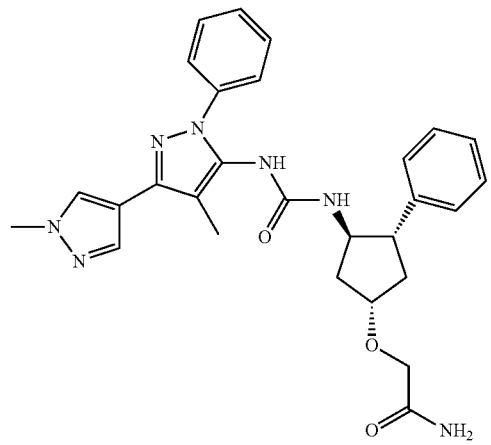
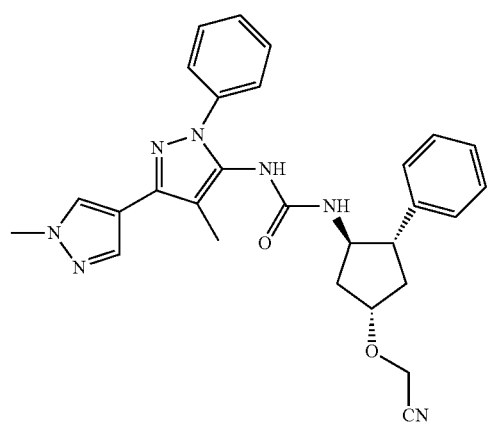
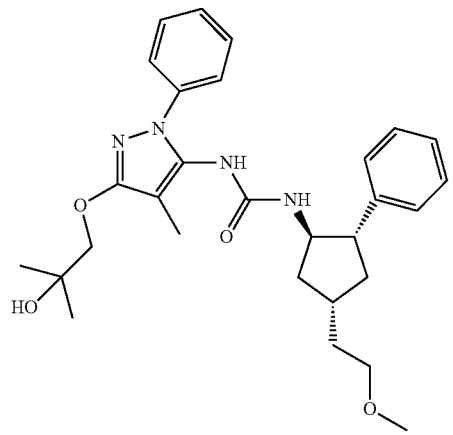

317
-continued
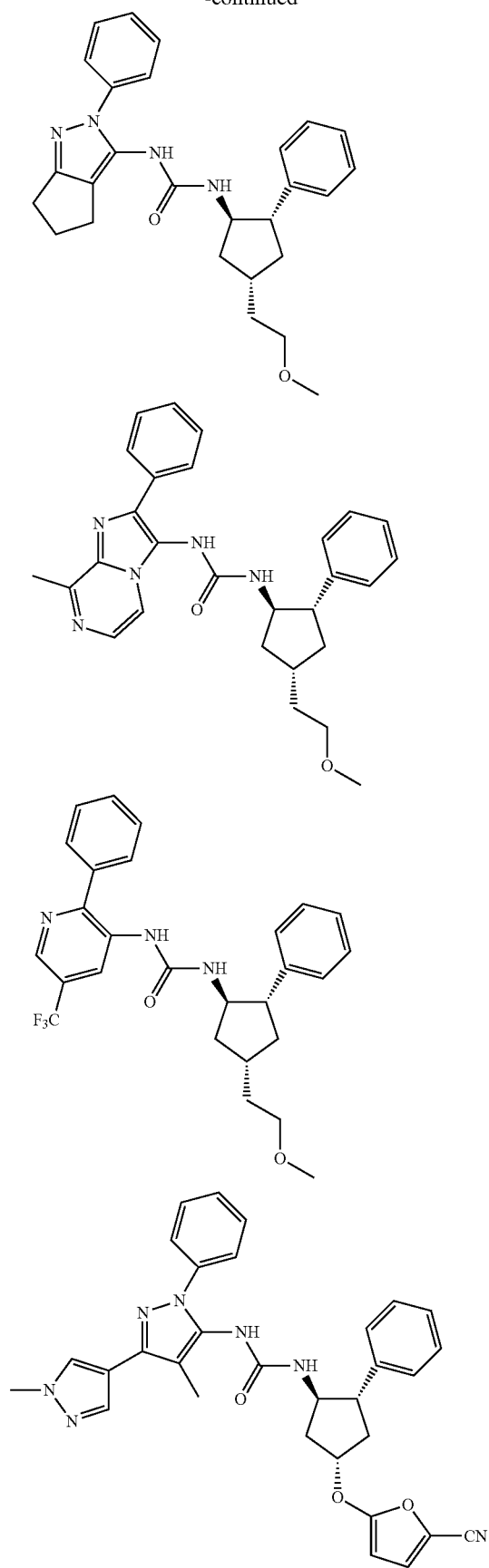
318
-continued
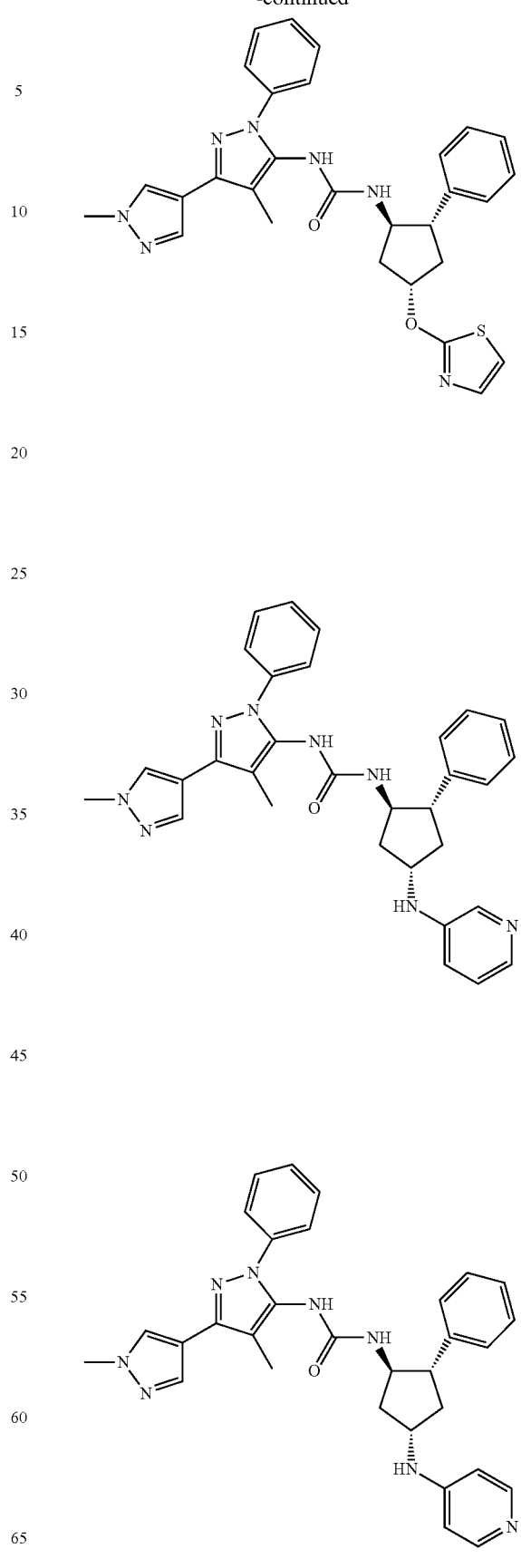

319
-continued
[Chemical Formula 90]
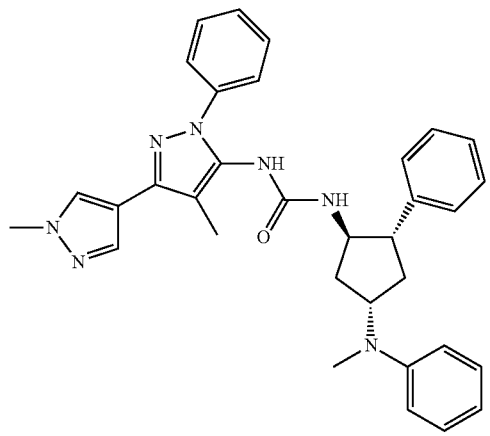
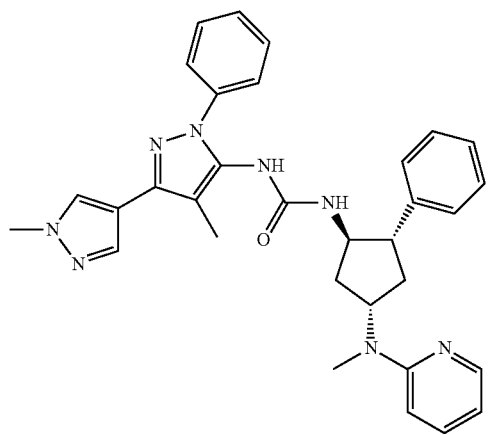
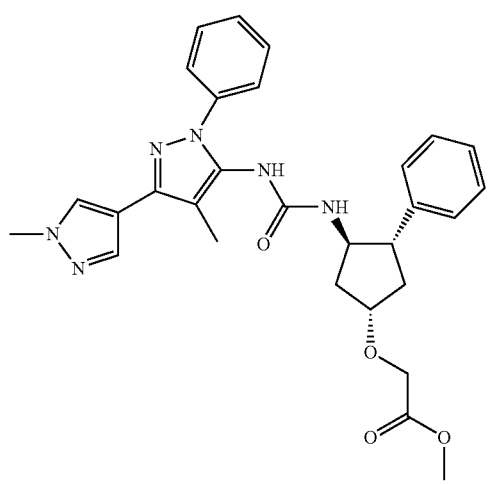
320
-continued
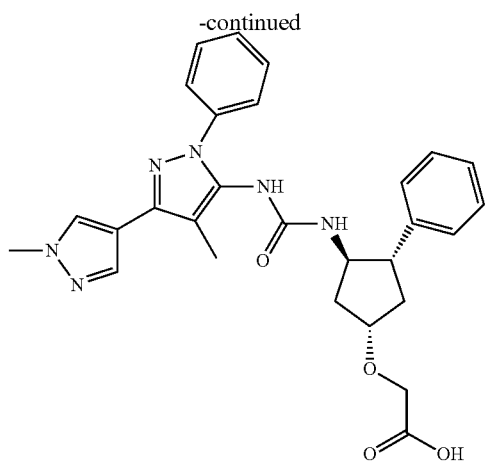
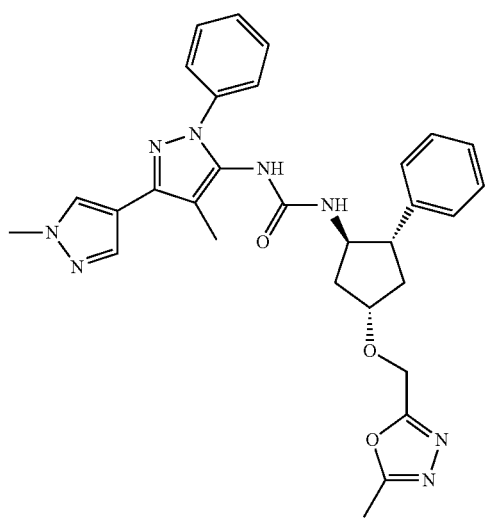
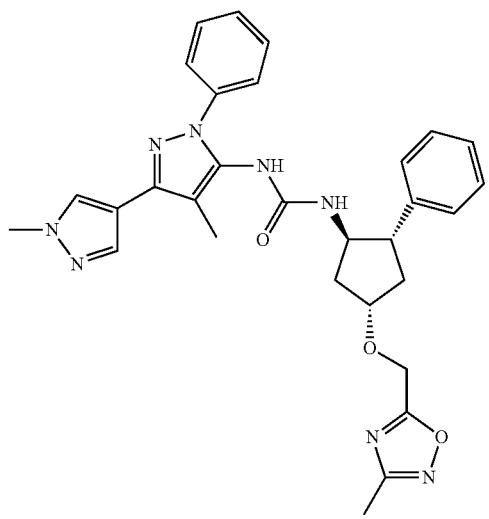

321
-continued
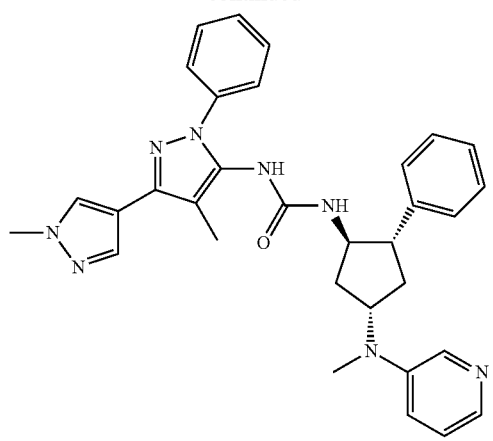
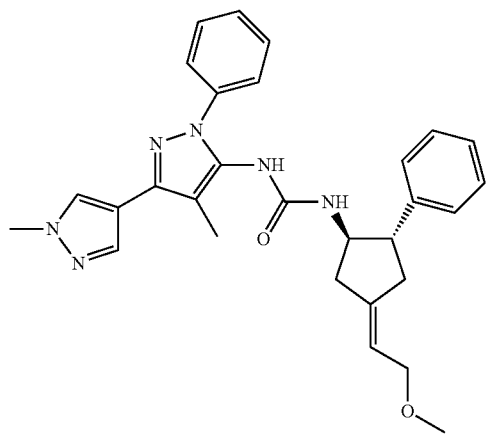
[Chemical Formula 91]
322
-continued
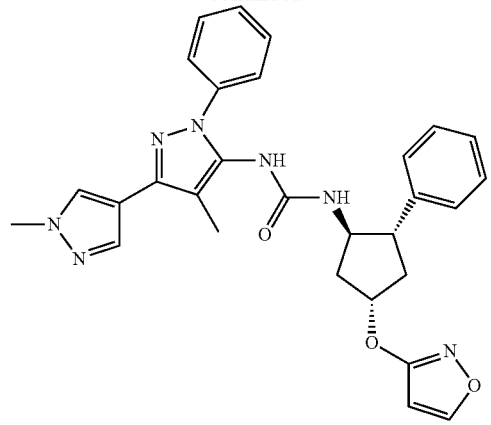
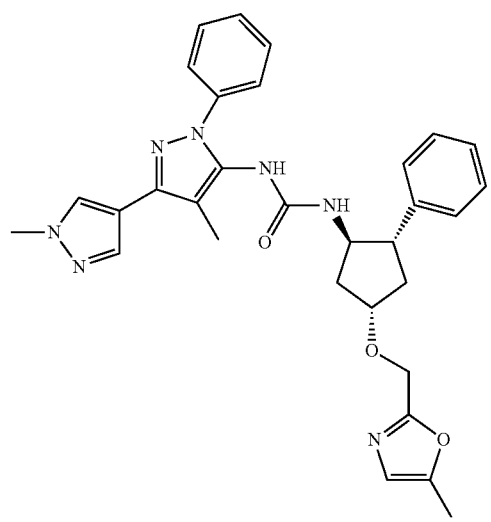
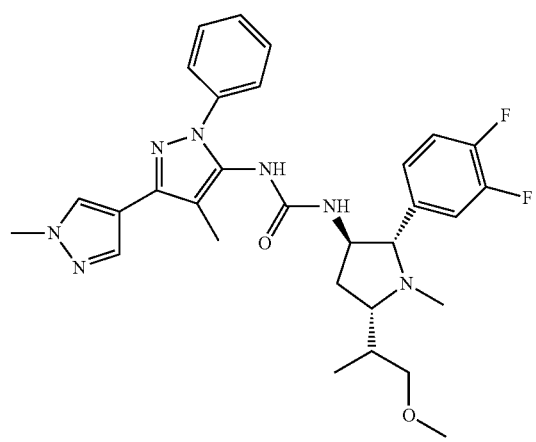

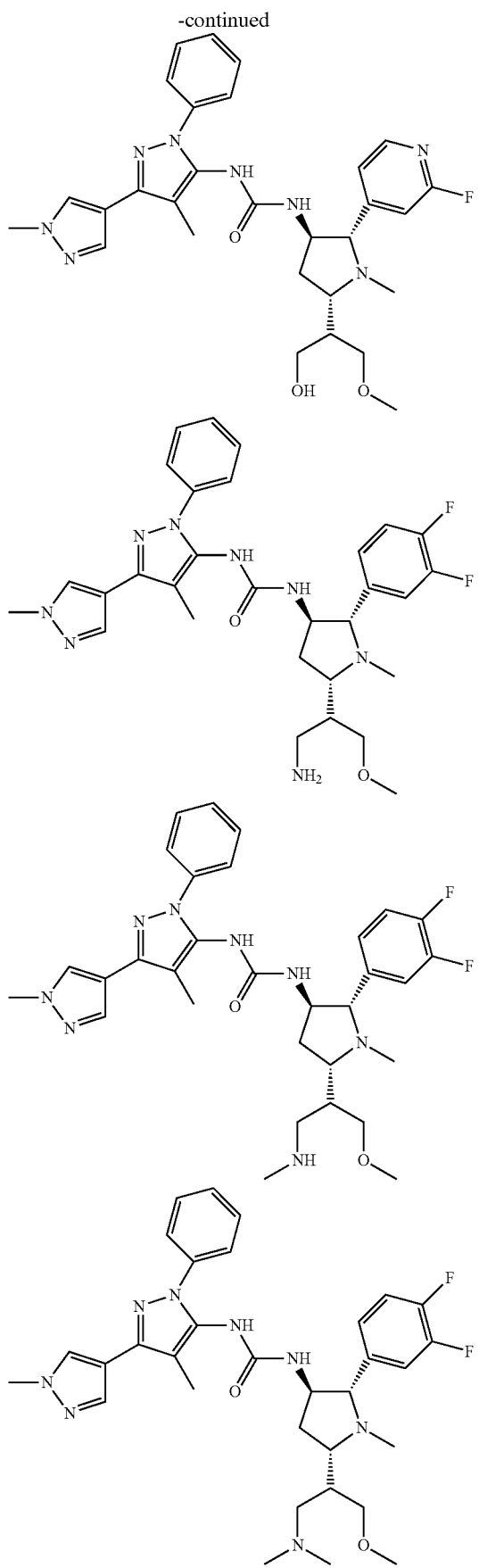

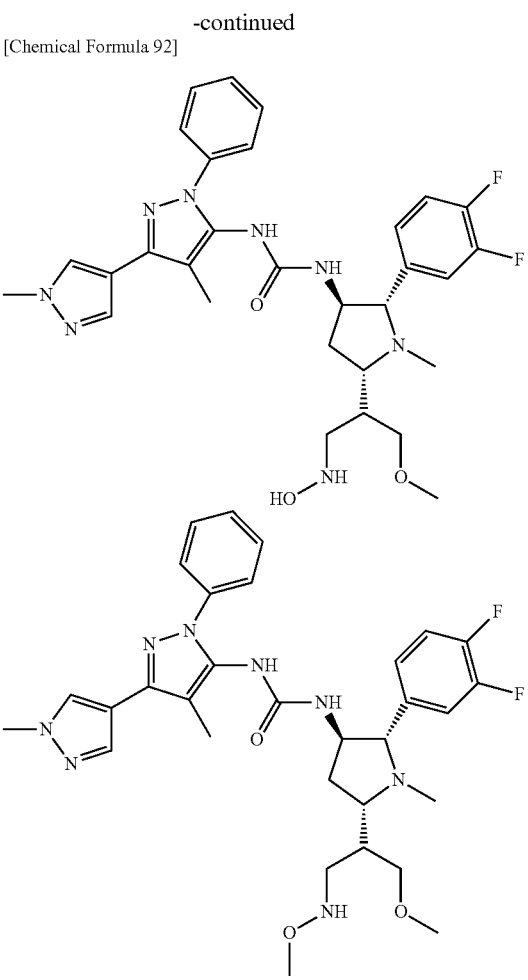

Test Example 1: The Growth Inhibition Assay Using TF-1 Cells

To produce the stable cells expressing two types of NT receptors (TrkA, TrkB, TrkC and p75) highly and simultaneously, each human NT receptor gene was transfected by a retrovirus vector into human erythroleukemic cell line TF-1 cells (ATCC Number: CRL-2003). The inhibition assay against NGF, BDNF and NT-3 were done in TF-1 cells expressing TrkA+p75, TrkB+p75 and TrkC+p75, respectively. The cells were suspended in RPMI-1640 medium containing 13% fetal bovine serum seeded in a white 96 well flat-bottom plate at 1000 cells (75 μL) per well and pre-incubated for 15 min at room temperature with 1 μLL of each compound (final concentration: 20 μmol/L to 1 nmol/L) dissolved in RPMI-1640 medium containing 20% DMSO. Twenty five LL of human NGF (final concentration: 2 ng/mL), human BDNF (final concentration: 1 ng/mL) or human NT-3 (final concentration: 2 ng/mL) was added in each well and the plate was incubated for 3 days. Then, one hundred LL of CellTiter-Glo reagent for CellTiter-Glo Luminescent Cell Viability Assay (manufactured by Promega) was added in each well and chemiluminescence was measured by a microplate reader to evaluate the growth of TF-1 cells. Luminescence value in the well incubated with or without each growth factor is 0% or 100% inhibition, respectively. The inhibitory activity of each compound was calculated by the following formula.

Inhibition (%)=(1−(luminescence value with compound−luminescence value of 100% inhibitory activity)/(luminescence value of 0% inhibitory activity−luminescence value of 100% inhibitory activity))×100

The 50% inhibitory concentration (IC50) was determined by the logistic regression using the inhibition data in 10 points at a range of 20 μmol/L to 1 nmol/L).

Test Example 1-2: The Growth Inhibition Assay Using TF-1 Cells

To produce the stable cells expressing two types of NT receptors (TrkA, TrkB, TrkC and p75) highly and simultaneously, each human NT receptor gene was transfected by a retrovirus vector into human erythroleukemic cell line TF-1 cells (ATCC Number: CRL-2003). The inhibition assay against NGF, BDNF and NT-3 were done in TF-1 cells expressing TrkA+p75, TrkB+p75 and TrkC+p75, respectively. Two hundred nL per well of each compound (final concentration: 20 μmol/L-1 nmol/L) dissolved in DMSO was applied in a white 384 well flat-bottom plate. The cells were suspended in RPMI-1640 medium containing 10% fetal bovine serum and seeded in each well at 400 cells for the TF1 cells expressing TrkA and p75 or TrkC and p75, and 800 cells for the TF cells expressing TrkB and p75. Forty L of human NGF (final concentration: 4 ng/mL), human BDNF (final concentration: 8 ng/mL) or human NT-3 (final concentration: 8 ng/mL) was added in each well and the plate was incubated for 3 days. Then, twenty L of CellTiter-Glo reagent for CellTiter-Glo Luminescent Cell Viability Assay (manufactured by Promega) was added in each well and chemiluminescence was measured by a microplate reader to evaluate the growth of TF-1 cells. Luminescence value in the well incubated with or without each growth factor is 0% or 100% inhibition, respectively. The inhibitory activity of each compound was calculated by the following formula.

Inhibition (%)=(1−(luminescence value with compound−luminescence value of 100% inhibitory activity)/(luminescence value of 0% inhibitory activity−luminescence value of 100% inhibitory activity))×100

The 50% inhibitory concentration (IC50) was determined by the logistic regression using the inhibition data in 10 points at a range of 20 μmol/L to 1 nmol/L).

Test Example 2: Human TrkA Inhibition Assay

Five μL per well of human TrkA (PV3144, Lifetechnologies, final concentration: 2.5 nmol/L) suspended in the assay buffer (100 mmol/L 4-(2-hydroxyethyl)-1-piperazineethanesulfonic acid (HEPES), 10 mmol/L magnesium chloride, 0.003 vol % Brij-35, 0.004 vol % Tween20 and 1 mmol/L dithiothreitol (DTT)) was applied in a 384 well plate and the plate was pre-incubated for 15 min at room temperature with 200 nL of each compound (final concentration: 200 μmol/L to 0.1 nmol/L) dissolved in DMSO. Then, fluorescent substrate (FL-peptide 27, 760424, PerkinElmer, final concentration: 1.5 μmol/L) and ATP (final concentration: 500 μmol/L) were added in each well. After the incubation for 90 min at room temperature, ten μL of termination buffer (100 mmol/L HEPES, 40 mmol/L ethylenediaminetetraacetic acid (EDTA), 10 mmol/L magnesium chloride, 0.003 vol % Brij-35, 0.004 vol % Tween20, 1 mmol/L DTT and 0.16 vol % Coating Reagent 3) was added in each well to stop the enzyme reaction. Fluorescent intensities (FI) of phosphorylated and non-phosphorylated fluorescent substrates were measured by LabChip EZReader II (Caliper LifeSciences, Inc.) and conversion ratio (CR) was calculated by the following formula-1. The CR in the well applied with DMSO alone was used as a negative control and the CR in the well without applying TrkA was used as a positive control. The inhibitory effect of each compound on TrkA phosphorylation was calculated by the following formula-2.

CR (%)=(FI of phosphorylated substrate/(FI of phosphorylated substrate+FI of non-phosphorylated substrate))×100    (Formula-1)

Inhibitory effect on TrkA phosphorylation (%)=(1−(CR in compound treated well−CR in positive control)/(CR in negative control−CR in positive control))×100.    (Formula-2)

The 50% inhibitory concentration (IC50) was determined by the logistic regression using the inhibition data in 10 points at a range of 2 μmol/L to 0.1 nmol/L or 200 μmol/L to 10 nmol/L).

(Result)

The evaluation results of the compounds in the present invention on TrkA inhibitory activity are indicated as follows. IC50 values of 0 to 100 nM, 100 to 1000 nM and over 1000 nM were shown as "A", "B" and "C", respectively.

Compound I-1: 83 nM,
Compound I-3: 65 nM,
Compound I-8: 26 nM,
Compound I-15: 143 nM,
Compound I-16: 121 nM,
Compound I-22: 35 nM,
Compound I-44: 700 nM,
Compound I-71: 300 nM,
Compound I-84: 0.72 nM,
Compound I-86: 1.1 nM,
Compound I-87: 1.8 nM,
Compound I-91: 7.8 nM,
Compound I-93: 21 nM,
Compound I-94: 22 nM,
Compound I-96: 29 nM,
Compound I-100: 34 nM,
Compound I-102: 43 nM,
Compound I-106: 79 nM,
Compound I-109: 95 nM,
Compound I-114: 120 nM,
Compound I-129: 440 nM,
Compound I-130: 460 nM,
Compound I-132: 480 nM,
Compound I-141: 1100 nM,
Compound I-142: 1300 nM,
Compound I-146: 1800 nM,
Compound I-157: 3300 nM,
Compound I-161: 4200 nM,
Compound I-168: 7000 nM.

TABLE 78

| No. | IC50_nM |
|---|---|
| I-2 | C |
| I-4 | C |
| I-5 | C |
| I-6 | C |
| I-7 | C |
| I-9 | B |
| I-10 | C |
| I-11 | C |
| I-12 | C |
| I-13 | C |

TABLE 78-continued

| No. | IC50_nM |
|---|---|
| I-14 | C |
| I-17 | C |
| I-18 | C |
| I-19 | C |
| I-20 | B |
| I-21 | C |
| I-23 | B |
| I-24 | B |
| I-25 | C |
| I-26 | C |
| I-27 | C |
| I-28 | C |
| I-29 | A |
| I-30 | C |
| I-31 | C |
| I-32 | C |
| I-33 | B |
| I-34 | C |
| I-35 | C |
| I-36 | A |
| I-37 | B |
| I-38 | C |
| I-39 | C |
| I-40 | C |
| I-41 | C |
| I-42 | B |
| I-43 | C |
| I-45 | C |
| I-46 | C |
| I-47 | C |
| I-48 | A |
| I-49 | A |
| I-50 | A |
| I-51 | A |
| I-52 | B |
| I-53 | C |
| I-54 | C |
| I-55 | B |
| I-56 | C |
| I-57 | B |
| I-58 | C |
| I-59 | C |
| I-60 | C |
| I-62 | C |
| I-63 | C |
| I-64 | C |
| I-65 | A |
| I-66 | B |
| I-67 | C |
| I-68 | C |
| I-69 | C |
| I-70 | C |
| I-72 | C |
| I-73 | C |
| I-74 | C |
| I-75 | B |
| I-76 | C |
| I-77 | C |
| I-78 | C |
| I-79 | B |
| I-80 | B |
| I-81 | B |
| I-82 | C |
| I-83 | C |

TABLE 79

| No. | IC50_nM |
|---|---|
| I-85 | A |
| I-88 | A |
| I-89 | A |
| I-90 | A |
| I-92 | A |
| I-95 | A |
| I-97 | A |
| I-98 | A |
| I-99 | A |
| I-101 | A |
| I-103 | A |
| I-104 | A |
| I-105 | A |
| I-107 | A |
| I-108 | A |
| I-110 | A |
| I-111 | A |
| I-112 | B |
| I-113 | B |
| I-115 | B |
| I-116 | B |
| I-117 | B |
| I-118 | B |
| I-119 | B |
| I-120 | B |
| I-121 | B |
| I-122 | B |
| I-123 | B |
| I-124 | B |
| I-125 | B |
| I-126 | B |
| I-127 | B |
| I-128 | B |
| I-131 | B |
| I-133 | B |
| I-134 | B |
| I-135 | B |
| I-136 | B |
| I-137 | B |
| I-138 | B |
| I-139 | B |
| I-140 | B |
| I-143 | C |
| I-144 | C |
| I-145 | C |
| I-147 | C |
| I-148 | C |
| I-149 | C |
| I-150 | C |
| I-151 | C |
| I-152 | C |
| I-153 | C |
| I-154 | C |
| I-155 | C |
| I-156 | C |
| I-158 | C |
| I-159 | C |
| I-160 | C |
| I-162 | C |
| I-164 | C |
| I-165 | C |
| I-166 | C |
| I-167 | C |
| I-169 | C |
| I-170 | C |
| I-171 | C |
| I-172 | C |
| I-173 | C |
| I-174 | C |
| I-175 | C |
| I-176 | C |

Test Example 2-2: Human TrkA Inhibition Assay

Seven point five μL per well of human TrkA (PV3144, Lifetechnologies, final concentration: 1 nmol/L) suspended in the assay buffer (100 mmol/L 4-(2-hydroxyethyl)-1-piperazineethanesulfonic acid (HEPES), 10 mmol/L magnesium chloride, 0.003 vol % Brij-35, 0.004 vol % Tween20 and 1 mmol/L dithiothreitol (DTT)) was applied in a 384 well plate and the plate was pre-incubated for 15 min at room temperature with 0.4 μLL of each compound (final concentration: 200 μmol/L-0.1 nmol/L) dissolved in DMSO. Then, fluorescent substrate (FL-peptide 27, 760424, PerkinElmer, final concentration: 1.5 μmol/L) and ATP (final concentration 500 μmol/L) dissolved in the assay buffer was added in each well. After the incubation of 120 min at 37° C., fifteen LL of termination buffer (100 mmol/L HEPES, 40 mmol/L ethylenediaminetetraacetic acid (EDTA), 10 mmol/L magnesium chloride, 0.003 vol % Brij-35, 0.004 vol % Tween20, 1 mmol/L DTT and 0.16 vol % Coating Reagent 3) was added in each well to stop the enzyme reaction. Fluorescent intensities (FI) of phosphorylated and non-phosphorylated fluorescent substrates were measured by LabChip EZReader II (Caliper LifeSciences, Inc.), and conversion ratio (CR) was calculated by the following formula-1. The CR in the well applied with DMSO alone was used as a negative control and the CR in the well without applying TrkA was used as a positive control. The inhibitory effect of each compound on TrkA phosphorylation was calculated by the following formula-2.

CR (%)=(FI of phosphorylated substrate/(FI of phosphorylated substrate+FI of non-phosphorylated substrate))×100 (Formula-1)

Phosphorylation inhibition (%)=(1−(CR with compound treatment−CR of positive control)/(CR of negative control−CR of positive control))×100

Inhibitory effect on TrkA phosphorylation (%)=(1−(CR in compound treated well−CR in positive control)/(CR in negative control−CR in positive control))×100. (Formula-2)

The 50% inhibitory concentration (IC50) was determined by the logistic regression using the inhibition data in 10 points at a range of 2 μmol/L to 0.1 nmol/L or 200 μmol/L to 10 nmol/L).
(Result)

The evaluation results of the compounds in the present invention are indicated as follows. IC50 values of 0 to 100 nM, 100 to 1000 nM and over 1000 nM were shown as "A", "B" and "C", respectively. IC50 values of the compounds in the present invention are as follows.

Compound I-1: 120 nM,
Compound I-3: 50 nM,
Compound I-8: 71 nM,
Compound I-16: 410 nM,
Compound I-22: 170 nM,
Compound I-84: 1.5 nM,
Compound I-86: 1.8 nM,
Compound I-87: 5.4 nM,
Compound I-91: 37 nM,
Compound I-94: 210 nM,
Compound I-96: 160 nM,
Compound I-102: 21 nM,
Compound I-109: 220 nM,
Compound I-184: 47 nM,
Compound I-185: 1500 nM,
Compound I-190: 1.3 nM,
Compound I-202: 0.71 nM,
Compound I-209: 10 nM,
Compound I-218: 270 nM,
Compound I-225: 120 nM,
Compound I-239: 76 nM,
Compound I-241: 0.9 nM,
Compound I-248: 18 nM,
Compound I-252: 3.6 nM,
Compound I-254: 0.73 nM,
Compound I-255: 1.1 nM,
Compound I-256: 8.2 nM,
Compound I-262: 4.8 nM,
Compound I-267: 24 nM,
Compound I-269: 1.3 nM,
Compound I-270: 0.67 nM.

TABLE 80

| No. | IC50_nM |
| --- | --- |
| I-163 | B |
| I-177 | B |
| I-178 | A |
| I-179 | B |
| I-180 | B |
| I-181 | C |
| I-182 | B |
| I-183 | A |
| I-186 | B |
| I-187 | A |
| I-188 | C |
| I-189 | A |
| I-191 | B |
| I-192 | B |
| I-193 | A |
| I-194 | C |
| I-195 | C |
| I-196 | C |
| I-197 | C |
| I-198 | C |

TABLE 81

| No. | IC50_nM |
| --- | --- |
| I-199 | C |
| I-200 | C |
| I-201 | A |
| I-203 | B |
| I-204 | A |
| I-205 | A |
| I-206 | A |
| I-207 | A |
| I-208 | A |
| I-210 | B |
| I-211 | C |
| I-212 | A |
| I-213 | B |
| I-214 | A |
| I-215 | B |
| I-216 | B |
| I-217 | A |
| I-219 | C |
| I-220 | B |
| I-221 | A |
| I-222 | A |
| I-223 | C |
| I-224 | B |
| I-226 | B |
| I-227 | B |
| I-228 | B |
| I-229 | A |
| I-230 | B |
| I-231 | C |
| I-232 | B |
| I-233 | C |
| I-234 | A |
| I-235 | A |
| I-236 | A |
| I-237 | A |
| I-238 | C |
| I-240 | B |
| I-242 | B |
| I-243 | C |
| I-244 | B |
| I-245 | C |
| I-246 | A |
| I-247 | A |

TABLE 81-continued

| No. | IC50_nM |
| --- | --- |
| I-249 | A |
| I-250 | A |
| I-251 | B |
| I-253 | A |
| I-257 | A |
| I-258 | A |
| I-259 | A |
| I-260 | A |
| I-261 | A |
| I-263 | A |
| I-264 | A |
| I-265 | A |
| I-266 | A |

TABLE 82

| No. | IC50_nM |
| --- | --- |
| I-268 | A |
| I-271 | B |
| I-272 | A |
| I-273 | C |
| I-274 | B |
| I-275 | A |

Test Example 3: hERG Test

For the purpose of assessing risk of an electrocardiogram QT interval prolongation of the compound of the present invention, effects of the compound of the present invention on delayed rectifier K$^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S), IKr induced by leak potential at −50 mV, and then depolarization pulse stimulation at +20 mV for 2 seconds and, further, repolarization pulse stimulation at −50 mV for 2 seconds, was recorded. After the generated current was stabilized, extracellular solution (NaCl: 145 mmol/L, KCl: 4 mmol/L, CaCl$_2$: 2 mmol/L, MgCl$_2$: 1 mmol/L, glucose: 10 mmol/L, HEPES (4-(2-hydroxyethyl)-1-piperazineethanesulfonic acid): 10 mmol/L, pH7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (Falster Patch; Sophion Bioscience A/S). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.

(Result) % inhibition was shown at 5 mol/L of test compound.
Compound I-29: 21.2%
Compound I-3: 20.4%
Compound I-262: 20.1%
Compound I-255: 10.2%
Compound I-084: 10.0%
Compound I-214: 20.2%
Compound I-221: 13.2%
Compound I-026: 3.3%

Test Example 4: CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a compound of the present invention is assessed.

The reaction conditions are as follows: substrate, 0.5 μmol/L ethoxyresorufin (CYP1A2), 100 μmol/L tolbutamide (CYP2C9), 50 μmol/L S-mephenytoinmephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; concentration of a compound of the present invention, 1, 5, 10, 20 μmol/L (four points).

Each five kinds of substrates, human hepatic microsome, or a compound of the present invention in 50 mmol/L Hepes buffer as a reaction solution is added to a 96-well plate at the composition as described above, NADPH, as a cofactor is added to initiate metabolism reactions as markers and, after the incubation at 37° C. for 15 minutes, a methanol/acetonitrile=1/1 (v/v) solution is added to stop the reaction. After the centrifugation at 3000 rpm for 15 minutes, resorufin (CYP1A2 metabolite) in the supernatant is quantified by a fluorescent multilabel counter and toltributamide hydroxide (CYP2C9P metabolite), mephenytoin 4' hydroxide (CYP2C19 metabolite), dextromethorphan (CYP2D6 metabolite), and terfenadine alcohol (CYP3A4 metabolite) are quantified by LC/MS/MS.

Addition of only DMSO being a solvent dissolving a compound of the present invention to a reaction system is adopted as a control (100%), remaining activity (%) is calculated at each concentration of a compound of the present invention added as the solution and IC$_{50}$ is calculated by reverse presumption by a logistic model using a concentration and an inhibition rate.

Test Example 5: CYP3A4(MDZ) MBI Test

CYP3A4(MDZ) MBI test is a test of investigating mechanism based inhibition (MBI) ability on CYP3A4 inhibition of a compound by enhancement of a metabolism reaction. CYP3A4 inhibition is evaluated using 1-hydroxylation reaction of midazolam (MDZ) by pooled human liver microsomes as an index.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 pmg/mL (at 10-fold dilution); concentrations of the compound of the present invention, 1, 5, 10, 20 μmol/L (four points).

Pooled human liver microsomes in a K-Pi buffer (pH 7.4) and a compound of the present invention solution as a pre-reaction solution are added to a 96-well plate at the composition of the pre-reaction. A part of pre-reaction solution is transferred to another 96-well plate, and 1/10 diluted by a substrate in a K-Pi buffer. NADPH as a co-factor is added to initiate a reaction as an index (without preincubation). After a predetermined time of a reaction, methanol/acetonitrile=1/1 (v/v) solution is added to stop the reaction. On the other hand, NADPH is also added to a remaining pre-reaction solution in order to initiate a preincubation (with preincubation). After a predetermined time of a pre-incubation, a part is transferred to another 96-well plate, and 1/10 diluted by a substrate in a K-Pi buffer in order to initiate a reaction as an index. After a predetermined time of a reaction, methanol/acetonitrile=1/1 (v/v) solution is added to stop the reaction. After centrifuged at 3000 rpm for 15 minutes, 1-hydroxymidazolam in the supernatant is quantified by LC/MS/MS.

The sample adding DMSO to a reaction system instead of compound of the present invention solution is adopted as a control (100%) because DMSO is used as a solvent to dissolve a compound of the present invention. Remaining activity (%) is calculated at each concentration of the compound of the present invention added as the solution, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as Positive. When a shifted IC is 1.0 or less, this is defined as Negative.

Test Example 6: BA Test

Materials and Methods for Experiments to Evaluate Oral Absorption
(1) Experimental animals: mice or SD rats are used.
(2) Rearing condition: mice or SD rats are allowed free access to solid feed and sterilized tap water.
(3) Setting of dosage and grouping: Oral administration and intravenous administration are performed with the pre-determined dosage. Grouping is set as below. (Dosage is changed per compound)
Oral administration 1 to 30 mg/kg (n=2 to 3)
Intravenous administration 0.5 to 10 mg/kg (n=2 to 3)
(4) Preparation of administration solutions: Oral administration is performed as solution or suspension. Intravenous administration is performed after solubilization.
(5) Routes of administration: Oral administration is performed mandatory into the stomach by oral sonde. Intravenous administration is performed from caudal vein by syringes with needle.
(6) Evaluation items: Blood is collected serially and concentration of a compound of the present invention in plasma is measured by LC/MS/MS.
(7) Statistical analysis: About transition of concentration of a compound of the present invention in plasma, the area under the plasma concentration versus time curve (AUC) is calculated by non-linear least-squares method program, WinNonlin (a registered trademark), and bioavailability (BA) of a compound of the present invention is calculated from AUCs of the oral administration group and the intravenous administration group.

Test Example 7: Clearance Test

Materials and Methods for Experiments
(1) Experimental animals: mice or SD rats are used.
(2) Rearing condition: mice or SD rats are allowed free access to solid feed and sterilized tap water.
(3) Setting of dosage and grouping: Intravenous administration is performed with the predetermined dosage. Grouping is set as below. (Dosage is changed per compound) Intravenous administration 0.5 to 10 mg/kg (n=2 to 3)
(4) Preparation of administration solutions: Intravenous administration is performed after solubilization.
(5) Routes of administration: Intravenous administration is performed from caudal vein by syringes with needle.
(6) Evaluation items: Blood is collected serially and concentration of a compound of the present invention in plasma is measured by LC/MS/MS.
(7) Statistical analysis: About transition of concentration of a compound of the present invention in plasma, the area under the plasma concentration versus time curve (AUC) is calculated by non-linear least-squares method program, WinNonlin (a registered trademark), and Total Clearance (CLtot) of a compound of the present invention is calculated.

Test Example 8: Fluctuation Ames Test

Mutagenicity of compounds of the present invention is evaluated.
20 μL of freezing-stored mice typhoid *bacillus* (*Salmonella typhimurium* TA98 strain, TA100 strain) is inoculated on 10 mL of a liquid nutrient medium (2.5% Oxoid nutrient broth No. 2), and this is cultured before shaking at 37° C. for 10 hours. 7.70 mL of a bacterial solution of the TA98 strain is centrifuged (2000×g, 10 minutes) to remove a culturing solution. The bacteria is suspended in 7.70 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), the suspension is added to 120 mL of an Exposure medium (Micro F buffer containing Biotin: 8 μg/mL, histidine: 0.2 μg/mL, glucose: 8 mg/mL). The TA100 strain is added to 130 mL of the Exposure medium relative to 3.42 mL of the bacterial solution to prepare a test bacterial solution. Each 12 μL of DMSO solution of a compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) are mixed, and this is shaking-cultured at 37° C. for 90 minutes. 460 μL of the bacterial solution exposed to a compound of the present invention is mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group. (−) means that mutagenicity is negative and (+) is positive.

Test Example 9: Metabolism Stability Test

Using commercially available pooled human hepatic microsomes, a compound of the present invention was reacted for a constant time, and a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%.

(Result)
Compound I-180: 90%

Test Example 9-2: Metabolism Stability Test

Using commercially available pooled human hepatic microsomes, a compound of the present invention was reacted for a constant time, and a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The compound of the present invention in the supernatant was quantified by LC/MS/MS or Solid Phase Extraction (SPE)/MS, and a remaining amount of the compound of the present invention after the reaction was calculated, letting a compound amount at 0 minute reaction time to be 100%.

(Result)
Compound I-96: 90%
Compound I-107: 92%
Compound I-136: 104%

Test Example 10: Powder Solubility Test

Appropriate quantity of the compound of the present invention is put in a suitable container and 200 µL of JP-1 fluid (water is added to 2.0 g of sodium chloride and 7.0 mL of hydrochloric acid to reach 1000 mL), JP-2 fluid (1 volume of water are added to 1 volume of the solution which 3.40 g of potassium dihydrogen phosphate and 3.55 g of anhydrous disodium hydrogen phosphate to reach 1000 mL) or 20 mmol/L sodium taurocholate (TCA)/JP-2 fluid (JP-2 fluid is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 µL of methanol is added to 100 µL of each filtrate to dilute two-fold. The dilution rate is changed as necessary. After checking that there is no bubble and deposit, the container is sealed and shaken. The compound of the present invention is measured using HPLC by absolute calibration curve method.

Test Example 11: Solubility Test

The solubility of the compound of the present invention is determined under 1% DMSO addition conditions. A 10 mmol/L solution of the compound is prepared with DMSO, and 2 µL of the solution of the compound of the present invention is added, respectively, to 198 µL of JP-2 fluid (see below). The mixture is shaked for 1 hour at a room temperature, and the mixture is filtered. The filtrate is ten or hundred-fold diluted with methanol/water=1/1 (v/v) or acetonitrile/methanol/water=1/1/2 (V/V/V) and the compound concentration in the filtrate is measured with LC/MS or Solid Phase Extraction (SPE)/MS by the absolute calibration method.

A: About 200 mL of 0.2 mol/L sodium hydrate reagent is added to 200 mL of 0.2 mol/L potassium dihydrogen phosphate reagent to adjust pH to 6.8, and then added 600 mL of water.

B: 3.40 g of potassium dihydrogen phosphate and 3.55 g of anhydrous disodium hydrogen phosphate is dissolved in water to reach 1000 mL.

C: 1 volume of water is added 1 volume of the solution that 3.40 g of potassium dihydrogen phosphate and 3.55 g of sodium dihydrogen phosphate anhydrous are dissolved in water to be 1000 mL.

Formulation Example

The following Formulation Examples are only exemplified and not intended to limit the scope of the invention.

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Disintegrated Tablets

The compounds of the present invention and crystalline cellulose are mixed, granulated and tablets are made to give orally disintegrated tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injection.

Formulation Example 7: Infusions

The compounds of the present invention and phosphate buffer are mixed to give injection.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compound of the present invention has TrkA inhibitory activity and it can be useful for a TrkA mediated disorder such as pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease, immune disease, visceral disease, infection disease and the like.

What is claimed is:
1. A compound represented by Formula (I"):

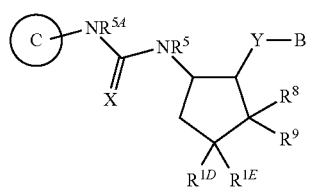

wherein
=X is =O, =S, =NR$^{10}$ or =CR$^{11}$R$^{12}$;
—Y— is a bond;
B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl;
Ring C is a substituted or unsubstituted aromatic heterocycle, or a substituted or unsubstituted non-aromatic heterocycle;
R$^{1D}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
R$^{1E}$ is a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or
R$^{1D}$ and R$^{1E}$ may be taken together to form =CR$^{1F}$R$^{1G}$, oxo, —N—O—R$^{1H}$ or a substituted or unsubstituted non-aromatic carbocycle, or a substituted or unsubstituted non-aromatic heterocycle;
R$^{1F}$ and R$^{1G}$ are each independently a hydrogen atom, substituted or unsubstituted alkyl, substituted or unsubstituted alkyloxy, or substituted or unsubstituted alkyloxycarbonyl;
R$^{1H}$ is a hydrogen atom, substituted or unsubstituted alkyl, substituted or unsubstituted alkenyl, or substituted or unsubstituted alkynyl;
R$^5$ and R$^{5A}$ are each independently a hydrogen atom, or substituted or unsubstituted alkyl;
R$^8$ is each independently a hydrogen atom, halogen, hydroxy, substituted or unsubstituted alkyl, substituted or unsubstituted alkenyl, substituted or unsubstituted alkynyl, or substituted or unsubstituted alkyloxy;
R$^9$ is each independently a hydrogen atom, halogen, hydroxy, substituted or unsubstituted alkyl, substituted or unsubstituted alkenyl, substituted or unsubstituted alkynyl, or substituted or unsubstituted alkyloxy, or
R$^8$ and R$^9$ may be taken together to form oxo;
R$^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxyl;
R$^{11}$ is a hydrogen atom, cyano, substituted or unsubstituted acyl, substituted or unsubstituted alkyloxycarbonyl, substituted or unsubstituted alkylcarbamoyl, substituted or unsubstituted alkylsulfonyl, or nitro;
R$^{12}$ is a hydrogen atom or cyano,
or its pharmaceutically acceptable salt.
2. The compound according to claim 1,
wherein =X is =O and R$^5$ and R$^{5A}$ are hydrogen atoms, or its pharmaceutically acceptable salt.
3. The compound according to claim 1,
wherein R$^8$ and R$^9$ are hydrogen atoms, or R$^8$ and R$^9$ are taken together to form oxo,
or its pharmaceutically acceptable salt.

4. The compound according to claim 1,
wherein Ring C is a substituted or unsubstituted aromatic heterocycle,
or its pharmaceutically acceptable salt.

5. The compound according to claim 4,
wherein Ring C is substituted or unsubstituted pyrazole,
or its pharmaceutically acceptable salt.

6. The compound according to claim 5,
wherein Ring C is a group represented by Formula:

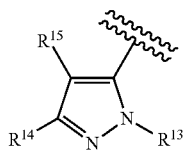

(6)

wherein $R^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkylsulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylthio, substituted or unsubstituted alkenylthio, substituted or unsubstituted alkynylthio, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ and $R^{15}$ may be taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle, or its pharmaceutically acceptable salt.

7. The compound according to claim 6,
wherein $R^{13}$ is a hydrogen atom, or substituted or unsubstituted aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, and $R^{15}$ is substituted or unsubstituted alkyl,
or its pharmaceutically acceptable salt.

8. The compound according to claim 1,
wherein $R^{1D}$ is substituted or unsubstituted alkyl and $R^{1E}$ is a hydrogen atom, or its pharmaceutically acceptable salt.

9. The compound according to claim 1,
wherein the compound is selected from the group consisting of

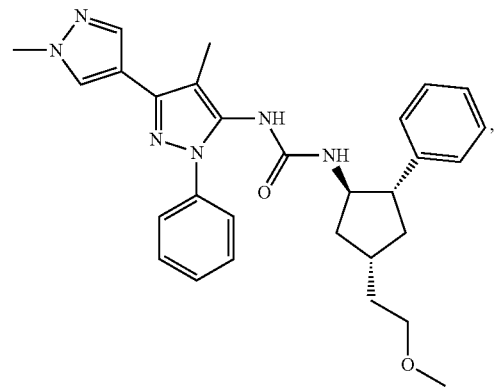

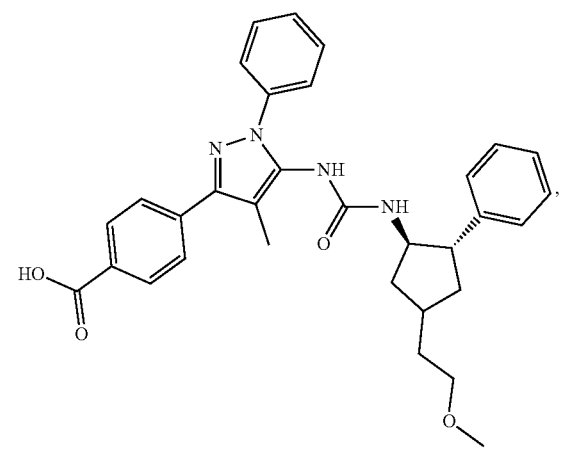

341

-continued

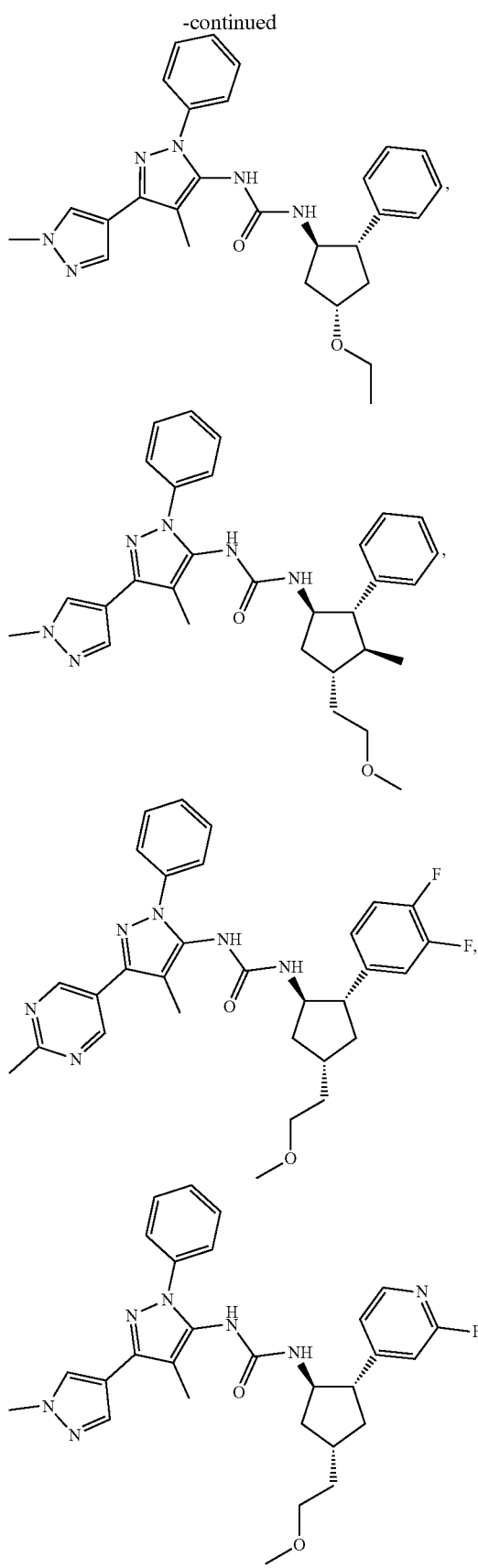

342

-continued

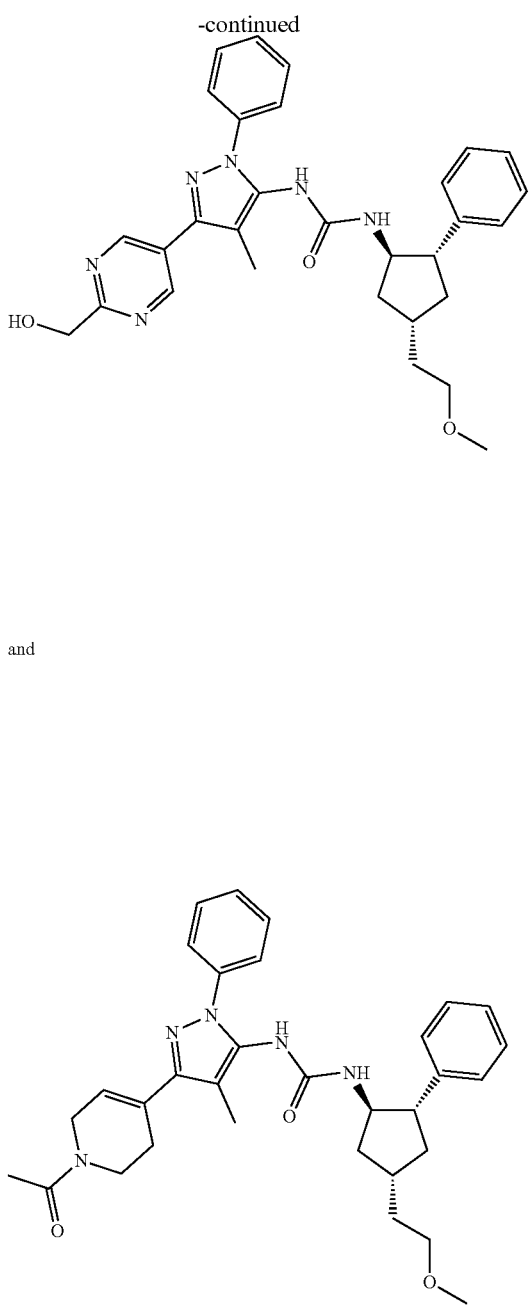

or its pharmaceutically acceptable salt.

10. The compound according to claim 1, wherein B is substituted or unsubstituted aromatic carbocyclyl or substituted or unsubstituted aromatic heterocyclyl, or its pharmaceutically acceptable salt.

11. A pharmaceutical composition comprising the compound according to claim 1, or its pharmaceutically acceptable salt.

12. A pharmaceutical composition comprising the compound according to claim 9, or its pharmaceutically acceptable salt.

* * * * *